(12) United States Patent
Fukuoka et al.

(10) Patent No.: US 8,530,490 B2
(45) Date of Patent: Sep. 10, 2013

(54) URACIL COMPOUND OR SALT THEREOF HAVING HUMAN DEOXYURIDINE TRIPHOSPHATASE INHIBITORY ACTIVITY

(75) Inventors: Masayoshi Fukuoka, Tsukuba (JP); Tatsushi Yokogawa, Tsukuba (JP); Seiji Miyahara, Tsukuba (JP); Hitoshi Miyakoshi, Tsukuba (JP); Wakako Yano, Tsukuba (JP); Junko Taguchi, Tsukuba (JP); Yayoi Takao, Chiyoda-ku (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 171 days.

(21) Appl. No.: 12/996,079

(22) PCT Filed: Jun. 2, 2009

(86) PCT No.: PCT/JP2009/002481
§ 371 (c)(1),
(2), (4) Date: Dec. 3, 2010

(87) PCT Pub. No.: WO2009/147843
PCT Pub. Date: Dec. 10, 2009

(65) Prior Publication Data
US 2011/0082163 A1    Apr. 7, 2011

(30) Foreign Application Priority Data
Jun. 3, 2008    (JP) .................. 2008-146334

(51) Int. Cl.
*A61K 31/505* (2006.01)
*C07D 401/02* (2006.01)
*C07D 239/02* (2006.01)

(52) U.S. Cl.
USPC .................. 514/274; 544/310; 544/312

(58) Field of Classification Search
USPC .................. 514/274; 544/312, 310
See application file for complete search history.

(56) References Cited

U.S. PATENT DOCUMENTS

| | | |
|---|---|---|
| 2008/0070920 A1 | 3/2008 | Guo et al. |
| 2008/0300216 A1 | 12/2008 | Gilbert et al. |
| 2008/0312183 A1 | 12/2008 | Gilbert et al. |
| 2012/0225838 A1 | 9/2012 | Fukuoka et al. |

FOREIGN PATENT DOCUMENTS

| | | |
|---|---|---|
| JP | 2002 284686 | 10/2002 |
| WO | 95 15332 | 6/1995 |
| WO | 03 089461 | 10/2003 |
| WO | 2005 065689 | 7/2005 |
| WO | 2005 066160 | 7/2005 |
| WO | 2008 016522 | 2/2008 |

OTHER PUBLICATIONS

Supplementary European Search Report, issued Aug. 11, 2011, in PCT/JP2009-002481 (EP 09 758 110.2).

Yong J. Lee, et al., "Energy Transfer inFluorescent Derivates of Uracil and Thymine," Journal of the American Chemical Society, vol. 99, No. 23, (Nov. 1, 1977), pp. 7679-7685 (XP55003084).

Yu S. Shvetsov, et al., "Synthesis and Properties of Pyrimidinyalkylsulfonamides," Bulletin of the Academy of Sciences of the USSR, Division of Chemical Science, vol. 27, No. 1, (1978), p. 149-153 (XP002652197).

Y.L. Jiang, et al., "Synthesis and High-Throughput Evaluation of Triskelion Uracil Libraries for Inhibition of Human dUTPase and UNG2," Bioorganic and Medicinal Chemistry, Pergamon, GB, vol. 14, No. 16 (Aug. 15, 2006), pp. 5666-5672 (XP025133468).

Nguyen, C., et al., "Acyclic Nucleoside Analogues as Inhibitors of *Plasmodium falciparum* dUTPase," Journal of Medicinal Chemistry, vol. 49, No. 14, pp. 4183-4195, (Jun. 13, 2006).

Nguyen, C., et al., "Deoxyuridine Triphosphate Nucleotidohydrolase as a Potential Antiparasitic Drug Target," Journal of Medicinal Chemistry, vol. 48, No. 19, pp. 5942-5954, (Aug. 19, 2005).

Mol, C.D., et al., "Human dUTP pyrophosphatase: uracil recognition by a β hairpin and active sites formed by three separate subunits," Structure, vol. 4, No. 9, pp. 1077-1092, (Sep. 15, 1996).

McIntosh, E.M., et al., "dUTP pyrophosphatase as a potential target for chemotherapeutic drug development," Acta Biochimica Polonica, vol. 44, No. 2, pp. 159-172, (1997).

(Continued)

*Primary Examiner* — James O Wilson
*Assistant Examiner* — Ebenezer O Sackey
(74) *Attorney, Agent, or Firm* — Oblon, Spivak, McClelland, Maier & Neustadt, L.L.P.

(57) ABSTRACT

Provided is a uracil compound or a salt thereof, which has potent human dUTPase inhibitory activity and is useful as, for example, an antitumor drug.

A uracil compound represented by the general formula (I) or a salt thereof:

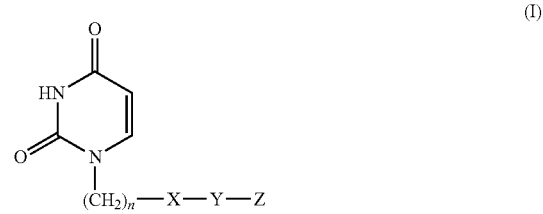

(I)

wherein n represents an integer of 1 to 3; X represents a bond, an oxygen atom, a sulfur atom, or the like; Y represents a linear or branched alkylene group having 1 to 8 carbon atoms, or the like; and Z represents $-SO_2NR^1R^2$ or $-NR^3SO_2-R^4$, wherein $R^1$ and $R^2$ each represent an alkyl group having 1 to 6 carbon atoms, an aralkyl group which is optionally substituted, or the like; $R^3$ represents an alkyl group having 1 to 6 carbon atoms, or the like; and $R^4$ represents an aromatic hydrocarbon group, an unsaturated heterocyclic group, or the like.

8 Claims, No Drawings

(56) References Cited

OTHER PUBLICATIONS

Ladner, R.D., et al., "dUTP Nucleotidohydrolase Isoform Expression in Normal and Neoplastic Tissues: Association with Survival and Response to 5-Fluorouracil in Colorectal Cancer," Cancer Research, vol. 60, pp. 3493-3503, (Jul. 1, 2000).

Ladner, R.D., "The Role of dUTPase and Uracil-DNA Repair in Cancer Chemotherapy," Current Protein and Peptide Science, vol. 2, No. 4, pp. 361-370, (2001).

Whittingham, J.L., et al., "dUTPase as a Platform for Antimalarial Drug Design: Structural Basis for the Selectivity of a Class of Nucleoside Inhibitors," Structure, vol. 13, pp. 329-338, (Feb. 2005).

Chan, S., et al., "Crystal Structure of the *Mycobacterium tuberculosis* dUTPase: Insights into the Catalytic Mechanism," J. Mol. Bio., vol. 341, pp. 503-517, (2004).

McCarthy, O.K., et al., "Design, synthesis and evaluation of novel uracil amino acid conjugates for the inhibition of *Trypanosoma cruzi* dUTPase," Bioorganic & Medicinal Chemistry Letters, vol. 16, pp. 3809-3812, (May 3, 2006).

Studebaker, A.W., et al., "The Herpesvirus Encoded dUTPase as a Potential Chemotherapeutic Target," Current Protein and Peptide Science, vol. 2, No. 4, pp. 371-379, (2001).

Samal, A., et al., "Structures of vaccinia virus dUTPase and its nucleotide complexes," Acta Cryst., vol. D63, pp. 571-580, (2007).

Williams, M.V., "Effects of Mercury (II) Compounds on the Activity of dUTPases from Various Sources," Molecular Pharmacology, vol. 29, pp. 288-292, (1986).

Marriott, J.H., et al., "Synthesis of Certain 2'-Deoxyuridine Derivatives Containing Substituted Phenoxy Groups Attached to C-5'; Evaluation as Potential dUTP Analogues," Nucleosides, Nucleotides & Nucleic Acids, vol. 20, No. 9, pp. 1691-1704, (2001).

International Search Report issued Jun. 30, 2009 in PCT/JP09/002481 filed Jun. 2, 2009.

Yu. S. Shvetsov, et al., "Synthesis and Properties of Pyrimidinylalkylsulfonamides, 2. Reaction of Several hydroxypyrimidines with N-phenyl-N-methyl-ω-chloroalkylsulfonamides", Bulletin of The Academy of Sciences of the USSR, Division of Chemical Science, vol. 26, No. 4, Apr. 1977, pp. 807-813 (English translation only).

URACIL COMPOUND OR SALT THEREOF HAVING HUMAN DEOXYURIDINE TRIPHOSPHATASE INHIBITORY ACTIVITY

FIELD OF THE INVENTION

The present invention relates to a novel uracil compound or a salt thereof, which has potent human deoxyuridine triphosphatase inhibitory activity and is useful as a therapeutic agent for disease associated with deoxyuridine triphosphatase, for example, an antitumor drug.

BACKGROUND OF THE INVENTION

Deoxyuridine triphosphatase (hereinafter, also referred to as dUTPase (EC3.6.1.23)) is a preventive DNA repair enzyme. This enzyme specifically recognizes only deoxyuridine triphosphate (hereinafter, referred to as dUTP) among canonical nucleoside triphosphates and hydrolyzes dUTP to deoxyuridine monophosphate (hereinafter, referred to as dUMP) and pyrophosphate (Non-Patent Document 1). The enzyme is thought to be responsible for two reactions, (1) decreasing the amount of the intracellular dUTP pools to prevent the misincorporation of uracil instead of thymine into DNA and (2) supplying a substrate dUMP for thymidylate synthase responsible for an important de novo pathway for thymine supply into DNA (Non-Patent Document 2).

dUTPase is known to be an essential enzyme for cell viability in both prokaryotes and eukaryotes. It has thus been suggested that this enzyme can be a target for antitumor drugs (Non-Patent Documents 3 and 4), antimalarial drugs (Patent Document 1 and Non-Patent Document 5), antituberculosis drugs (Non-Patent Document 6), anti-*Helicobacter pylori* drugs (Patent Document 2), antiparasitic drugs for *trypanosoma, leishmania*, or the like (Non-Patent Document 7), and antiviral drugs for herpesvirus (e.g., human herpes simplex virus, cytomegalovirus, or Epstein-Barr virus) (Non-Patent Document 8), vaccinia virus (Non-Patent Document 9), or the like.

Thus, dUTPase has been paid attention as a target for therapeutic agents against various diseases, and dUTPase inhibitors have also been studied widely.

For example, a low-molecular compound that mimics dUTP (e.g., Patent Document 3 and Non-Patent Document 10) and a 5'-O-substituted phenyl-deoxyuridine compound (Non-Patent Document 11) are known as the dUTPase inhibitors. However, none of these compounds has sufficient inhibitory activity against human dUTPase and is available as a medicament.

Therefore, the development of the potent human dUTPase inhibitors which are useful as therapeutic agents for disease associated with dUTPase, for example, an antitumor drug, are urgently required.

RELATED DOCUMENTS

Patent Documents

Patent Document 1: WO2005/065689 pamphlet
Patent Document 2: WO2003/089461 pamphlet
Patent Document 3: WO1995/15332 pamphlet

Non-Patent Documents

Non-Patent Document 1: Structure, 4, 1077-1092 (1996)
Non-Patent Document 2: Acta Biochim. Pol., 44, 159-171 (1997)
Non-Patent Document 3: Cancer Research, 60, 3493-3503, July 1 (2000)
Non-Patent Document 4: Curr. Protein Pept. Sci., 2, 361-370 (2001)
Non-Patent Document 5: Structure, 13, 329-338 (2005)
Non-Patent Document 6: J. Mol. Biol., 341, 503-517 (2004)
Non-Patent Document 7: Bioorg. Med. Chem. Lett., 16, 3809-3812 (2006)
Non-Patent Document 8: Curr. Protein Pept. Sci., 2, 371-379 (2001)
Non-Patent Document 9: Acta Crystallogr. D. Biol. Crystallogr, 63, 571-580 (2007)
Non-Patent Document 10: Mol. Pharmacol., 29, 288-292 (1986)
Non-Patent Document 11: Nucleosides Nucleotides & Nucleic acids, 20, 1691-1704 (2001)

SUMMARY OF THE INVENTION

Problems to be Solved by the Invention

An object of the present invention is to provide a uracil compound or a salt thereof, which has potent human dUTPase inhibitory activity and is useful as, for example, an antitumor drug.

Means for Solving the Problems

The present inventors have conducted diligent studies to attain the object, and as a result, have found that a uracil compound having a sulfonamide structure at the N–1 position of the uracil ring or a salt thereof has potent human dUTPase inhibitory activity and is useful as, for example, an antitumor drug. The present invention has been accomplished on the basis of this finding.

The present invention provides a uracil compound represented by the following formula (I) or a salt thereof:

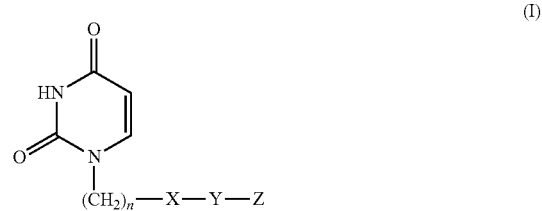

(I)

wherein n represents an integer of 1 to 3;
X represents a bond, an oxygen atom, a sulfur atom, an alkenylene group having 2 to 6 carbon atoms, a divalent aromatic hydrocarbon group which is optionally substituted, or a divalent saturated or unsaturated heterocyclic group which is optionally substituted;
Y represents a bond or a linear or branched alkylene group having 1 to 8 carbon atoms which optionally have a cycloalkylidene structure on one carbon atom; and
Z represents —$SO_2NR^1R^2$ or —$NR^3SO_2$—$R^4$, wherein $R^1$ and $R^2$ are the same or different and each represents a hydrogen atom, an alkyl group having 1 to 6 carbon atoms, or an aralkyl group which is optionally substituted, wherein when an aromatic hydrocarbon group constituting the aralkyl group is a phenyl group, the phenyl group may form a condensed bicyclic hydrocarbon group, together with the substituent, or $R^1$ and $R^2$ are taken together with the adjacent nitrogen atom to form a saturated heterocyclic group which is optionally substituted;

$R^3$ represents a hydrogen atom or an alkyl group having 1 to 6 carbon atoms; and $R^4$ represents an aromatic hydrocarbon group which is optionally substituted or an unsaturated heterocyclic group which is optionally substituted.

The present invention also provides a pharmaceutical composition containing the uracil compound represented by the formula (I) or the salt thereof.

The present invention also provides a human dUTPase inhibitor containing the uracil compound represented by the formula (I) or the salt thereof.

The present invention also provides use of the uracil compound represented by the formula (I) or the salt thereof for the production of a human dUTPase inhibitor.

The present invention also provides a method for treating disease attributed to human dUTPase, including administering the uracil compound represented by the formula (I) or the salt thereof to a patient in need thereof.

Effects of the Invention

The novel uracil compound of the present invention or the salt thereof has potent human dUTPase inhibitory activity and is useful as a therapeutic agent for disease associated with dUTPase, for example, an antitumor drug.

DETAILED DESCRIPTION OF THE INVENTION

A novel uracil compound of the present invention is represented by the general formula (I) and characterized by having a sulfonamide structure at the N-1 position of the uracil ring.

WO2005/065689 (Patent Document 1) discloses a uracil compound having a substituent such as a trityl or triphenylsilyl group (represented by a -E($R^6$)($R^7$)($R^8$) group therein) at the end of a substituent at the N-1 position of the uracil ring. The uracil compound described therein exhibits dUTPase inhibitory activity and is useful as an antimalarial drug. However, this document does not disclose a compound having a sulfonamide bond carried by the compound of the present invention.

JP-A-2002-284686 discloses a uracil compound having a sulfonamide bond via a hydroxamic acid residue as a substituent at the N-1 position of the uracil ring. Specifically, the uracil compound described therein differs from the compound of the present invention in that it has a substituent such as a hydroxamic acid group in an alkylene chain bonded to the N-1 position of the uracil ring. This document describes the MMP inhibitory effect of the uracil compound but makes no mention of dUTPase inhibitory activity.

As shown in Test Example described later, compounds described in Examples of WO2005/065689 (Patent Document 1) and JP-A-2002-284686 hardly exhibited human dUTPase inhibitory activity.

In the present specification, an "aromatic hydrocarbon group" is preferably an aromatic hydrocarbon group having 6 to 14 carbon atoms. Examples thereof include phenyl and naphthyl groups. The phenyl group is more preferable.

In the present specification, a "divalent aromatic hydrocarbon group" is preferably a divalent aromatic hydrocarbon group having 6 to 14 carbon atoms. Examples thereof include phenylene and naphthylene groups. The phenylene group is more preferable.

A "saturated or unsaturated heterocyclic group" is preferably a monocyclic or bicyclic saturated or unsaturated heterocyclic group having 1 or 2 atoms selected from oxygen, nitrogen, and sulfur atoms. Examples thereof include pyrrolidinyl, piperidinyl, piperazinyl, hexamethyleneimino, morpholino, thiomorpholino, homopiperidinyl, imidazolyl, thienyl, furyl, pyrrolyl, oxazolyl, isoxazolyl, thiazolyl, isothiazolyl, pyrazolinyl, triazolyl, tetrazolyl, pyridyl, pyrazyl, pyrimidinyl, pyridazyl, indolyl, isoindolyl, indazolyl, methylenedioxyphenyl, ethylenedioxyphenyl, benzofuranyl, dihydrobenzofuranyl, benzimidazolyl, benzoxazole, benzothiazolyl, purinyl, quinolyl, isoquinolyl, quinazolinyl, and quinoxalyl groups. Of these, 5- to 7-membered saturated or unsaturated heterocyclic groups having 1 nitrogen or sulfur atom are preferable. The piperidinyl, thienyl, and pyridyl groups are more preferable in terms of dUTPase inhibitory activity.

A "divalent saturated or unsaturated heterocyclic group" is preferably a monocyclic or bicyclic divalent saturated or unsaturated heterocyclic group having 1 or 2 atoms selected from oxygen, nitrogen, and sulfur atoms. Examples thereof include divalent groups derived from pyrrolidinyl, piperidinyl, piperazinyl, hexamethyleneimino, morpholino, thiomorpholino, homopiperidinyl, imidazolyl, thienyl, furyl, pyrrolyl, oxazolyl, isoxazolyl, thiazolyl, isothiazolyl, pyrazolinyl, triazolyl, tetrazolyl, pyridyl, pyrazyl, pyrimidinyl, pyridazyl, indolyl, isoindolyl, indazolyl, methylenedioxyphenyl, ethylenedioxyphenyl, benzofuranyl, dihydrobenzofuranyl, benzimidazolyl, benzoxazole, benzothiazolyl, purinyl, quinolyl, isoquinolyl, quinazolinyl, and quinoxalyl groups. Of these, 5- to 7-membered divalent saturated or unsaturated heterocyclic groups having 1 nitrogen or sulfur atom are preferable. The divalent groups derived from piperidinyl, thienyl, and pyridyl groups are more preferable in terms of dUTPase inhibitory activity.

A "saturated heterocyclic group" is preferably a monocyclic saturated heterocyclic group having 1 or 2 atoms selected from oxygen, nitrogen, and sulfur atoms. Examples thereof include pyrrolidinyl, piperidinyl, piperazinyl, hexamethyleneimino, morpholino, thiomorpholino, and homopiperidinyl groups. Of these, 5- to 7-membered saturated heterocyclic groups having 1 nitrogen atom are preferable. The piperidinyl and pyrrolidinyl groups are more preferable in terms of dUTPase inhibitory activity.

Examples of an "aralkyl group" include alkyl groups substituted by an aromatic hydrocarbon group having 6 to 10 carbon atoms and specifically include alkyl groups having 1 to 6 carbon atoms which are substituted by a phenyl group and alkyl groups having 1 to 6 carbon atoms which are substituted by a naphthyl group.

Examples of a group (substituent) by which the aromatic hydrocarbon group, the saturated or unsaturated heterocyclic group, and the aralkyl group may be substituted include a halogen atom, a hydroxyl group, a cyano group, a nitro group, an alkyl group, a halogenoalkyl group, a cycloalkyl group, a cycloalkyl-alkyl group, an aralkyl group, an alkenyl group, an alkynyl group, an alkoxy group, a halogenoalkoxy group, a cycloalkoxy group, a cycloalkyl-alkoxy group, an aralkyloxy group, an alkylthio group, a cycloalkyl-alkylthio group, an amino group, a mono- or dialkylamino group, a cycloalkyl-alkylamino group, a carboxyl group, an alkylcarbonyl group, an alkoxycarbonyl group, an acyl group, an acyloxy group, an oxo group, a saturated or unsaturated heterocyclic group, an aromatic hydrocarbon group, and a saturated heterocyclic oxy group. When the substituent is present, the number thereof is typically 1 to 3.

Examples of the halogen atom used as the substituent include chlorine, bromine, fluorine, and iodine atoms.

The alkyl or halogenoalkyl group used as the substituent refers to preferably a linear or branched alkyl group having 1 to 6 carbon atoms or this alkyl group which is substituted by the halogen atom exemplified above. Examples thereof include methyl, ethyl, n-propyl, isopropyl, and trifluoromethyl groups.

The cycloalkyl group used as the substituent is preferably a cycloalkyl group having 3 to 7 carbon atoms. Examples thereof include cyclopropyl, cyclobutyl, cyclopentyl, and cyclohexyl groups.

The cycloalkyl-alkyl group used as the substituent is preferably an alkyl group having 1 to 6 carbon atoms which is substituted by a cycloalkyl group having 3 to 7 carbon atoms. Examples thereof include cyclopropylmethyl, cyclopropylethyl, cyclobutylmethyl, and cyclopentylmethyl groups.

The aralkyl group used as the substituent refers to preferably a linear or branched alkyl group having 1 to 6 carbon atoms which is substituted by an aromatic hydrocarbon group having 6 to 14 carbon atoms. Examples thereof include benzyl, phenylethyl, phenylpropyl, naphthylmethyl, and naphthylethyl groups.

The alkenyl group used as the substituent contains a carbon-carbon double bond and refers to preferably an alkenyl group having 2 to 6 carbon atoms. Examples thereof include vinyl, allyl, methylvinyl, propenyl, butenyl, pentenyl, and hexenyl groups.

The alkynyl group used as the substituent contains a carbon-carbon triple bond and refers to preferably an alkynyl group having 2 to 6 carbon atoms. Examples thereof include ethynyl and propargyl groups.

The alkoxy or halogenoalkoxy group used as the substituent refers to preferably a linear or branched alkoxy group having 1 to 6 carbon atoms or this alkoxy group which is substituted by the halogen atom exemplified above. Examples thereof include methoxy, ethoxy, n-propoxy, isopropoxy, 1-methylpropoxy, n-butoxy, isobutoxy, 2-methylbutoxy, neopentyloxy, pentan-2-yloxy, fluoromethoxy, difluoromethoxy, trifluoromethoxy, 1,1-difluoroethoxy, 2,2-difluoroethoxy, 2,2,2-trifluoroethoxy, 1,1,2,2-tetrafluoroethoxy, perfluoroethoxy, 3-fluoro-2-(fluoromethyl)-propoxy, 1,3-difluoropropan-2-yloxy, and 2,2,3,3,3-pentafluoro-1-propoxy groups.

The cycloalkoxy group used as the substituent is preferably a cycloalkoxy group having 3 to 7 carbon atoms. Examples thereof include cyclopropoxy, cyclobutoxy, cyclopentyloxy, and cyclohexyloxy groups.

The cycloalkyl-alkoxy group used as the substituent is preferably an alkoxy group having 1 to 6 carbon atoms which is substituted by cycloalkyl having 3 to 7 carbon atoms. Examples thereof include cyclopropylmethoxy, cyclopropylethoxy, cyclobutylmethoxy, and cyclopentylmethoxy groups.

The aralkyloxy group used as the substituent refers to preferably an oxy group having the aralkyl group exemplified above. Examples thereof include benzyloxy, phenylethoxy, phenylpropoxy, naphthylmethoxy, and naphthylethoxy groups.

The alkylthio group used as the substituent refers to preferably a thio group having the alkyl group having 1 to 6 carbon atoms exemplified above. Examples thereof include methylthio, ethylthio, and n-propylthio groups.

The cycloalkyl-alkylthio group used as the substituent is preferably an alkylthio group having 1 to 6 carbon atoms which is substituted by a cycloalkyl group having 3 to 7 carbon atoms. Examples thereof include cyclopropylmethylthio, cyclopropylethylthio, cyclobutylmethylthio, and cyclopentylmethylthio groups.

The mono- or dialkylamino group used as the substituent refers to an amino group mono- or di-substituted by the alkyl group exemplified above. Examples thereof include methylamino, dimethylamino, ethylamino, diethylamino, and methylethylamino groups.

The cycloalkyl-alkylamino group used as the substituent refers to an alkylamino group substituted by the cycloalkyl group exemplified above. Examples thereof include cyclopropylmethylamino, cyclobutylmethylamino, and cyclopentylmethylamino groups.

The alkylcarbonyl group used as the substituent is preferably an alkylcarbonyl group having 1 to 6 carbon atoms. Examples thereof include methylcarbonyl and ethylcarbonyl groups.

The alkoxycarbonyl group used as the substituent is preferably an alkoxycarbonyl group having 1 to 6 carbon atoms. Examples thereof include methoxycarbonyl, ethoxycarbonyl, and tert-butoxycarbonyl groups.

Examples of the acyl group used as the substituent include linear or branched acyl groups having 1 to 6 carbon atoms, such as formyl, acetyl, propionyl, n-butyryl, isobutyryl, valeryl, isovaleryl, and pivaloyl groups, and a benzoyl group.

Examples of the acyloxy group used as the substituent include linear or branched acyloxy groups having 1 to 6 carbon atoms, such as acetoxy, propionyloxy, n-butyryloxy, isobutyryloxy, valeryloxy, isovaleryloxy, and pivaloyloxy groups, and a benzoyloxy group.

The saturated or unsaturated heterocyclic group used as the substituent refers to preferably a monocyclic or bicyclic saturated or unsaturated heterocyclic group having preferably 1 or 2 atoms selected from oxygen, nitrogen, and sulfur atoms. Examples thereof include pyrrolidinyl, piperidinyl, piperazinyl, hexamethyleneimino, morpholino, thiomorpholino, homopiperidinyl, tetrahydrofuryl, tetrahydropyryl, imidazolyl, thienyl, furyl, pyrrolyl, oxazolyl, isoxazolyl, thiazolyl, isothiazolyl, pyrazolinyl, triazolyl, tetrazolyl, pyridyl, pyrazyl, pyrimidinyl, pyridazyl, indolyl, isoindolyl, indazolyl, methylenedioxyphenyl, ethylenedioxyphenyl, benzofuranyl, dihydrobenzofuranyl, benzimidazolyl, benzoxazole, benzothiazolyl, purinyl, quinolyl, isoquinolyl, quinazolinyl, and quinoxalyl groups.

The aromatic hydrocarbon group used as the substituent refers to preferably an aromatic hydrocarbon group having 6 to 14 carbon atoms. Examples thereof include phenyl and naphthyl groups.

The saturated heterocyclic oxy group used as the substituent refers to an oxy group having the saturated heterocyclic group exemplified above. Examples thereof include tetrahydrofuryloxy and tetrahydropyryloxy groups.

In the general formula (I), n represents an integer of 1 to 3 and is preferably 1 or 3, more preferably 1, in terms of dUTPase inhibitory activity.

In the general formula (I), X represents a bond, an oxygen atom, a sulfur atom, an alkenylene group having 2 to 6 carbon atoms, a divalent aromatic hydrocarbon group which is optionally substituted, or a divalent saturated or unsaturated heterocyclic group which is optionally substituted.

The bond represented by X is preferably a single bond.

Examples of the "alkenylene group having 2 to 6 carbon atoms" represented by X include vinylene, allylene, methylvinylene, propenylene, butenylene, pentenylene, and hexenylene groups. Alkenylene groups having 2 to 4 carbon atoms are preferable. The vinylene group is more preferable.

Examples of the "divalent aromatic hydrocarbon group" or the "divalent saturated or unsaturated heterocyclic group" in the "divalent aromatic hydrocarbon group which is optionally substituted or the divalent saturated or unsaturated heterocyclic group which is optionally substituted" represented by X include the divalent aromatic hydrocarbon group exemplified above and the divalent saturated or unsaturated heterocyclic group exemplified above. The phenylene, naphthylene, thienylene, piperidinylene, and pyridylene groups are particularly preferable.

Preferable examples of the moiety X in terms of dUTPase inhibitory activity include a single bond, an oxygen atom, a sulfur atom, a vinylene group, a phenylene group, a thienylene group, a piperidinylene group, and a pyridylene group. In particular, the single bond, the oxygen atom, and the vinylene group are preferable.

In the general formula (I), Y represents a bond or a linear or branched alkylene group having 1 to 8 carbon atoms which optionally have a cycloalkylidene structure on one carbon atom.

In this context, examples of the "linear or branched alkylene group having 1 to 8 carbon atoms" in the "linear or branched alkylene group having 1 to 8 carbon atoms which optionally have a cycloalkylidene structure on one carbon atom" include methylene, ethylene, trimethylene, tetramethylene, pentamethylene, hexamethylene, propylene, butylene, dimethyltrimethylene, dimethyltetramethylene, ethyltrimethylene, and diethyltetramethylene groups. Linear or branched alkylene groups having 1 to 6 carbon atoms are preferable. Linear alkylene groups having 1 to 4 carbon atoms are more preferable.

The "cycloalkylidene" in the "linear or branched alkylene group having 1 to 8 carbon atoms which optionally have a cycloalkylidene structure on one carbon atom" is preferably cycloalkylidene having 3 to 6 carbon atoms. Examples thereof include cyclopropylidene, cyclobutylidene, cyclopentylidene, and cyclohexylidene.

In the general formula (I), when X represents a single bond, the moiety $(CH_2)_n$—X—Y is preferably an alkylene group having 3 to 6 carbon atoms. The group is more preferably a trimethylene or pentamethylene group.

Preferable examples of the moiety Y in terms of dUTPase inhibitory activity include a single bond, or a linear or branched alkylene group having 1 to 6 carbon atoms which optionally have a cycloalkylidene structure having 3 to 6 carbon atoms on one carbon atom (when X represents a single bond, the moiety $(CH_2)_n$—X—Y represents a trimethylene or pentamethylene group). The ethylene and trimethylene groups are more preferable.

In the general formula (I), Z is —$SO_2NR^1R^2$ or —$NR^3SO_2$—$R^4$ and is preferably —$SO_2NR^1R^2$.

In the moiety represented by Z, $R^1$ and $R^2$ are the same or different and each represents a hydrogen atom, an alkyl group having 1 to 6 carbon atoms, or an aralkyl group which is optionally substituted(s), wherein when an aromatic hydrocarbon group constituting the aralkyl group is a phenyl group, the phenyl group may form a condensed bicyclic hydrocarbon group, together with the substituent, or $R^1$ and $R^2$ are taken together with the adjacent nitrogen atom to form a saturated heterocyclic group which is optionally substituted.

The "alkyl group having 1 to 6 carbon atoms" represented by $R^1$ and $R^2$ refers to a linear or branched alkyl group having 1 to 6 carbon atoms. Examples thereof include methyl, ethyl, n-propyl, isopropyl, n-butyl, sec-butyl, tert-butyl, n-pentyl, and n-hexyl groups. Alkyl groups having 1 to 3 carbon atoms are preferable. The methyl group is more preferable.

The "aralkyl group" in the "aralkyl group which is optionally substituted" represented by $R^1$ and $R^2$ is preferably a linear or branched alkyl group having 1 to 6 carbon atoms which is substituted by an aromatic hydrocarbon group having 6 to 14 carbon atoms (each of the alkyl group and the aromatic hydrocarbon group is optionally substituted). Examples of the "linear or branched alkyl group having 1 to 6 carbon atoms which is substituted by an aromatic hydrocarbon group having 6 to 14 carbon atoms" include benzyl, phenylethyl, phenylpropyl, naphthylmethyl, and naphthylethyl groups. The benzyl and phenylethyl groups are preferable. The benzyl group is more preferable.

When an aromatic hydrocarbon group constituting the "aralkyl group" is a phenyl group, the "condensed bicyclic hydrocarbon group" which the phenyl group may form, together with the substituent refers to a phenyl ring-containing bicyclic hydrocarbon group having 9 to 10 carbon atoms. Examples thereof include 1,2,3,4-tetrahydronaphthalene, 1,4-dihydronaphthalene, 1,2-dihydronaphthalene, indene, and indane groups. The indane group is preferable.

When the alkyl group in the "aralkyl group"-constituting linear or branched alkyl group having 1 to 6 carbon atoms which is substituted by an aromatic hydrocarbon group having 6 to 14 carbon atoms (each of the alkyl group and the aromatic hydrocarbon group is optionally substituted) has a substituent(s), examples of the substituent include: a hydroxyl group; alkyl groups having 1 to 6 carbon atoms, such as methyl, ethyl, n-propyl, isopropyl, 2-methylpropyl, n-butyl, isobutyl, and n-pentyl groups; cycloalkyl groups having 3 to 7 carbon atoms, such as cyclopropyl, cyclobutyl, cyclopentyl, and cyclohexyl groups; alkylthio groups having 1 to 6 carbon atoms, such as methylthio, ethylthio, n-propylthio, and isopropylthio groups; and aromatic hydrocarbon (e.g., phenyl) or unsaturated heterocyclic (e.g., thienyl) groups which is optionally substituted such as a halogen atom (e.g., fluorine, chlorine, and bromine atoms), a methoxy group, an ethoxy group, a n-propoxy group, an isopropoxy group, an isobutoxy group, a cyclobutoxy group, a cyclopentyloxy group, and a cyclopropylmethoxy group. The alkyl group may have 1 to 3 substituents which are the same or different and each is selected from these substituents.

When two or more of the substituents are respectively an alkyl group having 1 to 6 carbon atoms, the carbon atoms of these alkyl groups may form together a cycloalkylidene structure.

When the aromatic hydrocarbon group in the "aralkyl group"-constituting linear or branched alkyl group having 1 to 6 carbon atoms which is substituted by an aromatic hydrocarbon group having 6 to 14 carbon atoms (each of the alkyl group and the aromatic hydrocarbon group is optionally substituted) has a substituent(s), examples of the substituent include: halogen atoms such as fluorine, chlorine, bromine, and iodine atoms; alkyl groups having 1 to 6 carbon atoms (e.g., methyl, ethyl, fluoromethyl, difluoromethyl, and trifluoromethyl) which is optionally substituted such as a halogen atom; alkynyl groups having 2 to 6 carbon atoms which is optionally substituted; linear or branched alkoxy groups having 1 to 6 carbon atoms (e.g., isobutoxy, 2-methylbutoxy, allyloxy, 2,2-difluoroethoxy, and 2,2,2-trifluoroethoxy groups) which is optionally substituted such as a hydroxyl group, a halogen atom (e.g., fluorine, chlorine, and bromine atoms), an alkenyl group having 2 to 6 carbon atoms (e.g., a vinyl group), and an alkynyl group having 2 to 6 carbon atoms (e.g., an ethynyl group), or a cycloalkylidene structure; cycloalkoxy groups having 3 to 7 carbon atoms, such as cyclopropoxy, cyclobutoxy, cyclopentyloxy, and cyclohexyloxy groups; cycloalkyl-alkoxy groups having 3 to 7 carbon atoms, such as cyclopropylmethoxy, cyclopropylethoxy, cyclobutylmethoxy, and cyclopentylmethoxy groups; saturated heterocyclic oxy groups such as tetrahydrofuran-3-yloxy and tetrahydro-2H-pyran-4-yloxy groups; and cycloalkyl-alkylthio groups having 3 to 7 carbon atoms, such as cyclopropylmethylthio and cyclobutylmethylthio groups.

The aromatic hydrocarbon group may have 1 to 2 substituents selected from these substituents.

In the general formula (I), examples of the "saturated heterocyclic group" in the "saturated heterocyclic group which is optionally substituted" which $R^1$ and $R^2$ may form, together with the adjacent nitrogen atom, include the saturated heterocyclic group exemplified above. The pyrrolidinyl group is preferable in terms of dUTPase inhibitory activity.

In the general formula (I), examples of the "substituent" in the "saturated heterocyclic group which is optionally substituted" which $R^1$ and $R^2$ may form, together with the adjacent nitrogen atom, include the substituent exemplified above. An aralkyl group which is optionally substituted(s) is preferable. A benzyl group which is optionally substituted is more preferable.

The substituent(s) which the aralkyl group may have is preferably a hydroxyl group, a halogen atom, or a phenyl group which is optionally substituted. The aralkyl group may have 1 to 3 substituents selected from these substituents.

A methylene group on the benzyl group may be substituted by a hydroxyl group and/or a phenyl group which may have fluorine substitution. Of these benzyl groups, a benzyl group which may have fluorine substitution on the phenyl ring thereof is preferable. The number of the substituent which the saturated heterocyclic group may have is preferably 1.

Specifically, preferable examples of the moiety $R^1$ include a hydrogen atom and an alkyl group having 1 to 3 carbon atoms in terms of dUTPase inhibitory activity, and the hydrogen atom is more preferable. Preferable examples of the moiety $R^2$ include a benzyl group which is optionally substituted and a phenylethyl group which is optionally substituted in terms of dUTPase inhibitory activity, and the benzyl group which is optionally substituted is more preferable. When a methylene group of the benzyl group or an ethylene group of the phenylethyl group has a substituent(s), it may have 1 to 3 substituents which are the same or different and each is selected from a hydroxyl group, an alkyl group having 1 to 6 carbon atoms, a cycloalkyl group having 3 to 7 carbon atoms, an alkylthio group having 1 to 6 carbon atoms, an aromatic hydrocarbon group which is optionally substituted, and an unsaturated heterocyclic group which is optionally substituted, wherein when two or more of the substituents are respectively an alkyl group having 1 to 6 carbon atoms, the carbon atoms of these alkyl groups may form together a cycloalkylidene structure. When a phenyl group of the benzyl or phenylethyl group has a substituent(s), it may have 1 to 2 substituents selected from a halogen atom, an ethynyl group, a linear or branched alkoxy group having 1 to 6 carbon atoms which is optionally substituted, a cycloalkoxy group having 3 to 7 carbon atoms, a cycloalkyl-alkoxy group having 3 to 7 carbon atoms, a cycloalkyl-alkylthio group having 3 to 7 carbon atoms, and a saturated heterocyclic oxy group.

Alternatively, $R^1$ and $R^2$ are preferably taken together with the adjacent nitrogen atom to form a pyrrolidinyl group which is optionally substituted.

In the moiety represented by Z, $R^3$ represents a hydrogen atom or an alkyl group having 1 to 6 carbon atoms. Examples of the "alkyl group having 1 to 6 carbon atoms" include the same alkyl group as exemplified for $R^1$ and $R^2$. Of these, the hydrogen atom is preferable in terms of dUTPase inhibitory activity.

In the moiety represented by Z, $R^4$ represents an aromatic hydrocarbon group which is optionally substituted or an unsaturated heterocyclic group which is optionally substituted.

Examples of the "aromatic hydrocarbon group" in the "aromatic hydrocarbon group which is optionally substituted" represented by $R^4$ include the aromatic hydrocarbon group exemplified above. The phenyl and naphthyl groups are preferable in terms of dUTPase inhibitory activity.

Examples of the "substituent" in the "aromatic hydrocarbon group which is optionally substituted" represented by $R^4$ include the "substituent" exemplified above. The substituent is preferably a halogen atom, a cyano group, a nitro group, an alkyl group having 1 to 6 carbon atoms, an alkenyl group having 2 to 6 carbon atoms, an alkoxy group having 1 to 6 carbon atoms which may be substituted by halogen, a cycloalkoxy group having 3 to 7 carbon atoms, a cycloalkyl-alkoxy group having 3 to 7 carbon atoms, a carboxyl group, an alkoxycarbonyl group having 1 to 6 carbon atoms, an acyloxy group, or a mono- or dialkylamino group. The acyloxy group is preferably an acyloxy group having 2 to 8 carbon atoms. Of these, preferable examples of the substituent specifically include a chlorine atom, a bromine atom, a fluorine atom, a nitro group, a methyl group, a propenyl group, a methoxy group, a cyclopropyloxy group, a cyclopropylmethoxy group, a difluoromethoxy group, a difluoroethoxy group, a trifluoromethoxy group, a benzoyloxy group, a methoxycarbonyl group, and a dimethylamino group. The number of the substituent is 0 to 2.

Examples of the "unsaturated heterocyclic group" in the "unsaturated heterocyclic group which is optionally substituted" represented by $R^4$ include the unsaturated heterocyclic group exemplified above, and the thienyl group is preferable in terms of dUTPase inhibitory activity.

Examples of the "substituent" in the "unsaturated heterocyclic group which is optionally substituted" represented by $R^4$ include the substituent exemplified above, and the halogen atom is preferable, and the chlorine atom is more preferable. The number of the substituent is preferably 0 to 2.

In the present invention, the uracil compound is preferably a uracil compound represented by the general formula (I) wherein n represents 1; X represents a single bond, an oxygen atom, or a vinylene group; Y represents an ethylene or trimethylene group, provided that when X represents a single bond, the moiety $(CH_2)_n$—X—Y represents a trimethylene or pentamethylene group; and Z represents $—SO_2NR^1R^2$, wherein $R^1$ represents a hydrogen atom, and $R^2$ represents a benzyl group which is optionally substituted [when a methylene group of the benzyl group has a substituent, it may have 1 substituent selected from a methyl group, an ethyl group, an isopropyl group, a phenyl group, a 3-cyclopropylmethoxyphenyl group, and 4-fluorophenyl group; when a phenyl group of the benzyl group has a substituent(s), it may have 1 to 2 substituents selected from a chlorine atom, a bromine atom, a fluorine atom, a methyl group, a trifluoromethyl group, an ethynyl group, an isobutoxy group, a 2-methylbutoxy group, an allyloxy group, a 2,2-difluoroethoxy group, a 2,2,2-trifluoroethoxy group, a cyclopentyloxy group, a cyclopropylmethoxy group, a tetrahydrofuran-3-yloxy group, and a tetrahydropyran-4-yloxy group].

In the present invention, particularly preferable examples of the uracil compound include the following compounds:
N-(3-(cyclopropylmethoxy)benzyl)-3-((2,4-dioxo-3,4-dihydropyrimidin-1(2H)-yl)methoxy)propane-1-sulfonamide,
(R)—N-(1-(3-(cyclopentyloxy)phenyl)ethyl)-3-((2,4-dioxo-3,4-dihydropyrimidin-1(2H)-yl)methoxy)propane-1-sulfonamide,
3-((2,4-dioxo-3,4-dihydropyrimidin-1(2H)-yl)methoxy)-N—((R)-1-(3-((R)-tetrahydrofuran-3-yloxy)phenyl)ethyl)propane-1-sulfonamide,
N-(3-(cyclopropylmethoxy)-4-fluorobenzyl)-3-((2,4-dioxo-3,4-dihydropyrimidin-1(2H)-yl)methoxy)propane-1-sulfonamide, (R)—N-(1-(3-(cyclopropylmethoxy)-4-fluorophenyl)ethyl)-3-((2,4-dioxo-3,4-dihydropyrimidin-1(2H)-yl)methoxy)propane-1-sulfonamide, N-(1-(3-(cyclopropylmethoxy)phenyl)ethyl)-3-((2,4-dioxo-3,4-dihydropyrimidin-1(2H)-yl)methoxy)propane-1-sulfonamide, N-(3-(cyclopentyloxy)benzyl)-3-((2,4-dioxo-3,4-dihydropyrimidin-1(2H)-yl)methoxy)propane-1-sulfonamide, (R)—N-(1-(3-(cyclopropylmethoxy)-4-fluorophenyl)propyl)-3-((2,4-dioxo-3,4-dihydropyrimidin-1(2H)-yl)methoxy)propane-1-sulfonamide, (R)—N-(1-(3-(cyclopropylmethoxy)phenyl)ethyl)-3-((2,4-dioxo-3,4-dihydropyrimidin-1(2H)-yl)methoxy)propane-1-sulfonamide, (R)—N-(1-(3-(cyclopentyloxy)-4-fluorophenyl)ethyl)-3-((2,4-dioxo-3,4-dihydropyrimidin-1(2H)-yl)methoxy)propane-1-sulfonamide, (R)-3-((2,4-dioxo-3,4-dihydropyrimidin-1(2H)-yl)methoxy)-N-(1-(3-(tetrahydro-2H-pyran-4-yloxy)phenyl)ethyl)propane-1-sulfonamide, (R)-3-((2,4-dioxo-3,4-dihydropyrimidin-1(2H)-yl)methoxy)-N-(1-(3-(2,2,2-trifluoroethoxy)phenyl)ethyl)propane-1-sulfonamide, (R)-3-((2,4-dioxo-3,4-dihydropyrimidin-1(2H)-yl)methoxy)-N-(1-(4-fluoro-3-(2,2,2-trifluoroethoxy)phenyl)ethyl)propane-1-sulfonamide, (R)-3-((2,4-dioxo-3,4-dihydropyrimidin-1(2H)-yl)methoxy)-N-(1-(3-isobutoxyphenyl)ethyl)propane-1-sulfonamide, 3-((2,4-dioxo-3,4-dihydropyrimidin-1(2H)-yl)methoxy)-N—((R)-1-(3-((S)-2-methylbutoxy)phenyl)ethyl)propane-1-sulfonamide, (R)—N-(1-(3-(2,2-difluoroethoxy)phenyl)ethyl)-3-((2,4-dioxo-3,4-dihydropyrimidin-1(2H)-yl)methoxy)propane-1-sulfonamide, (R)—N-(1-(3-(allyloxy)phenyl)ethyl)-3-((2,4-dioxo-3,4-dihydropyrimidin-1(2H)-yl)methoxy)propane-1-sulfonamide, (R)-3-((2,4-dioxo-3,4-dihydropyrimidin-1(2H)-yl)methoxy)-N-(1-phenylethyl)propane-1-sulfonamide, (R)—N-(1-(3-(cyclopropylmethoxy)phenyl)propyl)-3-(2,4-dioxo-3,4-dihydropyrimidin-1(2H)-yl)propane-1-sulfonamide, (R)-3-(2,4-dioxo-3,4-dihydropyrimidin-1(2H)-yl)-N-(1-phenylethyl)propane-1-sulfonamide, (R)-3-(2,4-dioxo-3,4-dihydropyrimidin-1(2H)-yl)-N-(1-(2-fluorophenyl)ethyl)propane-1-sulfonamide, (R)—N-(1-(2-chlorophenyl)ethyl)-3-(2,4-dioxo-3,4-dihydropyrimidin-1(2H)-yl)propane-1-sulfonamide, (R)-3-(2,4-dioxo-3,4-dihydropyrimidin-1(2H)-yl)-N-(1-(2-ethynylphenyl)ethyl)propane-1-sulfonamide, (R)—N-(1-(2-bromophenyl)ethyl)-3-(2,4-dioxo-3,4-dihydropyrimidin-1(2H)-yl)propane-1-sulfonamide, and (R)-3-(2,4-dioxo-3,4-dihydropyrimidin-1(2H)-yl)-N-(1-O— tolylethyl)propane-1-sulfonamide.

The uracil compound of the present invention can be produced according to the following reaction schemes:
[Step A]

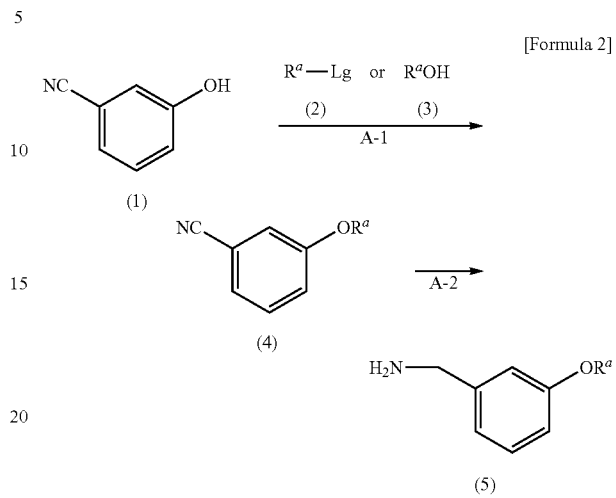

wherein $R^a$ represents any of a hydrogen atom, an ethynyl group, a linear or branched alkyl group having 1 to 6 carbon atoms which may have a substituent(s), a cycloalkyl group having 3 to 7 carbon atoms, a cycloalkyl-alkyl group having 3 to 7 carbon atoms, and a saturated heterocyclic group; and Lg represents a leaving group such as a halogen atom, a methanesulfonyloxy group, a p-toluenesulfonyloxy group, or a trifluoromethanesulfonyloxy group.

[A-1]

(a) In this step, easily available 3-cyanophenol (1) and alkyl halide, alkyl mesilate, alkyl tosylate, or alkyl trifluoromethanesulfonate represented by the general formula (2) can be reacted in the presence of a base to produce a compound represented by the general formula (4).

Any reaction solvent that does not affect the reaction can be used without limitations. Examples thereof include diethyl ether, tetrahydrofuran (hereinafter, referred to as THF), dioxane, acetone, dimethoxyethane, acetonitrile, N,N-dimethylformamide (hereinafter, referred to as DMF), N,N-dimethylacetamide (hereinafter, referred to as DMA), and dimethyl sulfoxide (hereinafter, referred to as DMSO). Preferably, the reaction solvent is DMF.

Examples of the base include: inorganic bases such as sodium bicarbonate, sodium carbonate, potassium carbonate, cesium carbonate, sodium hydride, potassium hydride, sodium hydroxide, and potassium hydroxide; and organic amines such as trimethylamine, triethylamine, tripropylamine, diisopropylethylamine, N-methylmorpholine, pyridine, lutidine, and collidine. Preferably, the base is potassium carbonate. The equivalent number thereof is 0.8 to 10 equivalents, preferably 1.0 to 5.0 equivalents.

The equivalent number of the compound of the general formula (2) is 0.8 to 10 equivalents, preferably 1.0 to 5.0 equivalents. The reaction temperature is 20 to 150° C., preferably 50 to 130° C. The reaction time is 0.5 to 24 hours, preferably 1.0 to 12 hours.

(b) In this step, easily available 3-cyanophenol (1) and alcohol represented by the general formula (3) can be condensed by Mitsunobu reaction to produce the compound represented by the general formula (4).

Any reaction solvent that does not affect the reaction can be used without limitations. Examples thereof include dichloromethane, 1,2-dichloroethane (hereinafter, referred to as DCE), benzene, xylene, toluene, ethyl acetate, propyl acetate, butyl acetate, diethyl ether, THF, dioxane, acetone, dimethoxyethane, acetonitrile, and DMF. Preferably, the reaction solvent is THF.

Any reagent that can usually be used in the Mitsunobu reaction can be used in this reaction without limitations. Examples thereof include combinations of di-lower alkyl azodicarboxylate (e.g., diethyl azodicarboxylate (hereinafter, referred to as DEAD) or diisopropyl azodicarboxylate (hereinafter, referred to as DIAD)) or an azo compound (e.g., azodicarbonyl such as 1,1'-(azodicarbonyl)dipiperidine) with triarylphosphine (e.g., triphenylphosphine) or tri-lower alkylphosphine (e.g., tri-n-butylphosphine). Preferably, the reagent is a combination of DEAD with triphenylphosphine.

The equivalent numbers of the alcohol of the general formula (3), the di-lower alkyl azodicarboxylate or azo compound, and the triarylphosphine or tri-lower alkylphosphine are respectively 0.8 to 5.0 equivalents, preferably 1.0 to 2.0 equivalents. The reaction temperature is −20 to 120° C., preferably 0 to 60° C. The reaction time is 0.1 to 24 hours, preferably 0.2 to 6.0 hours.

[A-2]

In this step, the cyano compound represented by the general formula (4) can be reacted with a generally known reducing agent to produce a compound represented by the general formula (5).

A reaction solvent differs depending on the type of reduction reaction. Examples thereof include methanol, ethanol, 1-propanol, 2-propanol, tert-butyl alcohol, dimethoxyethane, diethylene glycol dimethyl ether, diisopropyl ether, diethyl ether, THF, and dioxane. Preferably, the reaction solvent is THF.

Examples of the reducing agent include lithium aluminum hydride (hereinafter, referred to as LAH), lithium diethoxyaluminum hydride, lithium triethoxyaluminum hydride, lithium tri-tert-butoxyaluminum hydride, magnesium aluminum hydride, aluminum hydride with magnesium chloride, sodium aluminum hydride, sodium triethoxyaluminum hydride, sodium bis(2-methoxyethoxy)aluminum hydride, and catalysts used for hydrogenation, such as palladium/carbon, palladium hydroxide, and platinum. Preferably, the reducing agent is LAH. The equivalent number thereof is 0.5 to 5.0 equivalents, preferably 0.8 to 2.0 equivalents. The reaction temperature is 0 to 100° C., preferably 20 to 60° C. The reaction time is 0.1 to 24 hours, preferably 0.2 to 6.0 hours.

[Step B]

[Formula 3]

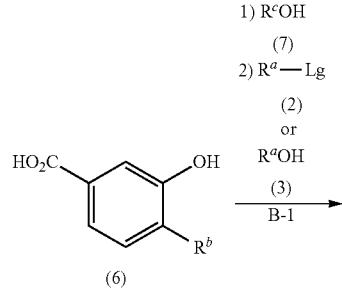

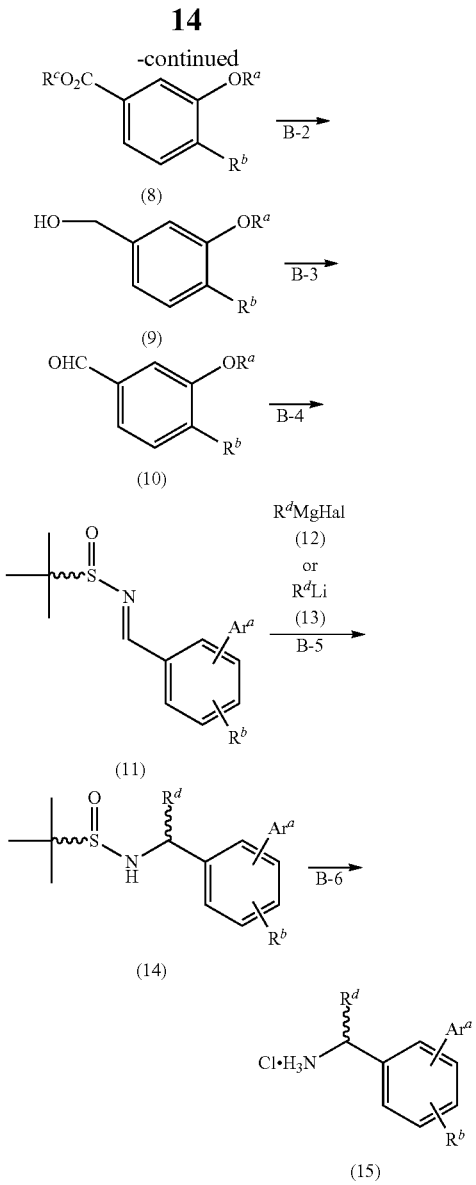

wherein $R^a$ and Lg are as defined above; A represents a hydrogen atom, an oxygen atom, a sulfur atom, or a bond; $R^b$ represents a hydrogen or halogen atom; $R^c$ represents a linear or branched alkyl group having 1 to 6 carbon atoms which may have a substituent(s); $R^d$ represents a linear or branched alkyl group having 1 to 6 carbon atoms, a cycloalkyl group having 3 to 7 carbon atoms, an aromatic hydrocarbon group which may have a substituent(s), or an unsaturated heterocyclic group which may have a substituent(s); and Hal represents a halogen atom.

[B-1]

In this step, the carboxy group of an easily available compound (6) is esterified with an alcohol compound (7) by a usually known method, and the resultant compound can then be reacted in the same way as in the step [A-1] to produce a compound represented by the general formula (8).

[B-2]

In this step, the compound represented by the general formula (8) can be reacted with a usually known reducing agent to produce a compound represented by the general formula (9).

Any reaction solvent that does not affect the reaction can be used without limitations. Examples thereof include diethyl ether, diisopropyl ether, THF, and dioxane. Preferably, the reaction solvent is THF.

Examples of the reducing agent used include LAH, lithium diethoxyaluminum hydride, lithium triethoxyaluminum hydride, lithium tri-tert-butoxyaluminum hydride, magnesium aluminum hydride, aluminum hydride with magnesium chloride, sodium aluminum hydride, sodium triethoxyaluminum hydride, sodium bis(2-methoxyethoxy)aluminum hydride, diisobutylaluminum hydride (hereinafter, referred to as DIBAL), and lithium borohydride. Preferably, the reducing agent is lithium borohydride. The equivalent number thereof is 0.8 to 10 equivalents, preferably 1.0 to 5.0 equivalents. The reaction temperature is 0 to the boiling point of the solvent, preferably the boiling point of the solvent. The reaction time is 0.1 to 24 hours, preferably 0.5 to 12 hours.

[B-3]

In this step, the compound represented by the general formula (9) can be reacted with a usually known oxidizing agent to produce an aldehyde compound represented by the general formula (10).

Any reaction solvent that does not affect the reaction can be used without limitations. Examples thereof include dichloromethane, chloroform, carbon tetrachloride, DCE, chlorobenzene, toluene, and xylene. Preferably, the reaction solvent is dichloromethane.

Examples of the oxidizing agent include: a complex reagent of chromic anhydride, pyridine, and acetic anhydride; chromium-based oxidizing agents such as pyridinium chlorochromate and pyridinium dichromate; hypervalent iodine oxidizing agents such as a Dess-Martin reagent; DMSO-based oxidizing agents such as DMSO used in combination with acetic anhydride, oxalyl chloride, dicyclohexylcarbodiimide (hereinafter, referred to as DCC), or 1-ethyl-3-(3-dimethylaminopropyl)carbodiimide hydrochloride (hereinafter, referred to as EDC.HCl); manganese(IV) oxide; and 2,2,6,6-tetramethylpiperidine-1-oxyl radicals. Preferably, the oxidizing agent is manganese(IV) oxide. The equivalent number thereof is 0.8 to 30 equivalents, preferably 1.0 to 20 equivalents. The reaction temperature is −20 to 150° C., preferably 0 to 100° C. The reaction time is 0.1 to 24 hours, preferably 0.5 to 12 hours.

When $R^b$ is a hydrogen atom, easily available 3-hydroxybenzaldehyde can be reacted as a starting material in the same way as in the step [A-1] to produce the compound represented by the general formula (10). Furthermore, the nitrile compound represented by the general formula (4) can be reduced by a usually known reduction reaction, for example, a DIBAL reduction method, to produce the compound represented by the general formula (10).

[B-4]

In this step, the compound represented by the general formula (10) or easily available aldehyde can be reacted with easily available 2-methyl-2-propanesulfinamide under acidic conditions to produce a compound represented by the general formula (11).

Any reaction solvent that does not affect the reaction can be used without limitations. Examples thereof include diethyl ether, diisopropyl ether, THF, dioxane, dichloromethane, chloroform, carbon tetrachloride, toluene, and xylene. Preferably, the reaction solvent is toluene.

Examples of the acid include hydrochloric acid, sulfuric acid, p-toluenesulfonic acid, and Lewis acid (e.g., titanium tetraisopropoxide and titanium tetraethoxide). Preferably, the acid is titanium tetraisopropoxide. The equivalent numbers of the 2-methyl-2-propanesulfinamide and the titanium tetraisopropoxide are respectively 0.8 to 10 equivalents, preferably 1.0 to 3.0 equivalents. The reaction temperature is 20 to 150° C., preferably 50 to 120° C. The reaction time is 0.1 to 24 hours, preferably 0.5 to 6.0 hours.

[B-5]

In this step, the compound represented by the general formula (11) can be reacted with a Grignard reagent (12) represented by $R^d$MgHal or an organic lithium reagent (13) represented by $R^d$Li to produce a compound represented by the general formula (14) diastereoselectively.

Any reaction solvent that does not affect the reaction can be used without limitations. Examples thereof include diethyl ether, diisopropyl ether, tert-butyl methyl ether, cyclopentyl methyl ether, THF, dimethoxyethane, dioxane, dichloromethane, chloroform, carbon tetrachloride, toluene, and xylene. The equivalent of the Grignard reagent or organic lithium reagent is 0.8 to 20 equivalents, preferably 1.0 to 10 equivalents. The reaction temperature is −100 to 100° C., preferably −78 to 50° C. The reaction time is 0.1 to 24 hours, preferably 0.5 to 12 hours.

[B-6]

In this step, the compound represented by the general formula (14) can be treated with an acid to produce a compound represented by the general formula (15).

Any solvent that does not affect the reaction can be used without limitations. Examples thereof include: alcohols such as methanol, ethanol, 1-propanol, 2-propanol, 1-butanol, and 2-butanol; dioxane; and ethyl acetate. Preferably, the solvent is methanol.

Examples of the acid include hydrochloric acid, sulfuric acid, and phosphoric acid. Preferably, the acid is hydrochloric acid. The equivalent number thereof is 0.1 to 10 equivalents, preferably 1.0 to 2.0 equivalents. The reaction temperature is −20 to 100° C., preferably 0 to 50° C. The reaction time is 0.01 to 24 hours, preferably 0.1 to 1.0 hours.

[Step C]

[Formula 4]

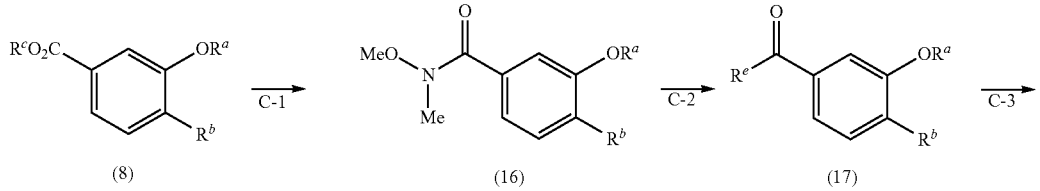

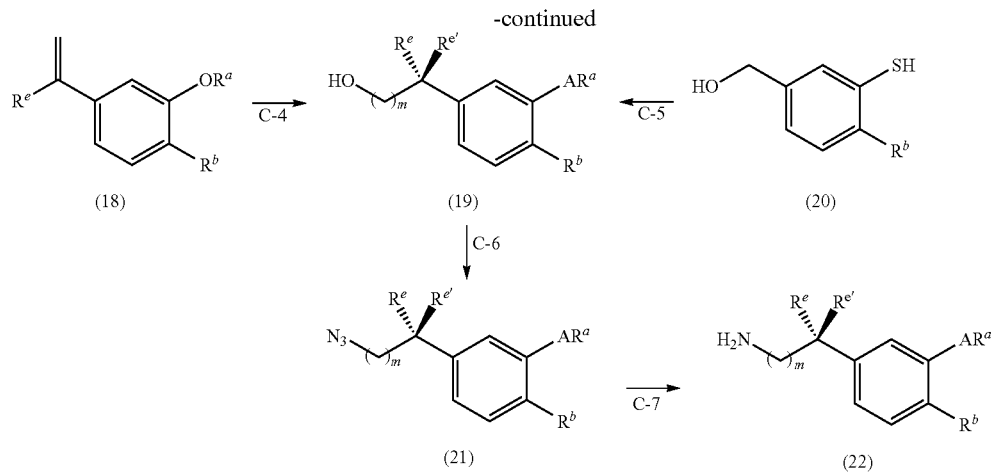

wherein $R^a$, $R^b$, and $R^c$ are as defined above; $R^e$ and $R^{e'}$ are the same or different and each represents a hydrogen atom, a hydroxyl group, an alkyl group having 1 to 6 carbon atoms, a cycloalkyl group having 3 to 7 carbon atoms, an aromatic hydrocarbon group which may have a substituent(s), or an unsaturated heterocyclic group which may have a substituent(s); A represents an oxygen or sulfur atom; and m represents an integer of 0 to 1.

[C-1]

In this step, the compound represented by the general formula (8) can be hydrolyzed by a general method and then condensed with N,O-dimethylhydroxylamine hydrochloride in the presence of a base to produce a compound represented by the general formula (16).

Any reaction solvent that does not affect the reaction can be used without limitations. Examples thereof include DMF, toluene, dichloromethane, acetonitrile, and THF. Preferably, the reaction solvent is DMF.

Examples of a condensing agent include DCC, EDC.HCl, and 1-hydroxybenzotriazole (hereinafter, referred to as HOBt). Preferably, the condensing agent is a combination of EDC.HCl with HOBt. The equivalent numbers thereof are respectively 0.8 to 2.0 equivalents, preferably 1.0 to 1.5 equivalents. The equivalent number of the N,O-dimethylhydroxylamine hydrochloride is 0.8 to 2.0 equivalents, preferably 1.0 to 1.5 equivalents.

Examples of the base include organic amines such as trimethylamine, triethylamine, tripropylamine, diisopropylethylamine, N-methylmorpholine, pyridine, lutidine, and collidine. Preferably, the base is triethylamine. The equivalent number thereof is 0.8 to 3.0 equivalents, preferably 1.0 to 2.0 equivalents. The reaction temperature is 0 to 100° C., preferably 10 to 40° C. The reaction time is 0.1 to 24 hours, preferably 0.5 to 4.0 hours.

[C-2]

In this step, the compound represented by the general formula (16) can be reacted with a Grignard reagent represented by $R^eMgHal$ to produce a compound represented by the general formula (17).

Any reaction solvent that does not affect the reaction can be used without limitations. Examples thereof include toluene, THF, dichloromethane, and dioxane. Preferably, the reaction solvent is THF.

The equivalent number of the Grignard reagent is 1.0 to 5.0 equivalents, preferably 3.0 to 4.0 equivalents. The reaction temperature is −80 to 50° C., preferably −78 to 30° C. The reaction time is 0.5 to 12 hours, preferably 1.0 to 6.0 hours.

[C-3]

In this step, the compound represented by the general formula (17) can be reacted with methyltriphenylphosphonium bromide under basic conditions to produce a compound represented by the general formula (18).

Any reaction solvent that does not affect the reaction can be used without limitations. Examples thereof include DMF, toluene, dichloromethane, acetonitrile, and THF. Preferably, the reaction solvent is THF. Examples of a base include bis(trimethylsilyl)amide sodium salt (hereinafter, referred to as NaHMDS), n-butyllithium, sec-butyllithium, and a metal hydride salt (e.g., sodium hydride and potassium hydride). Preferably, the base is NaHMDS. The equivalent number thereof is 0.8 to 2.0 equivalents, preferably 1.0 to 1.5 equivalents. The equivalent number of the methyltriphenylphosphonium bromide is 0.9 to 5.0 equivalents, preferably 1.0 to 1.5 equivalents. The reaction temperature is −100 to 100° C., preferably −78 to 40° C. The reaction time is 0.5 to 24 hours, preferably 1.0 to 5.0 hours.

[C-4]

In this step, the compound represented by the general formula (18) can be reacted with AD-mix or osmium tetroxide to produce a compound represented by the general formula (19).

Any reaction solvent that does not affect the reaction can be used without limitations. Examples thereof include DMF, toluene, dichloromethane, acetonitrile, THF, water, and alkyl alcohol. Preferably, the reaction solvent is a tert-butanol/water (1/1) solution. The reaction temperature is −20 to 100° C., preferably 0 to 10° C. The reaction time is 0.5 to 24 hours, preferably 1.0 to 5.0 hours.

The compound represented by the general formula (19) can also be produced from the compound represented by the general formula (10) in the same way as in the step [B-5].

[C-5]

In this step, 3-(mercaptophenyl)methanol (20) obtained according to a method described in, for example, the document (Chemistry Express, 7, 865-868 (1992)) is led to the compound represented by the general formula (19) in the same way as in the step [A-1].

[C-6]

(a) m=0 and Either $R^e$ or $R^{e'}$=Hydrogen Atom

In this step, the compound represented by the general formula (19) can be reacted with a general azidation reagent to produce a compound represented by the general formula (21).

Any reaction solvent that does not affect the reaction can be used without limitations. Examples thereof include dimethoxyethane, diethylene glycol dimethyl ether, diisopropyl ether, diethyl ether, THF, and dioxane. Preferably, the reaction solvent is THF.

Examples of a base include: inorganic bases such as sodium bicarbonate, sodium carbonate, potassium carbonate, cesium carbonate, sodium hydride, potassium hydride, sodium hydroxide, and potassium hydroxide; and organic amines such as trimethylamine, triethylamine, tripropylamine, diisopropylethylamine, 1,8-diazabicyclo[5.4.0]-7-undecene (hereinafter, referred to as DBU), N-methylmorpholine, pyridine, lutidine, and collidine. Preferably, the base is DBU. The equivalent number thereof is 0.8 to 5.0 equivalents, preferably 1.0 to 2.0 equivalents.

Examples of the azidation reagent include diphenylphosphoryl azide, carbon tetrabromide triphenylphosphine and sodium azide, bis(2,4-dichlorophenyl)chlorophosphate and sodium azide. Preferably, the azidation reagent is diphenylphosphoryl azide. The equivalent number thereof is 0.8 to 5.0 equivalents, preferably 1.0 to 3.0 equivalents. The reaction temperature is 0 to 120° C., preferably 20 to 100° C. The reaction time is 0.1 to 24 hours, preferably 0.5 to 12 hours.

(b) m=1 and $R^{e'}$=Hydroxyl Group

In this step, the primary hydroxyl group of the compound represented by the general formula (19) is methanesulfonylated by a general method, and the resultant compound can then be reacted with an azidation reagent to produce a compound represented by the general formula (21).

Any reaction solvent that does not affect the reaction can be used in the azidation without limitations. Examples thereof include dimethoxyethane, diethylene glycol dimethyl ether, diisopropyl ether, diethyl ether, THF, dioxane, and DMF. Preferably, the reaction solvent is DMF.

Examples of the azidation reagent used include sodium azide and lithium azide. Preferably, the azidating reagent is sodium azide. The equivalent number thereof is 0.8 to 10 equivalents, preferably 1.0 to 5.0 equivalents. The reaction temperature is 0 to 150° C., preferably 20 to 120° C. The reaction time is 0.1 to 24 hours, preferably 0.5 to 12 hours.

The compound represented by the general formula (21) wherein m=1 and $R^{e'}$=a hydroxyl group, its tertiary hydroxyl group can further be protected with trimethylsilyl group in the presence of a base by a general method.

Any reaction solvent that does not affect the reaction can be used without limitations. Examples thereof include dichloromethane, chloroform, carbon tetrachloride, toluene, and xylene. Preferably, the reaction solvent is dichloromethane.

Examples of the base include: inorganic bases such as sodium bicarbonate, sodium carbonate, potassium carbonate, cesium carbonate, sodium hydride, potassium hydride, sodium hydroxide, and potassium hydroxide; and organic amines such as trimethylamine, triethylamine, tripropylamine, diisopropylethylamine, DBU, N-methylmorpholine, pyridine, lutidine, and collidine. Preferably, the base is lutidine. The equivalent number thereof is 0.8 to 10 equivalents, preferably 1.0 to 5.0 equivalents. Examples of a trimethylsilylating reagent include trimethylsilyl trifluoromethanesulfonate, N,O-bistrimethylsilylacetamide, and trimethylsilylimidazole. Preferably, the trimethylsilylating reagent is trimethylsilyl trifluoromethanesulfonate. The equivalent number thereof is 0.8 to 10 equivalents, preferably 1.0 to 5.0 equivalents. The reaction temperature is −20 to 120° C., preferably 0 to 50° C. The reaction time is 0.1 to 24 hours, preferably 0.5 to 12 hours.

[C-7]

In this step, the compound represented by the general formula (21) can be reduced with a metal hydride to produce a compound represented by the general formula (22).

Any reaction solvent that does not affect the reaction can be used without limitations. Examples thereof include dimethoxyethane, diethylene glycol dimethyl ether, diisopropyl ether, diethyl ether, THF, and dioxane. Preferably, the reaction solvent is THF.

Examples of the metal hydride include LAH, lithium diethoxyaluminum hydride, lithium triethoxyaluminum hydride, lithium tri-tert-butoxyaluminum hydride, magnesium aluminum hydride, aluminum hydride with magnesium chloride, sodium aluminum hydride, and sodium triethoxyaluminum hydride. Preferably, the metal hydride is LAH. The equivalent number thereof is 0.8 to 5.0 equivalents, preferably 1.0 to 3.0 equivalents. The reaction temperature is −20 to 100° C., preferably 0 to 60° C. The reaction time is 0.1 to 24 hours, preferably 0.5 to 6.0 hours.

The compound represented by the general formula (21) can also be reduced by the general method for hydrogenation or Staudinger reaction (Hely. Chim. Acta, 2, 635 (1919)) to produce the compound represented by the general formula (22).

[Step D]

[Formula 5]

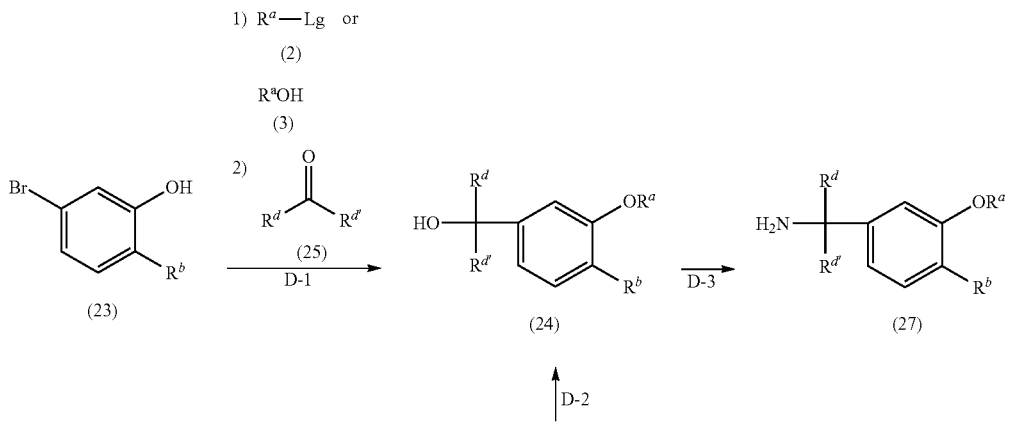

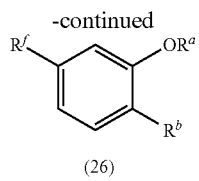

(26)

wherein $R^a$, $R^b$, $R^d$, and Lg are as defined above; $R^{d'}$ is the same as or different from $R^d$ and represents a hydrogen atom, an alkyl group having 1 to 6 carbon atoms, a cycloalkyl group having 3 to 7 carbon atoms, a cycloalkyl-alkylthio group having 3 to 7 carbon atoms, an aromatic hydrocarbon group which may have a substituent(s), or an unsaturated heterocyclic group which may have a substituent(s); and $R^f$ represents an electron-withdrawing group such as a formyl, acyl, or ester group.

[D-1]

In this step, a compound represented by the general formula (23) is alkylated in the same way as in the step [A-1] and then reacted by a general method, for example, with magnesium turnings, to prepare a Grignard reagent, which can then be reacted with known ketone or aldehyde (represented by the general formula (25)) to produce a compound represented by the general formula (24).

Any reaction solvent that does not affect the reaction can be used without limitations. Examples thereof include dimethoxyethane, diethylene glycol dimethyl ether, diisopropyl ether, diethyl ether, THF, and dioxane. Preferably, the reaction solvent is THF. The equivalent number of the compound represented by the general formula (25) is 0.8 to 5.0 equivalents, preferably 1.0 to 2.0 equivalents. The reaction temperature is −78 to 100° C., preferably 0 to 60° C. The reaction time is 0.1 to 24 hours, preferably 0.5 to 6.0 hours.

[D-2]

In this step, the compound represented by the general formula (26) can be reacted in the same way as in the step [B-5] to produce the compound represented by the general formula (24).

[D-3]

In this step, the compound represented by the general formula (24) can be azidated in the same way as in the steps [C-6] and [C-7] to produce an amine compound represented by the general formula (27).

[Step E]

[Formula 6]

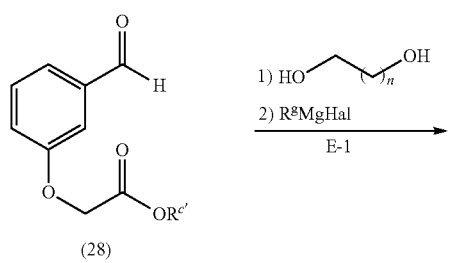

(28)

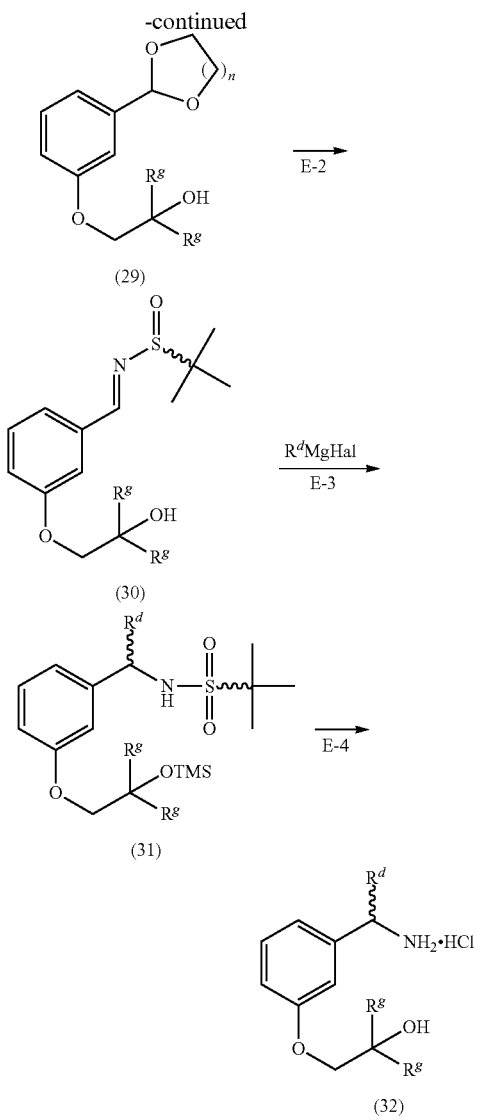

wherein $R^{c'}$ and $R^g$ represent a linear or blanched alkyl group having 1 to 6 carbon atoms which may have a substituent(s); $R^d$ and Hal are as defined above; and n represents 1 or 2.

[E-1]

In this step, an easily available aldehyde compound represented by the general formula (28) can be acetal-protected with, for example, diol, by a general method and then is reacted with a Grignard reagent in the same way as in the step [B-5] to produce a compound represented by the general formula (29).

[E-2]

In this step, the compound represented by the general formula (29) is deprotected by a general method to obtain an aldehyde compound, which can then be reacted in the same way as in the step [B-4] to produce a compound represented by the general formula (30).

[E-3]

In this step, the tertiary hydroxyl group of the compound represented by the general formula (30) is protected with, for example, a silylating agent, and the moiety $R^d$ can then be introduced into the resultant compound in the same way as in the step [B-5] to produce a compound represented by the general formula (31).

[E-4]

In this step, the compound represented by the general formula (31) can be reacted in the same way as in the step [B-6] to produce a compound represented by the general formula (32).

[Step F]

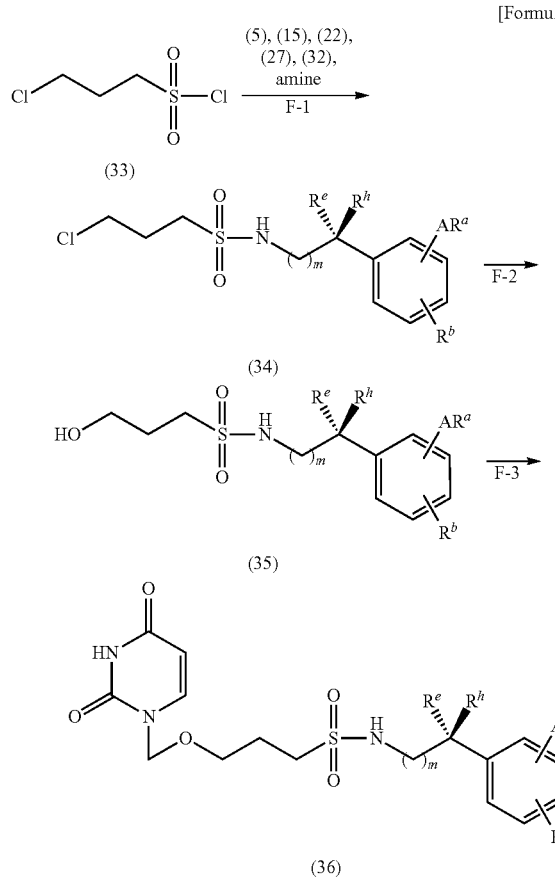

wherein $R^a$, $R^b$, $R^e$, A, and m are as defined above; and $R^h$ represents a hydrogen atom, a hydroxyl group, a trialkylsilyloxy group, an alkyl group having 1 to 6 carbon atoms, a cycloalkyl group having 3 to 7 carbon atoms, an aromatic hydrocarbon group which may have a substituent(s), or an unsaturated heterocyclic group which may have a substituent(s), provided that when both $R^e$ and $R^h$ are an alkyl group having 1 to 6 carbon atoms, the carbon atoms of these alkyl groups may form together a cycloalkylidene structure.

[F-1]

In this step, an easily available compound (33) can be reacted with any amine represented by the general formulas (5), (15), (22), (27), and (32) or easily available amine in the presence of a base to produce a compound represented by the general formula (34). When $R^h$ is a hydroxyl group, it can be protected with, for example, a silylating agent in the same way as in the step [E-3].

Any reaction solvent that does not affect the reaction can be used without limitations. Examples thereof include acetone, THF, diethyl ether, diisopropyl ether, dioxane, dichloromethane, chloroform, carbon tetrachloride, DMF, DMA, and acetonitrile. Preferably, the reaction solvent is dichloromethane.

Examples of the base include: inorganic bases such as sodium bicarbonate, sodium carbonate, and potassium carbonate; and organic amines such as trimethylamine, triethylamine, tripropylamine, diisopropylethylamine, N-methylmorpholine, pyridine, lutidine, and collidine. Preferably, the base is triethylamine. The equivalent numbers of the base and the amine are respectively 0.5 to 10 equivalents, preferably 0.7 to 5.0 equivalents. The reaction temperature is −20 to 100° C., preferably 0 to 50° C. The reaction time is 0.1 to 24 hours, preferably 0.2 to 6.0 hours.

[F-2]

In this step, the chloro compound represented by the general formula (34) can be acetoxylated through reaction with an acetoxylating reagent by a general method and then deacetylated by a general method to produce an alcohol compound represented by the general formula (35).

[F-3]

In this step, the compound represented by the general formula (35) can be methoxymethylated (MOM-induced) by a general method, subsequently treated with Lewis acid, and then reacted with 2,4-bis(trimethylsilyloxy)pyrimidine obtained according to a method described in the document (Nucleosides & Nucleotides, 4, 565-585 (1985)) in the presence of iodine to produce a compound represented by the general formula (36).

Any solvent that does not affect the reaction can be used in the Lewis acid treatment without limitations. Examples thereof include dichloromethane, chloroform, carbon tetrachloride, DCE, toluene, and xylene. Preferably, the solvent is dichloromethane. Examples of the Lewis acid include boron trichloride (hereinafter, referred to as $BCl_3$), boron trifluoride, and boron tribromide. Preferably, the Lewis acid is $BCl_3$. The equivalent number thereof is 0.01 to 10 equivalents, preferably 0.2 to 0.5 equivalents. The reaction temperature is −20 to 100° C., preferably 0 to 50° C. The reaction time is 0.1 to 24 hours, preferably 0.5 to 5.0 hours.

Any solvent that does not affect the reaction can be used in the reaction with 2,4-bis(trimethylsilyloxy)pyrimidine without limitations. Examples thereof include dichloromethane, chloroform, carbon tetrachloride, DCE, toluene, and xylene. Preferably, the solvent is DCE or toluene. The equivalent number of the 2,4-bis(trimethylsilyloxy)pyrimidine is 0.8 to 10 equivalents, preferably 0.9 to 5.0 equivalents. The equivalent number of the iodine is 0.001 to 1.0 equivalents, preferably 0.05 to 0.5 equivalents. The reaction temperature is 20 to 150° C., preferably 50 to 100° C. The reaction time is 0.1 to 120 hours, preferably 0.5 to 100 hours.

[Step G]

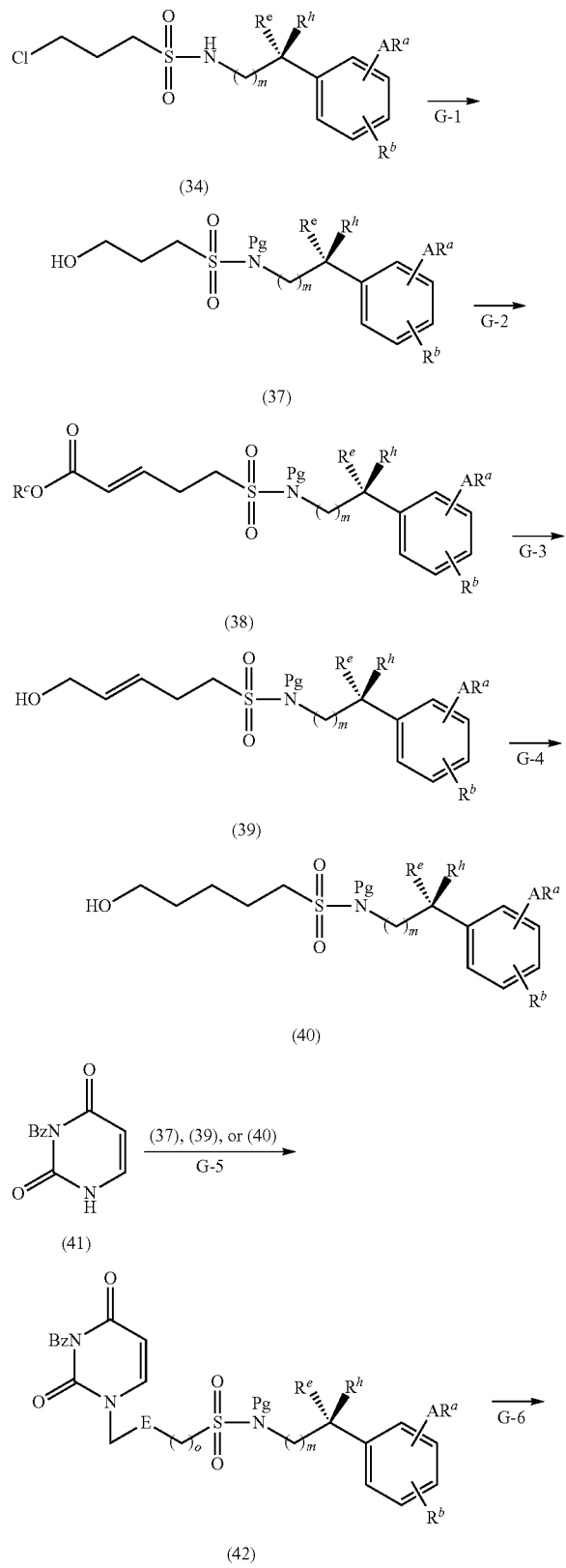

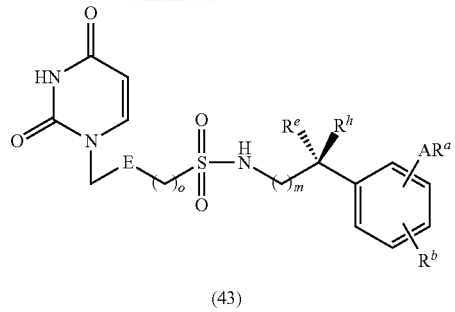

wherein $R^a$, $R^b$, $R^c$, $R^e$, $R^h$, A, and m are as defined above; Pg represents a protecting group for the nitrogen atom on the sulfonamide group; E represents a bond or a vinylene group, provided that when E represents a bond, the moiety $CH_2$-E-$(CH_2)$o represents n-propylene or n-pentylene group; o represents an integer of 1 to 3; and Bz represents a benzoyl group.

[G-1]

In this step, the nitrogen atom on the sulfonamide group of the compound represented by the general formula (34) is protected with a protecting group, for example, a methoxymethyl or tert-butoxycarbonyl group, by a general method, and the resultant compound can then be reacted in the same way as in the step [F-2] to produce a compound represented by the general formula (37).

[G-2]

In this step, the alcohol compound represented by the general formula (37) can be converted to an aldehyde compound in the same way as in the step [B-3] and then reacted with a Horner-Wadsworth-Emmons reagent to produce a compound represented by the general formula (38).

Any reaction solvent that does not affect the reaction can be used without limitations. Examples thereof include benzene, toluene, diethyl ether, diisopropyl ether, THF, diethylene glycol dimethyl ether, dimethoxyethane, and DMSO. Preferably, the reaction solvent is THF.

The Horner-Wadsworth-Emmons reagent is prepared by treating triethyl phosphonoacetate with a base, for example, sodium hydride, sodium amide, lithium diisopropylamide, or sodium methoxide. The equivalent number of the base is 0.1 to 10 equivalents, preferably 0.8 to 2.0 equivalents. The reaction temperature is $-20$ to $100°$ C., preferably 0 to $70°$ C. The reaction time is 0.05 to 12 hours, preferably 0.1 to 2.0 hours.

The equivalent number of the Horner-Wadsworth-Emmons reagent is 0.1 to 10 equivalents, preferably 0.3 to 5.0 equivalents. The reaction temperature is 0 to $150°$ C., preferably 10 to $100°$ C. The reaction time is 0.05 to 12 hours, preferably 0.1 to 4.0 hours.

[G-3]

In this step, the compound represented by the general formula (38) can be reacted by a general reduction method, preferably a DIBAL reduction method, to produce a compound represented by the general formula (39).

[G-4]

In this step, the compound represented by the general formula (39) can be reacted by a general method for hydrogenation to produce a compound represented by the general formula (40).

Any reaction solvent that does not affect the reaction can be used without limitations. Examples thereof include methanol, ethanol, 1-propanol, 2-propanol, tert-butyl alcohol, dimethoxyethane, diethylene glycol dimethyl ether, diisopropyl ether, diethyl ether, THF, dioxane, ethyl acetate, and butyl acetate. Preferably, the reaction solvent is methanol or ethyl acetate.

Examples of a catalyst include 5 to 10% palladium/carbon, palladium hydroxide, platinum, Raney nickel, platinum oxide, and rhodium-aluminum oxide. Preferably, the catalyst is 5 to 10% palladium/carbon. The equivalent number thereof is 0.001 to 10 equivalents, preferably 0.01 to 5.0 equivalents. The reaction temperature is 0 to 100° C., preferably 20 to 60° C. The reaction time is 0.1 to 24 hours, preferably 0.2 to 6.0 hours.

[G-5]

In this step, 3-benzoylpyrimidine-2,4(1H, 3H)-dione (41) obtained according to a method described in the document (J. Med. Chem., 50, 6032-6038 (2007)) and any alcohol compound represented by the general formulas (37), (39), and (40) can be treated with Mitsunobu reaction in the same way as in the step [A-1] (b) to produce a compound represented by the general formula (42).

[G-6]

In this step, a compound represented by the general formula (42) can be debenzoylated and Pg-deprotected by a general deprotection method to produce a compound represented by the general formula (43).

[Step H]

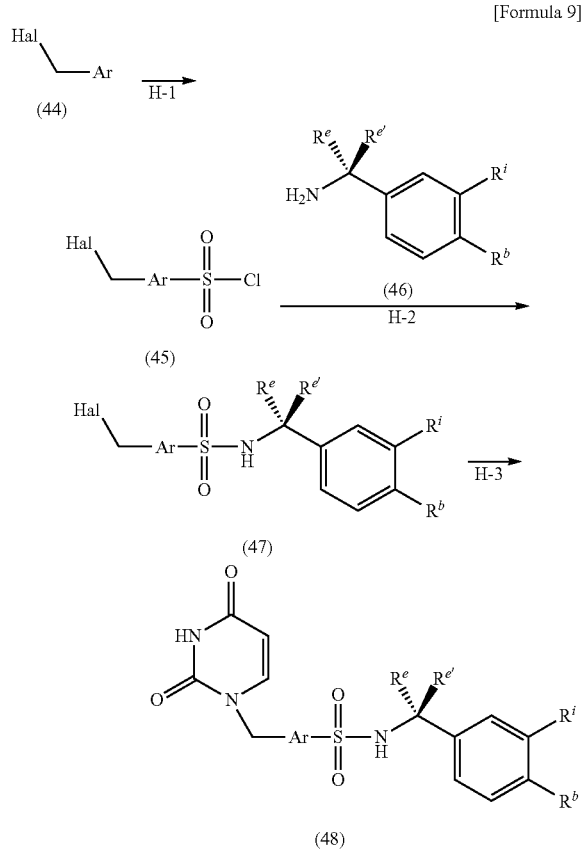

wherein Hal, $R^b$, $R^e$, and $R^{e'}$ are as defined above; $R^i$ represents any of a hydrogen atom, a linear or branched alkoxy group having 1 to 6 carbon atoms which may have a substituent(s), a cycloalkoxy group having 3 to 7 carbon atoms, a cycloalkyl-alkoxy group having 3 to 7 carbon atoms, a saturated heterocyclic oxy group, and a cycloalkyl-alkylthio group having 3 to 7 carbon atoms; and Ar represents an aromatic hydrocarbon group or an unsaturated heterocyclic group.

[H-1]

In this step, a compound represented by the general formula (44) can be reacted with a general chlorosulfonylating reagent to produce a compound represented by the general formula (45).

Any reaction solvent that does not affect the reaction can be used without limitations. Examples thereof include dichloromethane, chloroform, and carbon tetrachloride. Preferably, the reaction solvent is dichloromethane.

Examples of the chlorosulfonylating reagent include chlorosulfonic acid, sulfuryl chloride, a combination of chlorosulfonic acid with phosphorus pentachloride or phosphorus oxychloride, and a combination of sulfuryl chloride with DMF. Preferably, the chlorosulfonylating reagent is a combination of chlorosulfonic acid with phosphorus pentachloride. The equivalent numbers thereof are respectively 0.8 to 5.0 equivalents, preferably 1.0 to 3.0 equivalents. The reaction temperature is −20 to 100° C., preferably 0 to 80° C. The reaction time is 0.1 to 24 hours, preferably 0.2 to 5.0 hours.

[H-2]

In this step, the compound represented by the general formula (45) and an amine compound represented by the general formula (46) can be reacted in the same way as in the step [F-1] to produce a compound represented by the general formula (47).

[H-3]

In this step, the compound represented by the general formula (47) and 2,4-bis(trimethylsilyloxy)pyrimidine obtained according to a method described in the document (Nucleosides & Nucleotides, 4, 565-585 (1985)) can be reacted in the presence of iodine and, if necessary, in the presence of tetra-n-butylammonium iodide to produce a compound represented by the general formula (48).

Any solvent that does not affect the reaction can be used without limitations. Examples thereof include DCE, THF, dioxane, acetonitrile, and toluene. Preferably, the solvent is DCE or toluene.

The equivalent number of the 2,4-bis(trimethylsilyloxy) pyrimidine is 0.5 to 5.0 equivalents, preferably 1.0 to 1.5 equivalents. The equivalent numbers of the iodine and the tetra-n-butylammonium iodide are respectively 0.01 to 1.0 equivalents, preferably 0.1 to 0.5 equivalents.

The reaction temperature is 10 to 100° C., preferably 70 to 95° C. The reaction time is 0.1 to 120 hours, preferably 0.5 to 100 hours.

[Step I]

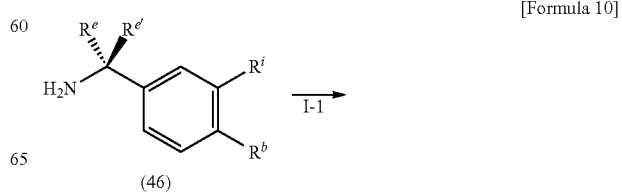

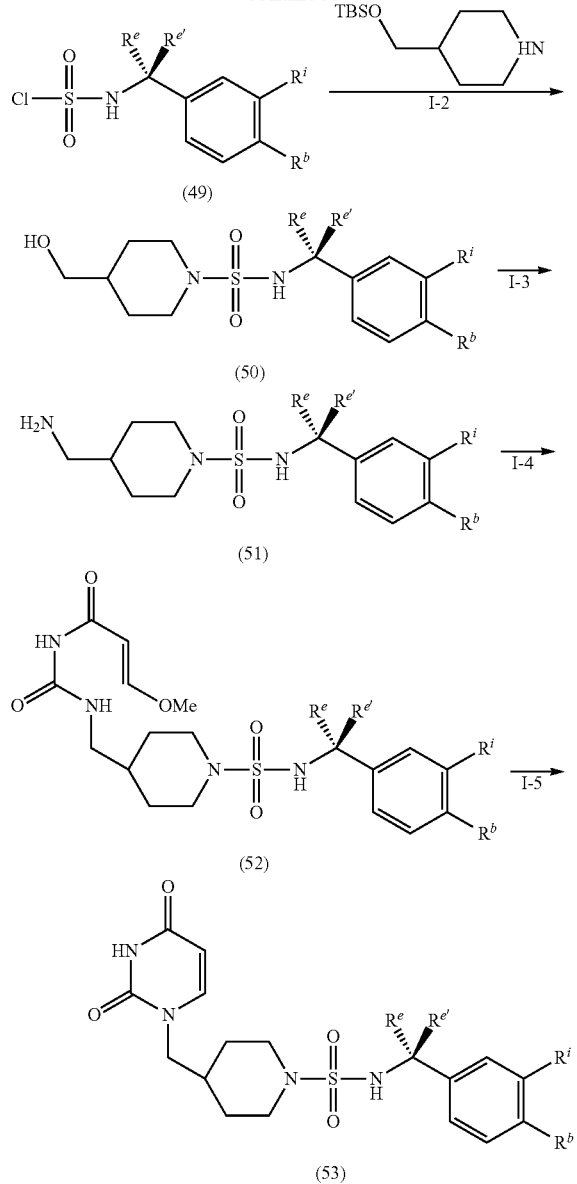

wherein $R^b$, $R^e$, and $R^{e'}$ are as defined above; Ie represents any of a hydrogen atom, a linear or branched alkoxy group having 1 to 6 carbon atoms which may have a substituent(s), a cycloalkoxy group having 3 to 7 carbon atoms, a cycloalkyl-alkoxy group having 3 to 7 carbon atoms, a saturated heterocyclic oxy group, and a cycloalkyl-alkylthio group having 3 to 7 carbon atoms; and TBS represents a tert-butyldimethylsilyl group.

[I-1]

In this step, the compound represented by the general formula (46) can be reacted in the same way as in the step [H-1] to produce a compound represented by the general formula (49).

[I-2]

In this step, the compound represented by the general formula (49) and 4-((tert-butyldimethylsilyloxy)methyl)piperidine obtained according to a method described in the document (J. Org. Chem., 71, 9045-9050 (2006)) can be reacted and then TBS group was deprotected by a general method to produce a compound represented by a the general formula (50).

[I-3]

In this step, the hydroxyl group of the compound represented by the general formula (50) is methanesulfonylated, and is then azidated and reduced to produce a compound represented by the general formula (51) in the same way as in the steps [C-6] and [C-7].

[I-4]

In this step, the amine compound represented by the general formula (51) can be reacted with 3-methoxy-2-propenoyl isocyanate obtained according to a method described in the document (J. Heterocyclic Chem., 36, 293 (1999)) in the presence of a molecular sieve 4A (hereinafter, referred to as MS 4A) to produce a compound represented by the general formula (52).

Examples of a reaction solvent used include dimethoxyethane, diethylene glycol dimethyl ether, diisopropyl ether, diethyl ether, THF, dioxane, and DMF. Preferably, the reaction solvent is DMF and toluene. The equivalent number of the 3-methoxy-2-propenoyl isocyanate is 0.5 to 5.0 equivalents, preferably 1.0 to 2.0 equivalents. The reaction temperature is −80 to 100° C., preferably −50 to 50° C. The reaction time is 0.1 to 24 hours, preferably 0.2 to 16 hours.

[I-5]

In this step, the compound represented by the general formula (52) can be reacted with a general acid to produce a compound represented by the general formula (53).

Examples of a reaction solvent used include water, methanol, ethanol, 1-propanol, 2-propanol, tert-butyl alcohol, dioxane, THF, ethyl acetate, and butyl acetate. Preferably, the reaction solvent is ethanol or dioxane. Examples of the acid include: Broensted acid such as inorganic acids including hydrochloric acid, hydrobromic acid, sulfuric acid, perchloric acid, and phosphoric acid, and organic acids including acetic acid, formic acid, oxalic acid, methanesulfonic acid, p-toluenesulfonic acid, trifluoroacetic acid, and trifluoromethanesulfonic acid; Lewis acid such as $BCl_3$, boron trifluoride, and boron tribromide; and acidic ion-exchanged resins. Preferably, the acid is hydrochloric acid or sulfuric acid. The equivalent number thereof is 0.5 to 100 equivalents, preferably 1.0 to 50 equivalents. The reaction temperature is 0 to 120° C., preferably 10 to 80° C. The reaction time is 0.1 to 5.0 hours, preferably 0.2 to 2.5 hours.

[Step J]

[Formula 11]

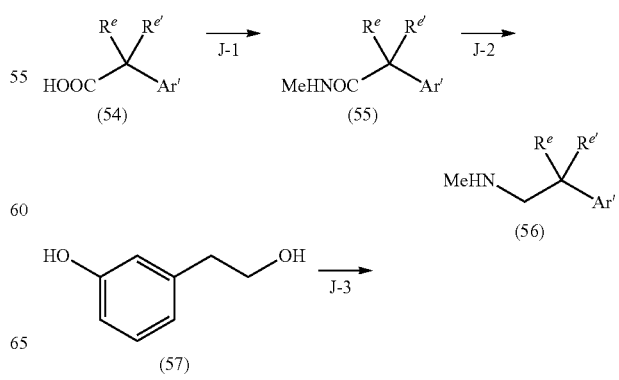

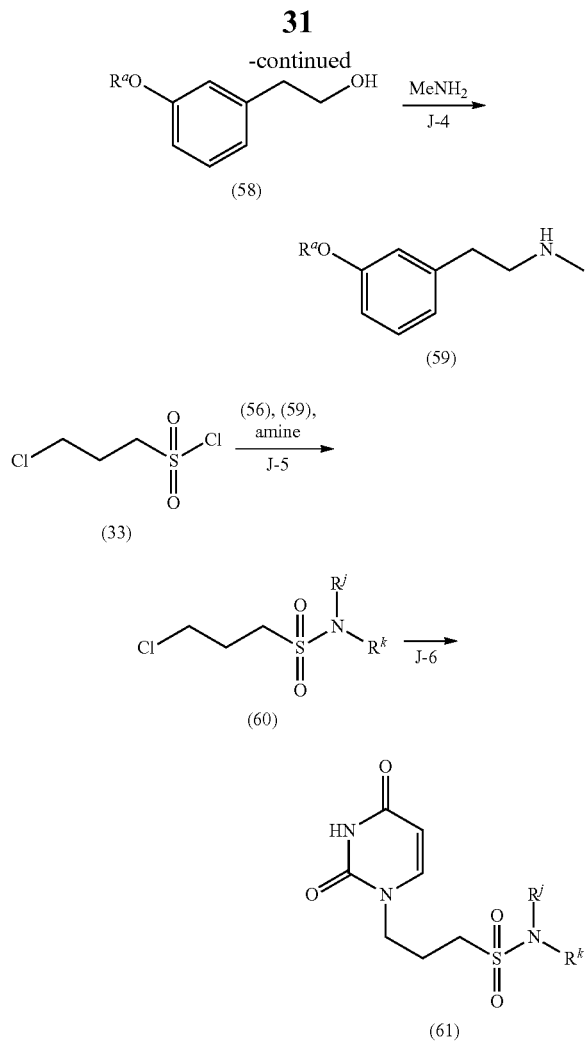

wherein $R^a$, $R^e$, and $R^{e'}$ are as defined above, provided that when both $R^e$ and $R^{e'}$ are an alkyl group having 1 to 6 carbon atoms, the carbon atoms of these alkyl groups may form together a cycloalkylidene structure; $R^j$ represents a hydrogen atom or an alkyl group having 1 to 3 carbon atoms, and $R^k$ represents a phenylethyl group which may have a substituent(s) (when an ethylene group of the phenylethyl group has a substituent(s), it may have 1 to 3 substituents which are the same or different and each is selected from an alkyl group having 1 to 6 carbon atoms and a cycloalkyl group having 3 to 7 carbon atoms, wherein when two or more of the substituents are respectively an alkyl group having 1 to 6 carbon atoms, the carbon atoms of these alkyl groups may form together a cycloalkylidene structure; when a phenyl group of the phenylethyl group has a substituent(s), it may have 1 to 2 substituents selected from a halogen atom, a linear or branched alkoxy group having 1 to 6 carbon atoms which may have a substituent(s), a cycloalkoxy group having 3 to 7 carbon atoms, and a cycloalkyl-alkoxy group having 3 to 7 carbon atoms), or $R^j$ and $R^k$ are taken together with the adjacent nitrogen atom to form a pyrrolidinyl group which may have a substituent(s); and Ar' represents an aromatic hydrocarbon group which may have a substituent(s) or an unsaturated heterocyclic group which may have a substituent(s).

[J-1]

In this step, an easily available compound (54) and amine, for example, methylamine, can be condensed to produce a compound represented by the general formula (55).

Any reaction solvent that does not affect the reaction can be used without limitations. Examples thereof include DMF, toluene, dichloromethane, acetonitrile, and THF. Preferably, the reaction solvent is DMF.

Examples of a condensing agent include DCC, EDC.HCl, and HOBt. Preferably, the condensing agent is a combination of EDC.HCl with HOBt. The equivalent numbers of the EDC.HCl and the HOBt are both 0.5 to 5.0 equivalents, preferably 1.0 to 1.8 equivalents. The reaction temperature is 0 to 100° C., preferably 10 to 40° C. The reaction time is 0.5 to 24 hours, preferably 1.0 to 5.0 hours.

In this step, the compound represented by the general formula (55) can be reduced with LAH to produce a compound represented by the general formula (56).

Any reaction solvent that does not affect the reaction can be used without limitations. Examples thereof include THF, dioxane, dialkyl ether, toluene, and dichloromethane. Preferably, the reaction solvent is THF. The equivalent number of the LAH is 0.5 to 10 equivalents, preferably 1.0 to 5.0 equivalents. The reaction temperature is 0 to 100° C., preferably 20 to 90° C. The reaction time is 0.5 to 48 hours, preferably 1.0 to 24 hours.

[J-3]

In this step, easily available 3-hydroxyphenethyl alcohol (57) can be reacted in the same way as in the step [A-1] to produce a compound represented by the general formula (58).

[J-4]

In this step, the compound represented by the general formula (58) can be methanesulfonylated in the same way as in the step [C-6] (b) and then reacted with methylamine in a sealed tube to synthesize a compound represented by the general formula (59).

Any solvent that does not affect the reaction can be used in the reaction with methylamine without limitations. Examples thereof include THF, dioxane, dialkyl ether, toluene, and dichloromethane. Preferably, the solvent is THF. The equivalent number of the methylamine is 0.1 to 10000 equivalents, preferably 1.0 to 1000 equivalents. The reaction temperature is -90 to 200° C., preferably 30 to 90° C. The reaction time is 0.5 to 48 hours, preferably 2.0 to 10 hours.

[J-5]

In this step, the amine represented by the general formula (56) or (59) or easily available amine (for example, when the amine is (R)-bis(4-fluorophenyl)(pyrrolidin-2-yl)methanol, it can be synthesized according to a method described in Tetrahedron Asymmetry, 14, 95-100 (2003)) and easily available 3-chloropropanesulfonyl chloride (33) can be reacted in the same way as in the step [F-1] to produce a compound represented by the general formula (60).

[J-6]

In this step, the chloro compound represented by the general formula (60) can be bromo-substituted through reaction with a bromide salt, preferably lithium bromide, by a general method and then reacted in the same way as in the step [H-3] to produce a compound represented by the general formula (61).

When a hydroxyl group of the compound represented by the general formula (61) is protected, it may be deprotected by a general method.

[Step K]

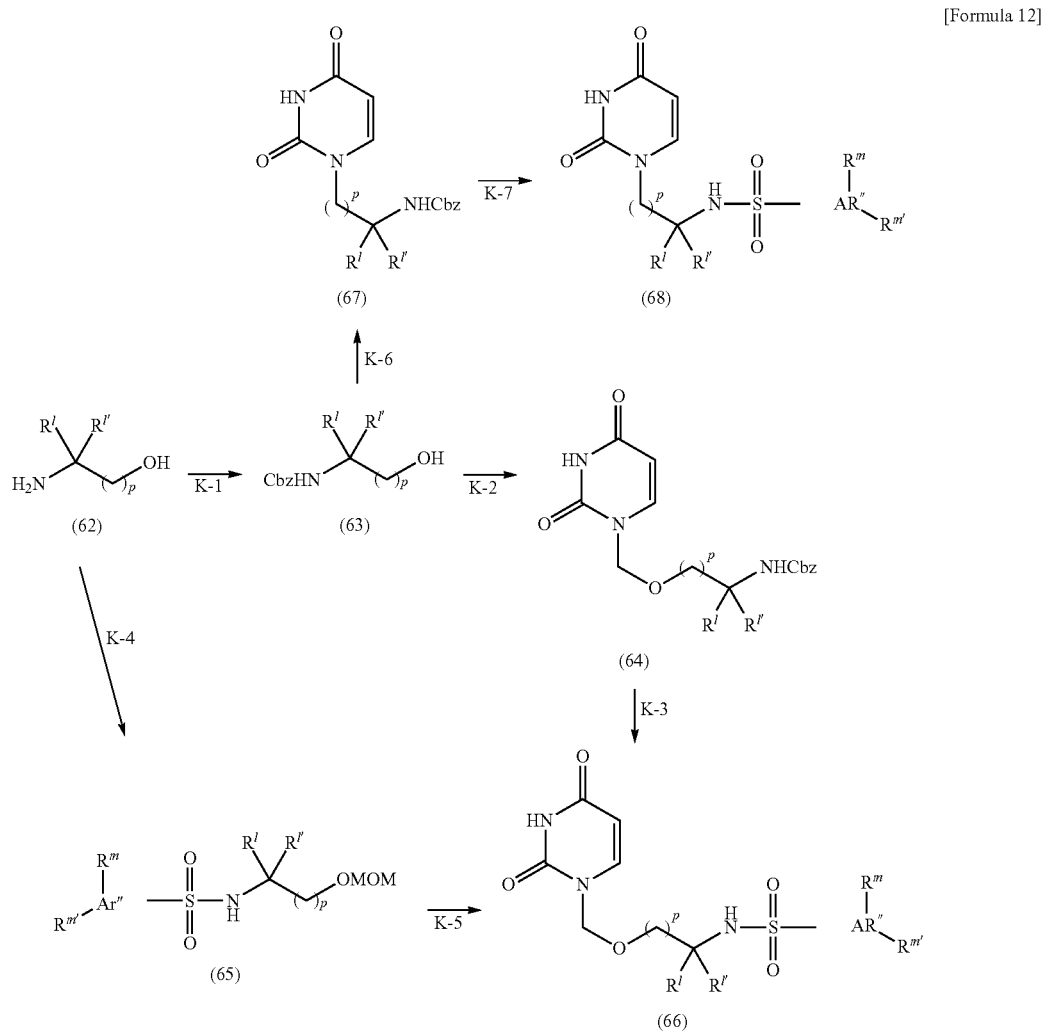

[Formula 12]

wherein $R^l$ and $R^{l'}$ are the same or different and each represents a hydrogen atom or an alkyl group having 1 to 6 carbon atoms, or the carbon atoms of these alkyl groups of $R^l$ and $R^{l'}$ may form together a cycloalkylidene structure; $R^m$ and $R^{m'}$ are the same or different and each represents a hydrogen atom, a halogen atom, a linear or branched alkyl group having 1 to 6 carbon atoms which may have a substituent(s), a cycloalkyl group having 3 to 7 carbon atoms, a linear or branched alkoxy group having 1 to 6 carbon atoms which may have a substituent(s), a cycloalkoxy group having 3 to 7 carbon atoms, a cycloalkyl-alkoxy group having 3 to 7 carbon atoms, a benzoyloxy group, a nitro group, a cyano group, an alkoxycarbonyl group having 1 to 6 carbon atoms, a dimethylamino group, a 1-alkenyl group having 3 to 6 carbon atoms, or a carboxyl group; Ar" is the same as Ar'; p represents an integer of 2 to 3; Cbz represents a benzyloxycarbonyl group; and MOM represents a methoxymethyl group.

[K-1]

In this step, the amino group of an easily available amino alcohol compound represented by the general formula (62) can be protected with Cbz group by a general method to produce a compound represented by the general formula (63).

The amino alcohol compound represented by the general formula (62) wherein, for example, P=2, can be produced by reducing ethyl 3-amino-3-methylbutanoate obtained according to a method described in J. Med. Chem., 34, 633-642 (1991) with LAH; the amino alcohol compound represented by the general formula (62) wherein $R^l$ and $R^{l'}$ are both methyl groups can be produced according to a method described in J. Am. Chem. Soc., 77, 1079-1083 (1955); and the amino alcohol compound represented by the general formula (62) wherein $R^l$ and $R^{l'}$ form a cyclopropane ring together with the interjacent carbon atom can be produced according to a method described in J. Heterocyclic. Chem., 25, 1769-1772 (1988).

[K-2]

In this step, the hydroxyl group of the compound represented by the general formula (63) is MOM-induced by a general method, and the resultant compound can then be reacted in the same way as in the step [F-3] to produce a compound represented by the general formula (64).

[K-3]

In this step, the compound represented by the general formula (64) can be deprotected by a general Cbz deprotection method, for example, is deprotected with palladium-carbon under a hydrogen atmosphere, and then treated with easily available arylsulfonyl chloride which may have a substituent(s) (which can be produced according to a method described in e.g., J. Pesticide. Chem., 13, 107-115 (1988)) under basic conditions to produce a sulfonamide compound represented by the general formula (66).

Any reaction solvent that does not affect the reaction can be used without limitations. Examples thereof include dichloromethane, DMF, ethyl acetate, THF, dioxane, diethyl ether, and acetonitrile. Preferably, the reaction solvent is dichloromethane.

The equivalent number of the arylsulfonyl chloride which may be substituted is 0.9 to 5.0 equivalents, preferably 1.0 to 1.5 equivalents.

Examples of a base include organic amines such as trimethylamine, triethylamine, tripropylamine, diisopropylethylamine, N-methylmorpholine, pyridine, lutidine, collidine, and DBU. Preferably, the base is triethylamine. The equivalent number thereof is 0.9 to 10 equivalents, preferably 1.0 to 3.0 equivalents.

The reaction temperature is 0 to 60° C., preferably 0 to 30° C. The reaction time is 0.1 to 100 hours, preferably 1.0 to 72 hours.

[K-4]

In this step, the amino alcohol compound represented by the general formula (62) can be reacted with easily available arylsulfonyl chloride which may be substituted (which can be produced according to a method described in, e.g., J. Pesticide. Chem., 13, 107-115 (1988)) in the same way as in the step [F-1] and then MOM-induced to produce a compound represented by the general formula (65).

In this step, the amino group of the amino alcohol compound represented by the general formula (62) can be protected, if necessary, with a protecting group by a general method. For example, a tert-butoxycarbonyl or benzyloxycarbonyl group can be used as the protecting group.

[K-5]

In this step, the compound represented by the general formula (65) can be reacted in the same way as in the step [F-3] to produce a compound represented by the general formula (66).

[K-6]

In this step, the compound represented by the general formula (63) can be reacted in the same way as in the steps [G-5] and [G-6] to produce a uracil compound represented by the general formula (67).

[K-7]

In this step, the compound represented by the general formula (67) can be reacted in the same way as in the step [K-3] to produce a compound represented by the general formula (68).

[Step L]

[Formula 13]

wherein Ar, $R^l$, $R^{l'}$, $R^m$, $R^{m'}$, and p are as defined above; and Boc represents a tert-butoxycarbonyl group.

[L-1]

In this step, the amino group of the compound represented by the general formula (62) is protected with a protecting group, preferably a Boc group, by a general method, and the hydroxyl group of the resultant compound is then methanesulfonylated by a general method. Furthermore, the resultant compound can be treated with thioacetic acid under basic conditions to produce a thioacetyl compound represented by the general formula (69).

Any reaction solvent that does not affect the reaction can be used in the thioacetylation without limitations. Examples thereof include dichloromethane, THF, and DMF. Preferably, the reaction solvent is DMF.

Examples of a base in the thioacetylation include: inorganic bases such as sodium bicarbonate, sodium carbonate, and potassium carbonate; and organic amines such as trimethylamine, triethylamine, tripropylamine, diisopropylethylamine, N-methylmorpholine, pyridine, lutidine, collidine, and DBU. Preferably, the base is potassium carbonate. The equivalent number thereof is 0.8 to 5.0 equivalents, preferably 1.0 to 4.0 equivalents.

The reaction temperature of the thioacetylation is 0 to 40° C., preferably 15 to 30° C. The reaction time is 0.1 to 12 hours, preferably 0.2 to 6.0 hours.

[L-2]

In this step, the thioacetyl compound represented by the general formula (69) is deacetylated by a general method to form a thiol group, which can then be MOM-induced by a general method and further reacted in the same way as in the step [F-3] to produce a compound represented by the general formula (70).

[L-3]

In this step, the Boc group of the compound represented by the general formula (70) is removed by a general method, and the resultant compound can then be reacted with easily available arylsulfonyl chloride which may be substituted in the same way as in the step [F-1] to produce a compound represented by the general formula (71).

[L-4]

In this step, a compound represented by the general formula (72) (see Reference Examples 240 described later) obtained in the process of producing the compound represented by the general formula (62) can be reacted with easily available ethyl(triphenylphosphoranylidene)acetate to produce a compound represented by the general formula (73).

Examples of a reaction solvent include toluene and xylene. Preferably, the reaction solvent is toluene. The equivalent number of the ethyl(triphenylphosphoranylidene)acetate is 0.8 to 3.0 equivalents, preferably 1.0 to 2.0 equivalents.

The reaction temperature is 80 to 150° C., preferably 100 to 130° C. The reaction time is 0.5 to 24 hours, preferably 1.0 to 18 hours.

[L-5]

In this step, the ester group of the compound represented by the general formula (73) is reduced by a general method to form an alcohol form, followed by removal of its amine protecting group, preferably the Boc group. Furthermore, the resultant compound can be reacted with easily available arylsulfonyl chloride which may be substituted in the same way as in the step [F-1] to produce a compound represented by the general formula (74).

[L-6]

In this step, the hydroxyl group of the compound represented by the general formula (74) is brominated with, for example, triphenylphosphine and carbon tetrabromide, by a general method usually known in the art, and the resultant compound can then be reacted in the same way as in the step [H-3] to produce a compound represented by the general formula (75).

[Step M]

[Formula 14]

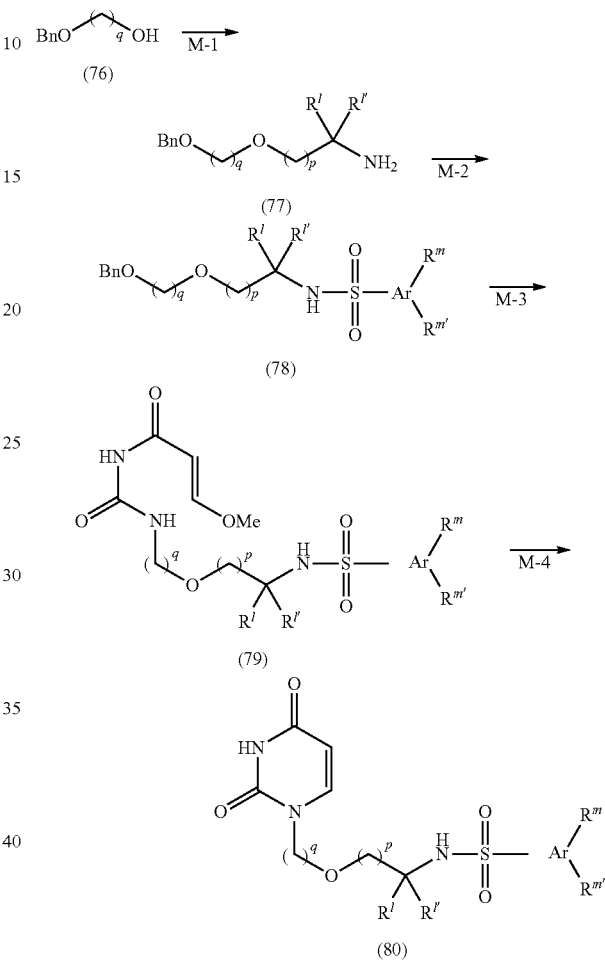

wherein Ar, $R^l$, $R^{l'}$, $R^m$, $R^{m'}$, and p are as defined above; q represents an integer of 2 to 3; and Bn represents a benzyl group.

[M-1]

In this step, the hydroxyl group of an easily available dialcohol compound represented by the general formula (76) whose one hydroxyl group is protected with a protecting group, for example, a benzyl group, is methanesulfonylated by a general method, and the resultant compound can then be reacted with the easily available compound represented by the general formula (62) under basic conditions to produce a compound represented by the general formula (77).

Examples of a solvent include THF and DMF. Preferably, the solvent is DMF. The equivalent number of the compound represented by the general formula (62) is 0.5 to 1.5 equivalents, preferably 0.8 to 1.2 equivalents. Examples of a base include sodium hydride and n-butyllithium. Preferably, the base is sodium hydride. The equivalent number thereof is 0.5 to 1.5 equivalents, preferably 0.8 to 1.2 equivalents.

The reaction temperature is −20 to 60° C., preferably 0 to 50° C. The reaction time is 0.5 to 10 hours, preferably 1.0 to 6.5 hours.

[M-2]

In this step, the amino group of the compound represented by the general formula (77) can be treated in the same way as in the step [F-1] to produce an arylsulfonamide compound represented by the general formula (78).

[M-3]

In this step, the protecting group for the hydroxyl group of the compound represented by the general formula (78) is removed, and an amine form thereof can then be produced in the same way as in the steps [C-6] and [C-7] and then reacted in the same way as in the step [1-4] to produce a compound represented by the general formula (79).

[M-4]

In this step, the compound represented by the general formula (79) can be reacted in the same way as in the step [I-5] to produce a compound represented by the general formula (80).

[Step N]

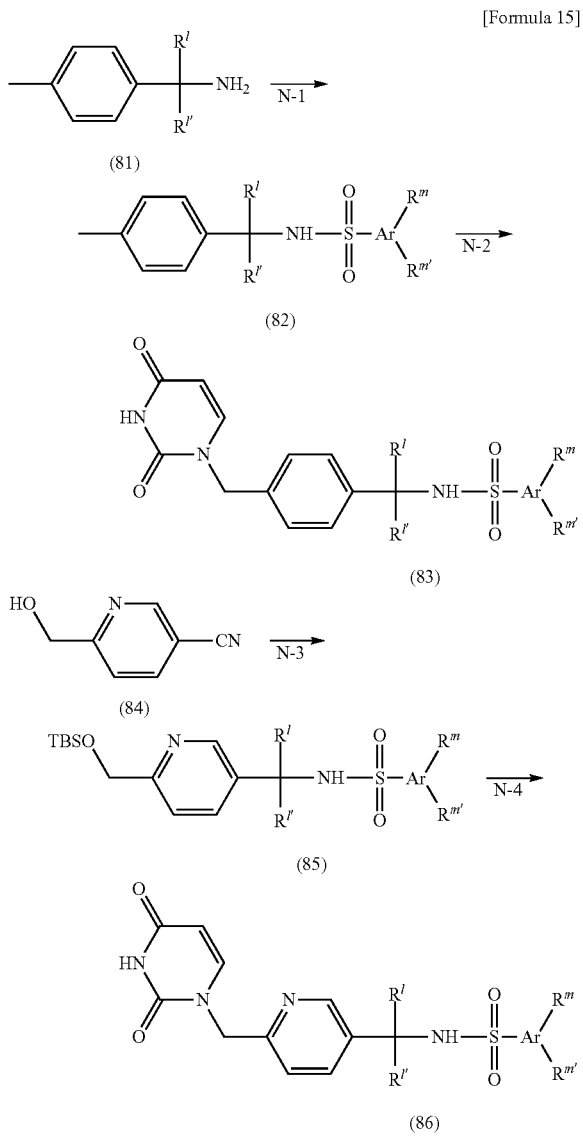

[Formula 15]

wherein Ar, $R^l$, $R^{l'}$, $R^m$, and $R^{m'}$ are as defined above.

[N-1]

In this step, an easily available compound represented by the general formula (81) (which can be produced according to a method described in, e.g., Tetrahedron Lett., 38, 1241-1244 (1997)) can be treated in the same way as in the step [F-1] to produce an arylsulfonamide compound represented by the general formula (82).

[N-2]

In this step, the methyl group of the compound represented by the general formula (82) can be brominated with a general brominating agent, for example, sodium bromate and sodium bisulfite or N-bromosuccinimide and azobisisobutyronitrile (AIBN), and the resultant compound can then be reacted in the same way as in the step [H-3] to produce a compound represented by the general formula (83).

[N-3]

In this step, a protecting group, preferably a TBS group, is introduced by a general method into the hydroxyl group of 6-(hydroxymethyl)nicotinonitrile (84) obtained according to a method described in JP-A-2006-508054, and the obtained compound can be reacted with a methylating agent that can be prepared from methyllithium and cerium chloride, and then reacted with easily available arylsulfonyl chloride which may be substituted in the same way as in the step [F-1] to produce a compound represented by the general formula (85).

Examples of a reaction solvent used in the methylation include THF, dioxane, and diethyl ether. Preferably, the reaction solvent is THF or diethyl ether. The equivalent number of the cerium chloride is 1.0 to 5.0 equivalents, preferably 2.0 to 4.0 equivalents. The equivalent number of the methyllithium is 1.0 to 5.0 equivalents, preferably 2.0 to 4.0 equivalents.

The reaction temperature of the methylation is −100 to 40° C., preferably −78 to 30° C. The reaction time is 0.5 to 5.0 hours, preferably 2.0 to 3.0 hours.

[N-4]

In this step, the protecting group for the hydroxyl group of the compound represented by the general formula (85) is removed, and the hydroxyl group of the resultant compound can then be brominated and then is reacted in the same way as in the step [L-6] to produce a uracil compound represented by the general formula (86).

The thus-produced compound of the present invention and the synthetic intermediates can usually be isolated and purified by the general separation/purification procedures, for example, recrystallization, crystallization, distillation, and column chromatography. The compound of the present invention and the synthetic intermediates can usually form pharmacologically acceptable salts thereof by a general method and can be interconverted with their respective salts.

As shown in Examples described later, the uracil compound of the present invention or the salt thereof has potent dUTPase inhibitory activity and is therefore useful as a medicament such as antitumor drugs.

The uracil compound of the present invention or the salt thereof, when contained in a pharmaceutical composition, is formulated, if necessary, with a pharmaceutical carrier and can be prepared into various administration forms adopted according to a preventive or therapeutic purpose. Examples of the form include oral agents, injections, suppositories, ointments, and patches. The oral agents are preferable. These administration forms can respectively be produced by a general formation method commonly used by those skilled.

Various organic or inorganic carrier substances commonly used as pharmaceutical materials are used as the pharmaceutical carrier. Examples of the pharmaceutical carrier formulated include: excipients, binders, disintegrants, lubricants, and coloring agents for solid preparations; and solvents, solubilizing agents, suspending agents, tonicity agents, buffers, and soothing agents for liquid preparations. Pharmaceutical additives such as preservatives, antioxidants, coloring agents, sweetening agents, and stabilizers can also be used, if necessary.

To prepare the oral solid preparations, an excipient and, if necessary, a binder, a disintegrant, a lubricant, a coloring agent, a flavoring/deodorizing agent, and the like can be added to the compound of the present invention and then prepared into tablets, coated tablets, granules, powders, capsules, and the like by a standard method.

Examples of the excipient include lactose, sucrose, D-mannitol, glucose, starch, calcium carbonate, kaolin, microcrystalline cellulose, and silicic anhydride.

Examples of the binder include water, ethanol, 1-propanol, 2-propanol, simple syrup, glucose solutions, α-starch solutions, gelatin solutions, D-mannitol, carboxymethylcellulose, hydroxypropylcellulose, hydroxypropyl starch, methylcellulose, ethylcellulose, shellac, calcium phosphate, and polyvinylpyrrolidone.

Examples of the disintegrant include dry starch, sodium alginate, powdered agar, sodium bicarbonate, calcium carbonate, sodium lauryl sulfate, monoglyceride stearate, and lactose.

Examples of the lubricant include purified talc, sodium stearate, magnesium stearate, borax, and polyethylene glycol.

Examples of the coloring agent include titanium oxide and iron oxide.

Examples of the flavoring/deodorizing agent include sucrose, orange peels, citric acid, and tartaric acid.

To prepare the oral liquid preparations, a flavoring agent, a buffer, a stabilizer, a deodorizing agent, and the like can be added to the compound of the present invention and prepared into solutions for oral administration, syrups, elixirs, and the like by a standard method. In this case, any of the flavoring/deodorizing agents exemplified above can be used. Examples of the buffer include sodium citrate. Examples of the stabilizer include tragacanth, arabic gum, and gelatin. The oral preparations can also be coated, if necessary, by enteric coating or by a method known in the art for the purpose of sustained effects. Examples of such a coating agent include hydroxypropylmethylcellulose, ethylcellulose, hydroxymethylcellulose, hydroxypropylcellulose, polyoxyethylene glycol, and Tween 80 (registered trademark).

To prepare the injections, a pH adjuster, a buffer, a stabilizer, a tonicity agent, a local anesthetic, and the like can be added to the compound of the present invention and prepared into subcutaneous, intramuscular, and intravenous injections by a standard method. In this case, examples of the pH adjuster and the buffer include sodium citrate, sodium acetate, and sodium phosphate. Examples of the stabilizer include sodium pyrosulfite, EDTA, thioglycolic acid, and thiolactic acid. Examples of the local anesthetic include procaine hydrochloride and lidocaine hydrochloride. Examples of the tonicity agent include sodium chloride, glucose, D-mannitol, and glycerin.

To prepare the suppositories, a pharmaceutical carrier known in the art, for example, polyethylene glycol, lanolin, cacao butter, or fatty acid triglyceride, and, if necessary, a surfactant such as Tween 80 (registered trademark) can be added to the compound of the present invention and then prepared into the suppositories by a standard method.

To prepare the ointments, a base, a stabilizer, a wetting agent, a preservative, and the like usually used can be formulated, if necessary, with the compound of the present invention and mixed and prepared into the ointments by a standard method. Examples of the base include liquid paraffin, white petrolatum, white beeswax, octyl dodecyl alcohol, and paraffin. Examples of the preservative include methyl p-hydroxybenzoate, ethyl p-hydroxybenzoate, and propyl p-hydroxybenzoate.

To prepare the patches, the ointments, cream, gel, paste, or the like can be applied to a usual support by a standard method. Examples of an appropriate support include woven or nonwoven fabric made of cotton, staple fiber, or chemical fiber, and films or foam sheets of soft vinyl chloride, polyethylene, or polyurethane.

The amount of the compound of the present invention to be formulated in any of the aforementioned dosage unit forms differs depending on, for example, the condition of a patient to which it is to be applied or the dosage form. In general, the amount is approximately 0.05 to 1000 mg for the oral agent, approximately 0.01 to 500 mg for the injection, and approximately 1 to 1000 mg for the suppository, per dosage unit form.

The daily dose of the drug having any of the aforementioned dosage forms differs depending on, for example, the condition, body weight, age, and sex of the patient and can be selected appropriately. The daily dose for an adult (body weight: 50 kg) is generally approximately 0.05 to 5000 mg, preferably 0.1 to 1000 mg. Preferably, the drug is administered at a single daily dose or in a divided (e.g., 2 or 3) manner.

Examples of disease that can be treated by the administration of the drug containing the compound of the present invention include malignant tumor, malaria, and tuberculosis. Examples of the malignant tumor include head and neck cancer, esophageal cancer, gastric cancer, colon cancer, rectum cancer, liver cancer, gallbladder/bile duct cancer, pancreas cancer, lung cancer, breast cancer, ovarian cancer, cervical cancer, endometrial cancer, kidney cancer, urinary bladder cancer, prostatic cancer, testicular tumor, osteogenic/soft-tissue sarcoma, leukemia, malignant lymphoma, multiple myeloma, skin cancer, and brain tumor. The compound of the present invention can also be used as an anti-*Helicobacter pylori*, antiparasitic, or antiviral drug.

EXAMPLES

Hereinafter, the present invention will be described more specifically with reference to Reference Examples, Examples, and Test Example. However, the present invention is not intended to be limited to these Examples.

Reference Example 1

Synthesis of (3-(cyclopropylmethoxy)phenyl)methanamine

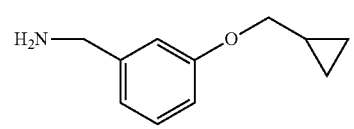

[Formula 16]

3-Cyanophenol (12.4 g) was dissolved in N,N-dimethylformamide (hereinafter, referred to as DMF; 100 mL). To the solution, potassium carbonate (30.5 g), potassium iodide (1.74 g), and (chloromethyl)cyclopropane (10.2 mL) were added, and the mixture was stirred at 90° C. for 4 hours. To the reaction mixture, water (130 mL) was added, and the resultant mixture was then extracted with toluene (130 mL). The organic layer was washed with brine (100 mL), dried over anhydrous sodium sulfate, and then concentrated under reduced pressure. The residue was dissolved in tetrahydrofuran (hereinafter, referred to as THF; 60 mL). To the solution, a solution of lithium aluminum hydride (hereinafter, referred to as LAH) in THF (2.4 M, 68 mL) was gradually added dropwise at 0° C., and the reaction mixture was then stirred at 45° C. for 4 hours. To the reaction mixture, water (10 mL), an aqueous sodium hydroxide solution (1.0 M, 10 mL), and water (5.0 mL) were gradually added at 0° C. The resultant precipitate was removed by filtration and washed with 10% methanol/THF (400 mL). Then, the combined filtrate was concentrated under reduced pressure. To the residue, water (50 mL) was added, and the resultant mixture was then extracted with ethyl acetate (50 mL×3). The organic layer was washed with brine (50 mL), dried over anhydrous sodium sulfate, and then concentrated under reduced pressure to obtain the title compound (18.1 g) as a crude product.

Reference Example 2

Synthesis of (3-cyclobutoxyphenyl)methanamine

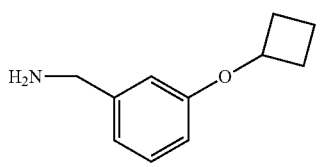

[Formula 17]

3-Cyanophenol (1.25 g), triphenylphosphine (2.9 g), and cyclobutanol (1.2 mL) were dissolved in THF (15 mL). To the solution, a toluene solution of diethyl azodicarboxylate (hereinafter, referred to as DEAD) (2.2 M, 5.0 mL) was gradually added dropwise at 0° C., and the mixture was then stirred at room temperature for 2 hours. The reaction mixture was concentrated under reduced pressure. To the residue, ethyl acetate (20 mL) was then added, and the organic layer was washed with an aqueous sodium hydroxide solution (1.0 M, 5.0 mL), dried over anhydrous sodium sulfate, and then concentrated under reduced pressure. The residue was purified by silica gel column chromatography (40% ethyl acetate/hexane). The obtained compound was dissolved in THF (5.0 mL). To the solution, a solution of LAH in THF (2.4 M, 5.3 mL) was gradually added dropwise at 0° C., and the mixture was stirred at 45° C. for 4 hours. To the reaction mixture, water (1.0 mL), an aqueous sodium hydroxide solution (1.0 M, 1.0 mL), and water (0.5 mL) were gradually added at 0° C. The resultant precipitate was removed by filtration and washed with 10% methanol/THF (40 mL). Then, the combined filtrate was concentrated under reduced pressure. To the residue, water (5.0 mL) was added, and the resultant mixture was then extracted with ethyl acetate (20 mL×3). The organic layer was washed with brine (20 mL), then dried over anhydrous sodium sulfate, and concentrated under reduced pressure to obtain the title compound (1.25 g) as a crude product.

Reference Example 3

Synthesis of (R)-1-(3-(cyclopentyloxy)phenyl)ethanamine hydrochloride

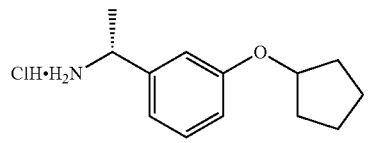

[Formula 18]

3-Hydroxybenzaldehyde (12.2 g) was dissolved in DMF (120 mL). To the solution, bromocyclopentane (32.8 mL), potassium carbonate (27.6 g), and potassium iodide (1.66 g) were added, and the mixture was stirred at 120° C. for 3.5 hours. The reaction mixture was cooled to room temperature, water (120 mL) was then added thereto, and the resultant mixture was then extracted with toluene (120 mL). The organic layer was washed with water (120 mL), an aqueous sodium hydroxide solution (1.0 M, 120 mL), and brine (100 mL), dried over anhydrous sodium sulfate, and then concentrated under reduced pressure. The residue was dissolved in toluene (250 mL). To the solution, (S)-(−)-2-methyl-2-propanesulfinamide (13.3 g) and titanium tetraisopropoxide (44.4 mL) were added, and the mixture was stirred at 70° C. for 6 hours. The reaction mixture was cooled to room temperature, and an aqueous saturated sodium bicarbonate solution (130 mL) was then added thereto. The resultant precipitate was removed by filtration and washed with ethyl acetate (200 mL×4). The combined filtrate was concentrated under reduced pressure. To the residue, brine (200 mL) was added, and the resultant mixture was then extracted with ethyl acetate (200 mL). The organic layer was dried over anhydrous magnesium sulfate and then concentrated under reduced pressure. An aliquot (1.47 g) of the residue (29.3 g) was dissolved in THF (7.5 mL). To the solution, a solution of methylmagnesium bromide in diethyl ether (3.0 M, 3.33 mL) was added dropwise at 0° C., and the mixture was stirred at 0° C. for 4 hours. To the reaction mixture, an aqueous saturated ammonium chloride solution (6.0 mL) was added at 0° C. over 5 minutes, and the resultant mixture was then extracted with ethyl acetate (10 mL). The organic layer was washed with brine (6.0 mL), dried over anhydrous sodium sulfate, and then concentrated under reduced pressure. The residue was purified by silica gel column chromatography (40% ethyl acetate/hexane). The obtained compound (1.09 g) was dissolved in methanol (10 mL). To the solution, a hydrochloric acid-dioxane solution (4.0 M, 1.1 mL) was added, and the mixture was stirred at room temperature for 30 minutes. The reaction mixture was concentrated under reduced pressure and then the residue was co-evaporated with toluene (5.0 mL×3) to obtain the title compound (845 mg).

Reference Example 4

Synthesis of (R)-1-(3-((R)-tetrahydrofuran-3-yloxy)phenyl)ethanamine hydrochloride

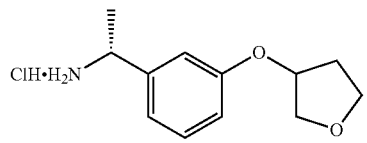

[Formula 19]

3-Hydroxybenzaldehyde (1.3 g), triphenylphosphine (3.6 g), and (S)-(+)-tetrahydro-3-furanol (1.2 mL) were dissolved in THF (20 mL). To the solution, a toluene solution of DEAD (2.2 M, 6.2 mL) was gradually added dropwise at 0° C., and the mixture was then stirred at room temperature for 2 hours. The reaction mixture was concentrated under reduced pressure, and ethyl acetate (20 mL) was then added thereto. The organic layer was washed with an aqueous sodium hydroxide solution (1.0 M, 5.0 mL), dried over anhydrous sodium sulfate, and then concentrated under reduced pressure. The residue was purified by silica gel column chromatography (50% ethyl acetate/hexane). The obtained compound was dissolved in toluene (6.5 mL). To the solution, (S)-(−)-2-methyl-2-propanesulfinamide (330 mg) and titanium tetraisopropoxide (1.1 mL) were added, and the mixture was stirred at 75° C. for 6 hours. The reaction mixture was cooled to room temperature, and an aqueous saturated sodium bicarbonate solution (10 mL) was then added thereto. The resultant precipitate was removed by filtration and washed with ethyl acetate (20 mL×4). The combined filtrate was concentrated under reduced pressure. To the residue, brine (30 mL) was added, and the resultant mixture was then extracted with ethyl acetate. The organic layer was dried over anhydrous magnesium sulfate and then concentrated under reduced pressure. The residue was dissolved in THF (7.5 mL). To the solution, a solution of methylmagnesium bromide in diethyl ether (3.0 M, 1.7 mL) was added dropwise at 0° C., and the mixture was stirred at room temperature for 2 hours. To the reaction mixture, an aqueous saturated ammonium chloride solution (10 mL) was added at 0° C. over 10 minutes, and the resultant mixture was then extracted with ethyl acetate (15 mL). The organic layer was washed with brine (10 mL), dried over anhydrous sodium sulfate, and then concentrated under reduced pressure. The residue was purified by silica gel column chromatography (100% ethyl acetate). The obtained compound was dissolved in methanol (5.0 mL). To the solution, a hydrochloric acid-dioxane solution (4.0 M, 470 µL) was added, and the mixture was stirred at room temperature for 30 minutes. The reaction mixture was concentrated under reduced pressure and then the residue was co-evaporated with toluene (4.0 mL×3) to obtain the title compound (244 mg).

Reference Example 5

Synthesis of (3-(cyclopropylmethoxy)-4-fluorophenyl)methanamine

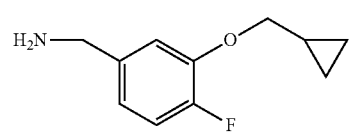

[Formula 20]

4-Fluoro-3-hydroxybenzoic acid (15.0 g) was dissolved in DMF (200 mL). To the solution, (chloromethyl)cyclopropane (18.0 mL), potassium carbonate (29.2 g), and potassium iodide (1.6 g) were added, and the mixture was stirred at 90° C. for 6 hours. The reaction mixture was cooled to room temperature, water (120 mL) was then added thereto, and the resultant mixture was then extracted with toluene (120 mL). The organic layer was washed with brine (100 mL), dried over anhydrous sodium sulfate, and then concentrated under reduced pressure. The residue was dissolved in toluene (65 mL). To the solution, a solution of diisobutylaluminum hydride in hexane (hereinafter, referred to as DIBAL) (1.0 M, 130 mL) was added dropwise at 0° C., and the reaction mixture was stirred at 0° C. for 2 hours. To the reaction mixture, water (10 mL) and an aqueous sodium hydroxide solution (1.0 M, 10 mL) were gradually added. The resultant precipitate was removed by filtration and washed with ethyl acetate (100 mL×5). Then, the combined filtrate was concentrated under reduced pressure. To the residue, water (100 mL) was added, and the resultant mixture was then extracted with ethyl acetate (150 mL). The organic layer was washed with brine (50 mL), dried over anhydrous sodium sulfate, and then concentrated under reduced pressure. The residue was purified by silica gel column chromatography (40% ethyl acetate/hexane). The obtained compound was dissolved in THF (75 mL). To the solution, diphenylphosphoryl azide (12.9 mL) and 1,8-diazabicyclo[5.4.0]-7-undecene (hereinafter, referred to as DBU) (9.4 mL) were added dropwise at room temperature, and the mixture was stirred at room temperature for 1 hour. To the reaction mixture, brine (100 mL) was added, and the aqueous layer was extracted with ethyl acetate (100 mL×2). The organic layer was washed with brine (100 mL), then dried over anhydrous sodium sulfate, and concentrated under reduced pressure. The residue was purified by silica gel column chromatography (20% ethyl acetate/hexane). The obtained compound was dissolved in THF (80 mL). To the solution, a solution of LAH in THF (2.4 M, 40 mL) was gradually added dropwise at 0° C., and the mixture was stirred at 0° C. for 1 hour. To the reaction mixture, water (5.0 mL) and aqueous sodium hydroxide solution (1.0 M, 5.0 mL) were gradually added dropwise at 0° C. The resultant precipitate was removed by filtration and washed with 10% methanol/THF (200 mL). Then, the combined filtrate was concentrated under reduced pressure. To the residue, brine (100 mL) was added, and the resultant mixture was then extracted with ethyl acetate (150 mL). The organic layer was dried over anhydrous sodium sulfate and concentrated under reduced pressure to obtain the title compound (10.5 g) as a crude product.

Reference Example 6

Synthesis of (R)-1-(3-(cyclopropylmethoxy)-4-fluorophenyl)ethanamine hydrochloride

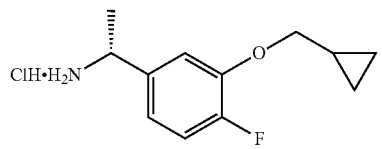

[Formula 21]

4-Fluoro-3-hydroxybenzoic acid (12.0 g) was dissolved in ethanol (200 mL). To the solution, sulfuric acid (3.5 mL) was added, and the mixture was heated to reflux at 105° C. for 4 hours. The reaction mixture was cooled to room temperature, and then concentrated under reduced pressure. To the residue, water (100 mL) and sodium carbonate (18.0 g) were added, and the aqueous layer was extracted with ethyl acetate (100 mL×2). The combined organic layer was washed with brine (100 mL), dried over anhydrous sodium sulfate, and then concentrated under reduced pressure. The residue was co-evaporated with toluene (15 mL×2), and the residue was then dissolved in DMF (100 mL). To the mixture, (chloromethyl)cyclopropane (6.9 mL), potassium carbonate (19.8 g), and potassium iodide (1.2 g) were added, and the mixture was stirred at 90° C. for 3.5 hours. The reaction mixture was cooled to room temperature, water (200 mL) was then added thereto, and the resultant mixture was then extracted with toluene (100 mL×2). The organic layer was washed with brine (100 mL), dried over anhydrous sodium sulfate, and then concentrated under reduced pressure. The residue was dissolved in THF (75 mL). To the mixture, a solution of lithium borohydride in THF (2.0 M, 54 mL) was added dropwise at room temperature, and the mixture was heated to reflux at 80° C. for 3.5 hours. The reaction mixture was cooled to room temperature, water (200 mL) was then added dropwise thereto at 0° C., and the resultant mixture was then extracted with ethyl acetate (100 mL×2). The organic layer was washed with brine (100 mL), dried over anhydrous sodium sulfate, and then concentrated under reduced pressure. The residue was dissolved in dichloromethane (250 mL). To the mixture, manganese dioxide (86 g) was added at room temperature, and the mixture was heated to reflux at 45° C. for 6 hours. The reaction mixture was cooled to room temperature, and the precipitate was removed by filtration and washed with chloroform (100 mL×4). Then, the combined filtrate was concentrated. The residue was dissolved in toluene (150 mL). To the solution, (S)-(−)-2-methyl-2-propanesulfinamide (8.5 g) and titanium tetraisopropoxide (28.4 mL) were added, and the mixture was stirred at 75° C. for 6 hours. The reaction mixture was cooled to room temperature, and an aqueous saturated sodium bicarbonate solution (150 mL) was then added thereto. The resultant precipitate was removed by filtration and washed with ethyl acetate (200 mL×6). The combined filtrate was concentrated under reduced pressure. To the residue, brine (150 mL) was added, and the resultant mixture was then extracted with ethyl acetate (200 mL). The organic layer was dried over anhydrous magnesium sulfate and then concentrated under reduced pressure. The residue was dissolved in THF (85 mL). To the mixture, a solution of methylmagnesium bromide in diethyl ether (3.0 M, 42 mL) was added dropwise at 0° C., and the mixture was stirred at room temperature for 2 hours. To the reaction mixture, an aqueous saturated ammonium chloride solution (100 mL) was added at 0° C. over 10 minutes, and the resultant mixture was then extracted with ethyl acetate (100 mL×2). The organic layer was washed with brine (100 mL), dried over anhydrous sodium sulfate, and then concentrated under reduced pressure. The residue was purified by silica gel column chromatography (50% ethyl acetate/hexane). The obtained compound was dissolved in methanol (70 mL). To the solution, a hydrochloric acid-dioxane solution (4.0 M, 13 mL) was added, and the mixture was stirred at room temperature for 30 minutes. The reaction mixture was concentrated under reduced pressure, and the residue was then co-evaporated with toluene (40 mL×3) to obtain the title compound (9.09 g).

Reference Example 7

Synthesis of (R)-1-(3-(cyclopropylmethoxy)-4-fluorophenyl)-2-methylpropan-1-amine hydrochloride

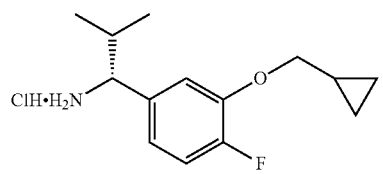

[Formula 22]

4-Fluoro-3-hydroxybenzoic acid (1.2 g) was dissolved in ethanol (20 mL). To the solution, sulfuric acid (350 μL) was added, and the mixture was heated to reflux at 105° C. for 4 hours. The reaction mixture was cooled to room temperature, and then concentrated under reduced pressure. To the residue, water (10 mL) and sodium carbonate (1.8 g) were added, and the aqueous layer was extracted with ethyl acetate (20 mL×2). The organic layer was washed with brine (20 mL), dried over anhydrous sodium sulfate, and then concentrated under reduced pressure. The residue was co-evaporated with toluene (4.0 mL×2), and the residue was then dissolved in DMF (50 mL). To the solution, (chloromethyl)cyclopropane (762 μL), potassium carbonate (2.1 g), and potassium iodide (133 mg) were added, and the mixture was stirred at 90° C. for 3.5 hours. The reaction mixture was cooled to room temperature, water (20 mL) was then added thereto, and the resultant mixture was then extracted with toluene (20 mL×2). The organic layer was washed with brine (20 mL), dried over anhydrous sodium sulfate, and then concentrated under reduced pressure. The residue was dissolved in THF (8.0 mL). To the mixture, a solution of lithium borohydride in THF (2.0 M, 7.5 mL) was added dropwise at room temperature, and the mixture was heated to reflux at 75° C. for 3.5 hours. The reaction mixture was cooled to 0° C., and water (20 mL) was then added dropwise thereto at the same temperature. The aqueous layer was extracted with ethyl acetate (20 mL×2). The organic layer was washed with brine (20 mL), dried over anhydrous sodium sulfate, and then concentrated under reduced pressure. The residue was dissolved in dichloromethane (25 mL). To the mixture, manganese dioxide (8.6 g) was added at room temperature, and the mixture was heated to reflux at 45° C. for 6 hours. The reaction mixture was cooled to room temperature, and the precipitate was then removed by filtration and washed with chloroform (20 mL×4). Then, the combined filtrate was concentrated. The residue was dissolved in toluene (17.5 mL). To the mixture, (R)-(−)-2-methyl-2-propanesulfinamide (985 mg) and titanium tetraisopropoxide (3.3 mL) were added, and the mixture was stirred at 75° C. for 6 hours. The reaction mixture was cooled to room temperature, and an aqueous saturated sodium bicarbonate solution (15 mL) was then added thereto. The resultant precipitate was removed by filtration and washed with ethyl acetate (20 mL×6). The combined filtrate was washed with brine (50 mL), dried over anhydrous magnesium sulfate, and then concentrated under reduced pressure. The residue was dissolved in THF (85 mL). To the mixture, a solution of isopropyllithium in THF (0.7 M, 12 mL) was added dropwise at −78° C., and the mixture was stirred at −78° C. for 45 minutes. To the reaction mixture, an aqueous saturated ammonium chloride solution (10 mL) was added at −78° C., and the aqueous layer was extracted with ethyl acetate (20 mL×2). The combined organic layer was washed with brine (20 mL), dried over anhydrous sodium sulfate, and then concentrated under reduced pressure. The residue was purified by silica gel column chromatography (50% ethyl acetate/hexane). The obtained compound was dissolved in methanol (7.0 mL). To the solution, a hydrochloric acid-dioxane solution (4.0 M, 470 μL) was added, and the mixture was stirred at room temperature for 30 minutes. The reaction mixture was concentrated under reduced pressure, and the residue was then co-evaporated with toluene (10 mL×3) to obtain the title compound (425 mg).

Reference Example 8

Synthesis of (3-(cyclopropylmethoxy)phenyl)(phenyl)methanamine

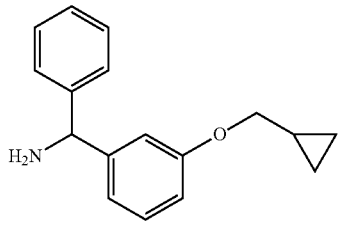

[Formula 23]

3-Hydroxybenzaldehyde (2.5 g) was dissolved in DMF (25 mL). To the solution, potassium carbonate (6.2 g), potassium iodide (350 mg), and (chloromethyl)cyclopropane (2.1 mL) were added, and the mixture was stirred at 90° C. for 4 hours. To the reaction mixture, water (30 mL) was added, and the resultant mixture was then extracted with toluene (30 mL). The organic layer was washed with brine (20 mL), dried over anhydrous sodium sulfate, and then concentrated under reduced pressure. The residue was dissolved in THF (3.0 mL). To the mixture, a solution of phenylmagnesium bromide in THF (1.0 M, 22.6 mL) was added dropwise at 0° C., and the mixture was stirred at room temperature for 2 hours. To the reaction mixture, an aqueous saturated ammonium chloride solution (10 mL) was added at 0° C., and the resultant mixture was then extracted with ethyl acetate (50 mL). The organic layer was washed with brine (30 mL), dried over anhydrous sodium sulfate, and then concentrated under reduced pressure. The residue was purified by silica gel column chromatography (40% ethyl acetate/hexane). The obtained compound was dissolved in chloroform (30 mL). To the solution, sodium azide (3.5 g) was added. To the reaction mixture, trifluoroacetic acid (6.6 mL) was added dropwise at 0° C., and the mixture was then stirred at room temperature for 1 hour. To the reaction mixture, water (20 mL) was added, and the resultant mixture was then extracted with chloroform (20 mL). The organic layer was washed with an aqueous saturated sodium bicarbonate solution (20 mL), dried over anhydrous sodium sulfate, and then concentrated under reduced pressure. The residue was purified by silica gel column chromatography (20% ethyl acetate/hexane). The obtained compound was dissolved in methanol (30 mL). To the solution, 10% palladium-carbon (600 mg) was added, and the reaction mixture was stirred at room temperature for 2 hours under a hydrogen atmosphere. The precipitate was removed by filtration through a pad of Celite and washed with methanol (100 mL). Then, the combined filtrate was concentrated under reduced pressure to obtain the title compound (2.79 g) as a crude product.

Reference Example 9

Synthesis of 1-(3-(cyclopropylmethoxy)phenyl)ethanamine

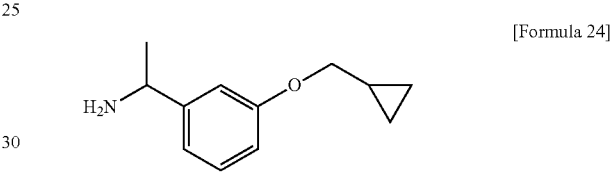

[Formula 24]

3-Hydroxybenzaldehyde (692 mg) was dissolved in DMF (25 mL). To the solution, potassium carbonate (1.56 g), potassium iodide (95 mg), and (chloromethyl)cyclopropane (578 μL) were added, and the mixture was stirred at 90° C. for 4 hours. To the reaction mixture, water (20 mL) was added, and the resultant mixture was then extracted with toluene (20 mL). The organic layer was washed with brine (20 mL), dried over anhydrous sodium sulfate, and then concentrated under reduced pressure. The residue was dissolved in THF (2.5 mL). To the mixture, a solution of methylmagnesium bromide in THF (1.0 M, 6.5 mL) was added dropwise at 0° C., and the mixture was stirred at room temperature for 2 hours. To the reaction mixture, an aqueous saturated ammonium chloride solution (10 mL) was added at 0° C., and the resultant mixture was then extracted with ethyl acetate (20 mL×2). The organic layer was washed with brine (20 mL), dried over anhydrous sodium sulfate, and then concentrated under reduced pressure. The residue was purified by silica gel column chromatography (40% ethyl acetate/hexane). The obtained compound was dissolved in THF (5.0 mL). To the solution, diphenylphosphoryl azide (875 μL) and DBU (592 μL) were added dropwise at room temperature, and the mixture was stirred for 1 hour. To the reaction mixture, brine (10 mL) was added, and the resultant mixture was then extracted with ethyl acetate (20 mL×2). The organic layer was washed with brine (10 mL), dried over anhydrous sodium sulfate, and then concentrated under reduced pressure. The residue was purified by silica gel column chromatography (20% ethyl acetate/hexane). The obtained compound was dissolved in methanol (7.5 mL). To the solution, 10% palladium-carbon (180 mg) was added, and the reaction mixture was stirred at room temperature for 2 hours under a hydrogen atmosphere. The precipitate was removed by filtration through a pad of Celite and washed with methanol (100 mL). Then, the combined filtrate was concentrated under reduced pressure to obtain the title compound (740 mg) as a crude product.

Reference Example 10

Synthesis of (3-(cyclopropylmethylthio))phenylmethanamine

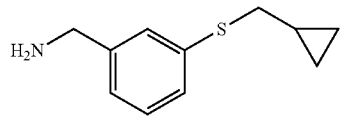

[Formula 25]

3-(Mercaptophenyl)methanol (1.77 g) obtained according to a method described in the document (Chemistry Express, 7, 865-868 (1992)) was dissolved in DMF (7.5 mL). To the solution, potassium carbonate (2.0 g) and (bromomethyl)cyclopropane (1.29 mL) were added, and the mixture was stirred at 90° C. for 4 hours. To the reaction mixture, water (20 mL) was added, and the resultant mixture was then extracted with toluene (20 mL). The organic layer was washed with brine (20 mL), dried over anhydrous sodium sulfate, and then concentrated under reduced pressure. The residue was dissolved in THF (25 mL). To the mixture, diphenylphosphoryl azide (3.5 mL) and DBU (2.7 mL) were added dropwise at room temperature, and the mixture was stirred for 1 hour. To the reaction mixture, brine (20 mL) was added, and the resultant mixture was then extracted with ethyl acetate (20 mL×2). The organic layer was washed with brine (20 mL), dried over anhydrous sodium sulfate, and then concentrated under reduced pressure. The residue was purified by silica gel column chromatography (20% ethyl acetate/hexane). The obtained compound was dissolved in THF (12.5 mL). To the solution, a solution of LAH in THF (2.4 M, 7.3 mL) was gradually added dropwise at room temperature, and the mixture was stirred for 1 hour. To the reaction mixture, water (1.0 mL) and an aqueous sodium hydroxide solution (1.0 M, 500 μL) were gradually added dropwise at 0° C. The resultant precipitate was removed by filtration and washed with 10% methanol/THF (100 mL). The combined filtrate was concentrated under reduced pressure. To the residue, water (20 mL) was added, and the resultant mixture was then extracted with ethyl acetate (20 mL×2). The organic layer was washed with brine (20 mL), dried over anhydrous sodium sulfate, and then concentrated under reduced pressure to obtain the title compound (1.55 g) as a crude product.

Reference Example 11

Synthesis of (R)-1-(3-cyclopropoxyphenyl)ethanamine hydrochloride

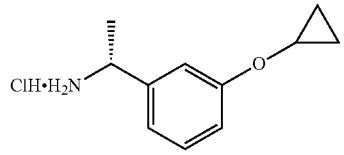

[Formula 26]

3-Cyclopropoxybenzonitrile (443 mg) obtained according to a method described in the document (Tetrahedron Lett., 40, 2633-2636 (1999)) was dissolved in diethyl ether (4.0 mL) and toluene (10 mL). To the solution, a solution of DIBAL in hexane (1.0 M, 6.8 mL) was added dropwise at −78° C., and the mixture was stirred at −78° C. for 2 hours. To the reaction mixture, methanol (2.0 mL) was added at −78° C., and the mixture was further stirred for 20 minutes. To the reaction mixture, dilute hydrochloric acid (1.0 M, 10 mL) was added at 0° C., and the mixture was stirred for 30 minutes. Water (20 mL) was then added thereto. The aqueous layer was extracted with ethyl acetate (20 mL×3). The organic layer was washed with brine (30 mL), dried over anhydrous sodium sulfate, and then concentrated under reduced pressure. The residue was purified by silica gel column chromatography (20% ethyl acetate/hexane). The obtained compound was dissolved in toluene (7.5 mL). To the solution, (S)-(−)-2-methyl-2-propanesulfinamide (267 mg) and titanium tetraisopropoxide (860 μL) were added, and the mixture was stirred at 75° C. for 6 hours. The reaction mixture was cooled to room temperature, and an aqueous saturated sodium bicarbonate solution (15 mL) was then added thereto. The resultant precipitate was removed by filtration and washed with ethyl acetate (20 mL×6). The combined filtrate was washed with brine (50 mL), dried over anhydrous magnesium sulfate, and then concentrated under reduced pressure. The residue was dissolved in THF (3.0 mL). To the mixture, a solution of methylmagnesium bromide in diethyl ether (3.0 M, 1.5 mL) was added dropwise at 0° C., and the mixture was stirred at room temperature for 2 hours. To the reaction mixture, an aqueous saturated ammonium chloride solution (10 mL) was added at 0° C., and the aqueous layer was extracted with ethyl acetate (20 mL×2). The organic layer was washed with brine (20 mL), dried over anhydrous sodium sulfate, and then concentrated under reduced pressure. The residue was purified by silica gel column chromatography (50% ethyl acetate/hexane). The obtained compound was dissolved in methanol (7.0 mL). To the solution, a hydrochloric acid-dioxane solution (4.0 M, 550 μL) was added, and the mixture was stirred at room temperature for 30 minutes. The reaction mixture was concentrated under reduced pressure, and the residue was then co-evaporated with toluene (5.0 mL×3) to obtain the title compound (374 mg).

Reference Example 12

Synthesis of 3-(3-(cyclopropylmethoxy)phenyl)pentan-3-amine

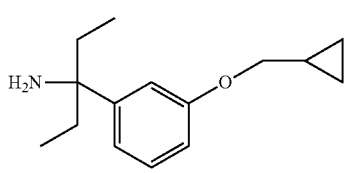

[Formula 27]

To a solution of magnesium (280 mg) in THF (2.5 mL), iodine (10 mg) was added at room temperature. Then, a small amount of a solution of 1-bromo-3-(cyclopropylmethoxy)benzene (2.27 g) obtained according to a method described in the document (Izvestiya akademii Nauk SSSR, Seriya Khimicheskaya, 12, 2752-2755 (1989)) in THF (3.5 mL) was added thereto, and the mixture was stirred at room temperature for 10 minutes until the iodine color disappeared. The remaining amount of the solution of 1-bromo-3-(cyclopropylmethoxy)benzene in THF was added thereto, and the mixture was stirred at room temperature for 1 hour until the magnesium disappeared. To the reaction mixture, a solution of 3-pentanone (1.02 g) in THF (3.0 mL) was added, and the mixture was stirred at room temperature for 2 hours. To the reaction mixture, an aqueous saturated ammonium chloride solution (10 ml) was added at 0° C., and the aqueous layer was extracted with ethyl acetate (20 mL×2). The organic layer was washed with brine (20 mL), dried over anhydrous sodium sulfate, and then concentrated under reduced pressure. The residue was purified by silica gel column chromatography (30% ethyl acetate/hexane). The obtained compound was dissolved in chloroform (20 mL). To the solution, sodium azide (1.7 g) was added. To the reaction mixture, trifluoroacetic acid (3.2 mL) was added dropwise at 0° C., and the mixture was then stirred at room temperature for 1 hour. To the reaction mixture, water (20 mL) was added, and the resultant mixture was then extracted with chloroform (20 mL). The organic layer was washed with an aqueous saturated sodium bicarbonate solution (20 mL), dried over anhydrous sodium sulfate, and then concentrated under reduced pressure. The residue was purified by silica gel column chromatography (10% ethyl acetate/hexane). The obtained compound was dissolved in methanol (10 mL). To the solution, 10% palladium-carbon (260 mg) was added, and the reaction mixture was stirred at room temperature for 2 hours under a hydrogen atmosphere. The precipitate was removed by filtration through a pad of Celite and washed with methanol (100 mL). Then, the combined filtrate was concentrated under reduced pressure to obtain the title compound (1.70 g) as a crude product.

Reference Example 13

Synthesis of (R)-1-(3-(1-aminoethyl)phenoxy)-2-methylpropan-2-ol hydrochloride

[Formula 28]

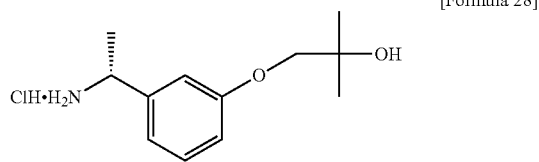

Methyl (3-formylphenoxy)acetate (1.05 g) was dissolved in toluene (12 mL). To the solution, 1,3-propanediol (477 µL) and p-toluenesulfonic acid monohydrate (10 mg) were added, and the mixture was heated to reflux at 125° C. for 18 hours using a Dean-Stark apparatus. The reaction mixture was cooled to room temperature, then washed with a 5% aqueous sodium carbonate solution (10 mL), dried over potassium carbonate, and then concentrated under reduced pressure. The residue was dissolved in THF (4.0 mL). To the mixture, a solution of methylmagnesium bromide in diethyl ether (3.0 M, 4.2 mL) was added dropwise at 0° C., and the mixture was stirred at room temperature for 2 hours. To the reaction mixture, an aqueous saturated ammonium chloride solution (10 mL) was added at 0° C., and the aqueous layer was extracted with ethyl acetate (20 mL×2). The organic layer was washed with brine (20 mL), dried over anhydrous sodium sulfate, and then concentrated under reduced pressure. The residue was purified by silica gel column chromatography (33% ethyl acetate/hexane). The obtained compound was dissolved in THF (15 mL). To the solution, concentrated hydrochloric acid (15 mL) was added, and the mixture was stirred at room temperature for 15 minutes. After extracted with ethyl acetate (50 mL×3), the combined organic layer was washed with an aqueous saturated sodium bicarbonate solution (50 mL) and brine (50 mL), dried over anhydrous sodium sulfate, and then concentrated under reduced pressure. The residue was dissolved in toluene (7.0 mL). To the mixture, (S)-(−)-2-methyl-2-propanesulfinamide (412 mg) and titanium tetraisopropoxide (1.3 mL) were added, and the mixture was stirred at 75° C. for 6 hours. The reaction mixture was cooled to room temperature, and an aqueous saturated sodium bicarbonate solution (15 mL) was then added thereto. The resultant precipitate was removed by filtration and washed with ethyl acetate (20 mL×6). The combined filtrate was washed with brine (50 mL), dried over anhydrous magnesium sulfate, and then concentrated under reduced pressure. The residue was dissolved in dichloromethane (6.0 mL). To the mixture, 2,6-lutidine (900 µL) and trimethylsilyl trifluoromethanesulfonate (hereinafter, referred to as TMSOTf; 840 µL) were added, and the mixture was stirred at room temperature for 1 hour. The reaction mixture was concentrated under reduced pressure, and the residue was then purified by silica gel column chromatography (25% ethyl acetate/hexane). The obtained compound was dissolved in THF (4.0 mL). To the solution, a solution of methylmagnesium bromide in diethyl ether (3.0 M, 1.4 mL) was added dropwise at 0° C., and the mixture was stirred at 0° C. for 3 hours. To the reaction mixture, an aqueous saturated ammonium chloride solution (10 mL) was added at 0° C., and the aqueous layer was extracted with ethyl acetate (20 mL×2). The organic layer was washed with brine (20 mL), dried over anhydrous sodium sulfate, and then concentrated under reduced pressure. The residue was purified by silica gel column chromatography (50% ethyl acetate/hexane). The obtained compound was dissolved in methanol (5.0 mL). To the solution, a hydrochloric acid-dioxane solution (4.0 M, 1.1 mL) was added, and the mixture was stirred at room temperature for 30 minutes. The reaction mixture was concentrated under reduced pressure, and the residue was then co-evaporated with toluene (5.0 mL×3) to obtain the title compound (348 mg).

Reference Example 14

Synthesis of (S)-2-(3-(cyclopentyloxy)-4-fluorophenyl)-2-(trimethylsilyloxy)butan-1-amine

[Formula 29]

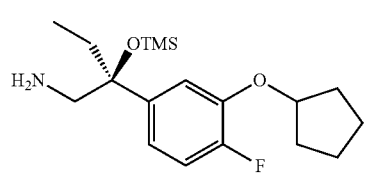

4-Fluoro-3-hydroxybenzoic acid (9.88 g) was dissolved in ethanol (165 mL). To the solution, sulfuric acid (2.10 mL) was added, and the mixture was heated to reflux at 90° C. for 2 hours. The reaction mixture was concentrated under reduced pressure. The residue was neutralized by the addition of water (100 mL) and sodium bicarbonate (7.0 g), and was then extracted with ethyl acetate (100 mL). The organic layer was washed with brine (100 mL), dried over anhydrous magnesium sulfate, and then concentrated under reduced pressure. The obtained ethyl ester compound (11.2 g) was dissolved in DMF (73 mL). To the solution, potassium carbonate (16.8 g) and bromocyclopentane (22.8 mL) were added, and the mixture was stirred at 125° C. for 3 hours. The reaction mixture was cooled to room temperature, water (150 mL) was then added thereto, and the resultant mixture was then extracted with toluene (150 mL). The organic layer was washed with water (150 mL) and brine (100 mL), dried over anhydrous sodium sulfate, and then concentrated under reduced pressure. The obtained ethyl 3-cyclopentyloxy-4-fluorobenzoate (16.0 g) was dissolved in ethanol (20 mL) and water (20 mL). To the mixture, an aqueous sodium hydroxide solution (4.0 M, 45.6 mL) was added, and the mixture was stirred at 55° C. for 3 hours. The reaction mixture was concentrated under reduced pressure. The residue was then acidified by the addition of hydrochloric acid (6.0 M, 41 mL), and was then extracted with ethyl acetate (200 mL). The organic layer was dried over anhydrous sodium sulfate and then concentrated under reduced pressure. The obtained 3-cyclopentyloxy-4-fluorobenzoic acid (13.6 g) was dissolved in DMF (150 mL). To the solution, 1-ethyl-3-(3-dimethylaminopropyl)carbodiimide hydrochloride (hereinafter, referred to as EDC.HCl; 17.4 g) and 1-hydroxybenzotriazole (hereinafter, referred to as HOBt; 9.79 g) were added, and the mixture was stirred at room temperature for 5 minutes. To the reaction mixture, N,O-dimethylhydroxylamine hydrochloride (7.07 g) and triethylamine (11.0 mL) were added, and the mixture was stirred at room temperature for 13 hours. To the reaction mixture, water (200 mL) was added, and the resultant mixture was then extracted with toluene (200 mL). The organic layer was washed with water (200 mL) and brine (200 mL), dried over anhydrous magnesium sulfate, and then concentrated under reduced pressure. The residue was purified by silica gel column chromatography (33% ethyl acetate/hexane). The obtained compound (16.1 g) was dissolved in THF (150 mL). To the solution, a solution of ethylmagnesium bromide in THF (1.0 M, 150 mL) was added dropwise at 0° C., and the mixture was stirred at 0° C. for 2.5 hours. An aqueous saturated ammonium chloride solution (100 mL) was added thereto at 0° C., and the resultant mixture was then extracted with ethyl acetate (100 mL). The organic layer was washed with brine (100 mL), dried over anhydrous sodium sulfate, and then concentrated under reduced pressure. The residue was purified by silica gel column chromatography (5% ethyl acetate/hexane). The obtained compound (12.9 g) was co-evaporated with toluene (30 mL×2).

(Methyl)triphenylphosphonium bromide (25.4 g) was suspended in THF (200 mL). To the suspension, a solution of bis(trimethylsilyl)amide sodium salt (hereinafter, referred to as NaHMDS) in THF (1.0 M, 71.0 mL) was added at 0° C., and the mixture was stirred at 0° C. for 30 minutes. The reaction mixture was cooled to −78° C. A THF (30 mL) solution of the above compound which was co-evaporated with toluene was added thereto, and the mixture was stirred at room temperature for 3 hours. To the reaction mixture, acetic acid (3.0 mL) was added, and the mixture was concentrated under reduced pressure. The residue was suspended in 10% ethyl acetate/hexane (50 mL). The precipitate was removed by filtration and then washed with 10% ethyl acetate/hexane (50 mL×3). The combined filtrate was concentrated under reduced pressure. The residue was purified by silica gel column chromatography (5% ethyl acetate/hexane). The obtained compound (12.8 g) was dissolved in tert-butanol (230 mL) and water (230 mL). To the solution, AD-mix α (76.0 g) was added at 0° C., and the mixture was vigorously stirred at 0° C. for 5 hours. To the reaction mixture, an aqueous saturated sodium bisulfite solution (150 mL) was added at 0° C. to dissolve the precipitate, and the resultant mixture was then extracted with ethyl acetate (150 mL). The organic layer was washed with brine (100 mL), dried over anhydrous sodium sulfate, and then concentrated under reduced pressure. The residue was purified by silica gel column chromatography (40% ethyl acetate/hexane). An aliquot (1.25 g) of the obtained compound (14.7 g) was dissolved in dichloromethane (8.0 mL). To the solution, triethylamine (975 µL) and methanesulfonyl chloride (400 µL) were added at 0° C., and the mixture was stirred at room temperature for 30 minutes. To the reaction mixture, an aqueous saturated sodium bicarbonate solution (10 mL) was added, and the aqueous layer was extracted with chloroform (20 mL×2). The organic layer was washed with brine (10 mL), dried over anhydrous sodium sulfate, and then concentrated under reduced pressure. The residue was dissolved in DMF (7.0 mL). To the solution, sodium azide (1.33 g) was added, and the mixture was stirred at 75° C. for 15 hours. The reaction mixture was cooled to room temperature, water (10 mL) was then added thereto, and the resultant mixture was then extracted with ethyl acetate (20 mL). The organic layer was washed with brine (10 mL), dried over anhydrous sodium sulfate, and then concentrated under reduced pressure. The residue was purified by silica gel column chromatography (20% ethyl acetate/hexane). The obtained compound was dissolved in a dichloromethane (8.0 mL). To the solution, 2,6-lutidine (700 µL) and TMSOTf (740 µL) were added, and the mixture was stirred at room temperature for 1 hour. The reaction mixture was concentrated under reduced pressure, and the residue was then purified by silica gel column chromatography (15% ethyl acetate/hexane). The obtained compound was dissolved in methanol (8.0 mL). To the solution, 10% palladium-carbon (180 mg) was further added, and the reaction mixture was stirred at room temperature for 1 hour under a hydrogen atmosphere. The precipitate was removed by filtration through a pad of Celite and washed with methanol (100 mL). Then, the combined filtrate was concentrated under reduced pressure to obtain the title compound (983 mg) as a crude product.

Reference Example 15 (3-(cyclopropylmethoxy)-4-fluorophenyl)(4-fluorophenyl)methanamine

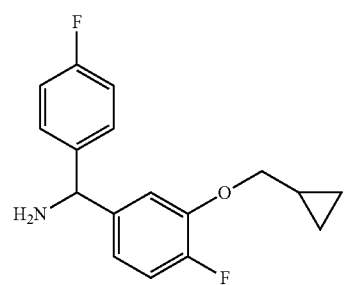

[Formula 30]

4-Fluoro-3-hydroxybenzoic acid (2.0 g) was dissolved in DMF (15 mL). To the solution, (chloromethyl)cyclopropane (2.4 mL), potassium carbonate (3.9 g), and potassium iodide (212 mg) were added, and the mixture was stirred at 90° C. for 6 hours. The reaction mixture was cooled to room temperature, water (30 mL) was then added thereto, and the resultant mixture was then extracted with toluene (30 mL). The organic layer was washed with brine (30 mL), dried over anhydrous sodium sulfate, and then concentrated under reduced pressure. The residue was dissolved in toluene (10 mL). To the mixture, a solution of DIBAL in hexane (1.0 M, 20 mL) was added dropwise at 0° C., and the reaction mixture was stirred at 0° C. for 2 hours. To the reaction mixture, water (1.0 mL) and an aqueous sodium hydroxide solution (1.0 M, 1.0 mL) were gradually added. The resultant precipitate was removed by filtration and washed with ethyl acetate (10 mL×5). Then, the combined filtrate was concentrated under reduced pressure. To the residue, water (20 mL) was added, and the resultant mixture was then extracted with ethyl acetate (30 mL). The organic layer was washed with brine (15 mL), dried over anhydrous sodium sulfate, and then concentrated under reduced pressure. The residue was purified by silica gel column chromatography (40% ethyl acetate/hexane). The obtained compound was dissolved in dichloromethane (20 mL). To the solution, manganese dioxide (8.6 g) was added at room temperature, and the mixture was heated to reflux at 45° C. for 6 hours. The reaction mixture was cooled to room temperature, and the precipitate was removed by filtraion and washed with chloroform (20 mL×4). Then, the combined filtrate was concentrated under reduced pressure. The residue was dissolved in THF (2.0 mL). To the mixture, a solution of 4-fluorophenylmagnesium bromide in THF (1.0 M, 12 mL) was added dropwise at 0° C., and the mixture was stirred at room temperature for 2 hours. To the reaction mixture, an aqueous saturated ammonium chloride solution (10 mL) was added at 0° C., and the resultant mixture was then extracted with ethyl acetate (15 mL×2). The organic layer was washed with brine (20 mL), dried over anhydrous sodium sulfate, and then concentrated under reduced pressure. The residue was purified by silica gel column chromatography (30% ethyl acetate/hexane). The obtained compound was dissolved in chloroform (10 mL). To the solution, sodium azide (1.9 g) was added. To the reaction mixture, trifluoroacetic acid (3.6 mL) was added dropwise at 0° C., and the mixture was then stirred at room temperature for 1 hour. To the reaction mixture, water (10 mL) was added, and the resultant mixture was then extracted with chloroform (10 mL). The organic layer was washed with an aqueous saturated sodium bicarbonate solution (10 mL), dried over anhydrous sodium sulfate, and then concentrated under reduced pressure. The residue was purified by silica gel column chromatography (20% ethyl acetate/hexane). The obtained compound was dissolved in methanol (30 mL). To the solution, 10% palladium-carbon (420 mg) was added, and the reaction mixture was stirred at room temperature for 2 hours under a hydrogen atmosphere. The precipitate was removed by filtration through a pad of Celite and washed with methanol (80 mL). Then, the combined filtrate was concentrated under reduced pressure to obtain the title compound (2.08 g) as a crude product.

Reference Example 16

2-(3-(cyclopropylmethoxy)-4-fluorophenyl)propan-2-amine

[Formula 31]

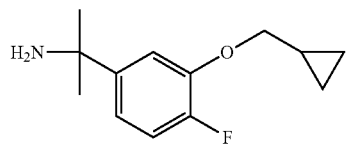

4-Fluoro-3-hydroxybenzoic acid (660 mg) was dissolved in DMF (5.0 mL). To the solution, (chloromethyl)cyclopropane (800 µL), potassium carbonate (1.3 g), and potassium iodide (71 mg) were added, and the mixture was stirred at 90° C. for 6 hours. The reaction mixture was cooled to room temperature, water (10 mL) was then added thereto, and the resultant mixture was then extracted with toluene (10 mL). The organic layer was washed with brine (10 mL), dried over anhydrous sodium sulfate, and then concentrated under reduced pressure. The residue was dissolved in THF (1.0 mL). To the mixture, a solution of methylmagnesium bromide in THF (1.0 M, 12 mL) was added dropwise at 0° C., and the mixture was heated to reflux at 85° C. for 2 hours. To the reaction mixture, an aqueous saturated ammonium chloride solution (10 mL) was added at 0° C., and the resultant mixture was then extracted with ethyl acetate (10 mL×2). The organic layer was washed with brine (10 mL), dried over anhydrous sodium sulfate, and then concentrated under reduced pressure. The residue was purified by silica gel column chromatography (20% ethyl acetate/hexane). The obtained compound was dissolved in chloroform (6.0 mL). To the solution, sodium azide (830 mg) was added. To the mixture, trifluoroacetic acid (1.3 mL) was added dropwise at 0° C., and the mixture was then stirred at room temperature for 1 hour. To the reaction mixture, water (5.0 mL) was added, and the resultant mixture was then extracted with chloroform (10 mL). The organic layer was washed with an aqueous saturated sodium bicarbonate solution (10 mL), dried over anhydrous sodium sulfate, and then concentrated under reduced pressure. The residue was purified by silica gel column chromatography (20% ethyl acetate/hexane). The obtained compound was dissolved in methanol (10 mL). To the solution, 10% palladium-carbon (250 mg) was added, and the reaction mixture was stirred at room temperature for 2 hours under a hydrogen atmosphere. The precipitate was removed by filtration through a pad of Celite and washed with methanol (80 mL). Then, the combined filtrate was concentrated under reduced pressure to obtain the title compound (610 mg) as a crude product.

Reference Example 17

1-(3-(cyclopropylmethoxy)-4-fluorophenyl)ethanamine

[Formula 32]

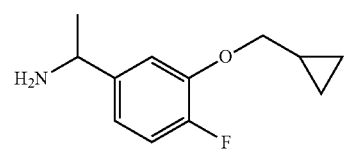

4-Fluoro-3-hydroxybenzoic acid (558 mg) was dissolved in DMF (5.0 mL). To the solution, (chloromethyl)cyclopropane (666 µL), potassium carbonate (990 mg), and potassium iodide (60 mg) were added, and the mixture was stirred at 90° C. for 6 hours. The reaction mixture was cooled to room temperature, water (10 mL) was then added thereto, and the resultant mixture was then extracted with toluene (10 mL). The organic layer was washed with brine (10 mL), dried over anhydrous sodium sulfate, and then concentrated under reduced pressure. The residue was dissolved in toluene (4.0 mL). To the mixture, a solution of DIBAL in hexane (1.0 M, 7.6 mL) was then added dropwise at 0° C., and the reaction mixture was stirred at 0° C. for 2 hours. To the reaction mixture, water (1.0 mL) and an aqueous sodium hydroxide solution (1.0 M, 1.0 mL) were gradually added. The precipitate was removed by filtration and washed with ethyl acetate (10 mL×5). Then, the combined filtrate was concentrated under reduced pressure. To the residue, water (10 mL) was added, and the resultant mixture was then extracted with ethyl acetate (15 mL). The organic layer was washed with brine (10 mL), dried over anhydrous sodium sulfate, and then concentrated under reduced pressure. The residue was purified by silica gel column chromatography (40% ethyl acetate/hexane). The residue was dissolved in dichloromethane (10 mL). To the solution, manganese dioxide (5.0 g) was added at room temperature, and the mixture was heated to reflux at 45° C. for 6 hours. The reaction mixture was cooled to room temperature, and the precipitate was removed by filtration and washed with chloroform (15 mL×4). Then, the combined filtrate was concentrated under reduced pressure. The residue was dissolved in THF (3.0 mL). To the mixture, a solution of methylmagnesium bromide in THF (1.0 M, 1.4 mL) was added dropwise at 0° C., and the mixture was stirred at room temperature for 2 hours. To the reaction mixture, an aqueous saturated ammonium chloride solution (3.0 mL) was added at 0° C., and the resultant mixture was then extracted with ethyl acetate (10 mL×2). The organic layer was washed with brine (10 mL), dried over anhydrous sodium sulfate, and then concentrated under reduced pressure. The obtained compound was dissolved in THF (5.0 mL). To the mixture, diphenylphosphoryl azide (650 μL) and DBU (494 μL) were added dropwise at room temperature, and the mixture was stirred for 1 hour. To the reaction mixture, brine (10 mL) was added, and the resultant mixture was then extracted with ethyl acetate (15 mL×2). The organic layer was washed with brine (10 mL), dried over anhydrous sodium sulfate, and then concentrated under reduced pressure. The residue was purified by silica gel column chromatography (20% ethyl acetate/hexane). The obtained compound was dissolved in methanol (5.5 mL). To the solution, 10% palladium-carbon (100 mg) was added, and the reaction mixture was stirred at room temperature for 2 hours under a hydrogen atmosphere. The precipitate was removed by filtration through a pad of Celite and washed with methanol (50 mL). Then, the combined filtrate was concentrated under reduced pressure to obtain the title compound (412 mg) as a crude product.

Reference Examples 18 to 87

Amines shown in tables below were synthesized according to any method of Reference Examples 1 to 9, 11, 12, and 15 to 17.

TABLE 1

| Reference Example | Starting material | Amine | Production method |
|---|---|---|---|
| 18 | 3-(OCF₂CHF₂)-benzaldehyde | α-(3-(OCF₂CHF₂)phenyl)benzylamine | 8 |
| 19 | 3-hydroxybenzaldehyde | α-(3-isobutoxyphenyl)benzylamine | 8 |
| 20 | 3-bromo-(cyclopropylmethoxy)benzene | bis(3-(cyclopropylmethoxy)phenyl)methanamine | 12 |

TABLE 1-continued

| Reference Example | Starting material | Amine | Production method |
|---|---|---|---|
| 21 | 3-hydroxybenzaldehyde | (S)-(3-(sec-butoxy)phenyl)(phenyl)methanamine | 8 |
| 22 | 3-hydroxy-4-fluorobenzoic acid | 3-(3-(cyclopropylmethoxy)-4-fluorophenyl)pentan-3-amine | 16 |
| 23 | 3-hydroxybenzonitrile | (3-(cyclopentyloxy)phenyl)methanamine | 1 |
| 24 | 3-hydroxy-4-fluorobenzoic acid | (S)-1-(3-(cyclopropylmethoxy)-4-fluorophenyl)propan-1-amine hydrochloride | 6 |

TABLE 2

| Reference Example | Starting material | Amine | Production method |
|---|---|---|---|
| 25 | 3-hydroxybenzaldehyde | (S)-1-(3-(cyclopropylmethoxy)phenyl)ethanamine hydrochloride | 3 |
| 26 | 3-hydroxy-4-fluorobenzoic acid | (S)-1-(3-(cyclopentyloxy)-4-fluorophenyl)ethanamine hydrochloride | 6 |
| 27 | 3-hydroxy-4-fluorobenzoic acid | 1-(3-(cyclopropylmethoxy)-4-fluorophenyl)-2-methylpropan-1-amine | 15 |
| 28 | methyl 3-hydroxybenzoate | 2-(3-(cyclopropylmethoxy)phenyl)propan-2-amine | 8 |

TABLE 2-continued

| Reference Example | Starting material | Amine | Production method |
|---|---|---|---|
| 29 | 3-hydroxybenzaldehyde | (S)-1-(3-(cyclopropylmethoxy)phenyl)propan-1-amine hydrochloride | 3 |
| 30 | 3-hydroxybenzaldehyde | (3-(cyclobutylmethoxy)phenyl)(phenyl)methanamine | 8 |
| 31 | 3-hydroxybenzaldehyde | cyclopropyl(3-(cyclopropylmethoxy)phenyl)methanamine | 8 |
| 32 | 3-hydroxybenzaldehyde | 1-(3-(cyclopropylmethoxy)phenyl)-2-methylpropan-1-amine | 8 |

TABLE 3

| Reference Example | Starting material | Amine | Production method |
|---|---|---|---|
| 33 | 3-hydroxybenzaldehyde | 1-(3-(cyclopentyloxy)phenyl)ethan-1-amine | 9 |
| 34 | 3-cyclopropoxybenzonitrile | (3-cyclopropoxyphenyl)methanamine | 1 |
| 35 | 3-hydroxy-4-fluorobenzoic acid | 1-(3-(cyclopropylmethoxy)-4-fluorophenyl)propan-1-amine | 17 |
| 36 | 3-hydroxy-4-fluorobenzoic acid | (S)-1-(3-(cyclopropylmethoxy)-4-fluorophenyl)-2-methylpropan-1-amine hydrochloride | 7 |

TABLE 3-continued

| Reference Example | Starting material | Amine | Production method |
|---|---|---|---|
| 37 | 4-fluoro-3-hydroxybenzoic acid | (4-fluorophenyl)(3-(cyclopropylmethoxy)-4-fluorophenyl)methanamine hydrochloride | 6 |
| 38 | 4-fluoro-3-hydroxybenzoic acid | (thiophen-2-yl)(3-(cyclopropylmethoxy)-4-fluorophenyl)methanamine hydrochloride | 6 |
| 39 | 1-bromo-3-(cyclopropylmethoxy)benzene | 1-(3-(cyclopropylmethoxy)phenyl)cyclopentan-1-amine | 12 |
| 40 | 4-fluoro-3-hydroxybenzoic acid | cyclopropyl(3-(cyclopropylmethoxy)-4-fluorophenyl)methanamine hydrochloride | 6 |

TABLE 4

| Reference Example | Starting material | Amine | Production method |
|---|---|---|---|
| 41 | 3-hydroxybenzaldehyde | 1-(3-(cyclopentyloxy)phenyl)propan-1-amine hydrochloride | 3 |
| 42 | 3-hydroxybenzaldehyde | cyclopropyl(3-(cyclopentyloxy)phenyl)methanamine hydrochloride | 3 |
| 43 | 3-cyclopropoxybenzonitrile | 1-(3-cyclopropoxyphenyl)propan-1-amine hydrochloride | 11 |

TABLE 4-continued

| Reference Example | Starting material | Amine | Production method |
|---|---|---|---|
| 44 | 4-fluoro-3-hydroxybenzoic acid | 3-(cyclopentyloxy)-4-fluorobenzylamine | 5 |
| 45 | 3-hydroxybenzonitrile | 3-(cyclohexyloxy)benzylamine | 2 |
| 46 | 3-hydroxybenzonitrile | 3-((tetrahydro-2H-pyran-4-yl)oxy)benzylamine | 2 |
| 47 | 3-hydroxybenzaldehyde | (S)-1-(3-((tetrahydro-2H-pyran-4-yl)oxy)phenyl)ethanamine | 4 |
| 48 | 4-fluoro-3-hydroxybenzoic acid | (S)-1-(4-fluoro-3-((tetrahydro-2H-pyran-4-yl)oxy)phenyl)ethanamine hydrochloride | 6 |

TABLE 5

| Reference Example | Starting material | Amine | Production method |
|---|---|---|---|
| 49 | 3-hydroxybenzaldehyde | (3-(cyclopropylmethoxy)phenyl)(4-fluorophenyl)methanamine hydrochloride | 3 |
| 50 | 3-hydroxybenzaldehyde | (S)-1-(3-(((S)-tetrahydrofuran-3-yl)oxy)phenyl)ethanamine hydrochloride | 4 |
| 51 | 3-hydroxybenzonitrile | 3-((1,3-difluoropropan-2-yl)oxy)benzylamine | 2 |
| 52 | 3-(1,1,2-trifluoroethoxy)benzaldehyde | (S)-1-(3-(1,1,2-trifluoroethoxy)phenyl)ethanamine hydrochloride | 3 |

TABLE 5-continued

| Reference Example | Starting material | Amine | Production method |
|---|---|---|---|
| 53 | 3-hydroxybenzaldehyde | (S)-1-(3-(neopentyloxy)phenyl)ethan-1-amine hydrochloride | 4 |
| 54 | 3-hydroxybenzaldehyde | (S)-1-(3-(2,2,2-trifluoroethoxy)phenyl)ethan-1-amine hydrochloride | 3 |
| 55 | 4-fluoro-3-hydroxybenzoic acid | (S)-1-(4-fluoro-3-(2,2,2-trifluoroethoxy)phenyl)ethan-1-amine hydrochloride | 6 |
| 56 | 3-hydroxybenzaldehyde | (S)-1-(3-((1,1,2,2-tetrafluoroethoxy))phenyl)ethan-1-amine hydrochloride | 3 |

TABLE 6

| Reference Example | Starting material | Amine | Production method |
|---|---|---|---|
| 57 | 3-hydroxybenzaldehyde | (S)-1-(3-((1,3-difluoropropan-2-yl)oxy)phenyl)ethan-1-amine hydrochloride | 3 |
| 58 | 3-hydroxybenzaldehyde | (S)-1-(3-(prop-2-yn-1-yloxy)phenyl)ethan-1-amine hydrochloride | 3 |
| 59 | 3-hydroxybenzaldehyde | (S)-1-(3-isobutoxyphenyl)ethan-1-amine hydrochloride | 3 |
| 60 | 3-hydroxybenzaldehyde | (S)-1-(3-(((S)-sec-butyl)oxy)phenyl)ethan-1-amine hydrochloride | 3 |
| 61 | 3-hydroxybenzaldehyde | (S)-1-(3-((1-methylcyclopropyl)methoxy)phenyl)ethan-1-amine hydrochloride | 4 |

TABLE 6-continued

| Reference Example | Starting material | Amine | Production method |
|---|---|---|---|
| 62 | 3-hydroxybenzaldehyde | (S)-1-[3-(2,2-difluoroethoxy)phenyl]ethylamine hydrochloride | 3 |
| 63 | 3-hydroxybenzaldehyde | (S)-1-{3-[(R)-1-methylprop-2-ynyloxy]phenyl}ethylamine hydrochloride | 4 |
| 64 | 3-hydroxybenzaldehyde | (S)-1-{3-[(S)-1-methylprop-2-ynyloxy]phenyl}ethylamine hydrochloride | 4 |
| 65 | 3-hydroxybenzaldehyde | (S)-1-[3-(2-fluoroethoxy)phenyl]ethylamine hydrochloride | 4 |

TABLE 7

| Reference Example | Starting material | Amine | Production method |
|---|---|---|---|
| 66 | 3-hydroxybenzaldehyde | (S)-1-[3-(cyclopentylmethoxy)phenyl]ethylamine hydrochloride | 4 |
| 67 | 3-hydroxybenzaldehyde | (S)-1-{3-[(R)-sec-butoxy]phenyl}ethylamine hydrochloride | 4 |
| 68 | 3-hydroxybenzaldehyde | (S)-1-{3-[(S)-sec-butoxy]phenyl}ethylamine hydrochloride | 4 |
| 69 | 4-fluoro-3-hydroxybenzoic acid | (S)-1-[3-(2,2-difluoroethoxy)-4-fluorophenyl]ethylamine hydrochloride | 6 |

TABLE 7-continued

| Reference Example | Starting material | Amine | Production method |
|---|---|---|---|
| 70 | 3-hydroxybenzaldehyde | (S)-1-(3-(allyloxy)phenyl)ethan-1-amine hydrochloride | 3 |
| 71 | 3-hydroxybenzaldehyde | (S)-1-(3-(((R)-pentan-2-yl)oxy)phenyl)ethan-1-amine hydrochloride | 4 |
| 72 | 3-hydroxybenzaldehyde | (S)-1-(3-(((S)-pentan-2-yl)oxy)phenyl)ethan-1-amine hydrochloride | 4 |
| 73 | 3-hydroxybenzaldehyde | (S)-1-(3-(2,2,3,3,3-pentafluoropropoxy)phenyl)ethan-1-amine hydrochloride | 3 |

TABLE 8

| Reference Example | Starting material | Amine | Production method |
|---|---|---|---|
| 74 | 3-hydroxybenzaldehyde | (S)-1-(3-(2-cyclopropylethoxy)phenyl)ethan-1-amine hydrochloride | 4 |
| 75 | benzaldehyde | (S)-1-phenylpropan-1-amine hydrochloride | 3 |
| 76 | 2-fluorobenzaldehyde | (S)-1-(2-fluorophenyl)ethan-1-amine hydrochloride | 3 |
| 77 | 2-methoxybenzaldehyde | (S)-1-(2-methoxyphenyl)ethan-1-amine hydrochloride | 3 |

TABLE 8-continued

| Reference Example | Starting material | Amine | Production method |
|---|---|---|---|
| 78 | 2-chlorobenzaldehyde | (1S)-1-(2-chlorophenyl)ethylamine hydrochloride | 3 |
| 79 | 3-fluorobenzaldehyde | (1S)-1-(3-fluorophenyl)ethylamine hydrochloride | 3 |
| 80 | 3-chlorobenzaldehyde | (1S)-1-(3-chlorophenyl)ethylamine hydrochloride | 3 |
| 81 | 3-bromobenzaldehyde | (1S)-1-(3-bromophenyl)ethylamine hydrochloride | 3 |
| 82 | 2-ethynylbenzaldehyde | (1S)-1-(2-ethynylphenyl)ethylamine hydrochloride | 3 |

TABLE 9

| Reference Example | Starting material | Amine | Production method |
|---|---|---|---|
| 83 | 2-bromobenzaldehyde | (1S)-1-(2-bromophenyl)ethylamine hydrochloride | 3 |
| 84 | 2-methylbenzaldehyde | (1S)-1-(2-methylphenyl)ethylamine hydrochloride | 3 |
| 85 | 2-(trifluoromethyl)benzaldehyde | (1S)-1-(2-(trifluoromethyl)phenyl)ethylamine hydrochloride | 3 |

TABLE 9-continued

| Reference Example | Starting material | Amine | Production method |
|---|---|---|---|
| 86 | 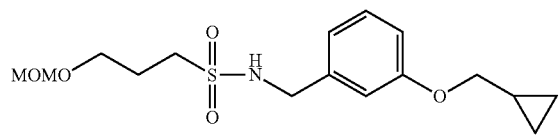 | | 8 |
| 87 | | | 8 |

Reference Example 88

Synthesis of N-(3-(cyclopropylmethoxy)benzyl)-3-(methoxymethoxy)propane-1-sulfonamide

[Formula 33]

The (3-(cyclopropylmethoxy)phenyl)methanamine (10.0 g) obtained in Reference Example 1 was dissolved in dichloromethane (50 mL). To the solution, triethylamine (11.9 g) and 3-chloropropanesulfonyl chloride (10.6 g) were added at 0° C., and the mixture was stirred at room temperature for 12 hours. To the reaction mixture, water (100 mL) was added, and the resultant mixture was then extracted with chloroform (50 mL). The organic layer washed with dilute hydrochloric acid (1.0 M, 100 mL) and brine (100 ml), dried over anhydrous sodium sulfate, and then concentrated under reduced pressure. The residue was dissolved in DMF (100 mL). To the mixture, sodium acetate (10.2 g) and sodium iodide (18.6 g) were added, and the mixture was stirred at 80° C. for 8 hours. The reaction mixture was cooled to room temperature, water (100 mL) was then added thereto, and the resultant mixture was then extracted with ethyl acetate (80 mL×2). The organic layer was washed with brine (100 mL), dried over anhydrous sodium sulfate, and then concentrated under reduced pressure. The residue was purified by silica gel column chromatography (50% ethyl acetate/hexane). The obtained compound was dissolved in a 5 to 10% hydrochloric acid/methanol solution (100 mL), and the solution was heated to reflux at 80° C. for 1 hour. The reaction mixture was cooled to room temperature and then concentrated under reduced pressure. The residue was purified by silica gel column chromatography (66% ethyl acetate/hexane). The obtained compound was dissolved in dichloromethane (80 mL). To the solution, N,N-diisopropylethylamine (14.1 mL) and chloromethyl methyl ether (4.1 mL) were added, and the mixture was stirred at room temperature for 1 hour. To the reaction mixture, an aqueous saturated ammonium chloride solution (50 mL) was added, and the resultant mixture was then extracted with chloroform (50 mL). The organic layer was washed with brine (30 mL), dried over anhydrous sodium sulfate, and then concentrated under reduced pressure. The residue was purified by silica gel column chromatography (25% ethyl acetate/hexane) to obtain the title compound (11.5 g).

Reference Example 89

Synthesis of (S)—N-(2-(3-(cyclopentyloxy)-4-fluorophenyl)-2-(trimethylsilyloxy)butyl)-3-(methoxymethoxy)propane-1-sulfonamide

[Formula 34]

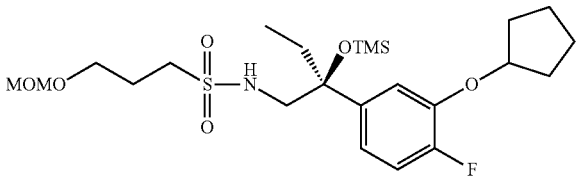

The (S)-2-(3-(cyclopentyloxy)-4-fluorophenyl)-2-(trimethylsilyloxy)butan-1-amine (983 mg) obtained in Reference Example 14 was dissolved in dichloromethane (5.0 mL). To the solution, triethylamine (560 mL) and 3-chloropropanesulfonyl chloride (380 µL) were added at 0° C., and the mixture was stirred at room temperature for 1.5 hours. To the reaction mixture, water (10 mL) was added, and the resultant mixture was then extracted with chloroform (20 mL). The organic layer was washed with dilute hydrochloric acid (1.0 M, 10 mL) and brine (10 mL), dried over anhydrous sodium sulfate, and then concentrated under reduced pressure. The residue was dissolved in DMF (7.0 mL). To the mixture, sodium acetate (385 mg) and sodium iodide (703 mg) were added, and the mixture was stirred at 80° C. for 8 hours. The reaction mixture was cooled to room temperature, water (10 mL) was then added to the reaction mixture, and the resultant mixture was then extracted with ethyl acetate (20 mL×2). The organic layer was washed with brine (100 mL), dried over anhydrous sodium sulfate, and then concentrated under reduced pressure. The residue was purified by silica gel column chromatography (20% ethyl acetate/hexane). The obtained compound was dissolved in a solution of methylamine in methanol (40%, 4.0 mL), and the solution was stirred at room temperature for 1 hour. The reaction mixture was concentrated under reduced pressure and then purified by silica gel column chromatography (40% ethyl acetate/hexane). The obtained compound was dissolved in dichloromethane (5.0 mL). To the solution, N,N-diisopropylethylamine (430 µL) and chloromethyl methyl ether (110 µL) were added, and the mixture was stirred at room temperature for 1 hour. To the reaction mixture, an aqueous saturated ammonium chloride solution (10 ml) was added, and the resultant mixture was then extracted with chloroform (20 mL). The organic layer was washed with brine (10 mL), dried over anhydrous sodium sulfate, and then concentrated under reduced pressure. The residue was purified by silica gel column chromatography (20% ethyl acetate/hexane) to obtain the title compound (238 mg).

Reference Example 90

Synthesis of (R)-3-(methoxymethoxy)-N-(1-(3-(2-methyl-2-(trimethylsilyloxy)propoxy)phenyl)ethyl)propane-1-sulfonamide

[Formula 35]

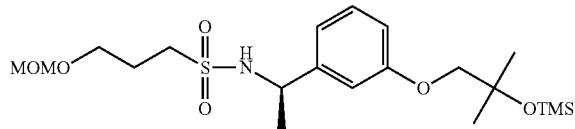

The (R)-1-(3-(1-aminoethoxy)phenoxy)-2-methylpropan-2-ol (348 mg) obtained in Reference Example 13 was dissolved in dichloromethane (5.0 mL). To the solution, triethylamine (665 µL) and 3-chloropropanesulfonyl chloride (231 µL) were added at 0° C., and the mixture was stirred at room temperature for 2 hours. To the reaction mixture, water (10 mL) was added, and the resultant mixture was then extracted with chloroform (20 mL). The organic layer was washed with dilute hydrochloric acid (1.0 M, 10 mL) and brine (10 mL), dried over anhydrous sodium sulfate, and then concentrated under reduced pressure. The residue was dissolved in a dichloromethane solution (3.0 mL). To the mixture, 2,6-lutidine (280 µL) and TMSOTf (275 µL) were added, and the mixture was stirred at room temperature for 1 hour. The reaction mixture was concentrated under reduced pressure, and the residue was then purified by silica gel column chromatography (20% ethyl acetate/hexane). The obtained compound was dissolved in DMF (5.0 mL). To the solution, sodium acetate (195 mg) and sodium iodide (354 mg) were added, and the mixture was stirred at 80° C. for 8 hours. The reaction mixture was cooled to room temperature, water (10 mL) was then added thereto, and the resultant mixture was then extracted with ethyl acetate (20 mL×2). The organic layer was washed with brine (10 mL), dried over anhydrous sodium sulfate, and then concentrated under reduced pressure. The residue was purified by silica gel column chromatography (25% ethyl acetate/hexane). The obtained compound was dissolved in a solution of methylamine in methanol (40%, 10 mL), and the solution was stirred at room temperature for 1 hour. The reaction mixture was concentrated under reduced pressure and then purified by silica gel column chromatography (40% ethyl acetate/hexane). The obtained compound was dissolved in dichloromethane (2.5 mL). To the solution, N,N-diisopropylethylamine (270 µL) and chloromethyl methyl ether (82 µL) were added, and the mixture was stirred at room temperature for 1.5 hours. To the reaction mixture, an aqueous saturated ammonium chloride solution (5.0 mL) was added, and the resultant mixture was then extracted with chloroform (10 mL). The organic layer was washed with brine (5.0 mL), dried over anhydrous sodium sulfate, and then concentrated under reduced pressure. The residue was purified by silica gel column chromatography (20% ethyl acetate/hexane) to obtain the title compound (146 mg).

Compounds shown in tables below were synthesized according to the method of Reference Example 88 using any amine obtained in Reference Examples 2 to 12, 15 to 48, and 50 to 87 or usually known amine.

TABLE 10

| Reference Example | Reference Example No. of amine (or structural formula of known amine) | Product |
|---|---|---|
| 91 | 2 | |
| 92 | 3 | |

TABLE 10-continued

| Reference Example | Reference Example No. of amine (or structural formula of known amine) | Product |
|---|---|---|
| 93 | 4 | MOMO-propylsulfonamide-N-[(S)-1-(3-((S)-tetrahydrofuran-3-yloxy)phenyl)ethyl] |
| 94 | 5 | MOMO-propylsulfonamide-N-[4-fluoro-3-(cyclopropylmethoxy)benzyl] |
| 95 | 6 | MOMO-propylsulfonamide-N-[(S)-1-(4-fluoro-3-(cyclopropylmethoxy)phenyl)ethyl] |
| 96 | 7 | MOMO-propylsulfonamide-N-[(S)-1-(4-fluoro-3-(cyclopropylmethoxy)phenyl)-2-methylpropyl] |

TABLE 11

| Reference Example | Reference Example No. of amine (or structural formula of known amine) | Product |
|---|---|---|
| 97 | 8 | MOMO-propylsulfonamide-N-[(3-(cyclopropylmethoxy)phenyl)(phenyl)methyl] |
| 98 | 9 | MOMO-propylsulfonamide-N-[1-(3-(cyclopropylmethoxy)phenyl)ethyl] |
| 99 | 10 | MOMO-propylsulfonamide-N-[3-(cyclopropylmethylthio)benzyl] |

TABLE 11-continued
| Reference Example | Reference Example No. of amine (or structural formula of known amine) | Product |
|---|---|---|
| 100 | 11 | 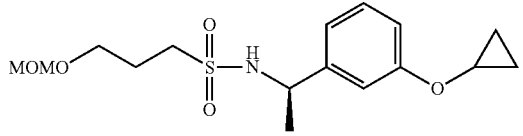 |
| 101 | 12 | 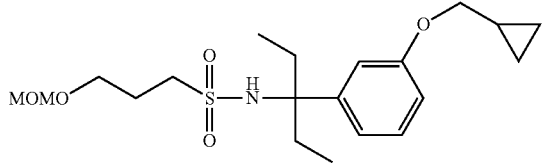 |
| 102 | 18 | 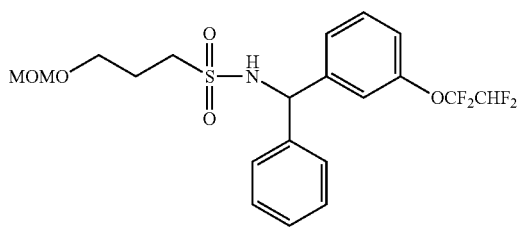 |
| 103 | 19 | 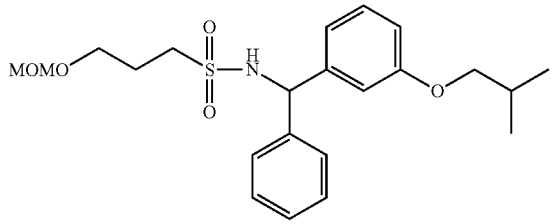 |
TABLE 12
| Reference Example | Reference Example No. of amine (or structural formula of known amine) | Product |
|---|---|---|
| 104 | 20 | 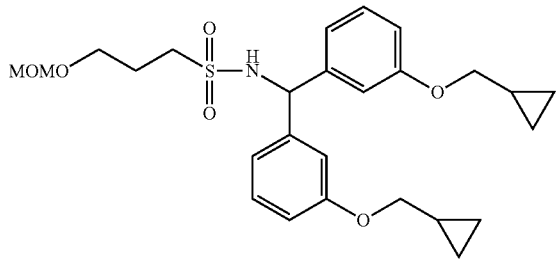 |

TABLE 12-continued

| Reference Example | Reference Example No. of amine (or structural formula of known amine) | Product |
|---|---|---|
| 105 | 21 | |
| 106 | 15 | |
| 107 | 22 | |
| 108 | 23 | |
| 109 | 24 | |
| 110 | 25 | |

TABLE 13
| Reference Example | Reference Example No. of amine (or structural formula of known amine) | Product |
|---|---|---|
| 111 | 26 | 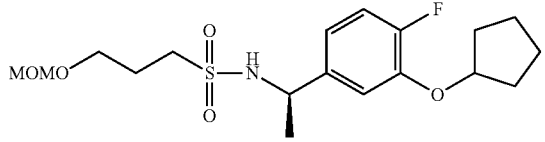 |
| 112 | 27 | 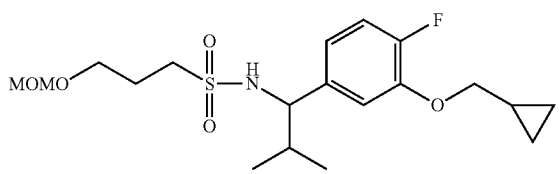 |
| 113 | 28 | 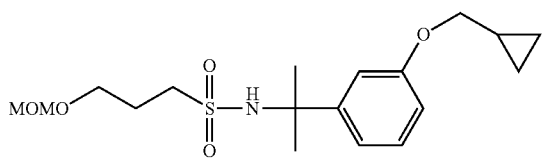 |
| 114 | 29 | 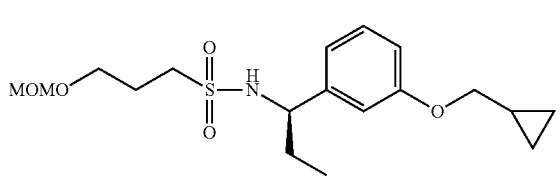 |
| 115 | 16 | 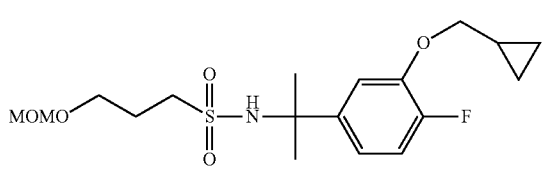 |
| 116 | 30 | 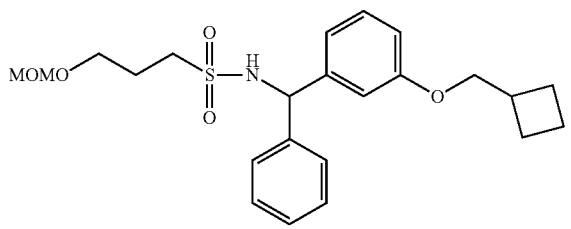 |
| 117 | 31 | 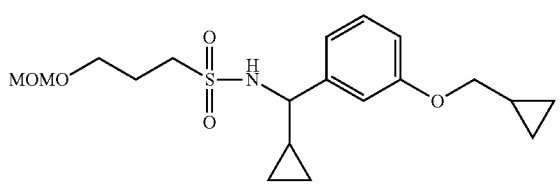 |
| 118 | 32 | 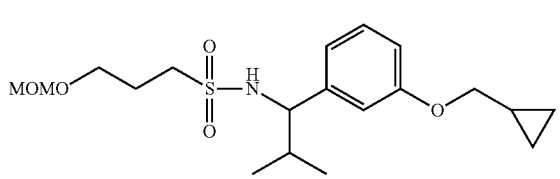 |

TABLE 14

| Reference Example | Reference Example No. of amine (or structural formula of known amine) | Product |
|---|---|---|
| 119 | 33 | (structure) |
| 120 | 34 | (structure) |
| 121 | 35 | (structure) |
| 122 | 36 | (structure) |
| 123 | 17 | (structure) |
| 124 | 37 | (structure) |
| 125 | 38 | (structure) |
| 126 | 39 | (structure) |

TABLE 15
| Reference Example | Reference Example No. of amine (or structural formula of known amine) | Product |
|---|---|---|
| 127 | 40 | 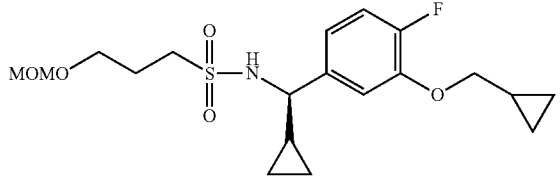 |
| 128 | 41 | 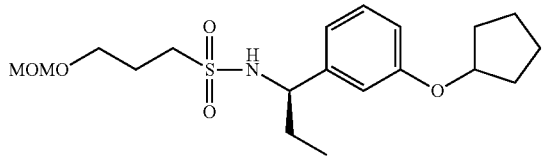 |
| 129 | 42 | 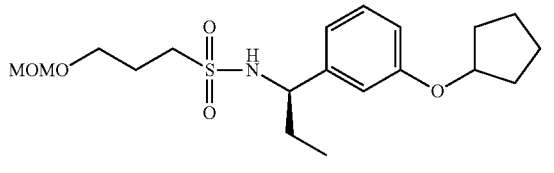 |
| 130 | 43 | 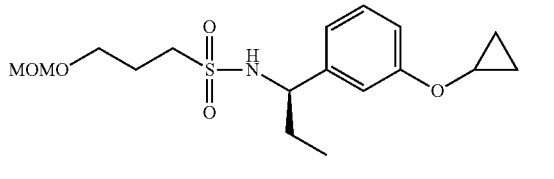 |
| 131 | 44 | 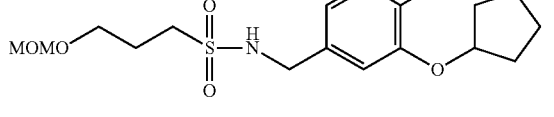 |
| 132 | 45 | 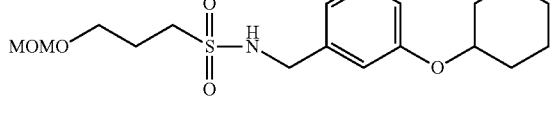 |
| 133 | 46 | 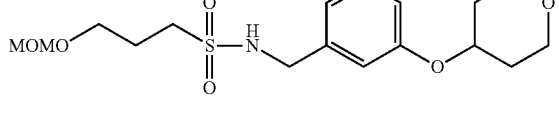 |
| 134 | 47 | 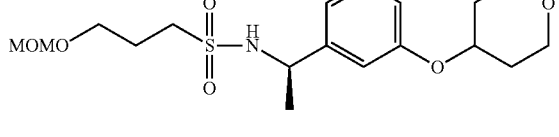 |
| 135 | 48 | 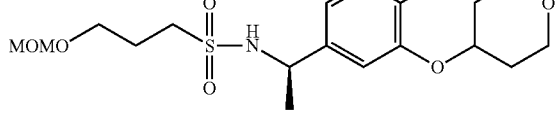 |

TABLE 16

| Reference Example | Reference Example No. of amine (or structural formula of known amine) | Product |
|---|---|---|
| 136 | 50 | MOMO-propylsulfonamide-N-[(R)-1-(3-((S)-tetrahydrofuran-3-yloxy)phenyl)ethyl] |
| 137 | 51 | MOMO-propylsulfonamide-N-[3-(1,3-difluoropropan-2-yloxy)benzyl] |
| 138 | 52 | MOMO-propylsulfonamide-N-[(R)-1-(3-(1,1,2,2-tetrafluoroethoxy)phenyl)ethyl] (OCF₂CHF₂) |
| 139 | 53 | MOMO-propylsulfonamide-N-[(R)-1-(3-(neopentyloxy)phenyl)ethyl] |
| 140 | 54 | MOMO-propylsulfonamide-N-[(R)-1-(3-(2,2,2-trifluoroethoxy)phenyl)ethyl] (CF₃) |
| 141 | 55 | MOMO-propylsulfonamide-N-[(R)-1-(4-fluoro-3-(2,2,2-trifluoroethoxy)phenyl)ethyl] |
| 142 | 56 | MOMO-propylsulfonamide-N-[(R)-1-(3-(1,1,2,2,2-pentafluoroethoxy)phenyl)ethyl] (OCF₂CF₃) |
| 143 | 57 | MOMO-propylsulfonamide-N-[(R)-1-(3-(1,3-difluoropropan-2-yloxy)phenyl)ethyl] |
| 144 | 58 | MOMO-propylsulfonamide-N-[(R)-1-(3-(prop-2-yn-1-yloxy)phenyl)ethyl] |

TABLE 17

| Reference Example | Reference Example No. of amine (or structural formula of known amine) | Product |
|---|---|---|
| 145 | 59 | MOMO-(CH₂)₃-SO₂-NH-CH(CH₃)-(3-isobutoxyphenyl) |
| 146 | 60 | MOMO-(CH₂)₃-SO₂-NH-CH(CH₃)-[3-((S)-2-methylbutoxy)phenyl] |
| 147 | 61 | MOMO-(CH₂)₃-SO₂-NH-CH(CH₃)-{3-[(1-methylcyclopropyl)methoxy]phenyl} |
| 148 | 62 | MOMO-(CH₂)₃-SO₂-NH-CH(CH₃)-[3-(2,2-difluoroethoxy)phenyl] |
| 149 | 63 | MOMO-(CH₂)₃-SO₂-NH-CH(CH₃)-{3-[(R)-1-methylprop-2-ynyloxy]phenyl} |
| 150 | 64 | MOMO-(CH₂)₃-SO₂-NH-CH(CH₃)-{3-[(S)-1-methylprop-2-ynyloxy]phenyl} |
| 151 | 65 | MOMO-(CH₂)₃-SO₂-NH-CH(CH₃)-[3-(2-fluoroethoxy)phenyl] |
| 152 | 66 | MOMO-(CH₂)₃-SO₂-NH-CH(CH₃)-[3-(cyclopentylmethoxy)phenyl] |
| 153 | 67 | MOMO-(CH₂)₃-SO₂-NH-CH(CH₃)-[3-((S)-sec-butoxy)phenyl] |

TABLE 18
| Reference Example | Reference Example No. of amine (or structural formula of known amine) | Product |
|---|---|---|
| 154 | 68 | 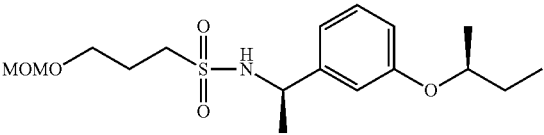 |
| 155 | 69 | 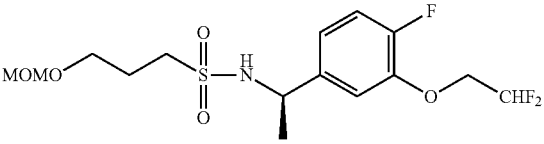 |
| 156 | 70 | 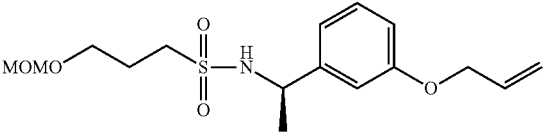 |
| 157 | 71 | 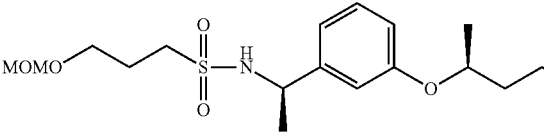 |
| 158 | 72 | 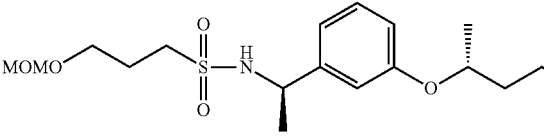 |
| 159 | 73 | 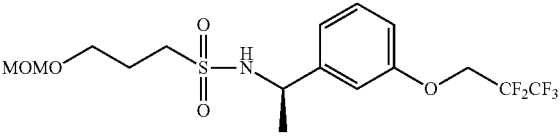 |
| 160 | 74 | 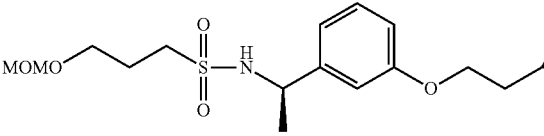 |
| 161 | 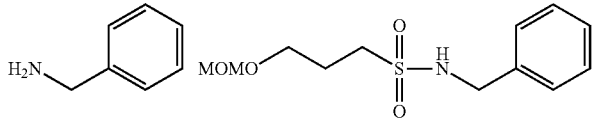 | |
| 162 | 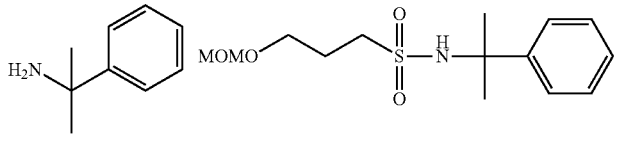 | |

TABLE 19
| Reference Example | Reference Example No. of amine (or structural formula of known amine) | Product |
|---|---|---|
| 163 | 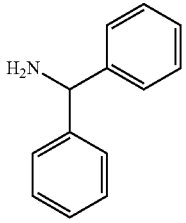 [SMILES: NC(c1ccccc1)c1ccccc1] | 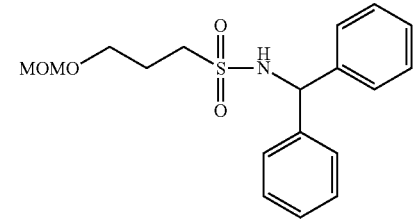 |
| 164 | 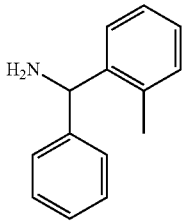 | 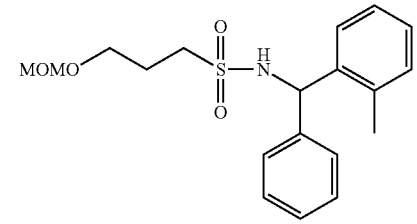 |
| 165 | 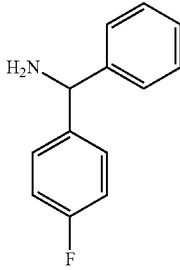 | 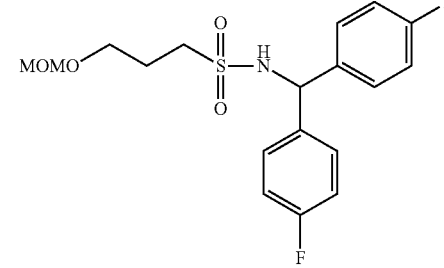 |
| 166 | 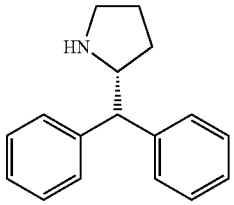 [SMILES: c1ccc(C(c2ccccc2)[C@H]2CCCN2)cc1] | 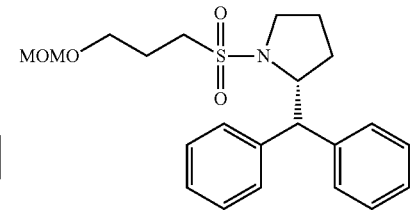 |
| 167 | 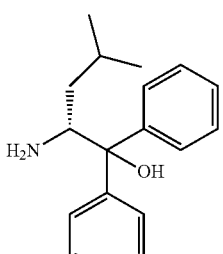 | 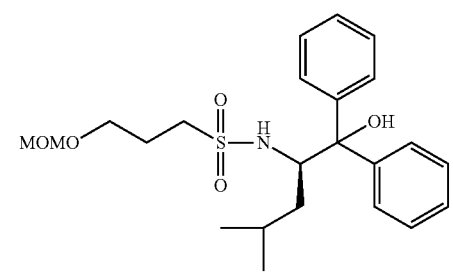 |
| 168 | 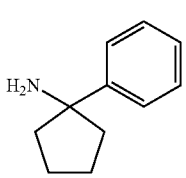 [SMILES: NC1(c2ccccc2)CCCC1] | 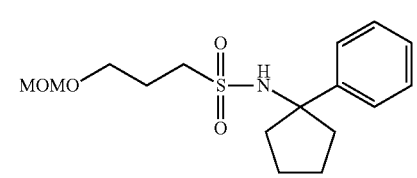 |

TABLE 20

| Reference Example | Reference Example No. of amine (or structural formula of known amine) | Product |
|---|---|---|
| 169 | H₂N-CH(CH₃)-Ph (chiral) | MOMO-(CH₂)₃-SO₂-NH-CH(CH₃)-Ph (chiral) |
| 170 | 75 | MOMO-(CH₂)₃-SO₂-NH-CH(Et)-Ph (chiral) |
| 171 | 76 | MOMO-(CH₂)₃-SO₂-NH-CH(CH₃)-(2-F-C₆H₄) (chiral) |
| 172 | 77 | MOMO-(CH₂)₃-SO₂-NH-CH(CH₃)-(2-OMe-C₆H₄) (chiral) |
| 173 | 78 | MOMO-(CH₂)₃-SO₂-NH-CH(CH₃)-(2-Cl-C₆H₄) (chiral) |
| 174 | 79 | MOMO-(CH₂)₃-SO₂-NH-CH(CH₃)-(3-F-C₆H₄) (chiral) |
| 175 | 80 | MOMO-(CH₂)₃-SO₂-NH-CH(CH₃)-(3-Cl-C₆H₄) (chiral) |
| 176 | 81 | MOMO-(CH₂)₃-SO₂-NH-CH(CH₃)-(3-Br-C₆H₄) (chiral) |
| 177 | 83 | MOMO-(CH₂)₃-SO₂-NH-CH(CH₃)-(2-Br-C₆H₄) (chiral) |

TABLE 21

| Reference Example | Reference Example No. of amine (or structural formula of known amine) | Product |
|---|---|---|
| 178 | 82 | 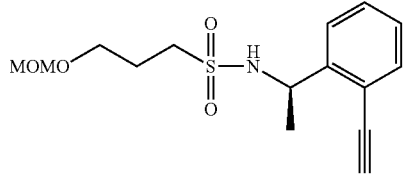 |
| 179 | 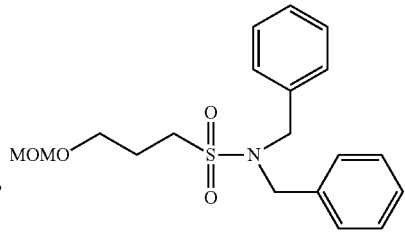 | 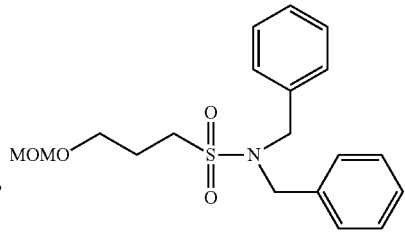 |
| 180 | 86 | 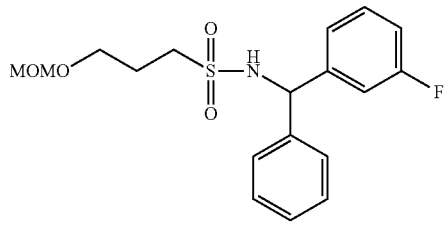 |
| 181 | 87 | 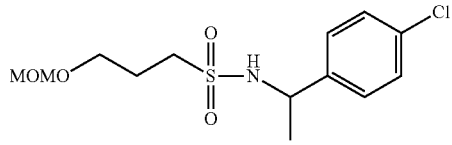 |

In the tables shown above, the amine used in Reference Example 165 was synthesized according to a method described in the document (J. Med. Chem., 44, 3937-3945 (2001)). Likewise, the amine used in Reference Example 168 was synthesized according to a method described in the document (Synthesis, 24-26 (1978)).

Reference Example 182

Synthesis of 5-(chloromethyl)-N-(1,2-diphenylethyl)thiophene-2-sulfonamide

[Formula 36]

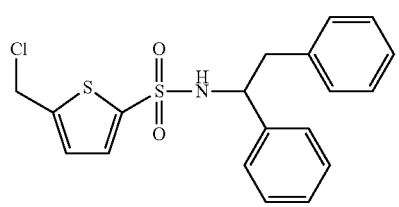

A chloroform solution (30 mL) of 2-(chloromethyl)thiophene (724 mg) was added to a mixture of chlorosulfonic acid (907 µL) and phosphorus pentachloride (1.14 g) at 0° C., and the mixture was stirred at room temperature for 30 minutes. To the reaction mixture, ice (20.0 g) was added, and the resultant mixture was then extracted with chloroform (20 mL×3). The organic layer was washed with brine (30 mL), dried over anhydrous sodium sulfate, and then concentrated under reduced pressure. The residue was dissolved in dichloromethane (12 mL). To the mixture, triethylamine (880 µL) and 1,2-diphenylethanamine (812 µL) were added at 0° C., and the mixture was stirred at room temperature for 2 hours. To the reaction mixture, water (10 mL) was added, and the resultant mixture was then extracted with chloroform (50 mL). The organic layer was washed with dilute hydrochloric acid (1.0 M, 10 mL) and brine (10 mL), dried over anhydrous sodium sulfate, and then concentrated under reduced pressure. The residue was purified by silica gel column chromatography (50% ethyl acetate/hexane) to obtain the title compound (204 mg).

Reference Example 183

Synthesis of N-benzhydryl-4-(bromomethyl)benzenesulfonamide

[Formula 37]

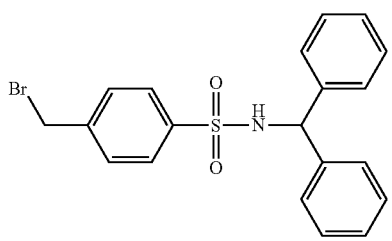

Benzhydrylamine (640 μL) was dissolved in dichloromethane (5.0 mL). To the solution, triethylamine (645 μl) and 4-(bromomethyl)benzenesulfonyl chloride (1.0 g) were added at 0° C., and the mixture was stirred at room temperature for 2 hours. To the reaction mixture, water (10 mL) was added, and the resultant mixture was then extracted with chloroform (30 mL). The organic layer was washed with brine (15 mL), dried over anhydrous sodium sulfate, and then concentrated under reduced pressure. The residue was purified by silica gel column chromatography (40% ethyl acetate/hexane) to obtain the title compound (753 mg).

Reference Example 184

Synthesis of (R)-4-(bromomethyl)-N-(1-(3-(cyclopropylmethoxy)-4-fluorophenyl)propyl)benzenesulfonamide

[Formula 38]

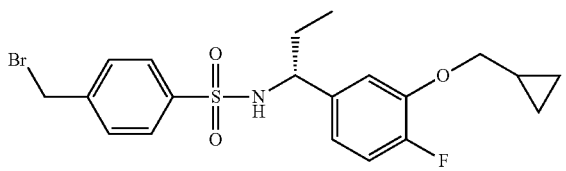

The title compound (216 mg) was obtained according to the method of Reference Example 183 from the (R)-1-(3-(cyclopropylmethoxy)-4-fluorophenyl)propan-1-amine hydrochloride (171 mg) obtained in Reference Example 24 and 4-(bromomethyl)benzenesulfonyl chloride (204 mg).

Reference Example 185

Synthesis of (R)—N-(1-(3-(cyclopropylmethoxy)-4-fluorophenyl)ethyl)-3-hydroxy-N-(methoxymethyl)propane-1-sulfonamide

[Formula 39]

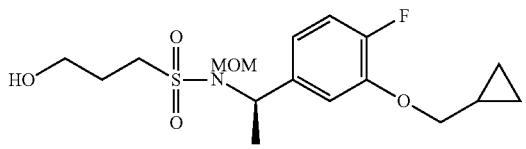

The (R)-1-(3-(cyclopropylmethoxy)-4-fluorophenyl)ethanamine hydrochloride (1.20 g) obtained in Reference Example 6 was dissolved in dichloromethane (7.5 mL). To the solution, triethylamine (1.6 mL) and 3-chloropropanesulfonyl chloride (550 μl) were added at 0° C., and the mixture was stirred at room temperature for 2 hours. To the reaction mixture, water (10 mL) was added, and the resultant mixture was then extracted with chloroform (30 mL). The organic layer was washed with brine (15 mL), dried over anhydrous sodium sulfate, and then concentrated under reduced pressure. The residue was purified by silica gel column chromatography (40% ethyl acetate/hexane). The obtained compound was dissolved in dichloromethane (7.0 mL). To the solution, N,N-diisopropylethylamine (5.0 mL) and chloromethyl methyl ether (1.5 mL) were added, and the mixture was stirred at 40° C. for 6 hours. To the reaction mixture, an aqueous saturated ammonium chloride solution (10 mL) was added, and the resultant mixture was then extracted with chloroform (20 mL). The organic layer was washed with brine (10 mL), dried over anhydrous sodium sulfate, and then concentrated under reduced pressure. The residue was purified by silica gel column chromatography (20% ethyl acetate/hexane). The obtained compound was dissolved in DMF (8.0 mL). To the solution, sodium acetate (887 mg) and sodium iodide (1.62 g) were added, and the mixture was stirred at 80° C. for 8 hours. The reaction mixture was cooled to room temperature, water (20 mL) was then added thereto, and the resultant mixture was then extracted with ethyl acetate (20 mL×2). The organic layer was washed with brine (20 mL), dried over anhydrous sodium sulfate, and then concentrated under reduced pressure. The residue was purified by silica gel column chromatography (50% ethyl acetate/hexane). The obtained compound was dissolved in a solution of methylamine in methanol (40%, 7.0 mL), and the mixture was stirred at room temperature for 1 hour. The reaction mixture was concentrated under reduced pressure and then purified by silica gel column chromatography (66% ethyl acetate/hexane) to obtain the title compound (932 mg).

Reference Example 186

Synthesis of (R,E)-N-(1-(3-(cyclopropylmethoxy)-4-fluorophenyl)ethyl)-5-hydroxy-N-(methoxymethyl)pent-3-ene-1-sulfonamide

[Formula 40]

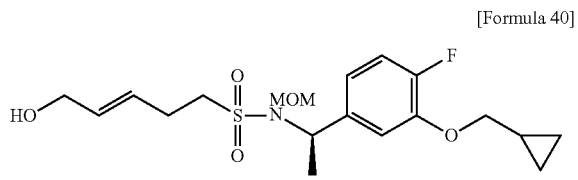

The (R)—N-(1-(3-(cyclopropylmethoxy)-4-fluorophenyl)ethyl)-3-hydroxy-N-(methoxymethyl)propane-1-sulfonamide (844 mg) obtained in Reference Example 185 was dissolved in dichloromethane (10 mL). To the solution, a Dess-Martin reagent (1.4 g) was added, and the mixture was stirred at room temperature for 1.5 hours. To the reaction mixture, an aqueous saturated sodium bicarbonate solution (20 mL) and an aqueous saturated sodium thiosulfate solution (20 mL) were added, and the aqueous layer was extracted with ethyl acetate (30 mL×2). The organic layer was washed with brine (15 mL), dried over anhydrous sodium sulfate, and then concentrated under reduced pressure. The residue was co-evaporated with toluene (15 mL×2), and the residue was then dissolved in THF (2.5 mL).

Triethyl phosphonoacetate (695 μL) was added to a suspension of sodium hydride (55%, 150 mg) in THF (5.0 mL) at 0° C., and the mixture was stirred at room temperature for 15 minutes. To the reaction mixture, a THF solution of the above compound which was co-evaporated with toluene was added thereto at 0° C., and the mixture was heated to reflux at 70° C. for 1 hour. The reaction mixture was cooled to room temperature, an aqueous saturated ammonium chloride solution (10 mL) was added thereto, and the resultant mixture was then extracted with ethyl acetate (20 mL×2). The organic layer was washed with brine (10 mL), dried over anhydrous sodium sulfate, and then concentrated under reduced pressure. The residue was purified by silica gel column chromatography (33% ethyl acetate/hexane). The obtained compound was dissolved in THF (8.0 mL). To the solution, a solution of DIBAL in THF (1.0 M, 4.0 mL) was added at −78° C., and the mixture was stirred at −78° C. for 1 hour. To the reaction mixture, water (10 mL) was added, and the resultant mixture was then extracted with ethyl acetate (20 mL×3). The organic layer was washed with brine (10 mL), dried over anhydrous sodium sulfate, and then concentrated under reduced pressure. The residue was purified by silica gel column chromatography (50% ethyl acetate/hexane) to obtain the title compound (330 mg).

Reference Example 187

Synthesis of (R)—N-(1-(3-(cyclopropylmethoxy)-4-fluorophenyl)ethyl)-5-hydroxy-N-(methoxymethyl)pentane-1-sulfonamide

[Formula 41]

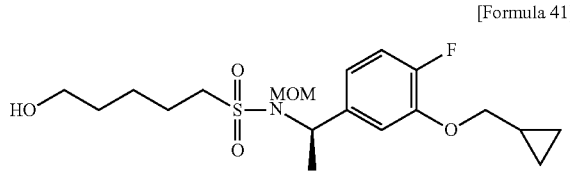

The (R,E)-N-(1-(3-(cyclopropylmethoxy)-4-fluorophenyl)ethyl)-5-hydroxy-N-(methoxymethyl)pent-3-ene-1-sulfonamide (296 mg) obtained in Reference Example 186 was dissolved in ethyl acetate (5.0 mL). To the solution, 10% palladium-carbon (170 mg) was added, and the reaction mixture was stirred at room temperature for 2 hours under a hydrogen atmosphere. The precipitate was removed by filtration through a pad of Celite and washed with ethyl acetate (100 mL). Then, the combined filtrate was concentrated under reduced pressure to obtain the title compound (208 mg) as a crude product.

Reference Example 188

Synthesis of (S)-tert-butyl-2-(3-(cyclopentyloxy)-4-fluorophenyl)-2-(trimethylsilyloxy)butyl(3-hydroxypropylsulfonyl)carbamate

[Formula 42]

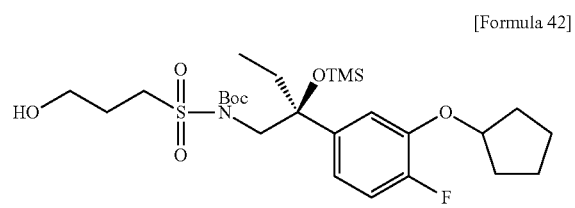

The (S)-2-(3-(cyclopentyloxy)-4-fluorophenyl)-2-(trimethylsilyloxy)butan-1-amine (983 mg) obtained in Reference Example 14 was dissolved in dichloromethane (5.0 mL). To the solution, triethylamine (560 μL) and 3-chloropropanesulfonyl chloride (380 μL) were added at 0° C., and the mixture was stirred at room temperature for 1.5 hours. To the reaction mixture, water (10 mL) was added, and the resultant mixture was then extracted with chloroform (20 mL). The organic layer was washed with dilute hydrochloric acid (1.0 M, 10 mL) and brine (10 mL), dried over anhydrous sodium sulfate, and then concentrated under reduced pressure. The residue was dissolved in DMF (7.0 mL). To the mixture, sodium acetate (385 mg) and sodium iodide (703 mg) were added, and the mixture was stirred at 80° C. for 8 hours. The reaction mixture was cooled to room temperature, water (10 mL) was then added thereto, and the resultant mixture was then extracted with ethyl acetate (20 mL×2). The organic layer was washed with brine (15 mL), dried over anhydrous sodium sulfate, and then concentrated under reduced pressure. The residue was purified by silica gel column chromatography (50% ethyl acetate/hexane). The obtained compound was dissolved in dichloromethane (5.0 mL). To the solution, N,N-dimethylamino-4-pyridine (hereinafter, referred to as DMAP; 21 mg) and di-tert-butyl dicarbonate (hereinafter, referred to as Boc₂O; 367 mg) were added at room temperature, and the mixture was stirred for 3 hours. The reaction mixture was concentrated under reduced pressure, and the residue was purified by silica gel column chromatography (25% ethyl acetate/hexane). The obtained compound was dissolved in a solution of methylamine in methanol (40%, 5.0 mL), and the mixture was stirred at room temperature for 1 hour. The reaction mixture was concentrated under reduced pressure, and the residue was then purified by silica gel column chromatography (50% ethyl acetate/hexane) to obtain the title compound (309 mg).

Reference Examples 189 to 214

Compounds shown in tables below were synthesized according to any method of Reference Examples 185 to 188 using any amine of Reference Examples 1, 3, 8, 24, 25, 29, 37, 49, 62, 75, 76, 78, 79, and 82 to 85 or commercially available amine.

TABLE 22
| Reference Example | Reference Example No. of amine (or structural formula of commercially available amine) | Product | Production method |
|---|---|---|---|
| 189 | 29 | 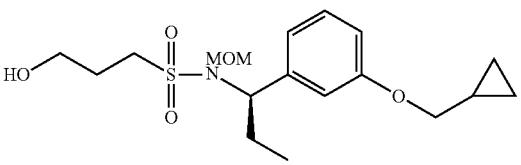 | 185 |
| 190 | 1 | 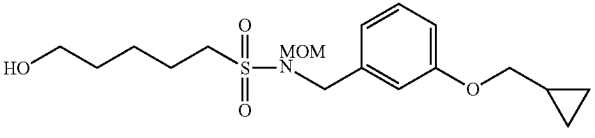 | 187 |
| 191 | 3 | 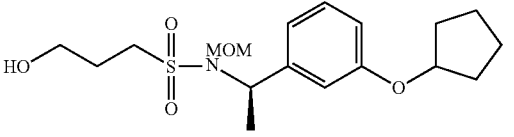 | 185 |
| 192 | 3 | 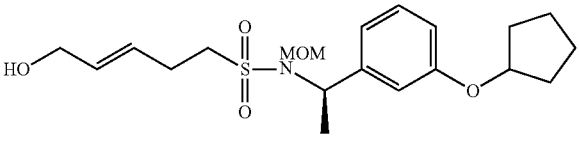 | 186 |
| 193 | 3 | 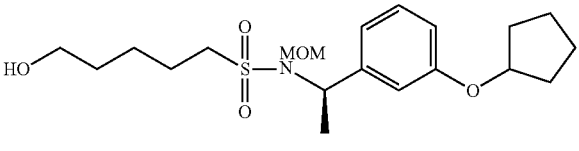 | 187 |
| 194 | 62 | 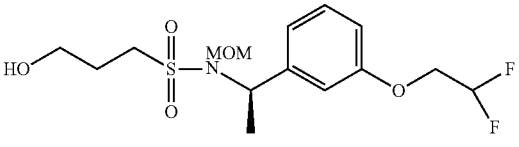 | 185 |
| 195 | 25 | 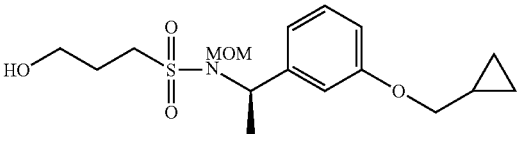 | 185 |
| 196 | 25 | 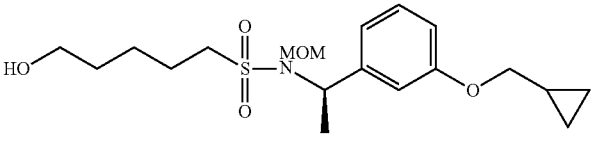 | 187 |
| 197 | 25 | 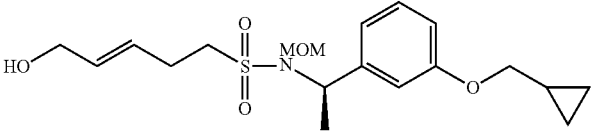 | 186 |

TABLE 23

| Reference Example | Reference Example No. of amine (or structural formula of commercially available amine) | Product | Production method |
|---|---|---|---|
| 198 | H₂N-CH(phenyl)₂ (diphenylmethylamine) | HO-(CH₂)₃-SO₂-N(MOM)-CH(phenyl)₂ | 185 |
| 199 | 8 | HO-(CH₂)₃-SO₂-N(MOM)-CH(phenyl)(3-(cyclopropylmethoxy)phenyl) | 185 |

TABLE 24

| Reference Example | Reference Example No. of amine (or structural formula of commercially available amine) | Product | Production method |
|---|---|---|---|
| 200 | 1 | HO-CH₂-CH=CH-CH₂-CH₂-SO₂-N(MOM)-CH₂-(3-(cyclopropylmethoxy)phenyl) | 186 |
| 201 | 49 | HO-(CH₂)₃-SO₂-N(MOM)-CH(3-cyclopropoxyphenyl)(4-fluorophenyl) | 185 |
| 202 | 24 | HO-(CH₂)₃-SO₂-N(MOM)-CH(Et)(4-fluoro-3-(cyclopropylmethoxy)phenyl) | 185 |

TABLE 24-continued
| Reference Example | Reference Example No. of amine (or structural formula of commercially available amine) | Product | Production method |
|---|---|---|---|
| 203 | 37 | 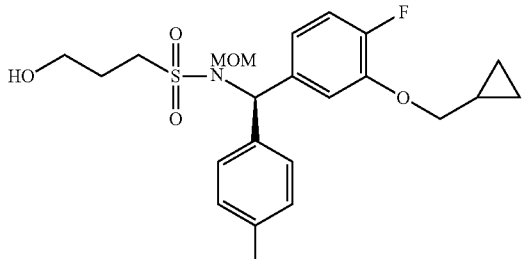 | 185 |
| 204 | 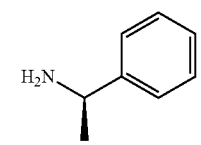 | 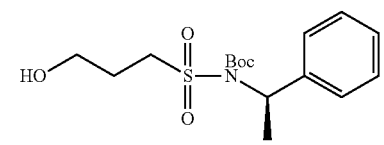 [SMILES: C[C@H](c1ccccc1)N(C(=O)OC(C)(C)C)S(=O)(=O)CCCO] | 188 |
| 205 | 75 | 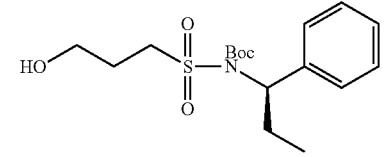 [SMILES: CC[C@H](c1ccccc1)N(C(=O)OC(C)(C)C)S(=O)(=O)CCCO] | 188 |
| 206 | 76 | 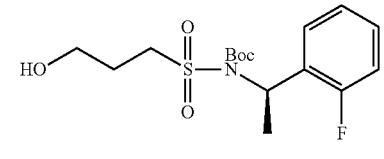 | 188 |
| 207 | 78 | 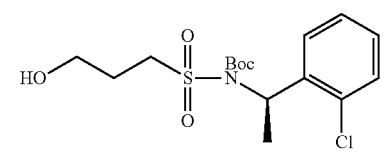 [SMILES: C[C@H](c1ccccc1Cl)N(C(=O)OC(C)(C)C)S(=O)(=O)CCCO] | 188 |
TABLE 25
| Reference Example | Reference Example No. of amine (or structural formula of commercially available amine) | Product | Production method |
|---|---|---|---|
| 208 | 79 | 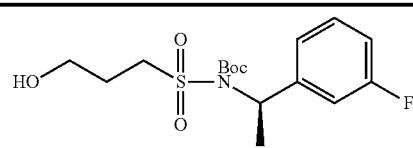 | 188 |
| 209 | 82 | 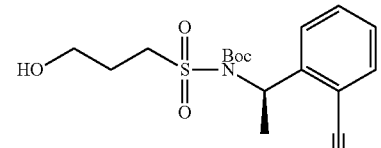 | 188 |

TABLE 25-continued

| Reference Example | Reference Example No. of amine (or structural formula of commercially available amine) | Product | Production method |
|---|---|---|---|
| 210 | 83 | HO–(CH₂)₃–S(O)₂–N(Boc)–CH(CH₃)–(2-Br-C₆H₄) | 188 |
| 211 | 84 | HO–(CH₂)₃–S(O)₂–N(Boc)–CH(CH₃)–(2-Me-C₆H₄) | 188 |
| 212 | 85 | HO–(CH₂)₃–S(O)₂–N(Boc)–CH(CH₃)–(2-CF₃-C₆H₄) | 188 |
| 213 | H₂N–CH(CH₃)–Ph | HO–(CH₂)₃–S(O)₂–N(Boc)–CH(CH₃)–Ph | 188 |
| 214 | H₂N–(indanyl) | HO–(CH₂)₃–S(O)₂–N(Boc)–(indanyl) | 188 |

Reference Example 215

Synthesis of 4-(aminomethyl)-N-(3-(cyclopropylmethoxy)benzyl)piperidine-1-sulfonamide

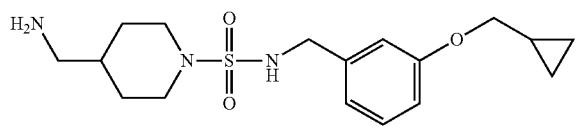

[Formula 43]

The (3-(cyclopropylmethoxy)phenyl)methanamine (817 mg) obtained in Reference Example 1 was dissolved in dichloromethane (4.0 mL). To the solution, chlorosulfonic acid (100 μL) was gradually added at 0° C., and the mixture was stirred at 0° C. for 30 minutes and at room temperature for 1 hour. The reaction mixture was concentrated under reduced pressure, and the residue was then co-evaporated with toluene (5.0 mL×3). The residue was dissolved in toluene (4.0 mL). To the mixture, phosphorus pentachloride (312 mg) was added, and the mixture was stirred at 70° C. for 1.5 hours. The precipitate was removed by filtration and washed with toluene (5.0 mL×3). Then, the combined filtrate was concentrated under reduced pressure. The residue was dissolved in THF (2.0 mL). The mixture was added to a THF (8.0 mL) solution of 4-((tert-butyldimethylsilyloxy)methyl)piperidine (344 mg) obtained according to a method described in the document (J. Org. Chem., 71, 9045-9050 (2006)) and triethylamine (280 μL), and the mixture was stirred at room temperature for 20 hours. To the reaction mixture, water (5.0 mL) was added, and the resultant mixture was then extracted with ethyl acetate (15 mL). The organic layer was washed with brine (5.0 mL), dried over anhydrous sodium sulfate, and then concentrated under reduced pressure. The residue was purified by silica gel column chromatography (10% ethyl acetate/hexane). The obtained yellow solid (212 mg) was dissolved in THF (2.0 mL). To the solution, a solution of tetrabutylammonium fluoride (hereinafter, referred to as TBAF) in THF (1.0 M, 700 μL) was added, and the mixture was stirred at room temperature for 30 minutes and at 50° C. for 1 hour. The reaction mixture was concentrated under reduced pressure, and the residue was then purified by silica gel column chromatography (60% ethyl acetate/hexane). The obtained pale yellow oil (122 mg) was dissolved in dichloromethane (1.0 mL). To the solution, triethylamine (58 μL) and methanesulfonyl chloride (29 μL) were added, and the mixture was stirred at room temperature for 30 minutes. To the reaction mixture, water (5.0 mL) was added, and the resultant mixture was then extracted with ethyl acetate (5.0 mL). The organic layer was washed with brine (3.0 mL), dried over anhydrous sodium sulfate, and then concentrated under reduced pressure. The residue was dissolved in DMF (2.0 mL). To the solution, sodium azide (67 mg) was added, and the mixture was stirred at 50° C. for 14 hours. To the reaction mixture, water (5.0 mL) was added, and the resultant mixture was then extracted with ethyl acetate (10 mL). The organic layer was washed with water (5.0 mL) and brine (3.0 mL), dried over anhydrous sodium sulfate, and then concentrated under reduced pressure. The residue was purified by silica gel column chromatography (20% ethyl acetate/hexane). The obtained colorless oil (106 mg) was dissolved in THF (2.5 mL). To the solution, water (500 μL) and polymer-supported triphenylphosphine (2.3 mmol/g, 365 mg) were added, and the mixture was stirred at room temperature for 30 minutes and at 50° C. for 1 hour. The resin was removed by filtration and washed with THF (5.0 mL×4). Then, the combined filtrate was concentrated. The residue was co-evaporated with ethanol (3.0 mL×3) and toluene (3.0 mL×3) to obtain the title compound (101 mg) as a crude product.

Reference Example 216

Synthesis of 4-(aminomethyl)-N-benzylpiperidine-1-sulfonamide

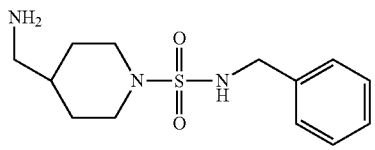

[Formula 44]

The title compound was obtained according to the method of Reference Example 215 from commercially available benzylamine.

Reference Example 217

Synthesis of (R)-1-(3-bromopropylsulfonyl)-2-((tert-butyldimethylsilyloxy)diphenylmethyl)pyrrolidine

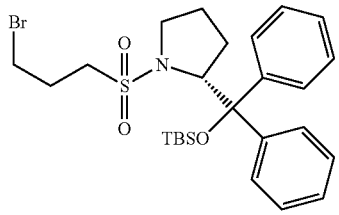

[Formula 45]

(R)-Diphenyl(pyrrolidin-2-yl)methanol (945 mg) and triethylamine (543 μL) were dissolved in diethyl ether (40 mL). To the solution, 3-chloropropanesulfonyl chloride (454 μL) was added at 0° C., and the mixture was stirred at room temperature for 3 hours. To the reaction mixture, water (20 mL) was added, and the resultant mixture was then extracted with ethyl acetate (30 mL). The organic layer was washed with brine (20 mL), dried over anhydrous magnesium sulfate, and then concentrated under reduced pressure. The residue was dissolved in dichloromethane (30 mL). To the mixture, 2,6-lutidine (1.05 mL) and tert-butyldimethylsilyl trifluoromethanesulfonate (1.72 mL) were added, and the mixture was heated to reflux at 55° C. for 10 hours. The reaction mixture was cooled to room temperature, an aqueous saturated ammonium chloride solution (20 mL) was then added thereto, and the resultant mixture was then partitioned. The organic layer was washed with water (20 mL) and brine (20 mL), dried over anhydrous magnesium sulfate, and then concentrated under reduced pressure. The residue was purified by silica gel column chromatography (17% ethyl acetate/hexane). The obtained compound was dissolved in 3-pentanone (50 mL). To the solution, lithium bromide (1.89 g) was added, and the mixture was heated to reflux at 120° C. for 3 hours. The reaction mixture was cooled to room temperature, water (20 mL) was then added thereto, and the resultant mixture was then extracted with ethyl acetate (20 mL). The organic layer was dried over anhydrous magnesium sulfate and then concentrated under reduced pressure. The obtained residue was reacted with lithium bromide again under the same conditions as above, and the obtained residue was co-evaporated with toluene (5.0 mL×3) to obtain the title compound (1.2 g) as a pale yellow oil.

Reference Example 218

Synthesis of (R)-1-(3-bromopropylsulfonyl)-2-((tert-butyldimethylsilyloxy)bis(4-fluorophenyl)methyl)pyrrolidine

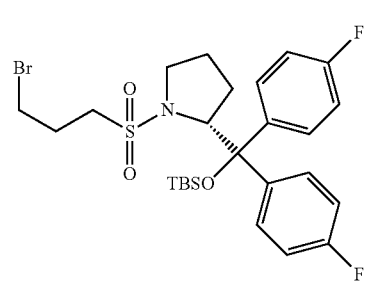

[Formula 46]

The title compound (930 mg) was obtained as a pale yellow oil according to the method of Reference Example 217 from (R)-bis(4-fluorophenyl)(pyrrolidin-2-yl)methanol (1.0 g) obtained according to a method described in the document (Tetrahedron Asymmetry, 14 (1), 95-100 (2003)).

Reference Example 219

Synthesis of (R)-1-(3-bromopropylsulfonyl)-2-((tert-butyldimethylsilyloxy)bis(3-fluorophenyl)methyl)pyrrolidine

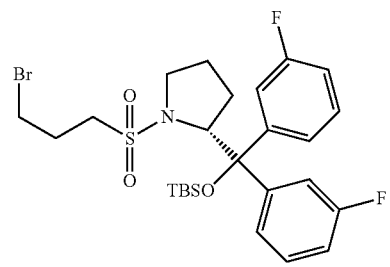

[Formula 47]

The title compound (910 mg) was obtained as a pale yellow oil according to the method of Reference Example 217 from (R)-bis(3-fluorophenyl)(pyrrolidin-2-yl)methanol (1.0 g)

obtained according to a method described in the document (Tetrahedron Asymmetry, 14 (1), 95-100 (2003)).

Reference Example 220

Synthesis of N-methyl-1-(1-phenylcyclopropyl)methanamine

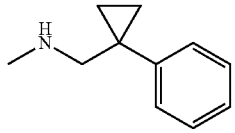

[Formula 48]

1-Phenylcyclopropanecarboxylic acid (2.95 g) was dissolved in DMF (120 mL). To the solution, EDC.HCl (5.2 g), HOBt (3.2 g), and a solution of methylamine in methanol (40%, 1.94 mL) were added, and the mixture was stirred at room temperature for 5 hours. The reaction mixture was concentrated under reduced pressure, and the residue was purified by silica gel column chromatography (50% ethyl acetate/hexane). An aliquot (1.1 g) of the obtained amide compound (2.9 g) was dissolved in THF (60 mL). To the solution, a solution of LAH in THF (2.4 M, 7.9 mL) was added dropwise at 0° C., and the mixture was heated to reflux at 80° C. for 12 hours. To the reaction mixture, water (4.0 mL) was gradually added dropwise at 0° C. The precipitate was removed by filtration and washed with THF (60 mL). Then, the combined filtrate was concentrated under reduced pressure to obtain the title compound (1.0 g) as a colorless oil.

Reference Example 221

Synthesis of 3-bromo-N-methyl-N-((1-phenylcyclopropyl)methyl)propane-1-sulfonamide

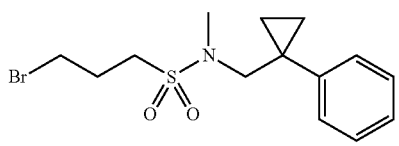

[Formula 49]

The N-methyl-1-(1-phenylcyclopropyl)methanamine (1.0 g) obtained in Reference Example 220 was dissolved in diethyl ether (40 mL). To the solution, triethylamine (887 µL) and 3-chloropropanesulfonyl chloride (703 µL) were added at 0° C., and the mixture was stirred at room temperature for 3 hours. To the reaction mixture, water (10 mL) was added, and the resultant mixture was then partitioned. The organic layer was dried over anhydrous magnesium sulfate and then concentrated under reduced pressure. The residue was purified by silica gel column chromatography (33% ethyl acetate/hexane). The obtained compound was dissolved in 3-pentanone (100 mL). To the solution, lithium bromide (4.27 g) was added, and the mixture was heated to reflux at 120° C. for 3 hours. The reaction mixture was cooled to room temperature, water (50 mL) was then added thereto, and the resultant mixture was then extracted with ethyl acetate (50 mL). The organic layer was dried over anhydrous magnesium sulfate and then concentrated under reduced pressure. The obtained residue was reacted with lithium bromide again under the same conditions as above, and the obtained residue was co-evaporated with toluene (20 mL×3) to obtain the title compound (1.69 g) as a colorless oil.

Reference Example 222

Synthesis of 2-(3-(cyclopropylmethoxy)phenyl)-N-methylethanamine

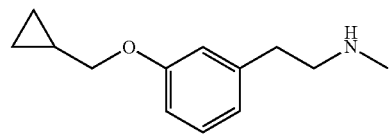

[Formula 50]

3-(2-Hydroxyethyl)phenol (2.5 g) was dissolved in DMF (18 mL). To the solution, potassium carbonate (5.0 g), sodium iodide (271 mg), and (chloromethyl)cyclopropane (1.75 mL) were added, and the mixture was stirred at 80° C. for 5 hours. The reaction mixture was cooled to room temperature, water (40 mL) was then added thereto, and the resultant mixture was then extracted with ethyl acetate (40 mL). The organic layer was dried over anhydrous magnesium sulfate and then concentrated under reduced pressure. The residue was purified by silica gel column chromatography (17% ethyl acetate/hexane). An aliquot (500 mg) of the obtained monoalcohol compound (2.6 g) was dissolved in dichloromethane (10 mL). To the solution, triethylamine (540 µL) and methanesulfonyl chloride (242 µL) were added, and the mixture was stirred at room temperature for 30 minutes. To the reaction mixture, an aqueous saturated sodium bicarbonate solution (10 mL) was added, and the resultant mixture was partitioned. The organic layer was washed with water (10 mL) and brine (10 mL), dried over anhydrous magnesium sulfate, and then concentrated under reduced pressure. The residue was dissolved in THF (6.0 mL). To the solution, an aqueous methylamine solution (40%, 6.0 mL) was added, and the mixture was stirred at 60° C. for 4 hours in a sealed tube. The reaction mixture was cooled to room temperature and then concentrated under reduced pressure. To the residue, an aqueous sodium hydroxide solution (1.0 M, 10 mL) was added, and the resultant mixture was then extracted with diethyl ether (20 mL). The organic layer was extracted with dilute hydrochloric acid (1.0 M, 20 mL), and the aqueous layer was turned into basic by the addition of an aqueous sodium hydroxide solution (4.0 M, 20 mL), and was then extracted with diethyl ether (20 mL). The organic layer was dried over potassium carbonate and concentrated under reduced pressure to obtain the title compound (310 mg) as a colorless oil.

Reference Example 223

Synthesis of 3-bromo-N-(3-(cyclopropylmethoxy) phenethyl)-N-methylpropane-1-sulfonamide

[Formula 51]

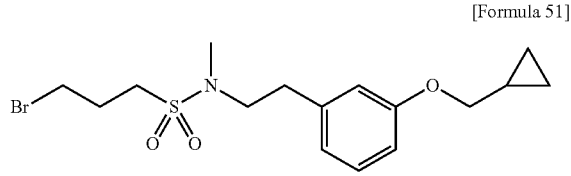 [SMILES: CN(CCc1cccc(OCC2CC2)c1)S(=O)(=O)CCCBr]

The 2-(3-(cyclopropylmethoxy)phenyl)-N-methylethanamine (140 mg) obtained in Reference Example 222 was dissolved in diethyl ether (3.0 mL). To the solution, triethylamine (170 µL) and 3-chloropropanesulfonyl chloride (108 µL) were added at 0° C., and the mixture was stirred at room temperature for 3 hours. To the reaction mixture, water (10 mL) was added, and the resultant mixture was partitioned. The organic layer was dried over anhydrous magnesium sulfate and concentrated under reduced pressure. The residue was purified by silica gel column chromatography (33% ethyl acetate/hexane). The obtained compound was dissolved in 3-pentanone (13 mL). To the solution, lithium bromide (560 mg) was added, and the mixture was heated to reflux at 120° C. for 3 hours. The reaction mixture was cooled to room temperature, water (10 mL) was then added thereto, and the resultant mixture was then extracted with ethyl acetate (10 mL). The organic layer was dried over anhydrous magnesium sulfate and then concentrated under reduced pressure. The obtained residue was reacted with lithium bromide again under the same conditions as above, and the obtained residue was co-evaporated with toluene (10 mL×3) to obtain the title compound (249 mg) as a colorless oil.

Reference Example 224

Synthesis of benzyl 4-(methoxymethoxy)-2-methylbutan-2-ylcarbamate

[Formula 52]

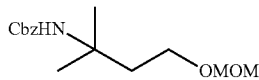

Ethyl 3-amino-3-methylbutanoate (480 mg) obtained according to a method described in the document (J. Med. Chem., 34, 633-642 (1991)) was dissolved in THF (3.0 mL). The solution was gradually added into a solution of LAH in THF (2.4 M, 2.1 mL) at room temperature, and the mixture was stirred at 45° C. for 16 hours. The reaction mixture was cooled to room temperature, and water (1.5 mL) was then added dropwise thereto at 0° C. The resultant precipitate was removed by filtration and washed with methanol (20 mL) and THF (20 mL). Then, the combined filtrate was concentrated under reduced pressure. The obtained residue was dissolved in methanol (10 mL). To the mixture, dibenzyl pyrocarbonate (1.2 mL) was added, and the mixture was stirred at room temperature for 14 hours. The reaction mixture was concentrated under reduced pressure, and the residue was then purified by silica gel column chromatography (40% ethyl acetate/hexane). The obtained colorless oil (486 mg) was dissolved in dichloromethane (4.0 mL). To the solution, N,N-diisopropylethylamine (3.5 mL) and chloromethyl methyl ether (789 µL) were added, and the mixture was stirred at room temperature for 14 hours. To the reaction mixture, an aqueous saturated ammonium chloride solution (10 mL) was added, and the resultant mixture was then extracted with ethyl acetate (15 mL). The organic layer was washed with an aqueous saturated ammonium chloride solution (10 mL×3) and brine (10 mL), dried over anhydrous sodium sulfate, and then concentrated under reduced pressure. The residue was purified by silica gel column chromatography (20% ethyl acetate/hexane) to obtain the title compound (529 mg) as a colorless oil. In this context, the benzyloxycarbonyl group is indicated as Cbz.

Reference Example 225

Synthesis of benzyl 5-(methoxymethoxy)-2-methylpentan-2-ylcarbamate

[Formula 53]

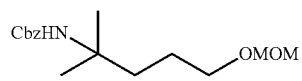

The title compound (1.24 g) was obtained as a pale yellow oil according to the method of Reference Example 224 from 4-hydroxy-1,1-dimethylbutylamine (527 mg) obtained according to a method described in the document (J. Am. Chem. Soc., 77, 1079-1083 (1955)).

Reference Example 226

Synthesis of benzyl 5-((2,4-dioxo-3,4-dihydropyrimidin-1(2H)-yl)methoxy)-2-methylpentan-2-ylcarbamate

[Formula 54]

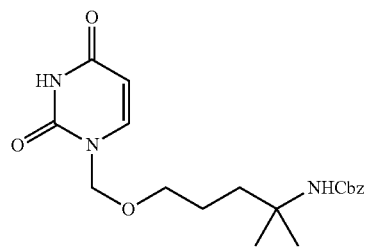

The benzyl 5-(methoxymethoxy)-2-methylpentan-2-ylcarbamate (369 mg) obtained in Reference Example 225 was dissolved in dichloromethane (1.0 mL). To the solution, a solution of boron trichloride (hereinafter, referred to as BCl₃) in dichloromethane (1.0 M, 330 µL) was gradually added at 0° C., and the mixture was stirred at room temperature for 2 hours. The reaction mixture was concentrated under reduced pressure, and the residue was then dissolved in 1,2-dichloroethane (hereinafter, referred to as DCE). To the mixture, 2,4-bis(trimethylsilyloxy)pyrimidine (256 mg) obtained according to a method described in the document (Nucleosides & Nucleotides, 4, 565-585 (1985)) and iodine (10 mg) were added, and the mixture was heated to reflux at 93° C. for 1.5 hours. The reaction mixture was cooled to room temperature, an aqueous saturated sodium bisulfite solution (10 mL) was then added thereto, and the resultant mixture was then extracted with ethyl acetate (30 mL). The organic layer was washed with brine, dried over anhydrous sodium sulfate, and then concentrated under reduced pressure. The residue was purified by silica gel column chromatography (5% methanol/chloroform) and $C_{18}$ reverse-phase column chromatography (50% methanol/water) to obtain the title compound (206 mg) as a colorless gum.

Reference Example 227

Synthesis of N-(4-(methoxymethoxy)-2-methylbutan-2-yl)benzenesulfonamide

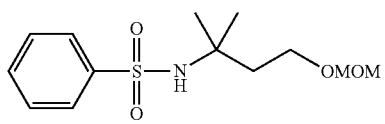

[Formula 55]

The benzyl 4-(methoxymethoxy)-2-methylbutan-2-ylcarbamate (525 mg) obtained in Reference Example 224 was dissolved in methanol (10 mL). To the solution, 5% palladium-carbon (400 mg) was added, and the reaction mixture was stirred at room temperature for 1 hour under a hydrogen atmosphere. The precipitate was removed by filtration through a pad of Celite and washed with methanol (30 mL). Then, the combined filtrate was concentrated under reduced pressure. The residue was dissolved in dichloromethane (5.0 mL). To the mixture, triethylamine (520 µL) and benzenesulfonyl chloride (360 µL) were added, and the mixture was stirred at room temperature for 15 hours. To the reaction mixture, water (10 mL) was added, and the resultant mixture was then extracted with ethyl acetate (10 mL). The organic layer was washed with brine (10 mL), dried over anhydrous sodium sulfate, and then concentrated under reduced pressure. The residue was purified by silica gel column chromatography (30% ethyl acetate/hexane) to obtain the title compound (285 mg) as a colorless oil.

Reference Example 228

Synthesis of N-(5-(methoxymethoxy)-2-methylpentan-2-yl)benzenesulfonamide

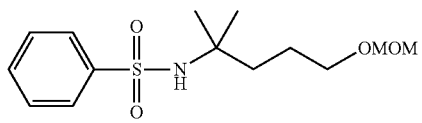

[Formula 56]

The title compound (197 mg) was obtained as a colorless oil according to the method of Reference Example 227 from the benzyl 5-(methoxymethoxy)-2-methylpentan-2-ylcarbamate (369 mg) obtained in Reference Example 225.

Reference Example 229

Synthesis of 3-(cyclopropylmethoxy)-N-(5-(methoxymethoxy)-2-methylpentan-2-yl)benzenesulfonamide

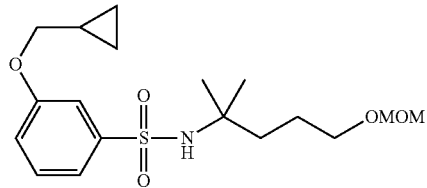

[Formula 57]

The benzyl 5-(methoxymethoxy)-2-methylpentan-2-ylcarbamate (242 mg) obtained in Reference Example 225 was dissolved in methanol (5.0 mL). To the solution, 10% palladium-carbon (250 mg) was added, and the reaction mixture was stirred at room temperature for 1 hour under a hydrogen atmosphere. The precipitate was removed by filtration through a pad of Celite and washed with methanol (20 mL). Then, the combined filtrate was concentrated under reduced pressure. The residue was dissolved in dichloromethane (3.0 mL). To the solution, triethylamine (170 µL) and 3-benzoyloxybenzenesulfonyl chloride (297 mg) obtained according to a method described in the document (J. Pesticide. Chem., 13, 107-115 (1988)) were added, and the mixture was stirred at room temperature for 2 hours. To the reaction mixture, water (7.0 mL) was added, and the resultant mixture was then extracted with ethyl acetate (10 mL). The organic layer was washed with brine (10 mL), dried over anhydrous sodium sulfate, and then concentrated under reduced pressure. The residue was purified by silica gel column chromatography (30% ethyl acetate/hexane). The obtained colorless oil (165 mg) was dissolved in a solution of methylamine in methanol (40%, 3.0 mL), and the solution was stirred at room temperature for 30 minutes. The reaction mixture was concentrated under reduced pressure, and the residue was then dissolved in DMF (3.0 mL). To the solution, potassium carbonate (102 mg), potassium iodide (6.0 mg), and (chloromethyl)cyclopropane (34 µL) were added, and the mixture was stirred at 90° C. for 14 hours. The reaction mixture was cooled to room temperature, water (10 mL) was then added thereto, and the resultant mixture was then extracted with ethyl acetate (15 mL). The organic layer was washed with water (10 mL) and brine (10 mL), dried over anhydrous sodium sulfate, and then concentrated under reduced pressure. The residue was purified by silica gel column chromatography (30% ethyl acetate/hexane) to obtain the title compound (124 mg) as a colorless oil.

Reference Example 230

Synthesis of 3-(2,2-difluoroethoxy)-N-(5-(methoxymethoxy)-2-methylpentan-2-yl)benzenesulfonamide

[Formula 58]

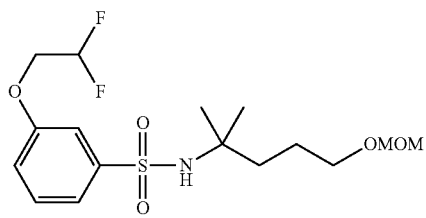

The title compound (367 mg) was obtained as a pale yellow gum according to the method of Reference Example 229 from the benzyl 5-(methoxymethoxy)-2-methylpentan-2-ylcarbamate (628 mg) obtained in Reference Example 225.

Reference Example 231

Synthesis of 3-(cyclopentyloxy)-N-(5-(methoxymethoxy)-2-methylpentan-2-yl)benzenesulfonamide

[Formula 59]

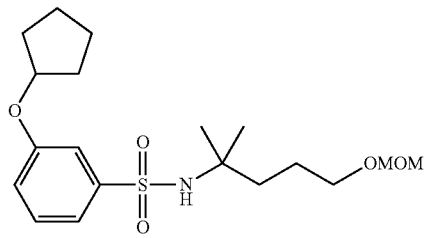

The title compound (379 mg) was obtained as a pale yellow gum according to the method of Reference Example 229 from the benzyl 5-(methoxymethoxy)-2-methylpentan-2-ylcarbamate (628 mg) obtained in Reference Example 225.

Reference Example 232

Synthesis of (Z)—N-(5-(methoxymethoxy)-2-methylpentan-2-yl)-3-(prop-1-enyl)benzenesulfonamide

[Formula 60]

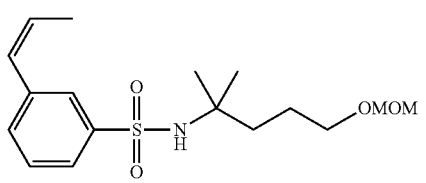

The benzyl 5-(methoxymethoxy)-2-methylpentan-2-ylcarbamate (3.24 g) obtained in Reference Example 225 was dissolved in methanol (25 mL). To the solution, 5% palladium-carbon (600 mg) was added, and the reaction mixture was stirred at room temperature for 3 hours under a hydrogen atmosphere. The precipitate was removed by filtration through a pad of Celite and washed with methanol (150 mL). Then, the combined filtrate was concentrated under reduced pressure. The residue was dissolved in dichloromethane (30 mL). To the mixture, triethylamine (2.45 mL) and 3-bromobenzenesulfonyl chloride (2.06 mL) were added, and the mixture was stirred at room temperature for 14 hours. To the reaction mixture, water (100 mL) was added, and the resultant mixture was then extracted with ethyl acetate (100 mL). The organic layer was washed with brine (100 mL), dried over anhydrous sodium sulfate, and then concentrated under reduced pressure. The residue was purified by silica gel column chromatography (25% ethyl acetate/hexane). An aliquot (951 mg) of the obtained colorless oil (2.85 g) was co-evaporated with toluene (10 mL×3), and the residue was then dissolved in THF (20 mL). To the solution, a solution of n-butyllithium in hexane (2.59 M, 2.0 mL) was gradually added dropwise at −78° C., and the mixture was stirred for 5 minutes. To the reaction mixture, DMF (0.48 mL) was added at −78° C., and the mixture was stirred at −78° C. for 1 hour. To the reaction mixture, acetic acid (740 µL) was added, and the mixture was stirred at room temperature for 20 minutes. To the reaction mixture, water (40 mL) was added, and the resultant mixture was then extracted with ethyl acetate (30 mL). The organic layer was washed with brine (30 mL), dried over anhydrous sodium sulfate, and then concentrated under reduced pressure. The residue was purified by silica gel column chromatography (40% ethyl acetate/hexane).

Ethyltriphenylphosphonium bromide (501 mg) was suspended in THF (4.5 mL). To the suspension, a solution of NaHMDS in THF (1.0 M, 1.35 mL) was added at 0° C., and the mixture was stirred at 0° C. for 30 minutes. To the reaction mixture, a THF (1.0 mL) solution of the above colorless oil (148 mg) which was obtained by column chromatography purification was gradually added at −78° C., and the mixture was stirred at room temperature for 1 hour. To the reaction mixture, an aqueous saturated ammonium chloride solution (10 mL) was added, and the resultant mixture was then extracted with ethyl acetate (20 mL). The organic layer was washed with brine (10 mL), dried over anhydrous sodium sulfate, and then concentrated under reduced pressure. The residue was purified by silica gel column chromatography (20% ethyl acetate/hexane) to obtain the title compound (138 mg) as a colorless oil.

Reference Example 233

Synthesis of N-(4-(methoxymethoxy)butyl)benzenesulfonamide

[Formula 61]

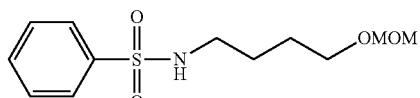

4-Aminobutanol (700 mg) was dissolved in THF (12.5 mL). To the solution, magnesium oxide (1.58 g), water (3.2 mL), and benzenesulfonyl chloride (1.15 mL) were added, and the mixture was stirred at room temperature for 2 hours. The precipitate was removed by filtration, and washed with chloroform (50 mL). Then, the combined filtrate was concentrated under reduced pressure. To the residue, water (20 mL) was added, and the resultant mixture was then extracted with ethyl acetate (20 mL). The organic layer was washed with brine (20 mL), dried over anhydrous sodium sulfate, and then concentrated under reduced pressure. The residue was purified by silica gel column chromatography (100% ethyl acetate). The obtained colorless oil (1.48 g) was dissolved in dichloromethane (7.5 mL). To the solution, N,N-diisopropylethylamine (3.43 mL) and chloromethyl methyl ether (1.0 mL) were added, and the mixture was stirred at room temperature for 1.5 hours. The reaction mixture was concentrated under reduced pressure, and the residue was then purified by silica gel column chromatography (50% ethyl acetate/hexane) to obtain the title compound (1.36 g) as a colorless oil.

Reference Example 234

Synthesis of N-(1-(3-(methoxymethoxy)propyl)cyclopropyl)benzenesulfonamide

[Formula 62]

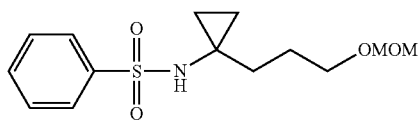

The title compound (178 mg) was obtained as a colorless oil according to the method of Reference Example 233 from 1-aminocyclopropanepropanol hydrochloride (138 mg) obtained according to a method described in the document (J. Heterocyclic. Chem., 25, 1769-1772 (1988)).

Reference Example 235

Synthesis of 3-methoxy-N-(1-(3-(methoxymethoxy)propyl)cyclopropyl)benzenesulfonamide

[Formula 63]

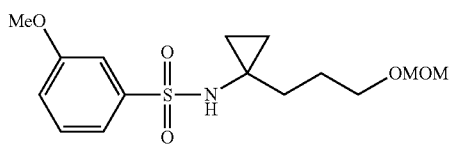

The title compound (192 mg) was obtained as a colorless oil according to the method of Reference Example 233 from 1-aminocyclopropanepropanol hydrochloride (138 mg) obtained according to a method described in the document (J. Heterocyclic. Chem., 25, 1769-1772 (1988)) and 3-methoxybenzenesulfonyl chloride (140 μL).

Reference Example 236

Synthesis of 3-(cyclopropylmethoxy)-N-(4-(methoxymethoxy)butyl)benzenesulfonamide

[Formula 64]

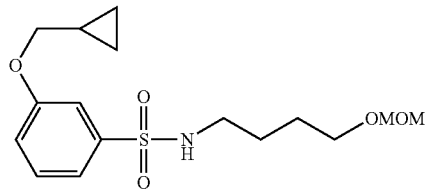

A colorless oil (285 mg) was obtained according to the method of Reference Example 233 from 4-aminobutanol (89 mg) and 3-benzoyloxybenzenesulfonyl chloride (300 mg) obtained according to a method described in the document (J. Pesticide. Chem., 13, 107-115 (1988)). This oil was dissolved in methanol (5.0 mL). To the solution, DBU (441 mg) was added, and the mixture was stirred at room temperature for 45 minutes. To the reaction mixture, acetic acid (210 μL) was added, and the mixture was stirred at room temperature for 10 minutes. The reaction mixture was then concentrated under reduced pressure. The residue was purified by silica gel column chromatography (100% ethyl acetate). The obtained colorless oil (147 mg) was dissolved in DMF (4.0 mL). To the solution, potassium carbonate (141 mg), potassium iodide (8.5 mg), and (chloromethyl)cyclopropane (47 μL) were added, and the mixture was stirred at 90° C. for 14 hours. The reaction mixture was cooled to room temperature, water (10 mL) was then added thereto, and the resultant mixture was then extracted with ethyl acetate (10 mL). The organic layer was washed with water (10 mL) and brine (10 mL), dried over anhydrous sodium sulfate, and then concentrated under reduced pressure. The residue was purified by silica gel column chromatography (30% ethyl acetate/hexane) to obtain the title compound (91 mg) as a colorless oil.

Reference Example 237

Synthesis of 3-(cyclopropylmethoxy)-N-(1-(3-(methoxymethoxy)propyl)cyclopropyl)benzenesulfonamide

[Formula 65]

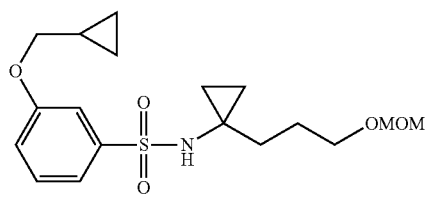

The title compound (312 mg) was obtained as a colorless oil according to the method of Reference Example 236 from 1-aminocyclopropanepropanol hydrochloride (258 mg) obtained according to a method described in the document (J. Heterocyclic. Chem., 25, 1769-1772 (1988)) and 3-benzoyloxybenzenesulfonyl chloride (504 mg) obtained according to a method described in the document (J. Pesticide. Chem., 13, 107-115 (1988)).

Reference Example 238

Synthesis of benzyl 5-(2,4-dioxo-3,4-dihydropyrimidin-1(2H)-yl)-2-methylpentan-2-ylcarbamate

[Formula 66]

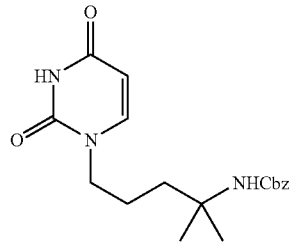

4-Hydroxy-1,1-dimethylbutylamine (7.34 g) obtained according to a method described in the document (J. Am. Chem. Soc., 77, 1079-1083 (1955)) was dissolved in dichloromethane (100 mL). To the solution, easily available N-(benzyloxycarbonyloxy)succinimide (18.0 g) was added, and the mixture was stirred at room temperature for 14 hours. The reaction mixture was concentrated under reduced pressure. To the residue, water (200 mL) was then added, and the resultant mixture was then extracted with ethyl acetate (200 mL). The organic layer was washed with brine (100 mL), dried over anhydrous sodium sulfate, and then concentrated under reduced pressure. The residue was purified by silica gel column chromatography (40% ethyl acetate/hexane). The obtained colorless oil (3.32 g) was dissolved in THF (130 mL). To the solution, triphenylphosphine (4.50 g) and 3-benzoylpyrimidine-2,4(1H, 3H)-dione (3.14 g) obtained according to a method described in the document (J. Med. Chem., 50, 6032-6038 (2007)) were added, and the mixture was stirred at room temperature for 5 minutes. To the reaction mixture, a toluene solution of DEAD (2.2 M, 7.81 mL) was gradually added dropwise, and the mixture was stirred at room temperature for 30 hours. The reaction mixture was concentrated under reduced pressure, and the residue was then purified by silica gel column chromatography (60% ethyl acetate/hexane). The obtained compound was dissolved in a solution of methylamine in methanol (40%, 50 mL), and the mixture was stirred at room temperature for 30 minutes. The reaction mixture was concentrated under reduced pressure, and the residue was then purified by silica gel column chromatography (3% methanol/chloroform) to obtain the title compound (3.59 g) as a foam.

Reference Examples 239 and 240

Synthesis of tert-butyl 5-hydroxy-2-methylpentan-2-ylcarbamate and tert-butyl 5-hydroxy-2,2-dimethylpyrrolidine-1-carboxylate

[Formula 67]

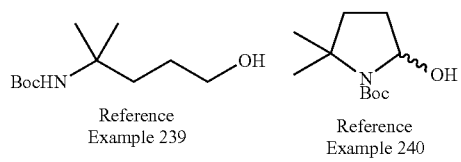

Reference Example 239

Reference Example 240

2-Amino-2-methyl-1-propanol (9.54 mL) was dissolved in methanol (200 mL). To the solution, Boc$_2$O (26.2 g) was added, and the mixture was stirred at room temperature for 2 hours. The reaction mixture was concentrated under reduced pressure, and the residue was then purified by silica gel column chromatography (30% ethyl acetate/hexane). An aliquot (15.5 g) of the obtained colorless solid (19.2 g) was dissolved in toluene (65 mL) and dimethyl sulfoxide (hereinafter, referred to as DMSO; 65 mL). To the solution, pyridine (9.71 mL), trifluoroacetic acid (4.46 mL), and EDC.HCl (46.0 g) were added, and the mixture was stirred at room temperature for 30 minutes. To the reaction mixture, water (250 mL) was added, and the resultant mixture was then extracted with ethyl acetate (250 mL×2). The organic layer was washed with brine (100 mL), dried over anhydrous sodium sulfate, and then concentrated under reduced pressure. The residue was co-evaporated with toluene (20 mL×3).

Sodium hydride (55%, 4.36 g) was suspended in THF (80 mL). To the suspension, triethyl phosphonoacetate (20.6 mL) was gradually added at 0° C., and the mixture was stirred at room temperature for 15 minutes. To the reaction mixture, a THF solution (80 mL) of the residue which was obtained by co-evaporation with toluene was added dropwise at 0° C., and the mixture was heated to reflux at 70° C. for 1 hour. The reaction mixture was concentrated under reduced pressure. To the residue, an aqueous saturated ammonium chloride solution (150 mL) was then added, and the resultant mixture was then extracted with 50% ethyl acetate/hexane (200 mL). The organic layer was washed with brine (100 mL), dried over anhydrous sodium sulfate, and then concentrated under reduced pressure. The residue was purified by silica gel column chromatography (15% ethyl acetate/hexane). The obtained pale yellow oil (17.2 g) was dissolved in ethyl acetate (100 mL). To the solution, 10% palladium-carbon (6.0 g) was added, and the reaction mixture was stirred at room temperature for 3 hours under a hydrogen atmosphere. The precipitate was removed by filtration through a pad of Celite and washed with ethyl acetate (600 mL). Then, the combined filtrate was concentrated under refuced pressure. The obtained colorless oil (17.2 g) was co-evaporated with toluene (20 mL×1), and the residue was then dissolved in THF (200 mL). To the mixture, a solution of lithium borohydride in THF (2.0 M, 55.4 mL) was added, and the mixture was stirred at room temperature for 3 days. To the reaction mixture, an aqueous saturated ammonium chloride solution (100 mL) was gradually added dropwise at 0° C., and the resultant mixture was then extracted with ethyl acetate (50 mL×3). The organic layer was washed with brine (100 mL), dried over anhydrous sodium sulfate, and then concentrated under reduced pressure. The residue was purified by silica gel column chromatography (Reference Example 240: 20% ethyl acetate/hexane, Reference Example 239: 70% ethyl acetate/hexane) to obtain the title compounds of Reference Examples 239 (5.9 g) and 240 (7.5 g) as a colorless gum and a colorless solid, respectively.

Reference Example 241

Synthesis of tert-butyl 5-(methoxymethylthio)-2-methylpentan-2-ylcarbamate

[Formula 68]

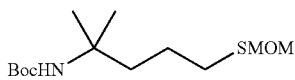

The tert-butyl 5-hydroxy-2-methylpentan-2-ylcarbamate (743 mg) obtained in Reference Example 239 was dissolved in pyridine (10 mL). To the solution, methanesulfonyl chloride (320 µL) was added, and the mixture was stirred at room temperature for 1 hour. To the reaction mixture, water (20 mL) was added, and the resultant mixture was then extracted with ethyl acetate (20 mL×4). The organic layer was dried over anhydrous sodium sulfate and then concentrated under reduced pressure. The residue was co-evaporated with toluene (10 mL×3), and the residue was then dissolved in DMF (13 mL). To the mixture, potassium carbonate (1.42 g) and thioacetic acid (490 μL) were added, and the mixture was stirred at room temperature for 2.5 hours. To the reaction mixture, water (25 mL) was added, and the resultant mixture was then extracted with ethyl acetate (25 mL). The organic layer was washed with water (20 mL) and brine (20 mL), dried over anhydrous sodium sulfate, and then concentrated under reduced pressure. The residue was dissolved in methanol (10 mL). To the mixture, sodium methoxide (369 mg) was added, and the mixture was stirred at room temperature for 30 minutes. The reaction mixture was concentrated under reduced pressure, an aqueous saturated ammonium chloride solution (15 mL) was then added thereto, and the resultant mixture was then extracted with ethyl acetate (20 mL×2). The organic layer was washed with brine (10 mL), dried over anhydrous sodium sulfate, and then concentrated under reduced pressure. The residue was dissolved in dichloromethane (5.0 mL). To the mixture, N,N-diisopropylethylamine (2.08 mL) and chloromethyl methyl ether (650 μL) were added, and the mixture was stirred at room temperature for 4 hours. To the reaction mixture, an aqueous saturated ammonium chloride solution (10 mL) was added, and the resultant mixture was then extracted with ethyl acetate (10 mL). The organic layer was washed with an aqueous saturated ammonium chloride solution (10 mL) and brine (10 mL), dried over anhydrous sodium sulfate, and then concentrated under reduced pressure. The residue was purified by silica gel column chromatography (15% ethyl acetate/hexane) to obtain the title compound (788 mg) as a colorless oil.

Reference Example 242

Synthesis of (E)-N-(7-bromo-2-methylhept-5-en-2-yl)-3-(cyclopropylmethoxy)benzenesulfonamide

[Formula 69]

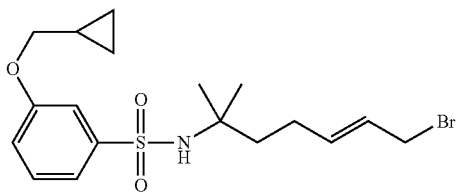

The tert-butyl 5-hydroxy-2,2-dimethylpyrrolidine-1-carboxylate (940 mg) obtained in Reference Example 240 was dissolved in toluene (20 mL). To the solution, ethyl(triphenylphosphoranylidene)acetate (1.74 g) was added, and the mixture was heated to reflux at 125° C. for 18 hours. The reaction mixture was concentrated under reduced pressure, and the residue was then purified by silica gel column chromatography (15% ethyl acetate/hexane). The obtained pale yellow gum (530 mg) was co-evaporated with toluene (10 mL×2), and the residue was then dissolved in THF (10 mL). To the solution, a solution of DIBAL in THF (1.0 M, 9.3 mL) was gradually added at −78° C., and the mixture was stirred at −78° C. for 2 hours. To the reaction mixture, a aqueous saturated Rochelle salt solution (20 mL) and brine (10 mL) were gradually added at −78° C., and the mixture was stirred at room temperature for 14 hours. After extracted with ethyl acetate (20 mL×3), the organic layer was dried over anhydrous sodium sulfate and then concentrated under reduced pressure. The residue was purified by silica gel column chromatography (40% ethyl acetate/hexane). The obtained colorless oil (450 mg) was dissolved in a hydrochloric acid-dioxane solution (4.0 M, 5.0 mL), and the mixture was stirred at room temperature for 50 minutes. The reaction mixture was concentrated under reduced pressure, and the residue was then co-evaporated with toluene (10 mL×3). The residue was dissolved in THF (4.0 mL) and water (1.0 mL). To the solution, triethylamine (340 μL), magnesium oxide (373 mg), and 3-benzoyloxybenzenesulfonyl chloride (604 mg) obtained according to a method described in the document (J. Pesticide. Chem., 13, 107-115 (1988)) were added, and the mixture was stirred at room temperature for 2 hours. The precipitate was removed by filtration and washed with ethyl acetate (50 mL) and water (10 mL). Then, the combined filtrate was concentrated under reduced pressure. To the residue, brine (20 mL) was added, and the resultant mixture was then extracted with ethyl acetate (20 mL). The organic layer was dried over anhydrous sodium sulfate and then concentrated under reduced pressure. The residue was purified by silica gel column chromatography (40% ethyl acetate/hexane). The obtained colorless oil (310 mg) was dissolved in a solution of methylamine in methanol (40%, 3.0 mL), and the solution was stirred at room temperature for 30 minutes. The reaction mixture was concentrated under reduced pressure, and the residue was then dissolved in DMF (4.0 mL). To the mixture, potassium carbonate (213 mg), potassium iodide (17 mg), and (chloromethyl)cyclopropane (78 μL) were added, and the mixture was stirred at 90° C. for 14 hours. The reaction mixture was cooled to room temperature, water (10 mL) was then added thereto, and the resultant mixture was then extracted with ethyl acetate (15 mL). The organic layer was washed with water (10 mL) and brine (10 mL), dried over anhydrous sodium sulfate, and then concentrated under reduced pressure. The residue was purified by silica gel column chromatography (30% ethyl acetate/hexane). The obtained pale yellow oil was dissolved in THF (4.5 mL). To the solution, triphenylphosphine (275 mg) and carbon tetrabromide (348 mg) were added, and the mixture was stirred at room temperature for 45 minutes. The reaction mixture was concentrated under reduced pressure, and the residue was then purified by silica gel column chromatography (20% ethyl acetate/hexane) to obtain the title compound (220 mg) as a colorless solid.

Reference Example 243

Synthesis of N-(1-(3-aminopropoxy)-2-methylpropan-2-yl)benzenesulfonamide

[Formula 70]

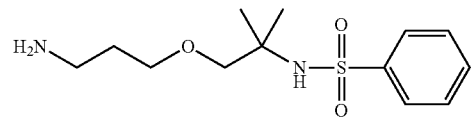

3-Benzyloxypropanol (1.25 g) was dissolved in dichloromethane (15 mL). To the solution, triethylamine (1.57 mL) and methanesulfonyl chloride (700 μL) were added, and the mixture was stirred at room temperature for 30 minutes. To the reaction mixture, water (30 mL) was added, and the resultant mixture was then extracted with ethyl acetate (30 mL). The organic layer was washed with brine (10 mL), dried over anhydrous sodium sulfate, and then concentrated under reduced pressure. The residue was co-evaporated with toluene (10 mL×2).

2-Amino-2-methyl-1-propanol (669 mg) was dissolved in DMF (20 mL). To the solution, sodium hydride (55%, 328 mg) was added, and the mixture was stirred at 50° C. for 1.5 hours. The reaction mixture was cooled to room temperature. A DMF (10 mL) solution of the above residue which was co-evaporated with toluene was then gradually added dropwise thereto at 0° C., and the mixture was stirred at 0° C. for 5 hours. To the reaction mixture, ethyl acetate (10 mL) was added, and the resultant mixture was then extracted with dilute hydrochloric acid (1.0 M, 20 mL). The aqueous layer was turned into basic (approximately pH 14) by the addition of an aqueous sodium hydroxide solution (1.0 M, 25 mL), and was then extracted with ethyl acetate. The organic layer was dried over anhydrous sodium sulfate and then concentrated under reduced pressure. The residue was co-evaporated with toluene (10 mL×2), and the residue was then dissolved in dichloromethane (20 mL). To the mixture, triethylamine (840 µL) and benzenesulfonyl chloride (570 mL) (570 µL) were added, and the mixture was stirred at room temperature for 14 hours. To the reaction mixture, water (30 mL) was added, and the resultant mixture was then extracted with ethyl acetate (50 mL). The organic layer was washed with brine (20 mL), dried over anhydrous sodium sulfate, and then concentrated under reduced pressure. The residue was purified by silica gel column chromatography (15% ethyl acetate/hexane). The obtained colorless oil (885 mg) was dissolved in methanol (15 mL). To the solution, 10% palladium-carbon (1.6 g) was added, and the reaction mixture was stirred at room temperature for 22 hours under a hydrogen atmosphere. The precipitate was removed by filtration through a pad of Celite and washed with methanol (150 mL). Then, the combined filtrate was concentrated. The residue (666 mg) was dissolved in dichloromethane (10 mL). To the solution, triethylamine (490 µL) and methanesulfonyl chloride (200 µL) were added, and the mixture was stirred at room temperature for 15 minutes. To the reaction mixture, water (20 mL) was added, and the resultant mixture was then extracted with ethyl acetate (30 mL). The organic layer was washed with brine (10 mL), dried over anhydrous sodium sulfate, and then concentrated under reduced pressure. The residue (847 mg) was dissolved in DMF (15 mL). To the solution, sodium azide (453 mg) was added, and the mixture was stirred at 60° C. for 45 minutes. The reaction mixture was cooled to room temperature, water (30 mL) was then added thereto, and the resultant mixture was then extracted with ethyl acetate (30 mL). The organic layer was washed with water (20 mL) and brine (20 mL), dried over anhydrous sodium sulfate, and then concentrated under reduced pressure. The residue was purified by silica gel column chromatography (20% ethyl acetate/hexane). The obtained colorless oil (643 mg) was dissolved in methanol (10 mL). To the solution, 5% palladium-carbon (640 mg) was added, and the reaction mixture was stirred at room temperature for 30 minutes under a hydrogen atmosphere. The precipitate was removed by filtration through a pad of Celite and washed with methanol (150 mL). Then, the filtrate was concentrated under reduced pressure to obtain the title compound (600 mg) as a crude product.

Reference Example 244

Synthesis of N-(1-(3-aminopropoxy)-2-methylpropan-2-yl)-3-(cyclopropylmethoxy)benzenesulfonamide

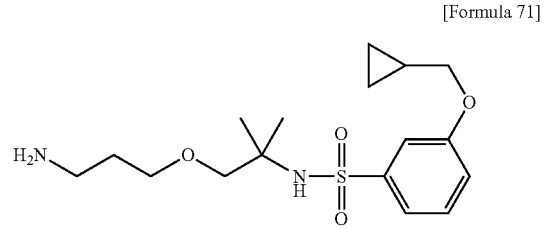 [SMILES: CC(C)(COCCCN)NS(=O)(=O)c1cccc(OCC2CC2)c1]

[Formula 71]

3-Benzyloxypropanol (1.33 g) was dissolved in dichloromethane (15 mL). To the solution, triethylamine (1.45 mL) and methanesulfonyl chloride (0.68 mL) were added, and the mixture was stirred at room temperature for 30 minutes. To the reaction mixture, water (30 mL) was added, and the resultant mixture was then extracted with ethyl acetate (30 mL). The organic layer was washed with brine (10 mL), dried over anhydrous sodium sulfate, and then concentrated under reduced pressure. The residue was co-evaporated with toluene (10 mL×2).

2-Amino-2-methyl-1-propanol (669 mg) was dissolved in DMF (20 mL). To the solution, sodium hydride (55%, 328 mg) was added, and the mixture was stirred at 50° C. for 2 hours. The reaction mixture was cooled to room temperature. A DMF (10 mL) solution of the above residue which was co-evaporated with toluene was then gradually added dropwise thereto at 0° C., and the mixture was stirred at 0° C. for 6.5 hours. To the reaction mixture, ethyl acetate (10 mL) was added, and the resultant mixture was then extracted with dilute hydrochloric acid (1.0 M, 20 mL). The aqueous layer was turned into basic (approximately pH 14) by the addition of an aqueous sodium hydroxide solution (1.0 M, 25 mL), and was then extracted with ethyl acetate. The organic layer was dried over anhydrous sodium sulfate and then concentrated under reduced pressure. The residue was co-evaporated with toluene (10 mL×2), and the residue was then dissolved in dichloromethane (20 mL). To the mixture, triethylamine (0.60 mL) and 3-benzoyloxybenzenesulfonyl chloride (976 mg) obtained according to a method described in the document (J. Pesticide. Chem., 13, 107-115 (1988)) were added, and the mixture was stirred at room temperature for 3 days. To the reaction mixture, water (30 mL) was added, and the resultant mixture was then extracted with ethyl acetate (50 mL). The organic layer was washed with brine (20 mL), dried over anhydrous sodium sulfate, and then concentrated under reduced pressure. The residue was purified by silica gel column chromatography (25% ethyl acetate/hexane).

The obtained colorless oil (1.26 g) was dissolved in a solution of methylamine in methanol (40%, 10 mL), and the solution was stirred at room temperature for 30 minutes. The reaction mixture was concentrated under reduced pressure, and the residue was then dissolved in methanol (30 mL). To the solution, 10% palladium-carbon (2.4 g) was added, and the reaction mixture was stirred under a hydrogen atmosphere at room temperature for 1.5 hours and at 45° C. for 2 hours. The precipitate was removed by filtration through a pad of Celite and washed with methanol (60 mL). Then, the combined filtrate was concentrated under reduced pressure. The residue was co-evaporated with toluene (10 mL), and the residue was then dissolved in DMF (12.5 mL). To the mixture, potassium carbonate (688 mg), potassium iodide (50 mg), and (chloromethyl)cyclopropane (250 µL) were added, and the mixture was stirred at 90° C. for 12 hours. To the reaction mixture, water (30 mL) was added, and the resultant mixture was then extracted with ethyl acetate (35 mL). The organic layer was washed with water (30 mL) and brine (20 mL), dried over anhydrous sodium sulfate, and then concentrated under reduced pressure. The residue was purified by silica gel column chromatography (40% ethyl acetate/hexane). The obtained crude product (1.10 g) was dissolved in dichloromethane (6.0 mL). To the solution, triethylamine (400 µL) and methanesulfonyl chloride (190 µL) were added, and the mixture was stirred at room temperature for 30 minutes. To the reaction mixture, water (20 mL) was added, and the resultant mixture was then extracted with ethyl acetate (30 mL). The organic layer was washed with brine (10 mL), dried over anhydrous sodium sulfate, and then concentrated under reduced pressure. The residue was dissolved in DMF (15 mL). To the mixture, sodium azide (435 mg) was added, and the mixture was stirred at 60° C. for 1 hour. The reaction mixture was cooled to room temperature, water (30 mL) was then added thereto, and the resultant mixture was then extracted with ethyl acetate (30 mL). The organic layer was washed with water (20 mL) and brine (20 mL), dried over anhydrous sodium sulfate, and then concentrated under reduced pressure. The residue was purified by silica gel column chromatography (20% ethyl acetate/hexane). The obtained colorless oil (790 mg) was dissolved in methanol (10 mL). To the solution, 5% palladium-carbon (300 mg) was added, and the reaction mixture was stirred at room temperature for 30 minutes under a hydrogen atmosphere. The precipitate was removed by filtration through a pad of Celite and washed with methanol (60 mL). Then, the combined filtrate was concentrated under reduced pressure to obtain the title compound (730 mg) as a crude product.

Reference Example 245

Synthesis of N-(2-(4-(bromomethyl)phenyl)propan-2-yl)benzenesulfonamide

[Formula 72]

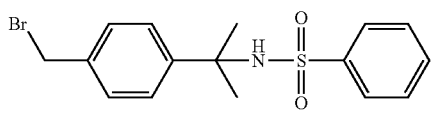

2-p-Tolylpropan-2-amine (550 mg) obtained according to a method described in the document (Tetrahedron Lett., 38, 1241-1244 (1997)) was dissolved in dichloromethane (10 mL). To the solution, triethylamine (1.04 mL) and benzenesulfonyl chloride (670 µL) were added, and the mixture was stirred at room temperature for 3 days. To the reaction mixture, water (30 mL) was added, and the resultant mixture was then extracted with ethyl acetate (30 mL). The organic layer was washed with brine (10 mL), dried over anhydrous sodium sulfate, and then concentrated under reduced pressure. The residue was purified by silica gel column chromatography (20% ethyl acetate/hexane). An aliquot (145 mg) of the obtained yellow solid (511 mg) was dissolved in ethyl acetate (1.5 mL), and the solution was added to an aqueous solution (1.0 mL) of sodium bromate (302 mg). To the reaction mixture, an aqueous solution (1.0 mL) of sodium bisulfite (208 mg) was further gradually added dropwise over 15 minutes, and the mixture was stirred at room temperature for 3.5 hours. To the reaction mixture, an aqueous saturated sodium thiosulfate solution (10 mL) was added, and the resultant mixture was then extracted with ethyl acetate (10 mL). The organic layer was washed with brine (10 mL), dried over anhydrous sodium sulfate, and then concentrated under reduced pressure to obtain the title compound (180 mg) as a crude product.

Reference Example 246

Synthesis of N-(2-(4-(bromomethyl)phenyl)propan-2-yl)-3-methoxybenzenesulfonamide

[Formula 73]

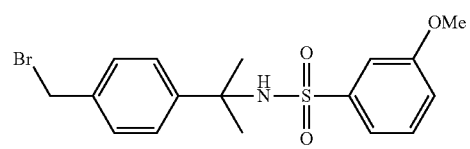

2-p-Tolylpropan-2-amine (745 mg) obtained according to a method described in the document (Tetrahedron Lett., 38, 1241-1244 (1997)) was dissolved in dichloromethane (5.0 mL). To the solution, triethylamine (1.39 mL) and 3-methoxybenzenesulfonyl chloride (1.06 mL) were added, and the mixture was stirred at room temperature for 20 hours. To the reaction mixture, water (30 mL) was added, and the resultant mixture was then extracted with ethyl acetate (30 mL). The organic layer was washed with brine (10 mL), dried over anhydrous sodium sulfate, and then concentrated under reduced pressure. The residue was purified by silica gel column chromatography (20% ethyl acetate/hexane). An aliquot (160 mg) of the obtained pale yellow oil (904 mg) was dissolved in carbon tetrachloride (5.0 mL). To the solution, N-bromosuccinimide (89 mg) and azobisisobutyronitrile (hereinafter, referred to as AIBN; 2.0 mg) were added, and the mixture was heated to reflux at 90° C. for 2 hours. The precipitate was removed by filtration and washed with chloroform (30 mL). Then, the combined filtrate was concentrated under reduced pressure. The residue was suspended in 50% chloroform/hexane (5.0 mL). The precipitate was removed by filtration again and washed with 50% chloroform/hexane (20 mL). Then, the combined filtrate was concentrated under reduced pressure to obtain the title compound (185 mg) as a crude product.

Reference Example 247

Synthesis of N-(2-(4-(bromomethyl)phenyl)propan-2-yl)-3-(cyclopropylmethoxy)benzenesulfonamide

[Formula 74]

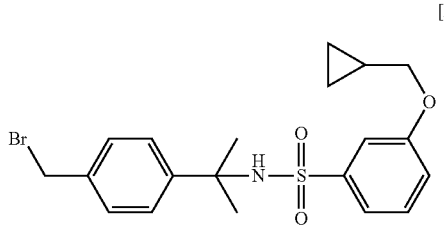

2-p-Tolylpropan-2-amine (298 mg) obtained according to a method described in the document (Tetrahedron Lett., 38, 1241-1244 (1997)) was dissolved in dichloromethane (5.0 mL). To the solution, triethylamine (420 µL) and 3-benzoyloxybenzenesulfonyl chloride (445 mg) obtained according to a method described in the document (J. Pesticide. Chem., 13, 107-115 (1988)) were added, and the mixture was stirred at room temperature for 16 hours. To the reaction mixture, water (15 mL) was added, and the resultant mixture was then extracted with ethyl acetate (20 mL). The organic layer was washed with brine (10 mL), dried over anhydrous sodium sulfate, and then concentrated under reduced pressure. The residue was purified by silica gel column chromatography (20% ethyl acetate/hexane). The obtained colorless gum (316 mg) was dissolved in a solution of methylamine in methanol (40%, 4.0 mL), and the mixture was stirred at room temperature for 30 minutes. The reaction mixture was concentrated under reduced pressure, and the residue was then co-evaporated with toluene (5.0 mL). The residue was then dissolved in DMF (5.0 mL). To the mixture, potassium carbonate (213 mg), potassium iodide (13 mg), and (chloromethyl)cyclopropane (78 µL) were added, and the mixture was stirred at 90° C. for 16 hours. The reaction mixture was cooled to room temperature, water (15 mL) was then added thereto, and the resultant mixture was then extracted with ethyl acetate (20 mL). The organic layer was washed with water (15 mL) and brine (10 mL), dried over anhydrous sodium sulfate, and then concentrated under reduced pressure. The residue was purified by silica gel column chromatography (20% ethyl acetate/hexane). The obtained colorless solid (233 mg) was dissolved in carbon tetrachloride (6.0 mL). To the solution, N-bromosuccinimide (125 mg) and AIBN (3.0 mg) were added, and the mixture was heated to reflux at 90° C. for 2 hours. The precipitate was removed by filtration and washed with chloroform (30 mL). Then, the combined filtrate was concentrated under reduced pressure. To the residue, brine (10 mL) was added, and the resultant mixture was then extracted with 50% ethyl acetate/hexane (10 mL). The organic layer was dried over anhydrous sodium sulfate and then concentrated under reduced pressure to obtain the title compound (255 mg) as a crude product.

Reference Example 248

Synthesis of N-(2-(6-(bromomethyl)pyridin-3-yl)propan-2-yl)-3-(cyclopropylmethoxy)benzenesulfonamide

[Formula 75]

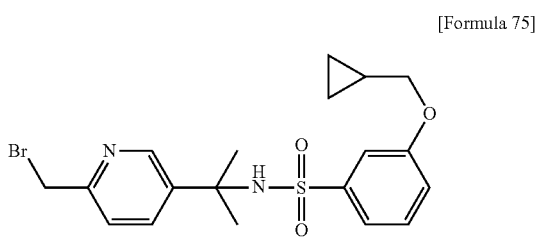 [SMILES: CC(C)(NS(=O)(=O)c1cccc(OCC2CC2)c1)c1ccc(CBr)nc1]

6-(Hydroxymethyl)nicotinonitrile (1.59 g) obtained according to a method described in JP-A-2006-508054 was dissolved in DMF (30 mL). To the solution, imidazole (2.1 g) and tert-butyldimethylsilyl chloride (2.33 g) were added, and the mixture was stirred at room temperature for 1.5 hours. To the reaction mixture, water (60 mL) was added, and the resultant mixture was then extracted with 50% ethyl acetate/hexane (60 mL). The organic layer was washed with brine (30 mL), dried over anhydrous sodium sulfate, and then concentrated under reduced pressure. The residue was purified by silica gel column chromatography (5% ethyl acetate/hexane). The obtained colorless solid (1.99 g) was co-evaporated with toluene (10 mL×3).

Cerium chloride was suspended in THF, and the suspension was vigorously stirred at room temperature for 2 hours. The reaction mixture was ultrasonicated for 5 minutes and then cooled to −78° C. A solution of methyllithium in diethyl ether (1.09 M, 5.5 mL) was gradually added dropwise thereto, and the reaction mixture was stirred at −78° C. for 30 minutes. An aliquot (497 mg) of the above colorless solid which was co-evaporated with toluene was dissolved in THF (2.0 mL), and this solution was gradually added to the reaction mixture at −78° C., and the mixture was stirred at room temperature for 2 hours. To the reaction mixture, an aqueous saturated ammonia solution (5.0 mL) was added, and the mixture was vigorously stirred at room temperature for 30 minutes. The precipitate was removed by filtration through a pad of Celite and washed with THF (100 mL). Then, the combined filtrate was concentrated under reduced pressure. To the residue, water (20 mL) was added, and the resultant mixture was then extracted with chloroform (30 mL). The organic layer was washed with brine (20 mL), dried over anhydrous sodium sulfate, and then concentrated under reduced pressure. The residue was dissolved in dichloromethane (6.0 mL). To the mixture, triethylamine (420 µL) and 3-benzoyloxybenzenesulfonyl chloride (593 mg) obtained according to a method described in the document (J. Pesticide. Chem., 13, 107-115 (1988)) were added, and the mixture was stirred at room temperature for 3 days. To the reaction mixture, water (10 mL) was added, and the resultant mixture was then extracted with ethyl acetate (15 mL). The organic layer was washed with brine (10 mL), dried over anhydrous sodium sulfate, and then concentrated under reduced pressure. The residue was purified by silica gel column chromatography (50% ethyl acetate/hexane). The obtained pale orange oil (700 mg) was dissolved in a solution of methylamine in methanol (40%, 3.0 mL), and the mixture was stirred at room temperature for 20 minutes. The reaction mixture was concentrated under reduced pressure, and the residue was then purified by silica gel column chromatography (60% ethyl acetate/hexane). The obtained pale yellow oil (522 mg) was dissolved in DMF (12 mL). To the solution, potassium carbonate (332 mg), potassium iodide (20 mg), and (chloromethyl)cyclopropane (122 μL) were added, and the mixture was stirred at 90° C. for 18 hours. The reaction mixture was cooled to room temperature, water (20 mL) was then added thereto, and the resultant mixture was then extracted with ethyl acetate (30 mL). The organic layer was washed with water (25 mL) and brine (20 mL), dried over anhydrous sodium sulfate, and then concentrated under reduced pressure. The residue was purified by silica gel column chromatography (5% methanol/chloroform) to obtain a desilylated compound (254 mg). The desilylated compound (249 mg) was dissolved in THF (3.0 mL). To the solution, triphenylphosphine (182 mg) and carbon tetrabromide (230 mg) were added, and the mixture was stirred at room temperature for 1 hour. The reaction mixture was concentrated under reduced pressure, and the residue was then purified by silica gel column chromatography (60% ethyl acetate/hexane) to obtain the title compound (226 mg) as a purple gum.

Example 1

Synthesis of N-(3-(cyclopropylmethoxy)benzyl)-3-((2,4-dioxo-3,4-dihydropyrimidin-1(2H)-yl)methoxy)propane-1-sulfonamide

[Formula 76]

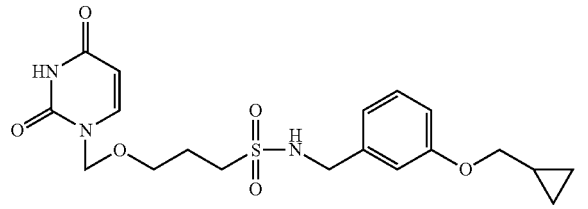

The N-(3-(cyclopropylmethoxy)benzyl)-3-(methoxymethoxy)propane-1-sulfonamide (6.8 g) obtained in Reference Example 88 was dissolved in dichloromethane (20 mL). To the solution, a solution of BCl₃ in dichloromethane (1.0 M, 6.7 mL) was added at 0° C., and the mixture was stirred at room temperature for 1.5 hours. The reaction mixture was concentrated under reduced pressure, and the residue was dissolved in DCE (25 mL).

2,4-Bis(trimethylsilyloxy)pyrimidine (7.1 g) obtained according to a method described in the document (Nucleosides & Nucleotides, 4, 565-585 (1985)) was dissolved in DCE (150 mL). To the solution, the DCE solution (30 mL) of the above residue and iodine (180 mg) were added, and the mixture was heated to reflux at 95° C. for 3.5 hours. The reaction mixture was cooled to room temperature, water (350 mL) and an aqueous saturated sodium thiosulfate solution (10 mL) were then added thereto, and the resultant mixture was then extracted with 10% methanol/chloroform (100 mL×3). The combined organic layer was washed with brine (150 mL), dried over anhydrous sodium sulfate, and then concentrated under reduced pressure. The residue was purified by silica gel column chromatography (100% ethyl acetate) to obtain the title compound (3.5 g, yield: 42%) as a white solid.

¹H-NMR (CDCl₃) δ (ppm): 0.30-0.39 (2H, m), 0.57-0.68 (2H, m), 1.20-1.31 (1H, m), 1.96-2.09 (2H, m), 3.0 (2H, t, J=7.2 Hz), 3.57-3.64 (2H, m), 3.81 (2H, d, J=6.9 Hz), 4.25 (2H, d, J=6.1 Hz), 4.89 (1H, brs), 5.09 (2H, s), 5.75 (1H, dd, J=7.9, 1.8 Hz), 6.76-6.90 (3H, m), 7.20-7.29 (2H, m), 8.9 (1H, brs)

Examples 2 to 94

Compounds shown below were synthesized according to the method of Example 1 from the compounds obtained in Reference Examples 89 to 181, respectively. The results are shown in tables below.

Example 2

(R)-3-((2,4-dioxo-3,4-dihydropyrimidin-1(2H)-yl)methoxy)-N-(1-(3-(2-hydroxy-2-methylpropoxy)phenyl)ethyl)propane-1-sulfonamide Example 3

(S)—N-(2-(3-(cyclopentyloxy)-4-fluorophenyl)-2-hydroxybutyl)-3-((2,4-dioxo-3,4-dihydropyrimidin-1(2H)-yl)methoxy)propane-1-sulfonamide Example 4

N-(3-cyclobutoxybenzyl)-3-((2,4-dioxo-3,4-dihydropyrimidin-1(2H)-yl)methoxy)propane-1-sulfonamide Example 5

(R)—N-(1-(3-(cyclopentyloxy)phenyl)ethyl)-3-((2,4-dioxo-3,4-dihydropyrimidin-1(2H)-yl)methoxy)propane-1-sulfonamide Example 6

3-((2,4-dioxo-3,4-dihydropyrimidin-1(2H)-yl)methoxy)-N—((R)-1-(3-((R)-tetrahydrofuran-3-yloxy)phenyl)ethyl)propane-1-sulfonamide Example 7

N-(3-(cyclopropylmethoxy)-4-fluorobenzyl)-3-((2,4-dioxo-3,4-dihydropyrimidin-1(2H)-yl)methoxy)propane-1-sulfonamide Example 8

(R)—N-(1-(3-(cyclopropylmethoxy)-4-fluorophenyl)ethyl)-3-((2,4-dioxo-3,4-dihydropyrimidin-1(2H)-yl)methoxy)propane-1-sulfonamide

Example 9

(R)—N-(1-(3-(cyclopropylmethoxy)-4-fluorophenyl)-2-methylpropyl)-3-((2,4-dioxo-3,4-dihydropyrimidin-1(2H)-yl)methoxy)propane-1-sulfonamide

Example 10

N-((3-(cyclopropylmethoxy)phenyl)(phenyl)methyl)-3-((2,4-dioxo-3,4-dihydropyrimidin-1(2H)-yl)methoxy)propane-1-sulfonamide

Example 11

N-(1-(3-(cyclopropylmethoxy)phenyl)ethyl)-3-((2,4-dioxo-3,4-dihydropyrimidin-1(2H)-yl)methoxy)propane-1-sulfonamide

Example 12

N-(3-(cyclopropylmethylthio)benzyl)-3-((2,4-dioxo-3,4-dihydropyrimidin-1(2H)-yl)methoxy)propane-1-sulfonamide

Example 13

(R)—N-(1-(3-cyclopropoxyphenyl)ethyl)-3-((2,4-dioxo-3,4-dihydropyrimidin-1(2H)-yl)methoxy)propane-1-sulfonamide

Example 14

N-(3-(3-(cyclopropylmethoxy)phenyl)pentan-3-yl)-3-((2,4-dioxo-3,4-dihydropyrimidin-1(2H)-yl)methoxy)propane-1-sulfonamide

Example 15

3-((2,4-dioxo-3,4-dihydropyrimidin-1(2H)-yl)methoxy)-N-(phenyl(3-(1,1,2,2-tetrafluoroethoxy)phenyl)methyl)propane-1-sulfonamide

Example 16

3-((2,4-dioxo-3,4-dihydropyrimidin-1(2H)-yl)methoxy)-N-((3-isobutoxyphenyl)(phenyl)methyl)propane-1-sulfonamide

Example 17

N-(bis(3-(cyclopropylmethoxy)phenyl)methyl)-3-((2,4-dioxo-3,4-dihydropyrimidin-1(2H)-yl)methoxy)propane-1-sulfonamide

Example 18

3-((2,4-dioxo-3,4-dihydropyrimidin-1(2H)-yl)methoxy)-N-((3-((S)-2-methylbutoxy)phenyl) (phenyl)methyl)propane-1-sulfonamide

Example 19

N-((3-(cyclopropylmethoxy)-4-fluorophenyl)(4-fluorophenyl)methyl)-3-((2,4-dioxo-3,4-dihydropyrimidin-1(2H)-yl)methoxy)propane-1-sulfonamide

Example 20

N-(3-(3-(cyclopropylmethoxy)-4-fluorophenyl)pentan-3-yl)-3-((2,4-dioxo-3,4-dihydropyrimidin-1(2H)-yl)methoxy)propane-1-sulfonamide

Example 21

N-(3-(cyclopentyloxy)benzyl)-3-((2,4-dioxo-3,4-dihydropyrimidin-1(2H)-yl)methoxy)propane-1-sulfonamide

Example 22

(R)—N-(1-(3-(cyclopropylmethoxy)-4-fluorophenyl)propyl)-3-((2,4-dioxo-3,4-dihydropyrimidin-1(2H)-yl)methoxy)propane-1-sulfonamide

Example 23

(R)—N-(1-(3-(cyclopropylmethoxy)phenyl)ethyl)-3-((2,4-dioxo-3,4-dihydropyrimidin-1(2H)-yl)methoxy)propane-1-sulfonamide

Example 24

(R)—N-(1-(3-(cyclopentyloxy)-4-fluorophenyl)ethyl)-3-((2,4-dioxo-3,4-dihydropyrimidin-1(2H)-yl)methoxy)propane-1-sulfonamide

Example 25

N-(1-(3-(cyclopropylmethoxy)-4-fluorophenyl)-2-methylpropyl)-3-((2,4-dioxo-3,4-dihydropyrimidin-1(2H)-yl)methoxy)propane-1-sulfonamide

Example 26

N-(2-(3-(cyclopropylmethoxy)phenyl)propan-2-yl)-3-((2,4-dioxo-3,4-dihydropyrimidin-1(2H)-yl)methoxy)propane-1-sulfonamide

Example 27

(R)—N-(1-(3-(cyclopropylmethoxy)phenyl)propyl)-3-((2,4-dioxo-3,4-dihydropyrimidin-1(2H)-yl)methoxy)propane-1-sulfonamide

Example 28

N-(2-(3-(cyclopropylmethoxy)-4-fluorophenyl)propan-2-yl)-3-((2,4-dioxo-3,4-dihydropyrimidin-1(2H)-yl)methoxy)propane-1-sulfonamide

Example 29

N-((3-(cyclobutylmethoxy)phenyl)(phenyl)methyl)-3-((2,4-dioxo-3,4-dihydropyrimidin-1(2H)-yl)methoxy)propane-1-sulfonamide

Example 30

N-(cyclopropyl(3-(cyclopropylmethoxy)phenyl)methyl)-3-((2,4-dioxo-3,4-dihydropyrimidin-1(2H)-yl)methoxy)propane-1-sulfonamide

Example 31

N-(1-(3-(cyclopropylmethoxy)phenyl)-2-methylpropyl)-3-((2,4-dioxo-3,4-dihydropyrimidin-1(2H)-yl)methoxy)propane-1-sulfonamide

Example 32

N-(1-(3-(cyclopentyloxy)phenyl)ethyl)-3-((2,4-dioxo-3,4-dihydropyrimidin-1(2H)-yl)methoxy)propane-1-sulfonamide

Example 33

N-(3-cyclopropoxybenzyl)-3-((2,4-dioxo-3,4-dihydropyrimidin-1(2H)-yl)methoxy)propane-1-sulfonamide

Example 34

N-(1-(3-(cyclopropylmethoxy)-4-fluorophenyl)propyl)-3-((2,4-dioxo-3,4-dihydropyrimidin-1(2H)-yl)methoxy)propane-1-sulfonamide

Example 35

(S)—N-(1-(3-(cyclopropylmethoxy)-4-fluorophenyl)-2-methylpropyl)-3-((2,4-dioxo-3,4-dihydropyrimidin-1(2H)-yl)methoxy)propane-1-sulfonamide

Example 36

N-(1-(3-(cyclopropylmethoxy)-4-fluorophenyl)ethyl)-3-((2,4-dioxo-3,4-dihydropyrimidin-1(2H)-yl)methoxy)propane-1-sulfonamide

Example 37

(R)—N-((3-(cyclopropylmethoxy)-4-fluorophenyl)(4-fluorophenyl)methyl)-3-((2,4-dioxo-3,4-dihydropyrimidin-1(2H)-yl)methoxy)propane-1-sulfonamide

Example 38

(S)—N-((3-(cyclopropylmethoxy)-4-fluorophenyl)(thiophen-2-yl)methyl)-3-((2,4-dioxo-3,4-dihydropyrimidin-1(2H)-yl)methoxy)propane-1-sulfonamide

Example 39

N-(1-(3-(cyclopropylmethoxy)phenyl)cyclopentyl)-3-((2,4-dioxo-3,4-dihydropyrimidin-1(2H)-yl)methoxy)propane-1-sulfonamide

Example 40

(R)—N-(cyclopropyl(3-(cyclopropylmethoxy)-4-fluorophenyl)methyl)-3-((2,4-dioxo-3,4-dihydropyrimidin-1(2H)-yl)methoxy)propane-1-sulfonamide

Example 41

(R)—N-(1-(3-(cyclopentyloxy)phenyl)propyl)-3-((2,4-dioxo-3,4-dihydropyrimidin-1(2H)-yl)methoxy)propane-1-sulfonamide

Example 42

(R)—N-((3-(cyclopentyloxy)phenyl)(cyclopropyl)methyl)-3-((2,4-dioxo-3,4-dihydropyrimidin-1(2H)-yl)methoxy)propane-1-sulfonamide

Example 43

(R)—N-(1-(3-cyclopropoxyphenyl)propyl)-3-((2,4-dioxo-3,4-dihydropyrimidin-1(2H)-yl)methoxy)propane-1-sulfonamide

Example 44

N-(3-(cyclopentyloxy)-4-fluorobenzyl)-3-((2,4-dioxo-3,4-dihydropyrimidin-1(2H)-yl)methoxy)propane-1-sulfonamide

Example 45

N-(3-(cyclohexyloxy)benzyl)-3-((2,4-dioxo-3,4-dihydropyrimidin-1(2H)-yl)methoxy)propane-1-sulfonamide

Example 46

3-((2,4-dioxo-3,4-dihydropyrimidin-1(2H)-yl)methoxy)-N-(3-(tetrahydro-2H-pyran-4-yloxy)benzyl)propane-1-sulfonamide

Example 47

(R)-3-((2,4-dioxo-3,4-dihydropyrimidin-1(2H)-yl)methoxy)-N-(1-(3-(tetrahydro-2H-pyran-4-yloxy)phenyl)ethyl)propane-1-sulfonamide

Example 48

(R)-3-((2,4-dioxo-3,4-dihydropyrimidin-1(2H)-yl)methoxy)-N-(1-(4-fluoro-3-(tetrahydro-2H-pyran-4-yloxy)phenyl)ethyl)propane-1-sulfonamide

Example 49

3-((2,4-dioxo-3,4-dihydropyrimidin-1(2H)-yl)methoxy)-N—((R)-1-(3-((S)-tetrahydrofuran-3-yloxy)phenyl)ethyl)propane-1-sulfonamide

Example 50

N-(3-(1,3-difluoropropan-2-yloxy)benzyl)-3-((2,4-dioxo-3,4-dihydropyrimidin-1(2H)-yl)methoxy)propane-1-sulfonamide

Example 51

(R)-3-((2,4-dioxo-3,4-dihydropyrimidin-1(2H)-yl)methoxy)-N-(1-(3-(1,1,2,2-tetrafluoroethoxy)phenyl)ethyl)propane-1-sulfonamide

Example 52

(R)-3-((2,4-dioxo-3,4-dihydropyrimidin-1(2H)-yl)methoxy)-N-(1-(3-(neopentyloxy)phenyl)ethyl)propane-1-sulfonamide

Example 53

(R)-3-((2,4-dioxo-3,4-dihydropyrimidin-1(2H)-yl)methoxy)-N-(1-(3-(2,2,2-trifluoroethoxy)phenyl)ethyl)propane-1-sulfonamide

Example 54

(R)-3-((2,4-dioxo-3,4-dihydropyrimidin-1(2H)-yl)methoxy)-N-(1-(4-fluoro-3-(2,2,2-trifluoroethoxy)phenyl)ethyl)propane-1-sulfonamide

Example 55

(R)-3-((2,4-dioxo-3,4-dihydropyrimidin-1(2H)-yl)methoxy)-N-(1-(3-(perfluoroethoxy)phenyl)ethyl)propane-1-sulfonamide

Example 56

(R)—N-(1-(3-(1,3-difluoropropan-2-yloxy)phenyl)ethyl)-3-((2,4-dioxo-3,4-dihydropyrimidin-1(2H)-yl)methoxy)propane-1-sulfonamide

Example 57

(R)-3-((2,4-dioxo-3,4-dihydropyrimidin-1(2H)-yl)methoxy)-N-(1-(3-(prop-2-ynyloxy)phenyl)ethyl)propane-1-sulfonamide

Example 58

(R)-3-((2,4-dioxo-3,4-dihydropyrimidin-1(2H)-yl)methoxy)-N-(1-(3-isobutoxyphenyl)ethyl)propane-1-sulfonamide

Example 59

3-((2,4-dioxo-3,4-dihydropyrimidin-1(2H)-yl)methoxy)-N—((R)-1-(3-((S)-2-methylbutoxy)phenyl)ethyl)propane-1-sulfonamide

Example 60

(R)-3-((2,4-dioxo-3,4-dihydropyrimidin-1(2H)-yl)methoxy)-N-(1-(3-((1-methylcyclopropyl)methoxy)phenyl)ethyl)propane-1-sulfonamide

Example 61

(R)—N-(1-(3-(2,2-difluoroethoxy)phenyl)ethyl)-3-((2,4-dioxo-3,4-dihydropyrimidin-1(2H)-yl)methoxy)propane-1-sulfonamide

Example 62

N—((R)-1-(3-((S)-but-3-yn-2-yloxy)phenyl)ethyl)-3-((2,4-dioxo-3,4-dihydropyrimidin-1(2H)-yl)methoxy)propane-1-sulfonamide

Example 63

N—((R)-1-(3-((R)-but-3-yn-2-yloxy)phenyl)ethyl)-3-((2,4-dioxo-3,4-dihydropyrimidin-1(2H)-yl)methoxy)propane-1-sulfonamide

Example 64

(R)-3-((2,4-dioxo-3,4-dihydropyrimidin-1(2H)-yl)methoxy)-N-(1-(3-(fluoromethoxy)phenyl)ethyl)propane-1-sulfonamide

Example 65

(R)—N-(1-(3-(cyclopentylmethoxy)phenyl)ethyl)-3-((2,4-dioxo-3,4-dihydropyrimidin-1(2H)-yl)methoxy)propane-1-sulfonamide

Example 66

N—((R)-1-(3-((R)-1-methylpropoxy)phenyl)ethyl)-3-((2,4-dioxo-3,4-dihydropyrimidin-1(2H)-yl)methoxy)propane-1-sulfonamide

Example 67

N—((R)-1-(3-((s)-1-methylpropoxy)phenyl)ethyl)-3-((2,4-dioxo-3,4-dihydropyrimidin-1(2H)-yl)methoxy)propane-1-sulfonamide

Example 68

(R)—N-(1-(3-(2,2-difluoroethoxy)-4-fluorophenyl)ethyl)-3-((2,4-dioxo-3,4-dihydropyrimidin-1(2H)-yl)methoxy)propane-1-sulfonamide

Example 69

(R)—N-(1-(3-(allyloxy)phenyl)ethyl)-3-((2,4-dioxo-3,4-dihydropyrimidin-1(2H)-yl)methoxy)propane-1-sulfonamide

Example 70

3-((2,4-dioxo-3,4-dihydropyrimidin-1(2H)-yl)methoxy)-N—((R)-1-(3-((S)-pentan-2-yloxy)phenyl)ethyl)propane-1-sulfonamide

Example 71

3-((2,4-dioxo-3,4-dihydropyrimidin-1(2H)-yl)methoxy)-N—((R)-1-(3-((R)-pentan-2-yloxy)phenyl)ethyl)propane-1-sulfonamide

Example 72

(R)-3-((2,4-dioxo-3,4-dihydropyrimidin-1(2H)-yl)methoxy)-N-(1-(3-(2,2,3,3,3-pentafluoropropoxy)phenyl)ethyl)propane-1-sulfonamide

Example 73

(R)—N-(1-(3-(2-cyclopropylethoxy)phenyl)ethyl)-3-((2,4-dioxo-3,4-dihydropyrimidin-1(2H)-yl)methoxy)propane-1-sulfonamide

Example 74

N-benzyl-3-((2,4-dioxo-3,4-dihydropyrimidin-1(2H)-yl)methoxy)propane-1-sulfonamide

Example 75

3-((2,4-dioxo-3,4-dihydropyrimidin-1(2H)-yl)methoxy)-N-(2-phenylpropan-2-yl)propane-1-sulfonamide

Example 76

N-benzhydryl-3-((2,4-dioxo-3,4-dihydropyrimidin-1(2H)-yl)methoxy)propane-1-sulfonamide

Example 77

3-((2,4-dioxo-3,4-dihydropyrimidin-1(2H)-yl)methoxy)-N-(phenyl(o-tolyl)methyl)propane-1-sulfonamide

Example 78

N-(bis(4-fluorophenyl)methyl)-3-((2,4-dioxo-3,4-dihydropyrimidin-1(2H)-yl)methoxy)propane-1-sulfonamide

Example 79

(R)-1-((3-(2-benzhydrylpyrrolidin-1-ylsulfonyl)propoxy)methyl)pyrimidine-2,4(1H, 3H)-dione

Example 80

(R)-3-((2,4-dioxo-3,4-dihydropyrimidin-1(2H)-yl)-methoxy)-N-(1-hydroxy-4-methyl-1,1-diphenylpentan-2-yl)propane-1-sulfonamide

Example 81

3-((2,4-dioxo-3,4-dihydropyrimidin-1(2H)-yl)methoxy)-N-(1-phenylcyclopentyl)propane-1-sulfonamide

Example 82

(R)-3-((2,4-dioxo-3,4-dihydropyrimidin-1(2H)-yl)methoxy)-N-(1-phenylethyl)propane-1-sulfonamide

Example 83

(R)-3-((2,4-dioxo-3,4-dihydropyrimidin-1(2H)-yl)methoxy)-N-(1-phenylpropyl)propane-1-sulfonamide

Example 84

(R)-3-((2,4-dioxo-3,4-dihydropyrimidin-1(2H)-yl)methoxy)-N-(1-(2-fluorophenyl)ethyl)propane-1-sulfonamide

Example 85

(R)-3-((2,4-dioxo-3,4-dihydropyrimidin-1(2H)-yl)methoxy)-N-(1-(2-methoxyphenyl)ethyl)propane-1-sulfonamide

Example 86

(R)—N-(1-(2-chlorophenyl)ethyl)-3-((2,4-dioxo-3,4-dihydropyrimidin-1(2H)-yl)methoxy)propane-1-sulfonamide

Example 87

(R)-3-((2,4-dioxo-3,4-dihydropyrimidin-1(2H)-yl)-methoxy)-N-(1-(3-fluorophenyl)ethyl)propane-1-sulfonamide

Example 88

(R)—N-(1-(3-chlorophenyl)ethyl)-3-((2,4-dioxo-3,4-dihydropyrimidin-1(2H)-yl)methoxy)propane-1-sulfonamide

Example 89

(R)—N-(1-(3-bromophenyl)ethyl)-3-((2,4-dioxo-3,4-dihydropyrimidin-1(2H)-yl)methoxy)propane-1-sulfonamide

Example 90

(R)—N-(1-(2-bromophenyl)ethyl)-3-((2,4-dioxo-3,4-dihydropyrimidin-1(2H)-yl)methoxy)propane-1-sulfonamide

Example 91

(R)-3-((2,4-dioxo-3,4-dihydropyrimidin-1(2H)-yl)methoxy)-N-(1-(2-ethynylphenyl)ethyl)propane-1-sulfonamide

Example 92

N,N-dibenzyl-3-((2,4-dioxo-3,4-dihydropyrimidin-1(2H)-yl)methoxy)propane-1-sulfonamide

Example 93

3-((2,4-dioxo-3,4-dihydropyrimidin-1(2H)-yl)methoxy)-N-((3-fluorophenyl)(phenyl)methyl)propane-1-sulfonamide

Example 94

N-(1-(4-chlorophenyl)ethyl)-3-((2,4-dioxo-3,4-dihydropyrimidin-1(2H)-yl)methoxy)propane-1-sulfonamide

TABLE 26

| Example | Reference Example No. | Product | Yield (%) | $^1$H-NMR δ (ppm) Form |
|---|---|---|---|---|
| 2 | 90 | 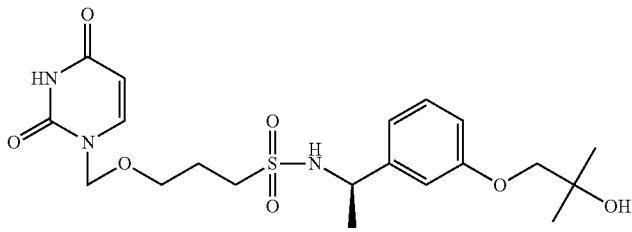 [SMILES: C[C@@H](NS(=O)(=O)CCCOCn1ccc(=O)[nH]c1=O)c1cccc(OCC(C)(C)O)c1] | 52 | (CDCl$_3$) 1.36 (6 H, s), 1.53 (3 H, d, J = 7.0 Hz), 1.88-1.96 (2 H, m), 2.61 (1 H, brs), 2.68-2.89 (2 H, m), 3.42-3.57 (2 H, m), 3.82 (2 H, s), 4.55-4.62 (1 H, m), 4.82 (1 H, brs), 5.03 (2 H, s), 5.75 (1 H, d, J = 8.1 Hz), 6.82-6.92 (3 H, m), 7.19-7.30 (2 H, m), 8.93 (1 H, brs) Foam |

TABLE 26-continued

| Example | Reference Example No. | Product | Yield (%) | ¹H-NMR δ (ppm) Form |
|---|---|---|---|---|
| 3 | 89 | | 49 | (CDCl₃) 0.76 (3 H, t, J = 7.3 Hz), 1.61-2.10 (12 H, m), 2.90-2.99 (3 H, m), 3.40-3.42 (2 H, m), 3.61 (2 H, t, J = 6.2 Hz), 4.82-4.89 (2 H, m), 5.10 (2 H, s), 5.75 (1 H, d, J = 8.1 Hz), 6.81-7.07 (3 H, m), 7.28 (1 H, d, J = 8.1 Hz), 9.20 (1 H, brs) Foam |
| 4 | 91 | | 34 | (CDCl₃) 1.50-2.21 (8 H, m), 2.40-2.52 (1 H, m), 2.99-3.08 (2 H, m), 3.60-3.69 (2 H, m), 4.20-4.29 (2 H, m), 4.60-4.68 (1 H, m), 5.10 (2 H, s), 5.76 (1 H, d, J = 8.1 Hz), 6.74-6.90 (3 H, m), 7.19-7.32 (2 H, m), 8.72 (1 H, brs) Foam |
| 5 | 92 | | 44 | (CDCl₃) 1.53 (3 H, d, J = 6.8 Hz), 1.56-1.98 (10 H, m), 2.67-2.78 (1 H, m), 2.80-2.91 (1 H, m), 3.42-3.60 (2 H, m), 4.51-4.63 (2 H, m), 4.74-4.89 (1 H, m), 5.05 (2 H, s), 5.76 (1 H, dd, J = 7.8, 2.2 Hz), 6.77-6.89 (3 H, m), 7.20-7.27 (2 H, m), 8.31 (1 H, brs) Foam |

TABLE 27

| Example | Reference Example No. | Product | Yield (%) | ¹H-NMR δ (ppm) Form |
|---|---|---|---|---|
| 6 | 93 | | 41 | (CDCl₃) 1.52 (3 H, d, J = 6.8 Hz), 1.85-1.92 (2 H, m), 2.10-2.29 (2 H, m), 2.68-2.88 (2 H, m), 3.43-3.56 (2 H, m), 3.89-4.04 (4 H, m), 4.53-4.61 (1 H, m), 4.92-4.96 (1 H, m), 5.05 (2 H, s), 5.12 (1 H, d, J = 7.0 Hz), 5.76 (1 H, d, J = 8.1 Hz), 6.75-6.92 (3 H, m), 7.20-7.29 (2 H, m), 9.11 (1 H, brs) Foam |
| 7 | 94 | | 27 | (CDCl₃) 0.31-0.40 (2 H, m), 0.55-0.69 (2 H, m), 1.19-1.36 (1 H, m), 1.90-2.10 (2 H, m), 2.98 (2 H, t, J = 7.8 Hz), 3.62 (2 H, t, J = 5.9 Hz), 3.87 (2 H, d, J = 6.8 Hz), 4.21 (2 H, d, J = 5.9 Hz), 5.09 (2 H, s), 5.28-5.39 (1 H, m), 5.77 (1 H, d, J = 7.8 Hz), 6.77-7.09 (3 H, m), 7.29 (1 H, d, J = 8.1 Hz), 9.51 (1 H, brs) Foam |

TABLE 27-continued

| Example | Reference Example No. | Product | Yield (%) | ¹H-NMR δ (ppm) Form |
|---|---|---|---|---|
| 8 | 95 | 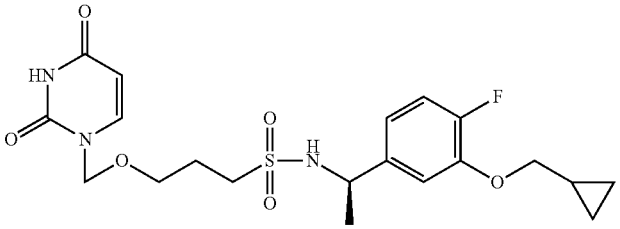 [SMILES: C[C@@H](NS(=O)(=O)CCCOCn1ccc(=O)[nH]c1=O)c1ccc(F)c(OCC2CC2)c1] | 46 | (CDCl₃) 0.31-0.38 (2 H, m), 0.59-0.69 (2 H, m), 1.20-1.38 (1 H, m), 1.52 (3 H, d, J = 6.8 Hz), 1.80-1.98 (2 H, m), 2.51-2.88 (2 H, m), 3.53 (2 H, t, J = 5.9 Hz), 3.88 (2 H, d, J = 7.0 Hz), 4.51-4.62 (1 H, m), 5.06 (2 H, s), 5.14 (1 H, d, J = 6.8 Hz), 5.77 (1 H, dd, J = 8.1 Hz, 1.6 Hz), 6.85-7.11 (3 H, m), 7.29 (1 H, d, J = 7.0 Hz), 9.12 (1 H, brs) Foam |

TABLE 28

| Example | Reference Example No. | Product | Yield (%) | ¹H-NMR δ (ppm) Form |
|---|---|---|---|---|
| 9 | 96 | 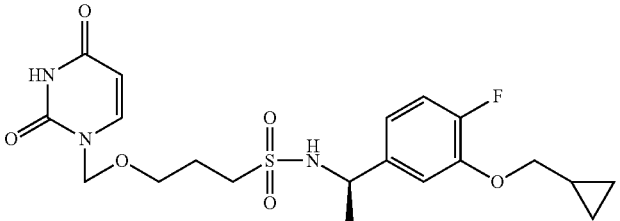 | 39 | (CDCl₃) 0.32-0.40 (2 H, m), 0.60-0.69 (2 H, m), 0.78-0.82 (3 H, m), 1.03-1.07 (3 H, m), 1.21-1.29 (1 H, m), 1.70-2.02 (3 H, m), 2.50-2.85 (2 H, m), 3.47 (2 H, t, J = 5.9 Hz), 3.89 (2 H, d, J = 7.0 Hz), 4.02-4.13 (1 H, m), 5.03 (2 H, s), 5.48 (1 H, brs), 5.78 (1 H, d, J = 8.1 Hz), 6.75-7.09 (3 H, m), 7.23 (1 H, d, J = 7.3 Hz), 9.30 (1 H, brs) Foam |
| 10 | 97 | 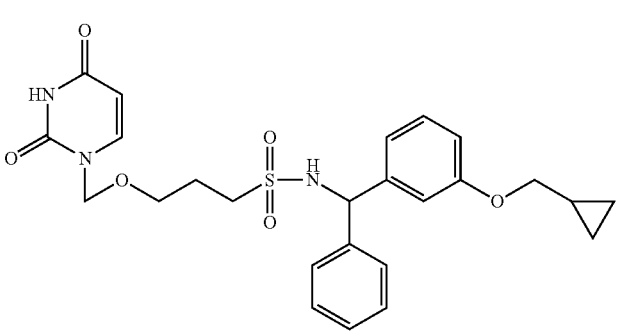 [SMILES: O=c1ccn(COCCCS(=O)(=O)NC(c2ccccc2)c2cccc(OCC3CC3)c2)c(=O)[nH]1] | 55 | (CDCl₃) 0.31-0.37 (2 H, m), 0.61-0.67 (2 H, m), 1.22-1.29 (1 H, m), 1.82-2.00 (2 H, m), 2.82 (2 H, t, J = 6.4 Hz), 3.48 (2 H, t, J = 6.2 Hz), 3.77 (2 H, d, J = 6.9 Hz), 5.02 (2 H, s), 5.33 (1 H, brs), 5.68 (1 H, d, J = 7.4 Hz), 5.74 (1 H, dd, J = 8.0, 2.1 Hz), 6.79-6.92 (3 H, m), 7.20-7.39 (7 H, m), 8.83 (1 H, brs) Foam |
| 11 | 98 | 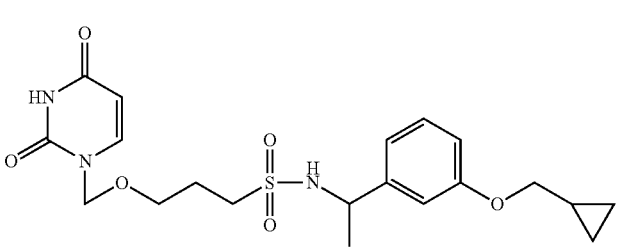 [SMILES: CC(NS(=O)(=O)CCCOCn1ccc(=O)[nH]c1=O)c1cccc(OCC2CC2)c1] | 52 | (CDCl₃) 0.31-0.38 (2 H, m), 0.59-0.67 (2 H, m), 1.19-1.30 (1 H, m), 1.52 (2 H, d, J = 6.8 Hz), 1.78-2.00 (2 H, m), 2.63-2.94 (2 H, m), 3.44-3.59 (2 H, m), 3.81 (2 H, d, J = 6.8 Hz), 4.51-4.62 (1 H, m), 4.84-4.91 (1 H, m), 5.06 (2 H, s), 5.14 (1 H, d, J = 6.8 Hz), 5.77 (1 H, dd, J = 8.1, 2.2 Hz), 6.85-7.05 (3 H, m), 7.20-7.30 (2 H, m), 8.69 (1 H, brs) Foam |

TABLE 29

| Example | Reference Example No. | Product | Yield (%) | ¹H-NMR δ (ppm) Form |
|---|---|---|---|---|
| 12 | 99 | (uracil-CH₂-O-(CH₂)₃-SO₂-NH-CH₂-phenyl-S-CH₂-cyclopropyl) | 32 | (CDCl₃) 0.24-0.28 (2 H, m), 0.56-0.62 (2 H, m), 1.00-1.08 (1 H, m), 1.96-2.09 (2 H, m), 2.87 (2 H, d, J = 7.0 Hz), 3.01 (2 H, t, J = 7.3 Hz), 3.62 (2 H, t, J = 6.2 Hz), 4.25 (2 H, d, J = 6.2 Hz), 5.05 (1 H, brs), 5.09 (2 H, s), 5.76 (1 H, dd, J = 7.8, J = 1.6 Hz), 7.10-7.29 (5 H, m), 9.03 (1 H, brs) Foam |
| 13 | 100 | (uracil-CH₂-O-(CH₂)₃-SO₂-NH-CH(CH₃)-phenyl-O-cyclopropyl) | 47 | (CDCl₃) 0.71-0.85 (4 H, m), 1.54 (3 H, d, J = 6.9 Hz), 1.78-1.96 (2 H, m), 2.62-2.90 (2 H, m), 3.49-3.61 (2 H, m), 3.75-3.88 (1 H, m), 4.51-4.62 (1 H, m), 5.01 (2 H, s), 5.13 (1 H, d, J = 6.9 Hz), 5.74 (1 H, d, J = 7.9 Hz), 6.90-7.10 (3 H, m), 7.19-7.32 (2 H, m), 9.11 (1 H, brs) Foam |
| 14 | 101 | (uracil-CH₂-O-(CH₂)₃-SO₂-NH-C(Et)₂-phenyl-O-CH₂-cyclopropyl) | 38 | (DMSO-d₆) 0.28-0.33 (2 H, m), 0.51-0.59 (2 H, m), 0.68 (6 H, t, J = 7.3 Hz), 1.11-1.23 (1 H, m), 1.71-1.98 (4 H, m), 2.00-2.18 (2 H, m), 2.32-2.39 (2 H, m), 3.35-3.44 (2 H, m), 3.78 (2 H, d, J = 7.0 Hz), 4.99 (2 H, s), 5.60 (1 H, d, J = 7.8 Hz), 6.74-7.22 (5 H, m), 7.62 (1 H, d, J = 7.8 Hz), 11.3 (1 H, brs) Foam |

TABLE 30

| Example | Reference Example No. | Product | Yield (%) | ¹H-NMR δ (ppm) Form |
|---|---|---|---|---|
| 15 | 102 | (uracil-CH₂-O-(CH₂)₃-SO₂-NH-CH(phenyl)-phenyl-OCF₂CHF₂) | 31 | (CDCl₃) 1.84-1.94 (2 H, m), 2.79-2.86 (2 H, m), 3.47 (2 H, t, J = 5.9 Hz), 5.00 (2 H, s), 5.70-6.12 (4 H, m), 7.14-7.39 (10 H, m), 9.25 (1 H, brs) Foam |

TABLE 30-continued

| Example | Reference Example No. | Product | Yield (%) | $^1$H-NMR δ (ppm) Form |
|---|---|---|---|---|
| 16 | 103 | | 42 | (CDCl$_3$)<br>1.00 (6 H, d, J = 6.5 Hz), 1.82-1.96 (2 H, m), 2.00-2.09 (1 H, m), 2.81 (2 H, t, J = 7.3 Hz), 3.48 (2 H, t, J = 5.9 Hz), 3.68 (2 H, d, J = 6.5 Hz), 5.01 (2 H, s), 5.37 (1 H, d, J = 7.6 Hz), 5.67 (1 H, d, J = 7.6 Hz), 5.74 (1 H, dd, J = 8.1, 2.2 Hz), 6.79-6.90 (3 H, m), 7.17-7.38 (7 H, m), 8.90 (1 H, brs)<br>Foam |
| 17 | 104 | | 39 | (CDCl$_3$)<br>0.26-0.31 (4 H, m), 0.51-0.58 (4 H, m), 1.12-1.24 (2 H, m), 1.61-1.78 (2 H, m), 2.69-2.78 (2 H, m), 3.32-3.40 (2 H, m), 3.76 (4 H, d, J = 6.8 Hz), 4.93 (2 H, s), 5.48 (1 H, brs), 5.59 (1 H, d, J = 8.1 Hz), 6.75-6.98 (7 H, m), 7.19 (2 H, t, J = 8.1 Hz), 7.57 (1 H, d, J = 8.1 Hz), 8.32 (1 H, brs)<br>Foam |

TABLE 31

| Example | Reference Example No. | Product | Yield (%) | $^1$H-NMR δ (ppm) Form |
|---|---|---|---|---|
| 18 | 105 | | 44 | (CDCl$_3$)<br>0.93 (3 H, t, J = 7.3 Hz), 0.99 (3 H, d, J = 6.5 Hz), 1.52-1.59 (2 H, m), 1.77-1.99 (3 H, m), 2.82 (2 H, t, J = 7.6 Hz), 3.50 (2 H, t, J = 6.2 Hz), 3.75 (2 H, ddd, J = 8.1, 8.1, 1.6 Hz), 5.00 (1 H, brs), 5.03 (2 H, s), 5.69 (1 H, d, J = 7.6 Hz), 5.74 (1 H, dd, J = 8.1, 2.2 Hz), 6.79-6.89 (3 H, m), 7.17-7.36 (7 H, m), 8.19 (1 H, brs)<br>Foam |
| 19 | 106 | | 34 | (CDCl$_3$)<br>0.31-0.37 (2 H, m), 0.61-0.67 (2 H, m), 1.23-1.30 (1 H, m), 1.86-2.05 (2 H, m), 2.81 (2 H, t, J = 7.3 Hz), 3.52 (2 H, t, J = 6.2 Hz), 3.83 (2 H, d, J = 7.0 Hz), 4.09-4.18 (1 H, m), 5.03 (2 H, s), 5.62-5.69 (1 H, m), 5.74 (1 H, d, J = 7.8 Hz), 6.77-7.31 (8 H, m), 8.99 (1 H, brs)<br>Foam |

TABLE 31-continued

| Example | Reference Example No. | Product | Yield (%) | $^1$H-NMR δ (ppm) Form |
|---|---|---|---|---|
| 20 | 107 | 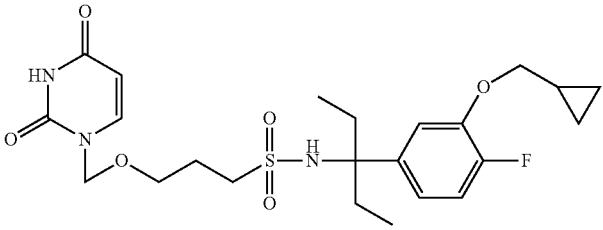 [SMILES: CCC(CC)(NS(=O)(=O)CCCOCn1ccc(=O)[nH]c1=O)c1ccc(F)c(OCC2CC2)c1] | 25 | (CDCl$_3$) 0.27-0.31 (2 H, m), 0.61-0.68 (2 H, m), 0.69 (6 H, t, J = 6.2 Hz), 1.21-1.29 (1 H, m), 1.81-1.98 (4 H, m), 2.08-2.22 (2 H, m), 2.64 (2 H, t, J = 6.8 Hz), 3.56 (2 H, t, J = 5.9 Hz), 3.78 (2 H, d, J = 7.0 Hz), 4.51 (1 H, brs), 5.08 (2 H, s), 5.77 (1 H, d, J = 7.8 Hz), 6.91-7.12 (3 H, m), 7.29 (1 H, d, J = 7.3 Hz), 8.40 (1 H, brs) Foam |

TABLE 32

| Example | Reference Example No. | Product | Yield (%) | $^1$H-NMR δ (ppm) Form |
|---|---|---|---|---|
| 21 | 108 | 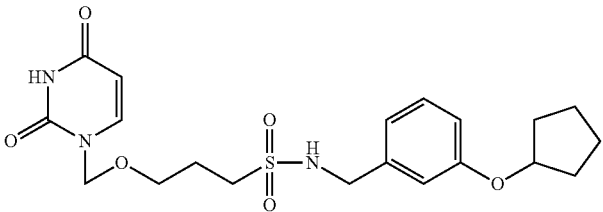 [SMILES: O=c1ccn(COCCCS(=O)(=O)NCc2cccc(OC3CCCC3)c2)c(=O)[nH]1] | 38 | (CDCl$_3$) 1.68-1.97 (8 H, m), 1.98-2.16 (2 H, m), 2.92-3.08 (2 H, m), 3.60-3.69 (2 H, m), 4.25 (2 H, d, J = 6.1 Hz), 4.74-4.79 (2 H, m), 5.01 (2 H, s), 5.76 (1 H, dd, J = 7.9, 2.1 Hz), 6.78-6.90 (3 H, m), 7.19-7.29 (2 H, m), 8.66 (1 H, brs) Foam |
| 22 | 109 | 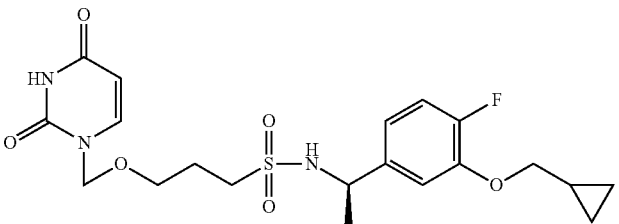 | 44 | (CDCl$_3$) 0.32-0.39 (2 H, m), 0.63-0.71 (2 H, m), 0.89 (3 H, t, J = 7.3 Hz), 1.20-1.38 (1 H, m), 1.71-1.99 (4 H, m), 2.53-2.89 (2 H, m), 3.41-3.50 (2 H, m), 3.88 (2 H, d, J = 7.1 Hz), 4.21-4.38 (1 H, m), 5.04 (2 H, s), 5.12 (1 H, d, J = 7.1 Hz), 5.78 (1 H, dd, J = 7.9, 2.0 Hz), 6.75-7.09 (3 H, m), 7.20 (1 H, d, J = 7.9 Hz), 8.97 (1 H, brs) Foam |
| 23 | 110 | 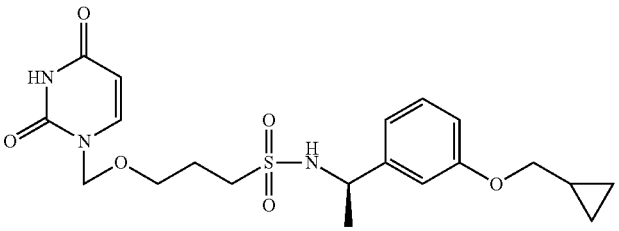 [SMILES: C[C@@H](NS(=O)(=O)CCCOCn1ccc(=O)[nH]c1=O)c1cccc(OCC2CC2)c1] | 40 | (CDCl$_3$) 0.31-0.38 (2 H, m), 0.59-0.67 (2 H, m), 1.19-1.30 (1 H, m), 1.52 (3 H, d, J = 6.8 Hz), 1.78-2.00 (2 H, m), 2.51-2.88 (2 H, m), 3.44-3.59 (2 H, m), 3.88 (2 H, d, J = 7.0 Hz), 4.52-4.62 (1 H, m), 5.06 (2 H, s), 5.14 (1 H, d, J = 7.0 Hz), 5.77 (1 H, d, J = 7.8 Hz), 6.85-6.99 (3 H, m), 7.20-7.30 (2 H, m), 9.12 (1 H, brs) Foam |

TABLE 33

| Example | Reference Example No. | Product | Yield (%) | ¹H-NMR δ (ppm) Form |
|---|---|---|---|---|
| 24 | 111 | (structure) | 40 | (CDCl$_3$) 1.52 (3 H, d, J = 7.0 Hz), 1.61-1.70 (2 H, m), 1.76-2.00 (8 H, m), 2.65-2.90 (2 H, m), 3.53 (2 H, t, J = 5.9 Hz), 4.52-4.61 (1 H, m), 4.77-4.85 (1 H, m), 5.05 (2 H, s), 5.06-5.11 (1 H, m), 5.77 (1 H, dd, J = 8.1, 2.2 Hz), 6.92-7.04 (3 H, m), 7.19 (1 H, d, J = 8.1 Hz), 9.04 (1 H, brs) Foam |
| 25 | 112 | (structure) | 46 | (CDCl$_3$) 0.32-0.40 (2 H, m), 0.60-0.69 (2 H, m), 0.78-0.82 (3 H, m), 1.03-1.07 (3 H, m), 1.21-1.29 (1 H, m), 1.70-2.02 (3 H, m), 2.50-2.85 (2 H, m), 3.47 (2 H, t, J = 5.9 Hz), 3.89 (2 H, d, J = 7.0 Hz), 4.02-4.13 (1 H, m), 5.03 (2 H, s), 5.23 (1 H, d, J = 8.1 Hz), 5.78 (1 H, d, J = 8.1 Hz), 6.75-7.09 (3 H, m), 7.23 (1 H, d, J = 7.8 Hz), 8.8 (1 H, brs) Foam |
| 26 | 113 | (structure) | 31 | (CDCl$_3$) 0.30-0.35 (2 H, m), 0.62-0.73 (2 H, m), 1.22-1.31 (1 H, m), 1.74 (6 H, s), 1.96-2.08 (2 H, m), 2.81 (2 H, t, J = 7.0 Hz), 3.59 (2 H, t, J = 5.9 Hz), 3.81 (2 H, d, J = 7.6 Hz), 4.63 (1 H, brs), 5.10 (2 H, s), 5.76 (1 H, dd, J = 7.8, 1.1 Hz), 6.76-6.88 (1 H, m), 7.05-7.10 (2 H, m), 7.24-7.30 (2 H, m), 8.35 (1 H, brs) Foam |

TABLE 34

| Example | Reference Example No. | Product | Yield (%) | ¹H-NMR δ (ppm) Form |
|---|---|---|---|---|
| 27 | 114 | (structure) | 42 | (CDCl$_3$) 0.32-0.37 (2 H, m), 0.60-0.70 (2 H, m), 0.88 (3 H, t, J = 7.4 Hz), 1.18-1.32 (1 H, m), 1.70-2.01 (4 H, m), 2.53-2.90 (2 H, m), 3.40-3.55 (2 H, m), 3.83 (2 H, d, J = 6.9 Hz), 4.21-4.38 (1 H, m), 4.85 (1 H, d, J = 7.4 Hz), 5.02 (2 H, s), 5.67 (1 H, d, J = 8.0 Hz), 6.80-6.91 (3 H, m), 7.20-7.35 (2 H, m), 8.58 (1 H, brs) Foam |
| 28 | 115 | (structure) | 25 | (DMSO-d$_6$) 0.30-0.35 (2 H, m), 0.54-0.62 (2 H, m), 1.18-1.26 (1 H, m), 1.56 (6 H, s), 1.74-1.88 (2 H, m), 2.62-2.78 (2 H, m), 3.42-3.50 (2 H, m), 3.87 (2 H, d, J = 7.3 Hz), 5.02 (2 H, s), 5.60 (1 H, d, J = 7.86 Hz), 6.90-7.48 (4 H, m), 7.65 (1 H, d, J = 7.8 Hz), 11.3 (1 H, brs) Foam |

TABLE 34-continued

| Example | Reference Example No. | Product | Yield (%) | ¹H-NMR δ (ppm) Form |
|---|---|---|---|---|
| 29 | 116 | (structure) | 36 | (CDCl₃) 1.68-1.78 (2 H, m), 1.81-2.02 (4 H, m), 2.06-2.21 (2 H, m), 2.68-2.83 (1 H, m), 2.83-2.90 (2 H, m), 3.41-3.50 (2 H, m), 3.89 (2 H, d, J = 6.8 Hz), 5.01 (2 H, s), 5.42 (1 H, d, J = 7.6 Hz), 5.67 (1 H, d, J = 7.3 Hz), 5.74 (1 H, d, J = 7.3 Hz), 6.76-6.90 (3 H, m), 7.19-7.40 (7 H, m), 9.00 (1 H, brs) Foam |

TABLE 35

| Example | Reference Example No. | Product | Yield (%) | ¹H-NMR δ (ppm) Form |
|---|---|---|---|---|
| 30 | 117 | (structure) | 23 | (CDCl₃) 0.31-0.40 (2 H, m), 0.46-0.71 (6 H, m), 1.16-1.29 (2 H, m), 1.82-2.00 (2 H, m), 2.60-2.89 (2 H, m), 3.42-3.53 (2 H, m), 3.67-3.88 (3 H, m), 5.04 (2 H, s), 5.12 (1 H, brs), 5.76 (1 H, d, J = 7.8 Hz), 6.82-7.00 (3 H, m), 7.20-7.29 (2 H, m), 9.16 (1 H, brs) Foam |
| 31 | 118 | (structure) | 46 | (CDCl₃) 0.32-0.38 (2 H, m), 0.61-0.68 (2 H, m), 0.75-0.81 (3 H, m), 1.01-1.05 (3 H, m), 1.20-1.28 (1 H, m), 1.68-2.00 (3 H, m), 2.50-2.82 (2 H, m), 3.38-3.49 (2 H, m), 3.80 (2 H, d, J = 6.8 Hz), 3.99-4.10 (1 H, m), 5.01 (2 H, s), 5.36 (1 H, d, J = 8.6 Hz), 5.77 (1 H, d, J = 7.8 Hz), 6.78-6.87 (3 H, m), 7.19-7.31 (2 H, m), 9.01 (1 H, brs) Foam |
| 32 | 119 | (structure) | 44 | (CDCl₃) 1.53 (3 H, d, J = 6.8 Hz), 1.56-1.98 (10 H, m), 2.67-2.78 (1 H, m), 2.80-2.91 (1 H, m), 3.42-3.60 (2 H, m), 4.51-4.63 (1 H, m), 4.74-4.89 (2 H, m), 5.05 (2 H, s), 5.76 (1 H, dd, J = 7.8 Hz, 2.2 Hz), 6.77-6.89 (3 H, m), 7.20-7.27 (2 H, m), 8.76 (1 H, brs) Foam |
| 33 | 120 | (structure) | 50 | (CDCl₃) 0.74-0.81 (4 H, m), 1.96-2.08 (2 H, m), 3.01 (2 H, t, J = 7.0 Hz), 3.62 (2 H, t, J = 5.94 Hz), 3.71-3.77 (1 H, m), 4.26 (2 H, d, J = 5.9 Hz), 5.05 (1 H, brs), 5.09 (2 H, s), 5.76 (1 H, dd, J = 8.1, 2.2 Hz), 6.91-7.02 (3 H, m), 7.23-7.29 (2 H, m), 9.11 (1 H, brs) Foam |

TABLE 36

| Example | Reference Example No. | Product | Yield (%) | ¹H-NMR δ (ppm) Form |
|---|---|---|---|---|
| 34 | 121 | | 46 | (CDCl₃) 0.32-0.39 (2 H, m), 0.63-0.71 (2 H, m), 0.89 (3 H, t, J = 7.3 Hz), 1.20-1.38 (1 H, m), 1.71-1.99 (4 H, m), 2.53-2.89 (2 H, m), 3.41-3.50 (2 H, m), 3.88 (2 H, d, J = 7.1 Hz), 4.21-4.38 (1 H, m), 5.04 (2 H, s), 5.22 (1 H, d, J = 7.0 Hz), 5.78 (1 H, dd, J = 7.9, 2.0 Hz), 6.75-7.09 (3 H, m), 7.20 (1 H, d, J = 8.1 Hz), 9.11 (1 H, brs) Foam |
| 35 | 122 | | 40 | (CDCl₃) 0.32-0.40 (2 H, m), 0.60-0.69 (2 H, m), 0.78-0.82 (3 H, m), 1.03-1.07 (3 H, m), 1.21-1.29 (1 H, m), 1.70-2.02 (3 H, m), 2.50-2.85 (2 H, m), 3.47 (2 H, t, J = 5.9 Hz), 3.89 (2 H, d, J = 7.0 Hz), 4.02-4.13 (1 H, m), 5.03 (2 H, s), 5.42 (1 H, d, 8.4 Hz), 5.78 (1 H, d, J = 8.1 Hz), 6.75-7.09 (3 H, m), 7.23 (1 H, d, J = 7.3 Hz), 9.20 (1 H, brs) Foam |
| 36 | 123 | | 48 | (CDCl₃) 0.31-0.38 (2 H, m), 0.59-0.69 (2 H, m), 1.20-1.38 (1 H, m), 1.52 (3 H, d, J = 6.8 Hz), 1.80-1.96 (2 H, m), 2.51-2.88 (2 H, m), 3.53 (2 H, t, J = 5.9 Hz), 3.88 (2 H, d, J = 7.0 Hz), 4.51-4.62 (1 H, m), 5.06 (2 H, s), 5.06-5.19 (1 H, m), 5.77 (1 H, d, J = 8.1 Hz), 6.85-7.11 (3 H, m), 7.29 (1 H, d, J = 7.0 Hz), 9.05 (1 H, brs) Foam |

TABLE 37

| Example | Reference Example No. | Product | Yield (%) | ¹H-NMR δ (ppm) Form |
|---|---|---|---|---|
| 37 | 124 | | 57 | (CDCl3) (0.31-0.37 (2 H, m), 0.61-0.67 (2 H, m), 1.23-1.30 (1 H, m), 1.86-2.05 (2 H, m), 2.81 (2 H, t, J = 7.3 Hz), 3.52 (2 H, t, J = 6.2 Hz), 3.83 (2 H, d, J = 7.0 Hz), 5.03 (2 H, s), 5.45 (1 H, brs), 5.62-5.69 (1 H, m), 5.74 (1 H, d, J = 7.8 Hz), 6.77-7.31 (8 H, m), 8.99 (1 H, brs) Foam |

TABLE 37-continued

| Example | Reference Example No. | Product | Yield (%) | $^1$H-NMR δ (ppm) Form |
|---|---|---|---|---|
| 38 | 125 | 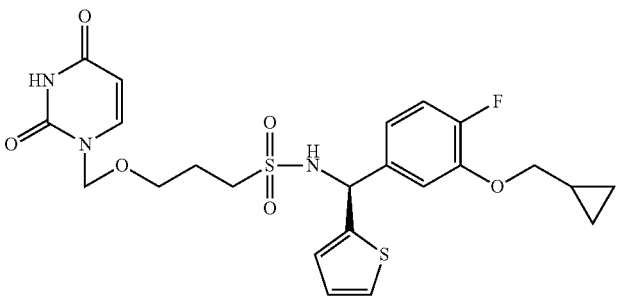 [SMILES: O=c1ccn(COCCCS(=O)(=O)N[C@@H](c2ccc(F)c(OCC3CC3)c2)c2cccs2)c(=O)[nH]1] | 33 | (CDCl$_3$) 0.31-0.38 (2 H, m), 0.61-0.68 (2 H, m), 1.23-1.33 (1 H, m), 1.92-2.01 (2 H, m), 2.85 (2 H, t, J = 6.9 Hz), 3.51-3.57 (1 H, m), 3.86 (2 H, d, J = 6.9 Hz), 5.05 (2 H, s), 5.32 (1 H, brs), 5.76 (1 H, d, J = 8.1 Hz), 5.84-5.89 (1 H, m), 6.89-7.14 (6 H, m), 7.19-7.32 (2 H, m) Foam |
| 39 | 126 | 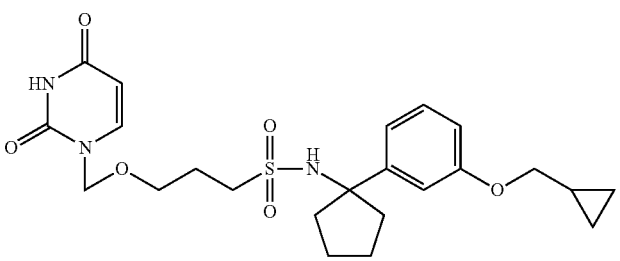 [SMILES: O=c1ccn(COCCCS(=O)(=O)NC2(c3cccc(OCC4CC4)c3)CCCC2)c(=O)[nH]1] | 21 | (CDCl$_3$) 0.31-0.38 (2 H, m), 0.60-0.69 (2 H, m), 1.23-1.31 (1 H, m), 1.74-2.38 (10 H, m), 2.42-2.53 (2 H, m), 3.38-3.45 (2 H, m), 3.81 (2 H, d, J = 6.9 Hz), 4.95 (1 H, brs), 5.06 (2 H, s), 5.77 (1 H, d, J = 7.9 Hz), 6.75-6.83 (1 H, m), 7.02-7.09 (2 H, m), 7.30-7.41 (2 H, m), 8.90 (1 H, brs) Foam |

TABLE 38

| Example | Reference Example No. | Product | Yield (%) | $^1$H-NMR δ (ppm) Form |
|---|---|---|---|---|
| 40 | 127 | 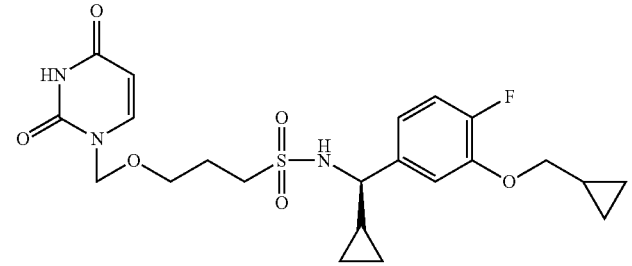 [SMILES: O=c1ccn(COCCCS(=O)(=O)N[C@@H](c2ccc(F)c(OCC3CC3)c2)C2CC2)c(=O)[nH]1] | 39 | (CDCl$_3$) 0.33-0.88 (8 H, m), 1.22-1.40 (2 H, m), 1.89-2.08 (2 H, m), 2.63-2.94 (2 H, m), 3.53-3.58 (2 H, m), 3.73-3.78 (1 H, m), 3.91 (2 H, d, J = 6.8 Hz), 5.08 (2 H, s), 5.20 (1 H, brs), 5.79 (1 H, d, J = 7.8 Hz), 6.90-7.09 (3 H, m), 7.27 (1 H, d, J = 8.1 Hz), 9.08 (1 H, brs) Foam |
| 41 | 128 | 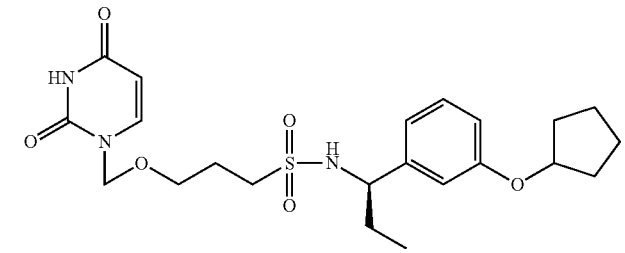 [SMILES: CC[C@@H](NS(=O)(=O)CCCOCn1ccc(=O)[nH]c1=O)c1cccc(OC2CCCC2)c1] | 33 | (CDCl$_3$) 0.90 (3 H, t, J = 7.6 Hz), 1.54-1.98 (12 H, m), 2.52-2.90 (2 H, m), 3.40-3.47 (2 H, m), 4.21-4.28 (1 H, m), 4.74-4.79 (1 H, m), 5.02 (2 H, s), 5.2 (1 H, brs), 5.76 (1 H, d, J = 7.8 Hz), 6.78-6.85 (3 H, m), 7.20-7.27 (2 H, m), 9.12 (1 H, brs) Foam |
| 42 | 129 | 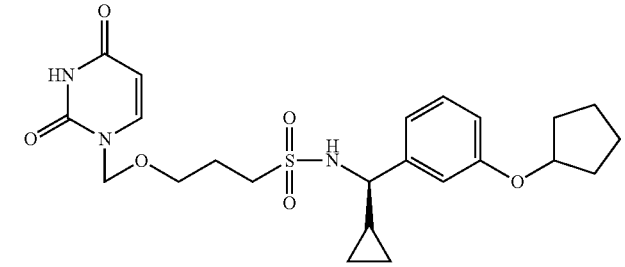 [SMILES: O=c1ccn(COCCCS(=O)(=O)N[C@@H](c2cccc(OC3CCCC3)c2)C2CC2)c(=O)[nH]1] | 50 | (CDCl$_3$) 0.30-0.77 (4 H, m), 1.14-1.29 (1 H, m), 1.63-2.00 (10 H, m), 2.61-2.89 (2 H, m), 3.42-3.56 (2 H, m), 3.67-3.81 (1 H, m), 4.74-4.79 (1 H, m), 4.90-4.98 (1 H, m), 5.04 (2 H, s), 5.76 (1 H, dd, J = 7.8, 1.9 Hz), 6.78-6.94 (3 H, m), 7.18-7.30 (2 H, m), 8.80 (1 H, brs) Foam |

TABLE 39

| Example | Reference Example No. | Product | Yield (%) | ¹H-NMR δ (ppm) Form |
|---|---|---|---|---|
| 43 | 130 | (structure) | 47 | (CDCl₃) 0.74-0.81 (4H, m), 0.90 (3H, t, J = 7.3 Hz), 1.81-1.96 (4H, m), 2.60-2.87 (2H, m), 3.34-3.51 (2H, m), 3.70-3.75 (1H, m), 4.11-4.22 (1H, m), 4.89-5.02 (1H, m), 5.03 (2H, s), 5.76 (1H, dd, J = 8.1, 2.2 Hz), 6.85-7.04 (3H, m), 7.19-7.29 (2H, m), 8.89 (1H, brs) Foam |
| 44 | 131 | (structure) | 31 | (CDCl₃) 1.73-1.96 (8H, m), 1.99-2.15 (2H, m), 2.99 (2H, t, J = 7.3 Hz), 3.61-3.66 (2H, m), 4.23 (2H, d, J = 5.9 Hz), 4.76-4.88 (2H, m), 5.1 (2H, s), 5.76 (1H, dd, J = 7.9, 2.1 Hz), 6.74-7.12 (3H, m), 7.26 (1H, d, J = 7.9 Hz), 8.66 (1H, brs) Foam |
| 45 | 132 | (structure) | 52 | (CDCl₃) 1.23-1.65 (8H, m), 1.74-1.88 (2H, m), 1.95-2.08 (2H, m), 3.01 (2H, t, J = 7.3 Hz), 3.62 (2H, t, J = 3.9 Hz), 4.23-4.35 (3H, m), 4.82-4.95 (1H, m), 5.09 (2H, s), 5.76 (1H, d, J = 7.8 Hz), 6.81-6.92 (3H, m), 7.21-7.28 (2H, m), 8.86 (1H, brs) Foam |

TABLE 40

| Example | Reference Example No. | Product | Yield (%) | ¹H-NMR δ (ppm) Form |
|---|---|---|---|---|
| 46 | 133 | (structure) | 30 | (CDCl₃) 1.72-1.86 (2H, m), 1.98-2.12 (4H, m), 3.04 (2H, t, J = 7.3 Hz), 3.54-3.68 (4H, m), 3.91-4.07 (2H, m), 4.26 (2H, d, J = 6.1 Hz), 4.45-4.52 (1H, m), 4.79 (1H, brs), 5.11 (2H, s), 5.77 (1H, dd, J = 8.1, 2.1 Hz), 6.81-6.92 (3H, m), 7.21-7.25 (2H, m), 8.66 (1H, brs) Foam |
| 47 | 134 | (structure) | 20 | (CDCl₃) 1.53 (3H, d, J = 7.0 Hz), 1.71-2.10 (6H, m), 2.64-2.91 (2H, m), 3.51-3.66 (4H, m), 3.92-4.05 (2H, m), 4.48-4.59 (2H, m), 5.06 (2H, s), 5.16 (1H, d, J = 6.8 Hz), 5.76 (1H, d, J = 8.1 Hz), 6.81-6.92 (3H, m), 7.21-7.27 (2H, m), 9.22 (1H, brs) Foam |

TABLE 40-continued

| Example | Reference Example No. | Product | Yield (%) | ¹H-NMR δ (ppm) Form |
|---|---|---|---|---|
| 48 | 135 | (uracil-CH₂-O-(CH₂)₃-SO₂-NH-CH(CH₃)-phenyl(4-F)(3-O-tetrahydropyranyl)) | 49 | (CDCl₃) 1.51 (3H, d, J = 6.8 Hz), 1.74-2.08 (6H, m), 2.62-2.91 (2H, m), 3.51-3.62 (4H, m), 3.96-4.04 (2H, m), 4.45-4.59 (2H, m), 5.06 (2H, s), 5.35 (1H, brs), 5.77 (1H, d, J = 7.83 Hz), 6.90-7.10 (3H, m), 7.26 (1H, d, J = 7.8 Hz), 9.38 (1H, brs) Foam |

TABLE 41

| Example | Reference Example No. | Product | Yield (%) | ¹H-NMR δ (ppm) Form |
|---|---|---|---|---|
| 49 | 136 | (uracil-CH₂-O-(CH₂)₃-SO₂-NH-CH(CH₃)-phenyl(3-O-tetrahydrofuranyl)) | 39 | (CDCl₃) 1.52 (3H, d, J = 6.8 Hz), 1.85-1.92 (2H, m), 2.10-2.29 (2H, m), 2.68-2.88 (2H, m), 3.43-3.56 (2H, m), 3.89-4.04 (4H, m), 4.53-4.61 (2H, m), 4.92-4.96 (1H, m), 5.05 (2H, s), 5.76 (1H, d, J = 8.1 Hz), 6.75-6.92 (3H, m), 7.20-7.29 (2H, m), 8.30 (1H, brs) Foam |
| 50 | 137 | (uracil-CH₂-O-(CH₂)₃-SO₂-NH-CH₂-phenyl(3-O-CH(CH₂F)₂)) | 44 | (CDCl₃) 2.00-2.12 (2H, m), 3.02 (2H, t, J = 7.0 Hz), 3.63 (2H, t, J = 5.7 Hz), 4.27 (2H, d, J = 5.4 Hz), 4.55-4.61 (2H, m), 4.69-4.81 (4H, m), 5.10 (2H, s), 5.75 (1H, d, J = 7.6 Hz), 6.87-7.03 (3H, m), 7.20-7.31 (2H, m), 8.49 (1H, brs) Foam |
| 51 | 138 | (uracil-CH₂-O-(CH₂)₃-SO₂-NH-CH(CH₃)-phenyl(3-OCF₂CHF₂)) | 70 | (CDCl₃) 1.56 (3H, t, J = 7.0 Hz), 1.88-1.96 (2H, m), 2.69-2.88 (2H, m), 3.53 (2H, t, J = 5.4 Hz), 4.62-4.70 (1H, m), 4.85 (1H, brs) 5.05 (2H, s), 5.75 (1H, t, J = 7.8 Hz, 2.2 Hz), 5.92-6.13 (1H, m), 7.13-7.29 (4H, m), 7.40 (1H, d, J = 7.8 Hz), 9.25 (1H, brs) Foam |

TABLE 42

| Example | Reference Example No. | Product | Yield (%) | ¹H-NMR δ (ppm) Form |
|---|---|---|---|---|
| 52 | 139 | 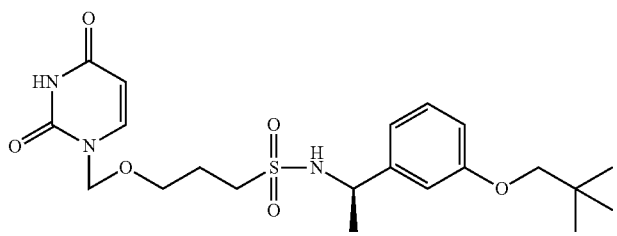 [SMILES: C[C@@H](NS(=O)(=O)CCCOCn1ccc(=O)[nH]c1=O)c1cccc(OCC(C)(C)C)c1] | 62 | (CDCl₃) 1.04 (9H, d, J = 6.8 Hz), 1.54 (3H, d, J = 6.8 Hz), 1.85-1.96 (2H, m), 2.65-2.90 (2H, m), 3.48-3.56 (2H, m), 3.60 (2H, s), 4.52-4.59 (1H, m), 4.61-4.69 (1H, m), 5.05 (2H, s), 5.75 (1H, dd, J = 8.1, 2.3 Hz), 6.79-6.88 (3H, m), 7.17-7.28 (2H, m), 8.47 (1H, brs) Foam |
| 53 | 140 | 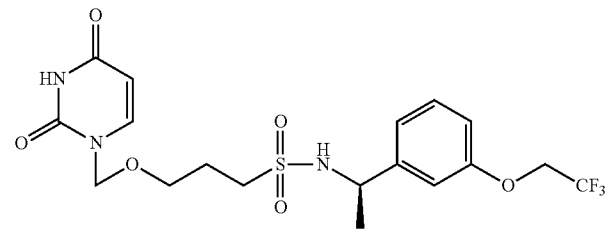 [SMILES: C[C@@H](NS(=O)(=O)CCCOCn1ccc(=O)[nH]c1=O)c1cccc(OCC(F)(F)F)c1] | 46 | (DMSO-d₆) 1.37 (3H, d, J = 6.8 Hz), 1.69-1.80 (2H, m), 2.58-2.70 (1H, m), 2.72-2.88 (1H, m), 3.31-3.46 (2H, m), 4.39-4.45 (1H, m), 4.69-4.79 (2H, m), 4.99 (2H, s), 5.60 (1H, dd, J = 8.1, 0.8 Hz), 6.91-7.08 (3H, m), 7.26-7.31 (1H, m), 7.63 (1H, dd, J = 8.1, 0.8 Hz), 7.73 (1H, d, J = 8.6 Hz), 11.3 (1H, brs) Foam |
| 54 | 141 | 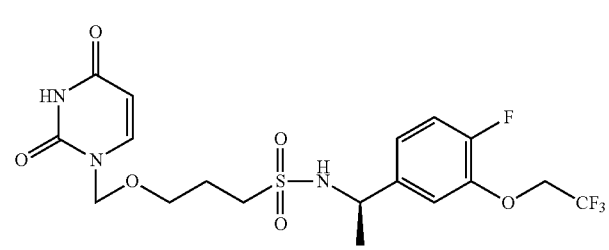 [SMILES: C[C@@H](NS(=O)(=O)CCCOCn1ccc(=O)[nH]c1=O)c1ccc(F)c(OCC(F)(F)F)c1] | 48 | (DMSO-d₆) 1.37 (3H, d, J = 6.8 Hz), 1.69-1.80 (2H, m), 2.56-2.90 (2H, m), 3.38-3.43 (2H, m), 4.37-4.48 (1H, m), 4.74-4.89 (2H, m), 5.00 (2H, s), 5.60 (1H, d, J = 7.8 Hz), 7.03-7.09 (1H, m), 7.20-7.32 (2H, m), 7.63 (1H, d, J = 7.8 Hz), 7.71 (1H, d, J = 8.4 Hz), 11.3 (1H, brs) Foam |
| 55 | 142 | 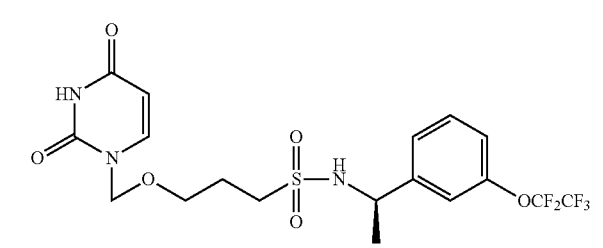 | 40 | (CDCl₃) 1.53 (3H, d, J = 6.8 Hz), 1.84-1.98 (2H, m), 2.67-2.85 (2H, m), 3.46-3.54 (2H, m), 4.58-4.63 (1H, m), 4.88 (1H, brs), 5.05 (2H, s), 5.75 (1H, d, J = 7.8 Hz), 6.82-7.29 (5H, m), 8.55 (1H, brs) Foam |

TABLE 43

| Example | Reference Example No. | Product | Yield (%) | ¹H-NMR δ (ppm) Form |
|---|---|---|---|---|
| 56 | 143 | 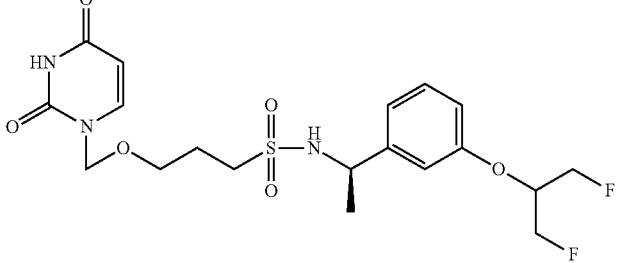 | 70 | (CDCl₃) 1.53 (3H, d, J = 7.0 Hz), 1.85-1.92 (2H, m), 2.67-2.90 (2H, m), 3.43-3.52 (2H, m), 4.55-4.63 (3H, m), 4.69-4.77 (3H, m), 5.00 (1H, brs), 5.05 (2H, s), 5.76 (1H, dd, J = 7.8, 2.2 Hz), 6.88-7.01 (3H, m), 7.20-7.29 (2H, m), 8.97 (1H, brs) Foam |

TABLE 43-continued

| Example | Reference Example No. | Product | Yield (%) | $^1$H-NMR δ (ppm) Form |
|---|---|---|---|---|
| 57 | 144 | | 35 | (CDCl$_3$) 1.53 (3H, d, J = 6.8 Hz), 1.84-1.97 (2H, m), 2.55 (1H, s), 2.61-2.89 (2H, m), 3.45-3.53 (2H, m), 4.52-4.58 (1H, m), 4.71 (2H, s), 5.05 (2H, s), 5.10 (1H, brs), 5.76 (1H, d, J = 7.8 Hz), 6.88-6.97 (3H, m), 7.21-7.32 (2H, m), 9.08 (1H, brs) Foam |
| 58 | 145 | | 54 | (CDCl$_3$) 1.01 (6H, d, J = 6.8 Hz), 1.52 (3H, d, J = 7.0 Hz), 1.82-1.96 (2H, m), 2.00-2.09 (1H, m), 2.65-2.90 (2H, m), 3.48-3.59 (2H, m), 3.71 (2H, d, J = 6.5 Hz), 4.50-4.57 (1H, m), 5.04 (2H, s), 5.50 (1H, d, J = 7.0 Hz), 5.75 (1H, d, J = 7.8 Hz), 6.79-6.90 (3H, m), 7.17-7.29 (2H, m), 8.90 (1H, brs) Foam |

TABLE 44

| Example | Reference Example No. | Product | Yield (%) | $^1$H-NMR δ (ppm) Form |
|---|---|---|---|---|
| 59 | 146 | | 48 | (CDCl$_3$) 0.95 (3H, t, J = 7.4 Hz), 1.02 (3H, d, J = 6.8 Hz), 1.53 (3H, d, J = 6.8 Hz), 1.54-1.62 (2H, m), 1.80-1.93 (3H, m), 2.67-2.88 (2H, m), 3.47-3.56 (2H, m), 3.71-3.88 (2H, m), 4.53-4.62 (1H, m), 5.05 (2H, s), 5.06 (1H, brs), 5.78 (1H, d, J = 7.9 Hz), 6.79-6.92 (3H, m), 7.22-7.31 (2H, m), 9.09 (1H, brs) Foam |
| 60 | 147 | | 48 | (CDCl$_3$) 0.41-0.46 (2H, m), 0.47-0.54 (2H, m), 1.23 (3H, s), 1.52 (3H, d, J = 7.0 Hz), 1.80-1.98 (2H, m), 2.66-2.90 (2H, m), 3.48-3.53 (2H, m), 3.73 (2H, s), 4.51-4.60 (1H, m), 5.05 (2H, s), 5.32 (1H, brs), 5.76 (1H, d, J = 7.8 Hz), 6.84-6.94 (3H, m), 7.20-7.31 (2H, m), 9.45 (1H, brs) Foam |
| 61 | 148 | | 40 | (DMSO-d$_6$) 1.37 (3H, d, J = 6.8 Hz), 1.61-1.84 (2H, m), 2.53-2.67 (1H, m), 2.71-2.90 (1H, m), 3.31-3.40 (2H, m), 4.23-4.46 (3H, m), 4.99 (2H, s), 5.60 (1H, d, J = 7.8 Hz), 6.39 (1H, tt, J = 54.6, 3.5 Hz), 6.86-7.03 (3H, m), 7.23-7.30 (1H, m), 7.62 (1H, d, J = 7.8 Hz), 7.73 (1H, d, J = 8.6 Hz), 11.3 (1H, brs) Foam |

TABLE 45

| Example | Reference Example No. | Product | Yield (%) | ¹H-NMR δ (ppm) Form |
|---|---|---|---|---|
| 62 | 149 | (structure) | 14 | (CDCl₃) 1.53 (3H, d, J = 6.5 Hz), 1.67 (3H, d, J = 6.8 Hz), 1.84-2.00 (2H, m), 2.50-2.78 (2H, m), 3.46-3.53 (2H, m), 4.56-4.66 (3H, m), 5.04 (1H, brs), 5.05 (2H, s), 5.75 (1H, dd, J = 8.1 Hz, 2.4 Hz), 6.79-6.97 (3H, m), 7.20-7.29 (2H, m), 8.35 (1H, brs) Foam |
| 63 | 150 | (structure) | 13 | (CDCl₃) 1.53 (3H, d, J = 6.5 Hz), 1.67 (3H, d, J = 6.8 Hz), 1.84-2.00 (2H, m), 2.50-2.78 (2H, m), 3.46-3.53 (2H, m), 4.56-4.66 (3H, m), 5.04 (1H, brs), 5.05 (2H, s), 5.75 (1H, dd, J = 8.1 Hz, 2.4 Hz), 6.79-6.97 (3H, m), 7.20-7.29 (2H, m), 8.52 (1H, brs) Foam |
| 64 | 151 | (structure) | 69 | (CDCl₃) 1.53 (3H, d, J = 6.8 Hz), 1.84-1.98 (2H, m), 2.67-2.85 (2H, m), 3.46-3.54 (2H, m), 4.16-4.20 (1H, m), 4.27-4.30 (1H, m), 4.56-4.67 (1H, m), 4.67-4.70 (1H, m), 4.80-4.85 (1H, m), 5.01-5.04 (1H, m), 5.04 (2H, s), 5.75 (1H, d, J = 7.8 Hz), 6.82-6.95 (3H, m), 7.21-7.31 (2H, m), 8.95 (1H, brs) Pale yellow oil |

TABLE 46

| Example | Reference Example No. | Product | Yield (%) | ¹H-NMR δ (ppm) Form |
|---|---|---|---|---|
| 65 | 152 | (structure) | 47 | (CDCl₃) 1.25-1.33 (2H, m), 1.53 (3H, d, J = 7.0 Hz), 1.54-1.78 (6H, m), 1.81-1.94 (2H, m), 2.32-2.38 (1H, m), 2.66-2.91 (2H, m), 3.45-3.55 (2H, m), 3.82 (2H, d, J = 7.0 Hz), 4.53-4.60 (1H, m), 4.95 (1H, brs), 5.05 (2H, s), 5.75 (1H, d, J = 7.8 Hz), 6.77-6.89 (3H, m), 7.20-7.27 (2H, m), 9.12 (1H, brs) Foam |
| 66 | 153 | (structure) | 51 | (CDCl₃) 0.98 (3H, t, J = 7.3 Hz), 1.29 (3H, d, J = 6.2 Hz), 1.53 (3H, d, J = 6.8 Hz), 1.62-1.78 (2H, m), 1.84-2.00 (2H, m), 2.74-2.94 (2H, m), 3.48-3.53 (2H, m), 4.33-4.42 (1H, m), 4.51-4.62 (1H, m), 4.66-4.72 (1H, m), 5.05 (2H, s), 5.75 (1H, d, J = 7.8 Hz), 6.79-6.90 (3H, m), 7.20-7.28 (2H, m), 8.43 (1H, brs) Foam |

TABLE 46-continued

| Example | Reference Example No. | Product | Yield (%) | $^1$H-NMR δ (ppm) Form |
|---|---|---|---|---|
| 67 | 154 | 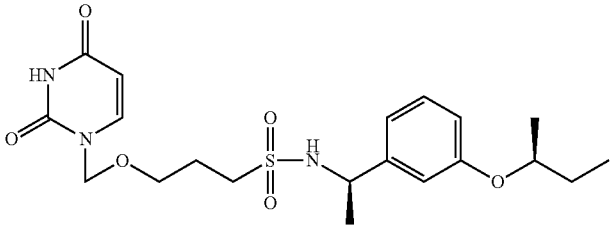 [SMILES: CC[C@H](C)Oc1cccc([C@@H](C)NS(=O)(=O)CCCOCn2ccc(=O)[nH]c2=O)c1] | 39 | (CDCl$_3$) 0.98 (3H, t, J = 7.3 Hz), 1.29 (3H, d, J = 6.2 Hz), 1.53 (3H, d, J = 6.8 Hz), 1.62-1.78 (2H, m), 1.84-2.00 (2H, m), 2.74-2.94 (2H, m), 3.48-3.53 (2H, m), 4.33-4.42 (1H, m), 4.51-4.67 (2H, m), 5.05 (2H, s), 5.75 (1H, d, J = 7.8 Hz), 6.79-6.90 (3H, m), 7.20-7.28 (2H, m), 8.19 (1H, brs) Foam |

TABLE 47

| Example | Reference Example No. | Product | Yield (%) | $^1$H-NMR δ (ppm) Form |
|---|---|---|---|---|
| 68 | 155 | 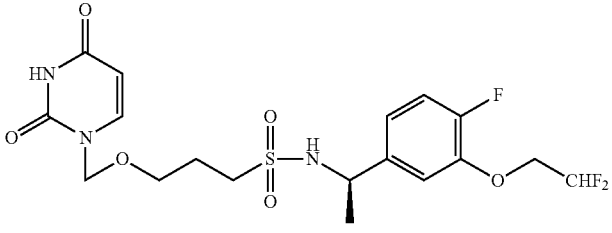 [SMILES: C[C@@H](NS(=O)(=O)CCCOCn1ccc(=O)[nH]c1=O)c1ccc(F)c(OCC(F)F)c1] | 45 | (DMSO-d$_6$) 1.37 (3H, d, J = 6.8 Hz), 1.61-1.84 (2H, m), 2.67-2.90 (2H, m), 3.42 (2H, t, J = 6.2 Hz), 4.31-4.48 (3H, m), 5.00 (2H, s), 5.60 (1H, d, J = 7.8 Hz), 6.42 (1H, tt, J = 54, 3.5 Hz), 6.98-7.04 (1H, m), 7.16-7.31 (2H, m), 7.64 (1H, d, J = 7.8 Hz), 7.71 (1H, d, J = 8.6 Hz), 11.3 (1H, brs) Foam |
| 69 | 156 | 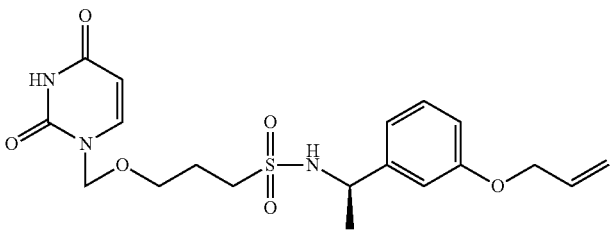 [SMILES: C=CCOc1cccc([C@@H](C)NS(=O)(=O)CCCOCn2ccc(=O)[nH]c2=O)c1] | 35 | (DMSO-d$_6$) 1.35 (3H, d, J = 7.0 Hz), 1.67-1.77 (2H, m), 2.49-2.60 (1H, m), 2.75-2.95 (1H, m), 3.25-3.40 (2H, m), 4.36-4.45 (1H, m), 4.52-4.55 (2H, m), 4.97 (2H, s), 5.24 (1H, d, J = 10.5 Hz), 5.38 (1H, d, J = 16.7 Hz), 5.59 (1H, d, J = 7.8 Hz), 5.95-6.08 (1H, m), 6.78-6.96 (3H, m), 7.17-7.24 (1H, m), 7.61 (1H, d, J = 7.8 Hz), 7.72 (1H, d, J = 8.6 Hz), 11.3 (1H, brs) Foam |
| 70 | 157 | 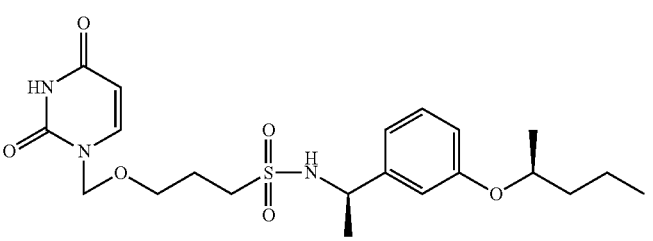 [SMILES: CCC[C@H](C)Oc1cccc([C@@H](C)NS(=O)(=O)CCCOCn2ccc(=O)[nH]c2=O)c1] | 23 | (CDCl$_3$) 0.94 (3H, t, J = 7.0 Hz), 1.26 (3H, d, J = 6.2 Hz), 1.38-1.50 (2H, m), 1.55 (3H, d, J = 6.8 Hz), 1.62-1.74 (2H, m), 1.84-1.99 (2H, m), 2.75-2.90 (2H, m), 3.48-3.55 (2H, m), 4.33-4.42 (1H, m), 4.51-4.62 (1H, m), 4.98 (1H, brs), 5.05 (2H, s), 5.75 (1H, d, J = 7.8 Hz), 6.79-6.90 (3H, m), 7.19-7.30 (2H, m), 8.94 (1H, brs) Foam |

TABLE 48

| Example | Reference Example No. | Product | Yield (%) | $^1$H-NMR δ (ppm) Form |
|---|---|---|---|---|
| 71 | 158 | 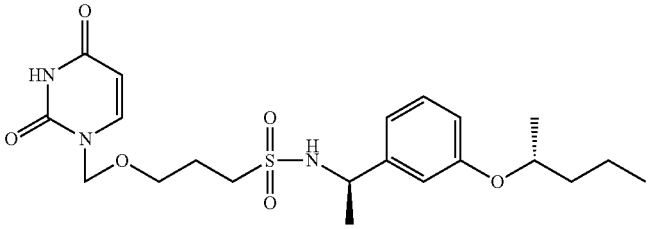 [SMILES: CCC[C@@H](C)Oc1cccc([C@@H](C)NS(=O)(=O)CCCOCn2ccc(=O)[nH]c2=O)c1] | 24 | (CDCl$_3$) 0.94 (3H, t, J = 7.0 Hz), 1.26 (3H, d, J = 6.2 Hz), 1.38-1.50 (2H, m), 1.55 (3H, d, J = 6.8 Hz), 1.62-1.74 (2H, m), 1.84-1.99 (2H, m), 2.75-2.90 (2H, m), 3.48-3.55 (2H, m), 4.33-4.42 (1H, m), 4.51-4.62 (1H, m), 4.94 (1H, brs), 5.05 (2H, s), 5.75 (1H, d, J = 7.8 Hz), 6.79-6.90 (3H, m), 7.19-7.30 (2H, m), 8.90 (1H, brs) Foam |
| 72 | 159 | 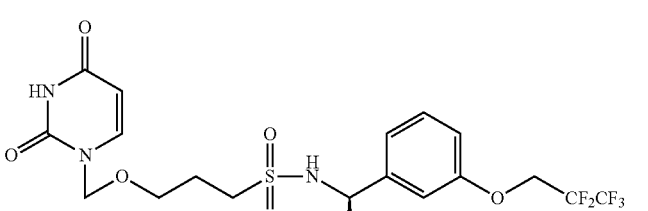 | 60 | (CDCl$_3$) 1.54 (3H, d, J = 6.8 Hz), 1.88-2.05 (2H, m), 2.70-2.88 (2H, m), 3.50-3.57 (2H, m), 4.40 (2H, t, 11.3 Hz), 4.59-4.65 (1H, m), 4.76 (1H, brs), 5.05 (2H, s), 5.75 (1H, dd, J = 7.8, 2.2 Hz), 6.82-7.04 (3H, m), 7.21-7.35 (2H, m), 8.42 (1H, brs) Foam |

TABLE 49

| Example | Reference Example No. | Product | Yield (%) | $^1$H-NMR δ (ppm) Form |
|---|---|---|---|---|
| 73 | 160 | 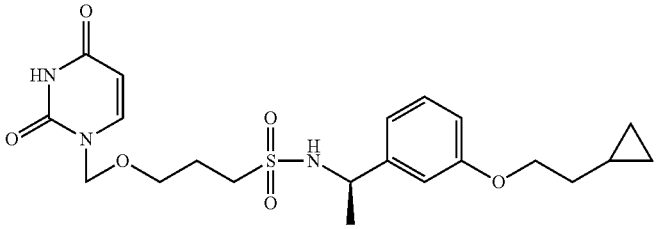 [SMILES: C[C@@H](NS(=O)(=O)CCCOCn1ccc(=O)[nH]c1=O)c1cccc(OCCC2CC2)c1] | 41 | (CDCl$_3$) 0.11-0.16 (2H, m), 0.43-0.53 (2H, m), 0.80-0.89 (1H, m), 1.53 (3H, d, J = 7.0 Hz), 1.67 (2H, q, J = 6.8 Hz), 1.85-2.01 (2H, m), 2.65-2.89 (2H, m), 3.48-3.55 (2H, m), 4.03 (2H, t, J = 6.8 Hz), 4.51-4.62 (1H, m), 5.05 (2H, s), 5.14 (1H, brs), 5.76 (1H, d, J = 7.8 Hz), 6.82-6.91 (3H, m), 7.21-7.29 (2H, m), 9.19 (1H, brs) Foam |
| 74 | 161 | 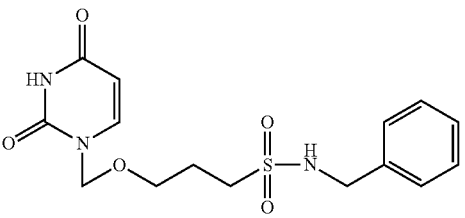 [SMILES: O=c1ccn(COCCCS(=O)(=O)NCc2ccccc2)c(=O)[nH]1] | 50 | (DMSO-d$_6$) 1.85-1.93 (2H, m), 2.95-3.00 (2H, m), 3.39 (2H, t, J = 6.5 Hz), 4.18 (2H, d, J = 6.2 Hz), 5.10 (2H, s), 5.68 (1H, d, J = 7.8 Hz), 7.30-7.40 (5H, m), 7.69-7.74 (2H, m), 11.4 (1H, brs) Foam |
| 75 | 162 | 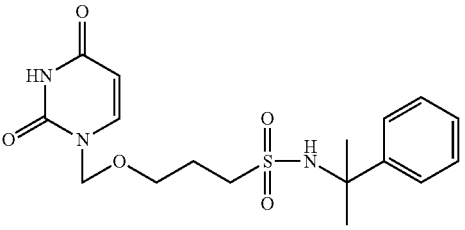 [SMILES: CC(C)(NS(=O)(=O)CCCOCn1ccc(=O)[nH]c1=O)c1ccccc1] | 29 | (DMSO-d$_6$) 1.54 (6H, s), 1.70-1.76 (2H, m), 2.54 (2H, t, J = 7.8 Hz), 3.30-3.39 (2H, m), 4.90 (2H, s), 5.57 (1H, d, J = 7.6 Hz), 7.16-7.45 (6H, m), 7.60 (1H, d, J = 7.8 Hz), 11.3 (1H, brs) Foam |

TABLE 50

| Example | Reference Example No. | Product | Yield (%) | ¹H-NMR δ (ppm) Form |
|---|---|---|---|---|
| 76 | 163 | | 32 | (CDCl₃) 1.82-1.93 (2H, m), 2.78 (2H, t, J = 5.7 Hz), 3.45 (2H, t, J = 5.9 Hz), 5.00 (2H, s), 5.56 (1H, d, J = 7.6 Hz), 5.70-5.75 (1H, m), 7.18 (1H, d, J = 7.8 Hz), 7.24-7.37 (11H, m), 9.15 (1H, brs) Foam |
| 77 | 164 | | 51 | (CDCl₃) 1.95-2.05 (2H, m), 2.32 (3H, s), 2.80 (2H, t, J = 6.2 Hz), 3.52 (2H, t, J = 5.9 Hz), 4.84 (1H, brs), 5.04 (2H, s), 5.74 (1H, dd, J = 7.8, 2.2 Hz), 5.96 (1H, d, J = 7.0 Hz), 7.17-7.36 (10H, m), 7.98 (1H, brs) Foam |
| 78 | 165 | | 25 | (CDCl₃) 1.89-2.04 (2H, m), 2.83 (2H, t, J = 7.6 Hz), 3.53 (2H, t, J = 6.2 Hz), 5.04 (2H, s), 5.71 (1H, brs), 5.75 (1H, d, J = 7.8 Hz), 7.02-7.08 (3H, m), 7.20 (1H, d, J = 7.8 Hz), 7.23-7.30 (6H, m), 9.15 (1H, brs) Foam |
| 79 | 166 | | 20 | (CDCl₃) 1.65-2.01 (6H, m), 2.04-2.32 (2H, m), 3.12-3.19 (1H, m), 3.39-3.44 (2H, m), 3.64-3.71 (1H, m), 4.05 (1H, d, J = 9.5 Hz), 4.96 (1H, t, J = 9.5 Hz), 5.07 (2H, s), 5.75 (1H, d, J = 7.8 Hz), 7.10-7.34 (11H, m), 8.86 (1H, brs) Foam |

TABLE 51

| Example | Reference Example No. | Product | Yield (%) | ¹H-NMR δ (ppm) Form |
|---|---|---|---|---|
| 80 | 167 | | 22 | (CDCl₃) 1.07 (3H, d, J = 6.5 Hz), 1.26 (3H, d, J = 6.5 Hz), 1.50-1.55 (2H, m), 1.82-2.50 (4H, m), 2.66-2.73 (1H, m), 3.60 (2H, t, J = 5.9 Hz), 4.35-4.42 (2H, m), 4.80-4.85 (1H, m), 5.24 (2H, s), 5.94 (1H, dd, J = 7.8 Hz, 2.2 Hz), 7.35-7.82 (11H, m), 8.35 (1H, brs) Foam |
| 81 | 168 | | 26 | (CDCl₃) 1.69-2.28 (10H, m), 2.42-2.55 (2H, m), 3.38 (2H, t, J = 6.2 Hz), 4.96 (1H, brs), 5.03 (2H, s), 5.77 (1H, d, J = 7.8 Hz), 7.20-7.36 (5H, m), 7.49 (1H, d, J = 7.3 Hz), 8.96 (1H, brs) Foam |
| 82 | 169 | | 42 | (DMSO-d₆) 1.37 (3H, d, J = 7.0 Hz), 1.61-1.81 (2H, m), 2.50-2.60 (1H, m), 2.72-2.83 (1H, m), 3.25-3.40 (2H, m), 4.35-4.46 (1H, m), 4.97 (2H, s), 5.60 (1H, d, J = 7.8 Hz), 7.19-7.37 (5H, m), 7.62 (1H, d, J = 7.8 Hz), 7.75 (1H, d, J = 8.64 Hz), 11.3 (1H, brs) Foam |

TABLE 52

| Example | Reference Example No. | Product | Yield (%) | ¹H-NMR δ (ppm) Form |
|---|---|---|---|---|
| 83 | 170 | | 41 | (DMSO-d₆) 0.82 (3H, t, J = 7.3 Hz), 1.55-1.82 (4H, m), 2.36-2.47 (1H, m), 2.66-2.77 (1H, m), 3.20-3.30 (2H, m), 4.08-4.17 (1H, m), 4.96 (2H, s), 5.61 (1H, d, J = 7.8 Hz), 7.20-7.35 (5H, m), 7.60 (1H, d, J = 7.8 Hz), 7.77 (1H, d, J = 8.9 Hz), 11.3 (1H, brs) Foam |
| 84 | 171 | | 37 | (DMSO-d₆) 1.39 (3H, d, J = 6.8 Hz), 1.71-1.83 (2H, m), 2.66-2.76 (1H, m), 2.84-2.95 (1H, m), 3.42 (2H, t, J = 6.2 Hz), 4.68-4.76 (1H, m), 5.01 (2H, s), 5.61 (1H, d, J = 7.8 Hz), 7.11-7.35 (3H, m), 7.48-7.54 (1H, m), 7.64 (1H, d, J = 7.8 Hz), 7.88 (1H, d, J = 7.8 Hz), 11.3 (1H, brs) Foam |

TABLE 52-continued

| Example | Reference Example No. | Product | Yield (%) | ¹H-NMR δ (ppm) Form |
|---|---|---|---|---|
| 85 | 172 | (structure) | 38 | (DMSO-$d_6$) 1.30 (3H, d, J = 7.0 Hz), 1.64-1.81 (2H, m), 2.57-2.67 (1H, m), 2.78-2.87 (1H, m), 3.27-3.32 (2H, m), 3.78 (3H, s), 4.72-4.80 (1H, m), 4.98 (2H, s), 5.60 (1H, d, J = 7.8 Hz), 6.89-6.97 (2H, m), 7.17-7.24 (1H, m), 7.36-7.39 (1H, m), 7.62 (1H, d, J = 7.8 Hz), 7.68 (1H, d, J = 8.9 Hz), 11.3 (1H, brs) Foam |

TABLE 53

| Example | Reference Example No. | Product | Yield (%) | ¹H-NMR δ (ppm) Form |
|---|---|---|---|---|
| 86 | 173 | (structure) | 37 | (DMSO-$d_6$) 1.35 (3H, d, J = 7.0 Hz), 1.68-1.85 (2H, m), 2.65-2.76 (1H, m), 2.79-2.95 (1H, m), 3.37-3.47 (2H, m), 4.80-4.89 (1H, m), 5.00 (2H, s), 5.61 (1H, d, J = 7.8 Hz), 7.24-7.45 (3H, m), 7.61 (1H, dd, J = 1.1, 8.4 Hz), 7.64 (1H, d, J = 7.8 Hz), 8.00 (1H, d, J = 8.1 Hz), 11.3 (1H, brs) Foam |
| 87 | 174 | (structure) | 35 | (DMSO-$d_6$) 1.37 (3H, d, J = 7.3 Hz), 1.69-1.82 (2H, m), 2.63-2.74 (1H, m), 2.81-2.92 (1H, m), 3.39-3.44 (2H, m), 4.44-4.51 (1H, m), 5.01 (2H, s), 5.61 (1H, d, J = 7.8 Hz), 7.02-7.10 (1H, m), 7.18-7.23 (2H, m), 7.33-7.41 (1H, m), 7.64 (1H, d, J = 7.8 Hz), 7.80 (1H, d, J = 8.4 Hz), 11.3 (1H, brs) Foam |
| 88 | 175 | (structure) | 39 | (DMSO-$d_6$) 1.37 (3H, d, J = 7.0 Hz), 1.68-1.86 (2H, m), 2.64-2.75 (1H, m), 2.83-2.95 (1H, m), 3.40-3.47 (2H, m), 4.41-4.52 (1H, m), 5.02 (2H, s), 5.61 (1H, d, J = 7.8 Hz), 7.25-7.39 (3H, m), 7.45 (1H, s), 7.65 (1H, d, J = 7.8 Hz), 7.81 (1H, d, J = 8.4 Hz), 11.3 (1H, brs) Foam |

TABLE 54

| Example | Reference Example No. | Product | Yield (%) | ¹H-NMR δ (ppm) Form |
|---|---|---|---|---|
| 89 | 176 | | 40 | (DMSO-d₆) 1.37 (3H, d, J = 6.8 Hz), 1.71-1.83 (2H, m), 2.65-2.75 (1H, m), 2.84-2.95 (1H, m), 3.40-3.47 (2H, m), 4.43-4.48 (1H, m), 5.02 (2H, s), 5.61 (1H, d, J = 8.1 Hz), 7.26-7.46 (3H, m), 7.58 (1H, brs), 7.65 (1H, d, J = 8.1 Hz), 7.80 (1H, d, J = 8.4 Hz), 11.3 (1H, brs) Foam |
| 90 | 177 | | 35 | (DMSO-d₆) 1.34 (3H, d, J = 7.0 Hz), 1.67-1.85 (2H, m), 2.63-2.74 (1H, m), 2.82-2.93 (1H, m), 3.32-3.43 (2H, m), 4.81-4.84 (1H, m), 5.00 (2H, s), 5.61 (1H, d, J = 8.1 Hz), 7.16-7.22 (1H, m), 7.38-7.44 (1H, m), 7.54-7.62 (2H, m), 7.64 (1H, d, J = 7.8 Hz), 8.04 (1H, d, J = 7.6 Hz), 11.3 (1H, brs) Foam |
| 91 | 178 | | 15 | (CDCl₃) 1.56 (3H, d, J = 7.0 Hz), 1.83-2.00 (2H, m), 2.70-2.93 (2H, m), 3.36-3.56 (2H, m), 4.97 (1H, s), 5.03 (2H, s), 5.25 (1H, d, J = 8.4 Hz), 5.76 (1H, d, J = 8.1 Hz), 7.20-7.41 (5H, m), 7.52 (1H, d, J = 8.1 Hz), 8.58 (1H, brs) Foam |
| 92 | 179 | | 35 | (DMSO-d₆) 1.88 (2H, t, J = 6.9 Hz), 3.11 (2H, t, J = 7.3 Hz), 3.52 (2H, t, J = 6.3 Hz), 4.30 (4H, s), 5.05 (2H, s), 5.61 (1H, d, J = 7.9 Hz), 7.21-7.33 (10H, m), 7.68 (1H, d, J = 7.9 Hz), 11.3 (1H, brs) Foam |

TABLE 55

| Example | Reference Example No. | Product | Yield (%) | ¹H-NMR δ (ppm) Form |
|---|---|---|---|---|
| 93 | 180 | | 27 | (CDCl₃) 1.84-1.94 (2H, m), 2.80-2.86 (2H, m), 3.45-3.50 (2H, t, J = 5.7 Hz), 5.01 (2H, s), 5.72 (1H, t, J = 8.4 Hz), 5.86 (1H, d, J = 7.8 Hz), 6.96-7.38 (11H, m), 9.39 (1H, brs) Foam |
| 94 | 181 | | 32 | (CDCl₃) 1.52 (3H, d, J = 6.8 Hz), 1.89-1.94 (2H, m), 2.71-2.83 (2H, m), 3.55 (2H, t, J = 5.9 Hz), 4.60-4.65 (1H, m), 4.85 (1H, d, J = 6.2 Hz), 5.77 (1H, d, J = 7.8 Hz), 5.06 (2H, s), 7.21-7.36 (5H, m), 8.60 (1H, brs) Foam |

Example 95

Synthesis of 5-((2,4-dioxo-3,4-dihydropyrimidin-1(2H)-yl)methyl)-N-(1,2-diphenylethyl)thiophene-2-sulfonamide

[Formula 77]

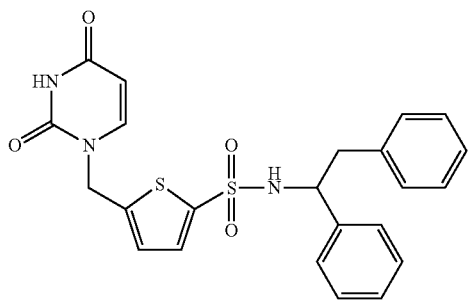

The 5-(chloromethyl)-N-(1,2-diphenylethyl)thiophene-2-sulfonamide (193 mg) obtained in Reference Example 182 was dissolved in DCE (4.0 mL). To the solution, a solution of 2,4-bis(trimethylsilyloxy)pyrimidine (190 mg) obtained according to a method described in the document (Nucleosides & Nucleotides, 4, 565-585 (1985)) in dichloromethane (2.0 mL), iodine (30 mg), and tetra-n-butylammonium iodide (36 mg) were added, and the mixture was heated to reflux at 95° C. for 15 hours. The reaction mixture was cooled to room temperature, water (50 mL) and an aqueous saturated sodium thiosulfate solution (5.0 mL) were then added thereto, and the resultant mixture was then extracted with 10% methanol/chloroform (30 mL×3). The organic layer was washed with brine (50 mL), dried over anhydrous sodium sulfate, and then concentrated under reduced pressure. The residue was purified by silica gel column chromatography (100% ethyl acetate) to obtain the title compound (58 mg, yield: 25%).

¹H-NMR (CDCl₃) δ (ppm): 3.03 (2H, d, J=6.7 Hz), 5.00 (2H, s), 5.61 (1H, brs), 5.70-5.77 (2H, m), 5.95-7.25 (13H, m), 8.92 (1H, brs)

Example 96

Synthesis of N-benzhydryl-4-((2,4-dioxo-3,4-dihydropyrimidin-1(2H)-yl)methyl)benzenesulfonamide

[Formula 78]

The title compound (118 mg, yield: 44%) was obtained according to the method of Example 95 from the N-benzhydryl-4-(bromomethyl)benzenesulfonamide (250 mg) obtained in Reference Example 183 and 2,4-bis(trimethylsilyloxy)pyrimidine (230 mg) obtained according to a method described in the document (Nucleosides & Nucleotides, 4, 565-585 (1985)).

¹H-NMR (CDCl₃) δ (ppm): 4.89 (2H, s), 5.25 (1H, d, J=7.6 Hz), 5.64 (1H, d, J=7.6 Hz), 5.76 (1H, d, J=8.1 Hz), 7.06-7.26 (13H, m), 7.62-7.65 (2H, m), 8.41 (1H, brs)

Example 97

(R)—N-(1-(3-(cyclopropylmethoxy)-4-fluorophenyl)propyl)-4-((2,4-dioxo-3,4-dihydropyrimidin-1(2H)-yl)methyl)benzenesulfonamide

[Formula 79]

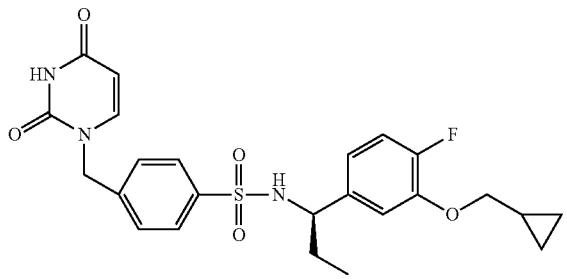

The title compound (140 mg, yield: 60%) was obtained according to the method of Example 95 from the (R)-4-(bromomethyl)-N-(1-(3-(cyclopropylmethoxy)-4-fluorophenyl)propyl)benzenesulfonamide (216 mg) obtained in Reference Example 184 and 2,4-bis(trimethylsilyloxy)pyrimidine (190 mg) obtained according to a method described in the document (Nucleosides & Nucleotides, 4, 565-585 (1985)).

$^1$H-NMR (CDCl$_3$) δ (ppm): 0.27-0.31 (2H, m), 0.59-0.62 (2H, m), 0.81 (3H, t, J=7.6 Hz), 1.18-1.29 (1H, m), 1.65-1.88 (2H, m), 3.62-3.70 (2H, m), 4.10-4.19 (1H, m), 4.88 (2H, s), 5.72 (1H, d, J=7.6 Hz), 5.78 (1H, d, J=8.1 Hz), 6.55-6.82 (3H, m), 7.14-7.56 (5H, m), 9.39 (1H, brs)

Example 98

Synthesis of (R)—N-(1-(3-(cyclopropylmethoxy)-4-fluorophenyl)ethyl)-3-(2,4-dioxo-3,4-dihydropyrimidin-1(2H)-yl)propane-1-sulfonamide

[Formula 80]

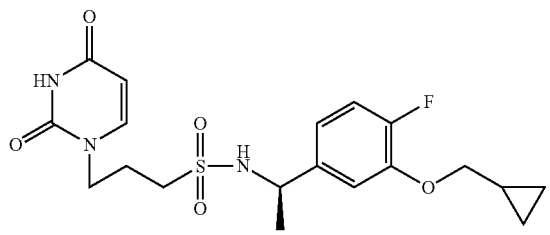

The (R)—N-(1-(3-(cyclopropylmethoxy)-4-fluorophenyl)ethyl)-3-hydroxy-N-(methoxymethyl)propane-1-sulfonamide (87 mg) obtained in Reference Example 185 was dissolved in THF (4.0 mL). To the solution, triphenylphosphine (131 mg) and 3-benzoylpyrimidine-2,4(1H, 3H)-dione (100 mg) obtained according to a method described in the document (J. Med. Chem., 50, 6032-6038 (2007)) were added, and the mixture was stirred at room temperature for 5 minutes. To the reaction mixture, a solution of DEAD in toluene (2.2 M, 210 μL) was gradually added dropwise, and the mixture was stirred at room temperature for 4 hours. The reaction mixture was concentrated under reduced pressure, and the residue was then purified by silica gel column chromatography (70% ethyl acetate/hexane). The obtained compound was dissolved in a solution of methylamine in methanol (40%, 2.0 mL), and the mixture was stirred at room temperature for 30 minutes. The reaction mixture was concentrated under reduced pressure, and the residue was then purified by silica gel column chromatography (100% ethyl acetate). The obtained compound was dissolved in dioxane (600 μL). To the solution, a hydrochloric acid-dioxane solution (4.0 M, 200 μL) was added, and the mixture was stirred at room temperature for 1 hour. The reaction mixture was neutralized by the addition of an aqueous saturated sodium bicarbonate solution (4.0 mL) at 0° C., and was then extracted with ethyl acetate (10 mL×2). The organic layer was washed with brine (10 mL), dried over anhydrous sodium sulfate, and then concentrated under reduced pressure. The residue was purified by silica gel column chromatography (100% ethyl acetate) to obtain the title compound (32 mg, yield: 33%).

$^1$H-NMR (CDCl$_3$) δ (ppm): 0.34-0.40 (2H, m), 0.63-0.71 (2H, m), 1.24-1.32 (1H, m), 1.52 (3H, d, J=6.8 Hz), 1.92-2.18 (2H, m), 2.64-2.73 (2H, m), 3.66-3.75 (2H, m), 3.83 (2H, d, J=6.5 Hz), 4.54-4.64 (1H, m), 4.93-5.08 (1H, m), 5.68 (1H, d, J=7.3 Hz), 6.82-6.90 (4H, m), 8.75 (1H, brs)

Example 99

Synthesis of (S)—N-(2-(3-(cyclopentyloxy)-4-fluorophenyl)-2-hydroxybutyl)-3-(2,4-dioxo-3,4-dihydroxypyrimidin-1(2H)-yl)propane-1-sulfonamide

[Formula 81]

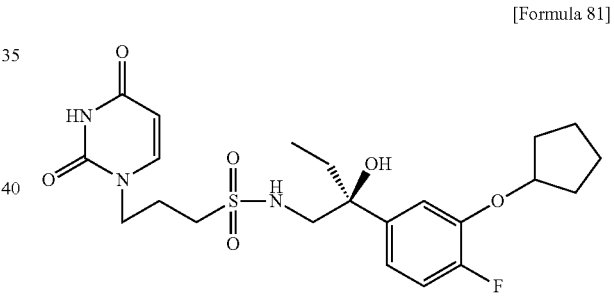

The (S)-tert-butyl 2-(3-(cyclopentyloxy)-4-fluorophenyl)-2-(trimethylsilyloxy)butyl(3-hydroxypropylsulfonyl)carbamate (249 mg) obtained in Reference Example 188 was dissolved in THF (4.5 mL). To the solution, triphenylphosphine (163 mg) and 3-benzoylpyrimidine-2,4(1H, 3H)-dione (114 mg) obtained according to a method described in the document (J. Med. Chem., 50, 6032-6038 (2007)) were added, and the mixture was stirred at room temperature for 5 minutes. To the reaction mixture, a solution of DEAD in toluene (2.2 M, 250 μL) was gradually added dropwise, and the mixture was stirred at room temperature for 4 hours. The reaction mixture was concentrated under reduced pressure, and the residue was then purified by silica gel column chromatography (50% ethyl acetate/hexane). The obtained compound was dissolved in a solution of methylamine in methanol (40%, 4.0 mL), and the solution was stirred at room temperature for 30 minutes. The reaction mixture was concentrated under reduced pressure, and the residue was then purified by silica gel column chromatography (100% ethyl acetate). The obtained compound was dissolved in dichloromethane (3.0 mL). To the solution, trifluoroacetic acid (470 μL) was added, and the mixture was stirred at room temperature for 2 hours. The reaction mixture was neutralized by the addition of an aqueous saturated sodium bicarbonate solution (10 mL) at 0° C., and was then extracted with chloroform (20 mL×2). The organic layer was washed with brine (10 mL), dried over anhydrous sodium sulfate, and then concentrated under reduced pressure. The residue was purified by silica gel column chromatography (100% ethyl acetate) to obtain the title compound (38.5 mg, yield: 18%).

$^1$H-NMR (CDCl$_3$) δ (ppm): 0.76 (3H, t, J=7.3 Hz), 1.59-1.92 (11H, m), 2.05-2.13 (2H, m), 2.90-2.99 (3H, m), 3.40-3.43 (2H, m), 3.81 (2H, t, J=6.8 Hz), 4.83 (1H, brs), 5.69 (1H, d, J=7.7 Hz), 6.82-7.06 (3H, m), 7.20 (1H, d, J=7.9 Hz)

Examples 100 to 127

Compounds shown below were synthesized according to the method of Example 98 from the compounds obtained in Reference Examples 186, 187, and 189 to 214, respectively. The results are shown in tables below.

Example 100

(R,E)-N-(1-(3-(cyclopropylmethoxy)-4-fluorophenyl)ethyl)-5-(2,4-dioxo-3,4-dihydropyrimidin-1(2H)-yl)pent-3-ene-1-sulfonamide Example 101

(R)—N-(1-(3-(cyclopropylmethoxy)-4-fluorophenyl)ethyl)-5-(2,4-dioxo-3,4-dihydropyrimidin-1(2H)-yl)pentane-1-sulfonamide Example 102

(R)—N-(1-(3-(cyclopropylmethoxy)phenyl)propyl)-3-(2,4-dioxo-3,4-dihydropyrimidin-1(2H)-yl)propane-1-sulfonamide Example 103

N-(3-(cyclopropylmethoxy)benzyl)-5-(2,4-dioxo-3,4-dihydropyrimidin-1(2H)-yl)pentane-1-sulfonamide Example 104

(R)—N-(1-(3-(cyclopentyloxy)phenyl)ethyl)-3-(2,4-dioxo-3,4-dihydropyrimidin-1(2H)-yl)propane-1-sulfonamide Example 105

(R,E)-N-(1-(3-(cyclopentyloxy)phenyl)ethyl)-5-(2,4-dioxo-3,4-dihydropyrimidin-1(2H)-yl)pent-3-ene-1-sulfonamide Example 106

(R)—N-(1-(3-(cyclopentyloxy)phenyl)ethyl)-5-(2,4-dioxo-3,4-dihydropyrimidin-1(2H)-yl)pentane-1-sulfonamide Example 107

(R)—N-(1-(3-(2,2-difluoroethoxy)phenyl)ethyl)-3-(2,4-dioxo-3,4-dihydropyrimidin-1(2H)-yl)propane-1-sulfonamide Example 108

(R)—N-(1-(3-(cyclopropylmethoxy)phenyl)ethyl)-3-(2,4-dioxo-3,4-dihydropyrimidin-1(2H)-yl)propane-1-sulfonamide Example 109

(R)—N-(1-(3-(cyclopropylmethoxy)phenyl)ethyl)-5-(2,4-dioxo-3,4-dihydropyrimidin-1(2H)-yl)pentane-1-sulfonamide Example 110

(R,E)-N-(1-(3-(cyclopropylmethoxy)phenyl)ethyl)-5-(2,4-dioxo-3,4-dihydropyrimidin-1(2H)-yl)pent-3-ene-1-sulfonamide Example 111

N-benzhydryl-3-(2,4-dioxo-3,4-dihydropyrimidin-1(2H)-yl)propane-1-sulfonamide

Example 112

N-((3-(cyclopropylmethoxy)phenyl)(phenyl)methyl)-3-(2,4-dioxo-3,4-dihydropyrimidin-1(2H)-yl)propane-1-sulfonamide Example 113

(E)-N-(3-(cyclopropylmethoxy)benzyl)-5-(2,4-dioxo-3,4-dihydropyrimidin-1(2H)-yl)pent-3-ene-1-sulfonamide Example 114

(R)—N-((3-(cyclopropylmethoxy)phenyl)(4-fluorophenyl)methyl)-3-(2,4-dioxo-3,4-dihydropyrimidin-1(2H)-yl)propane-1-sulfonamide

Example 115

(R)—N-(1-(3-(cyclopropylmethoxy)-4-fluorophenyl)propyl)-3-(2,4-dioxo-3,4-dihydropyrimidin-1(2H)-yl)propane-1-sulfonamide

Example 116

(R)—N-((3-(cyclopropylmethoxy)-4-fluorophenyl)(4-fluorophenyl)methyl)-3-(2,4-dioxo-3,4-dihydropyrimidin-1(2H)-yl)propane-1-sulfonamide

Example 117

(R)-3-(2,4-dioxo-3,4-dihydropyrimidin-1(2H)-yl)-N-(1-phenylethyl)propane-1-sulfonamide

Example 118

(R)-3-(2,4-dioxo-3,4-dihydropyrimidin-1(2H)-yl)-N-(1-phenylpropyl)propane-1-sulfonamide

Example 119

(R)-3-(2,4-dioxo-3,4-dihydropyrimidin-1(2H)-yl)-N-(1-(2-fluorophenyl)ethyl)propane-1-sulfonamide

Example 120

(R)—N-(1-(2-chlorophenyl)ethyl)-3-(2,4-dioxo-3,4-dihydropyrimidin-1(2H)-yl)propane-1-sulfonamide

Example 121

(R)-3-(2,4-dioxo-3,4-dihydropyrimidin-1(2H)-yl)-N-(1-(3-fluorophenyl)ethyl)propane-1-sulfonamide

Example 122

(R)-3-(2,4-dioxo-3,4-dihydropyrimidin-1(2H)-yl)-N-(1-(2-ethynylphenyl)ethyl) propane-1-sulfonamide

Example 123

(R)—N-(1-(2-bromophenyl)ethyl)-3-(2,4-dioxo-3,4-dihydropyrimidin-1(2H)-yl)propane-1-sulfonamide

Example 124

(R)-3-(2,4-dioxo-3,4-dihydropyrimidin-1(2H)-yl)-N-(1-o-tolylethyl)propane-1-sulfonamide

Example 125

(R)-3-(2,4-dioxo-3,4-dihydropyrimidin-1(2H)-yl)-N-(1-(2-(trifluoromethyl)phenyl)ethyl)propane-1-sulfonamide

Example 126

(S)-3-(2,4-dioxo-3,4-dihydropyrimidin-1(2H)-yl)-N-(1-phenylethyl)propane-1-sulfonamide

Example 127

(S)—N-(2,3-dihydro-1H-inden-1-yl)-3-(2,4-dioxo-3,4-dihydropyrimidin-1(2H)-yl)propane-1-sulfonamide

TABLE 56

| Example | Reference Example No. | Product | Yield (%) | $^1$H-NMR δ (ppm) Form |
|---|---|---|---|---|
| 100 | 186 | (structure) | 35 | (CDCl$_3$) 0.35-0.38 (2H, m), 0.63-0.68 (2H, m), 1.22-1.30 (1H, m), 1.70 (3H, d, J = 7.0 Hz), 2.50-2.61 (2H, m), 3.02-3.09 (2H, m), 3.88 (2H, d, J = 6.8 Hz), 4.22-4.26 (2H, m), 4.52-4.59 (1H, m), 5.06-5.12 (1H, m), 5.51-5.77 (3H, m), 6.82-7.19 (4H, m), 8.55 (1H, brs) Foam |
| 101 | 187 | (structure) | 17 | (CDCl$_3$) 0.33-0.37 (2H, m), 0.62-0.69 (2H, m), 1.22-1.39 (3H, m), 1.53 (3H, d, J = 7.0 Hz), 1.54-1.78 (4H, m), 2.61-2.82 (2H, m), 3.62-3.70 (3H, m), 3.89 (2H, d, J = 6.9 Hz), 4.52-4.63 (1H, m), 5.71 (1H, d, J = 7.8 Hz), 6.82-7.12 (4H, m) Foam |

TABLE 56-continued

| Example | Reference Example No. | Product | Yield (%) | ¹H-NMR δ (ppm) Form |
|---|---|---|---|---|
| 102 | 189 | 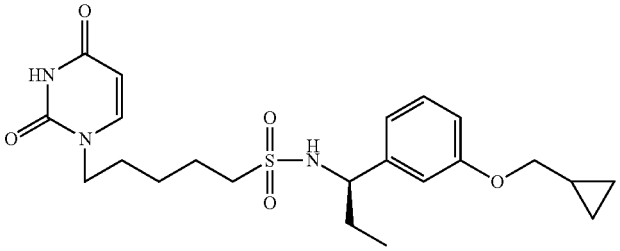 [SMILES: CC[C@@H](NS(=O)(=O)CCCCCn1ccc(=O)[nH]c1=O)c1cccc(OCC2CC2)c1] | 39 | (CDCl₃) 0.35-0.38 (2H, m), 0.62-0.70 (2H, m), 0.90 (3H, t, J = 7.3 Hz), 1.22-1.32 (1H, m), 1.75-2.01 (4H, m), 2.53-2.64 (2H, m), 3.57-3.79 (2H, m), 3.80 (2H, d, J = 6.8 Hz), 4.26-4.32 (1H, m), 4.80 (1H, brs), 5.65 (1H, d, J = 7.8 Hz), 6.82 (2H, d, J = 7.0 Hz), 7.10 (1H, d, J = 7.8 Hz), 7.22-7.29 (2H, m), 9.11 (1H, brs) Foam |

TABLE 57

| Example | Reference Example No. | Product | Yield (%) | ¹H-NMR δ (ppm) Form |
|---|---|---|---|---|
| 103 | 190 | 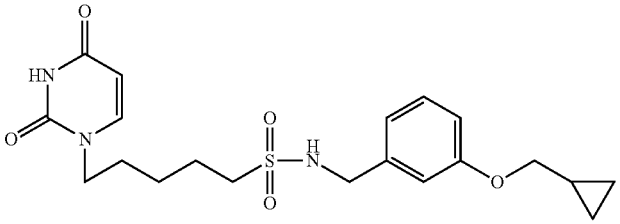 [SMILES: O=c1ccn(CCCCCS(=O)(=O)NCc2cccc(OCC3CC3)c2)c(=O)[nH]1] | 55 | (CDCl₃) 0.33-0.38 (2H, m), 0.61-0.68 (2H, m), 1.22-1.30 (1H, m), 1.39-1.44 (2H, m), 1.60-1.71 (2H, m), 1.79-1.86 (2H, m), 2.94 (2H, t, J = 7.6 Hz), 3.70 (2H, t, J = 7.0 Hz), 3.80 (2H, d, J = 7.0 Hz), 4.26 (2H, d, J = 5.9 Hz), 4.72 (1H, brs), 5.70 (1H, dd, J = 8.1, 1.9 Hz), 6.79-6.90 (3H, m), 7.11 (1H, d, J = 7.6 Hz), 7.22-7.29 (1H, m), 8.45 (1H, brs) Foam |
| 104 | 191 | 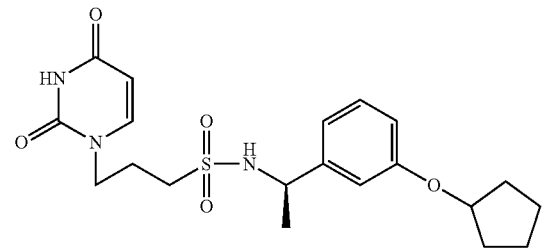 [SMILES: C[C@@H](NS(=O)(=O)CCCn1ccc(=O)[nH]c1=O)c1cccc(OC2CCCC2)c1] | 38 | (CDCl₃) 1.53 (3H, d, J = 6.8 Hz), 1.56-1.70 (2H, m), 1.72-2.09 (8H, m), 2.58-2.74 (2H, m), 3.64-3.89 (2H, m), 4.55-4.60 (1H, m), 4.65-4.73 (1H, m), 4.74-4.80 (1H, m), 5.66 (1H, d, J = 7.9 Hz), 6.81-6.88 (3H, m), 7.13 (1H, d, J = 7.9 Hz), 7.25-7.29 (1H, m), 8.22 (1H, brs) Foam |

TABLE 58

| Example | Reference Example No. | Product | Yield (%) | ¹H-NMR δ (ppm) Form |
|---|---|---|---|---|
| 105 | 192 | 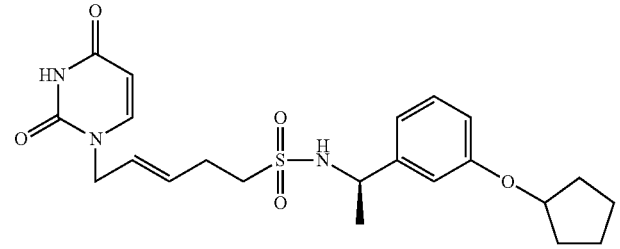 [SMILES: C[C@@H](NS(=O)(=O)CC/C=C/Cn1ccc(=O)[nH]c1=O)c1cccc(OC2CCCC2)c1] | 26 | (CDCl₃) 1.53 (3H, d, J = 6.8 Hz), 1.61-1.98 (8H, m), 2.33-2.48 (2H, m), 2.59-2.87 (2H, m), 4.18-4.23 (2H, m), 4.51-4.58 (1H, m), 4.73-4.79 (1H, m), 4.84-4.90 (1H, m), 5.37-5.60 (2H, m), 5.70 (1H, d, J = 8.1 Hz), 6.74-6.87 (3H, m), 7.12 (1H, d, J = 8.0 Hz), 7.21-7.26 (1H, m), 8.68 (1H, brs) Foam |

TABLE 58-continued

| Example | Reference Example No. | Product | Yield (%) | $^1$H-NMR δ (ppm) Form |
|---|---|---|---|---|
| 106 | 193 | | 47 | (CDCl$_3$) 1.26-1.38 (4H, m), 1.52 (3H, d, J = 7.0 Hz), 1.53-1.98 (10H, m), 2.53-2.80 (2H, m), 3.60-3.67 (2H, m), 4.48-4.60 (1H, m), 4.72-4.79 (1H, m), 5.46-5.52 (1H, m), 5.71 (1H, d, J = 8.1 Hz), 6.77-6.98 (3H, m), 7.13 (1H, d, J = 7.8 Hz), 7.16-7.27 (1H, m), 9.66 (1H, brs) Foam |

TABLE 59

| Example | Reference Example No. | Product | Yield (%) | 1H-NMR δ (ppm) Form |
|---|---|---|---|---|
| 107 | 194 | | 26 | (CDCl$_3$) 1.53 (3H, d, J = 6.9 Hz), 2.01-2.13 (2H, m), 2.67 (2H, t, J = 6.8 Hz), 3.63-3.91 (2H, m), 4.2 (2H, td, J = 13.0 Hz, 3.8 Hz), 4.53-4.62 (1H, m), 4.84-4.90 (1H, m), 5.67 (1H, d, J = 7.9 Hz), 6.10 (1H, tt, J = 55 Hz, 0.8 Hz), 6.81-6.95 (3H, m), 7.12 (1H, d, J = 7.9 Hz), 7.22-7.31 (1H, m), 8.44 (1H, brs) Foam |
| 108 | 195 | | 36 | (CDCl$_3$) 0.33-0.39 (2H, m), 0.62-0.70 (2H, m), 1.22-1.30 (1H, m), 1.53 (3H, d, J = 6.8 Hz), 1.92-2.18 (2H, m), 2.61-2.72 (2H, m), 3.61-3.70 (2H, m), 3.80 (2H, d, J = 6.8 Hz), 4.53-4.61 (1H, m), 4.80 (1H, brs), 5.66 (1H, d, J = 7.8 Hz), 6.82-6.90 (3H, m), 7.12 (1H, d, J = 7.8 Hz), 7.22-7.29 (1H, m), 8.85 (1H, brs) Foam |

TABLE 60

| Example | Reference Example No. | Product | Yield (%) | $^1$H-NMR δ (ppm) Form |
|---|---|---|---|---|
| 109 | 196 | | 33 | (CDCl$_3$) 0.33-0.37 (2H, m), 0.62-0.69 (2H, m), 1.22-1.36 (3H, m), 1.53 (3H, d, J = 6.8 Hz), 1.54-1.78 (4H, m), 2.61-2.82 (2H, m), 3.65 (2H, t, J = 8.1 Hz), 3.80 (2H, d, J = 7.0 Hz), 4.54-4.63 (1H, m), 4.77 (1H, brs), 5.69 (1H, dd, J = 8.1, 1.9 Hz), 6.81-6.90 (3H, m), 7.09 (1H, d, J = 7.8 Hz), 7.22-7.29 (1H, m), 8.55 (1H, brs) Foam |

TABLE 61

| Example | Reference Example No. | Product | Yield (%) | ¹H-NMR δ (ppm) Form |
|---|---|---|---|---|
| 110 | 197 | (structure) | 35 | (CDCl$_3$) 0.34-0.37 (2H, m), 0.62-0.69 (2H, m), 1.22-1.30 (1H, m), 1.53 (3H, d, J = 6.8 Hz), 2.32-2.41 (2H, m), 2.60-2.83 (2H, m), 3.80 (2H, d, J = 6.8 Hz), 4.20-4.24 (2H, m), 4.52-4.58 (2H, m), 5.48-5.58 (2H, m), 5.71 (1H, d, J = 8.1 Hz), 6.81-6.90 (3H, m), 7.11 (1H, d, J = 7.8 Hz), 7.22-7.29 (1H, m), 8.23 (1H, brs) Foam |
| 111 | 198 | (structure) | 38 | (DMSO-d$_6$) 1.73-1.81 (2H, m), 2.71-2.77 (2H, m), 3.52-3.59 (2H, m), 5.50 (1H, dd, J = 8.0, 2.2 Hz), 5.59 (1H, d, J = 9.6 Hz), 7.21-7.40 (11H, m), 8.4 (1H, d, J = 9.7 Hz), 11.2 (1H, brs) Foam |
| 112 | 199 | (structure) | 37 | (CDCl$_3$) 0.31-0.37 (2H, m), 0.61-0.68 (2H, m), 1.22-1.28 (1H, m), 2.00-2.09 (2H, m), 2.72 (2H, t, J = 7.3 Hz), 3.70-3.80 (4H, m), 5.13-5.18 (1H, m), 5.63-5.70 (2H, m), 6.82-6.91 (3H, m), 7.09 (1H, d, J = 7.8 Hz), 7.22-7.30 (6H, m), 8.22 (1H. brs) Foam |

TABLE 62

| Example | Reference Example No. | Product | Yield (%) | ¹H-NMR δ (ppm) Form |
|---|---|---|---|---|
| 113 | 200 | (structure) | 49 | (CDCl$_3$) 0.34-0.38 (2H, m), 0.61-0.67 (2H, m), 1.22-1.30 (1H, m), 2.60-2.70 (2H, m), 3.15 (2H, t, J = 7.0 Hz), 3.79 (2H, t, J = 7.0 Hz), 4.27-4.32 (2H, m), 4.75 (2H, d, J = 6.8 Hz), 5.55-5.81 (4H, m), 6.81-6.90 (3H, m), 7.17 (1H, d, J = 7.8 Hz), 7.22-7.29 (1H, m) Foam |

TABLE 62-continued

| Example | Reference Example No. | Product | Yield (%) | ¹H-NMR δ (ppm) Form |
|---|---|---|---|---|
| 114 | 201 | | 31 | (CDCl₃) 0.33-0.39 (2H, m), 0.62-0.69 (2H, m), 1.20-1.28 (1H, m), 2.00-2.09 (2H, m), 2.75 (2H, t, J = 7.1 Hz), 3.69-3.85 (4H, m), 5.62-5.70 (2H, m), 6.82-7.19 (3H, m), 7.22-7.29 (6H, m) Foam |
| 115 | 202 | | 43 | (CDCl₃) 0.35-0.38 (2H, m), 0.62-0.70 (2H, m), 0.90 (3H, t, J = 7.3 Hz), 1.22-1.32 (1H, m), 1.75-1.96 (2H, m), 1.98-2.07 (2H, m), 2.56-2.61 (2H, m), 3.57-3.79 (2H, m), 3.89 (2H, d, J = 7.1 Hz), 4.23-4.30 (1H, m), 5.68 (1H, d, J = 7.9 Hz), 6.82-7.10 (4H, m) Foam |

TABLE 63

| Example | Reference Example No. | Product | Yield (%) | ¹H-NMR δ (ppm) Form |
|---|---|---|---|---|
| 116 | 203 | | 55 | (CDCl₃) 0.33-0.39 (2H, m), 0.62-0.68 (2H, m), 1.20-1.28 (1H, m), 2.05-2.10 (2H, m), 2.76 (2H, t, J = 7.1 Hz), 3.69-3.82 (2H, m), 3.84 (2H, d, J = 7.1 Hz), 5.62-5.70 (2H, m), 6.82-7.12 (3H, m), 7.22-7.27 (5H, m) Foam |
| 117 | 204 | | 52 | (DMSO-d₆) 1.36 (3H, d, J = 7.0 Hz), 1.75-1.85 (2H, m), 2.55-2.61 (1H, m), 2.70-2.79 (1H, m), 3.49-3.66 (2H, m), 4.41-4.43 (1H, m), 5.51 (1H, d, J = 7.8 Hz), 7.20-7.36 (5H, m), 7.46 (1H, d, J = 7.8 Hz), 7.77 (1H, brs), 11.2 (1H, brs) Foam |

TABLE 63-continued

| Example | Reference Example No. | Product | Yield (%) | 1H-NMR δ (ppm) Form |
|---|---|---|---|---|
| 118 | 205 | 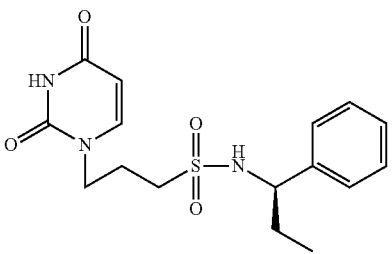 [SMILES: CC[C@@H](NS(=O)(=O)CCCn1ccc(=O)[nH]c1=O)c1ccccc1] | 55 | (DMSO-d$_6$) 0.80 (3H, t, J = 7.3 Hz), 1.53-1.85 (4H, m), 2.38-2.48 (1H, m), 2.62-2.73 (1H, m), 3.37-3.64 (2H, m), 4.11-4.15 (1H, m), 5.50 (1H, d, J = 7.8 Hz), 7.18-7.37 (5H, m), 7.40 (1H, d, J = 7.8 Hz), 7.77 (1H, d, J = 8.1 Hz), 11.2 (1H, brs) Foam |

TABLE 64

| Example | Reference Example No. | Product | Yield (%) | 1H-NMR δ (ppm) Form |
|---|---|---|---|---|
| 119 | 206 | 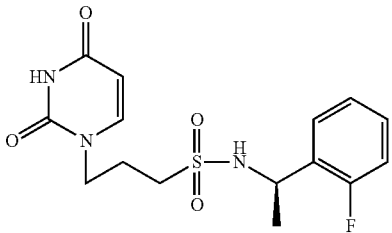 [SMILES: C[C@@H](NS(=O)(=O)CCCn1ccc(=O)[nH]c1=O)c1ccccc1F] | 49 | (DMSO-d$_6$) 1.39 (3H, d, J = 7.0 Hz), 1.85-1.90 (2H, m), 2.67-2.78 (1H, m), 2.83-2.91 (1H, m), 3.59-3.71 (2H, m), 4.69-4.80 (1H, m), 5.53 (1H, d, J = 7.8 Hz), 7.09-7.31 (3H, m), 7.46-7.53 (1H, m), 7.52 (1H, d, J = 7.8 Hz), 7.89 (1H, brs), 11.2 (1H, brs) Foam |
| 120 | 207 | 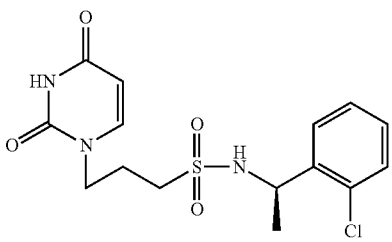 | 57 | (DMSO-d$_6$) 1.35 (3H, d, J = 6.8 Hz), 1.85-1.90 (2H, m), 2.69-2.77 (1H, m), 2.82-2.90 (1H, m), 3.61-3.70 (2H, m), 4.82-4.89 (1H, m), 5.53 (1H, d, J = 7.8 Hz), 7.24-7.30 (1H, m), 7.35-7.40 (2H, m), 7.51 (1H, d, J = 7.8 Hz), 7.57-7.60 (1H, m), 8.02 (1H, brs), 11.2 (1H, brs) Foam |
| 121 | 208 | 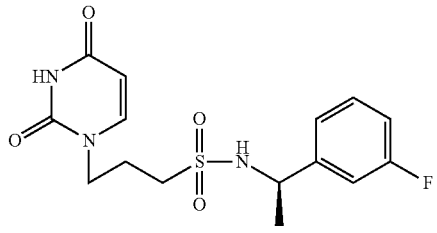 [SMILES: C[C@@H](NS(=O)(=O)CCCn1ccc(=O)[nH]c1=O)c1cccc(F)c1] | 54 | (DMSO-d$_6$) 1.37 (3H, d, J = 7.0 Hz), 1.82-1.92 (2H, m), 2.67-2.88 (2H, m), 3.62-3.68 (2H, m), 4.45-4.51 (1H, m), 5.53 (1H, d, J = 7.8 Hz), 7.03-7.09 (1H, m), 7.17-7.22 (2H, m), 7.33-7.41 (1H, m), 7.51 (1H, d, J = 7.8 Hz), 7.82 (1H, d, J = 6.2 Hz), 11.2 (1H, brs) Foam |

TABLE 65

| Example | Reference Example No. | Product | Yield (%) | ¹H-NMR δ (ppm) Form |
|---|---|---|---|---|
| 122 | 209 | | 49 | (DMSO-$d_6$) 1.36 (3H, d, J = 7.3 Hz), 1.77-1.87 (2H, m), 2.61-2.72 (1H, m), 2.77-2.88 (1H, m), 3.56 (2H, m), 4.43 (1H, s), 4.87-4.96 (1H, m), 5.52 (1H, d, J = 8.1 Hz), 7.25 (1H, t, J = 7.3 Hz), 7.40-7.50 (3H, m), 7.56 (1H, d, J = 8.1 Hz), 7.97 (1H, brs), 11.2 (1H, brs) Foam |
| 123 | 210 | | 55 | (DMSO-$d_6$) 1.34 (3H, d, J = 6.8 Hz), 1.84-1.92 (2H, m), 2.64-2.75 (1H, m), 2.80-2.91 (1H, m), 3.58-3.70 (2H, m), 4.78-4.85 (1H, m), 5.53 (1H, d, J = 7.8 Hz), 7.16-7.22 (1H, m), 7.42 (1H, t, J = 7.8 Hz), 7.50 (1H, d, J = 7.8 Hz), 7.53-7.61 (2H, m), 8.06 (1H, brs), 11.2 (1H, brs) Foam |

TABLE 66

| Example | Reference Example No. | Product | Yield (%) | ¹H-NMR δ (ppm) Form |
|---|---|---|---|---|
| 124 | 211 | | 52 | (DMSO-$d_6$) 1.34 (3H, d, J = 6.8 Hz), 1.78-1.89 (2H, m), 2.30 (3H, s), 2.45-2.56 (1H, m), 2.68-2.79 (1H, m), 3.49-3.69 (2H, m), 4.65-4.71 (1H, m), 5.52 (1H, d, J = 7.8 Hz), 7.08-7.23 (3H, m), 7.42 (1H, d, J = 7.6 Hz), 7.47 (1H, d, J = 7.8 Hz), 7.81 (1H, d, J = 7.6 Hz), 11.2 (1H, brs) Foam |
| 125 | 212 | | 50 | (DMSO-$d_6$) 1.38 (3H, d, J = 7.0 Hz), 1.75-1.90 (2H, m), 2.50-2.60 (1H, m), 2.71-2.82 (1H, m), 3.52-3.65 (2H, m), 4.77 (1H, d, J = 6.5 Hz), 5.50 (1H, d, J = 7.8 Hz), 7.46 (2H, t, J = 7.6 Hz), 7.62-7.74 (2H, m), 7.83 (1H, d, J = 7.8 Hz), 8.16 (1H, brs), 11.2 (1H, brs) Foam |

TABLE 67

| Example | Reference Example No. | Product | Yield (%) | 1H-NMR δ (ppm) Form |
|---|---|---|---|---|
| 126 | 213 | (structure) | 45 | (DMSO-d6) 1.36 (3H, d, J = 7.0 Hz), 1.74-1.86 (2H, m), 2.55-2.60 (1H, m), 2.70-2.77 (1H, m), 3.50-3.67 (2H, m), 4.41-4.42 (1H, m), 5.52 (1H, d, J = 7.8 Hz), 7.20-7.36 (5H, m), 7.47 (1H, d, J = 7.8 Hz), 7.78 (1H, brs), 11.2 (1H, brs) Foam |
| 127 | 214 | (structure) | 39 | (DMSO-d6) 1.77-1.91 (2H, m), 1.98-2.09 (2H, m), 2.68-2.94 (2H, m), 3.10-3.18 (2H, m), 3.80 (2H, t, J = 7.0 Hz), 4.72-4.81 (1H, m), 5.58 (1H, d, J = 7.8 Hz), 7.20-7.33 (4H, m), 7.62 (1H, d, J = 6.5 Hz), 7.65 (1H, d, J = 7.8 Hz), 11.2 (1H, brs) Foam |

Example 128

Synthesis of N-(3-(cyclopropylmethoxy)benzyl)-4-((2,4-dioxo-3,4-dihydropyrimidin-1(2H)-yl)methyl)piperidine-1-sulfonamide

[Formula 82]

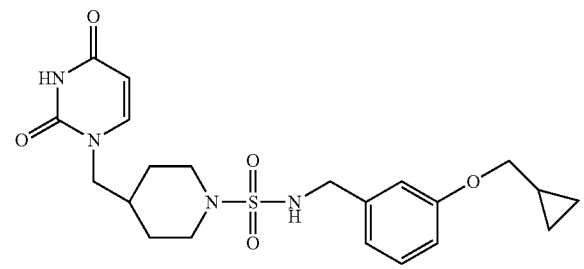

The 4-(aminomethyl)-N-(3-(cyclopropylmethoxy)benzyl)piperidine-1-sulfonamide (101 mg) obtained in Reference Example 215 was dissolved in DMF (1.0 mL). To the solution, a molecular sieve 4A (hereinafter, referred to as MS 4A; 20 mg) and an aliquot (1.2 mL) of a solution of 3-methoxy-2-propenoyl isocyanate (64 mg) in toluene (2.0 mL) obtained according to a method described in the document (J. Heterocyclic Chem., 36, 293 (1999)) were gradually added at 0° C., and the mixture was stirred at room temperature for 3 days. To the reaction mixture, water (5.0 mL) was added, and the resultant mixture was then extracted with ethyl acetate (10 mL). The organic layer was washed with water (5.0 mL) and brine (5.0 mL), dried over anhydrous sodium sulfate, and then concentrated under reduced pressure. The residue was purified by silica gel column chromatography (70% ethyl acetate/hexane). The obtained colorless oil (104 mg) was dissolved in a hydrochloric acid-dioxane solution (4.0 M, 2.0 mL), and the mixture was stirred at room temperature for 1.5 hours. The reaction mixture was concentrated under reduced pressure, and the residue was co-evaporated with toluene (5.0 mL). The residue was then purified by silica gel column chromatography (2% methanol/chloroform) to obtain the title compound (63 mg, yield: 64%) as a colorless solid.

1H-NMR (DMSO-d6) δ (ppm): 0.28-0.33 (2H, m), 0.53-0.57 (2H, m), 1.08-1.13 (3H, m), 1.54-1.60 (2H, m), 2.40-2.68 (2H, m), 3.46-3.55 (4H, m), 3.78 (2H, d, J=7.0 Hz), 4.01 (2H, d, J=5.9 Hz), 5.53 (1H, d, J=7.8 Hz), 6.75-6.90 (3H, m), 7.17-7.24 (2H, m), 7.57 (1H, d, J=8.1 Hz), 7.67 (1H, brs), 11.2 (1H, brs)

Example 129

Synthesis of N-benzyl-4-((2,4-dioxo-3,4-dihydropyrimidin-1(2H)-yl)methyl)piperidine-1-sulfonamide

[Formula 83]

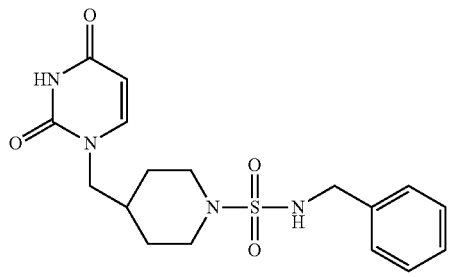

The title compound (9.2 mg) was obtained as a colorless solid according to the method of Example 128 from the compound obtained in Reference Example 216.

1H-NMR (DMSO-d6) δ (ppm): 1.03-1.15 (2H, m), 1.49-1.62 (2H, m), 1.62-1.82 (1H, m), 2.49-2.58 (2H, m), 3.47-3.54 (4H, m), 4.03 (2H, d, J=6.2 Hz), 5.53 (1H, d, J=7.9 Hz), 7.22-7.36 (5H, m), 7.58 (1H, d, J=7.9 Hz), 7.70 (1H, t, J=6.2 Hz), 11.2 (1H, brs)

Example 130

Synthesis of (R)-1-(3-(2-(hydroxydiphenylmethyl)pyrrolidin-1-ylsulfonyl)propyl)pyrimidine-2,4(1H,3H)-dione

[Formula 84]

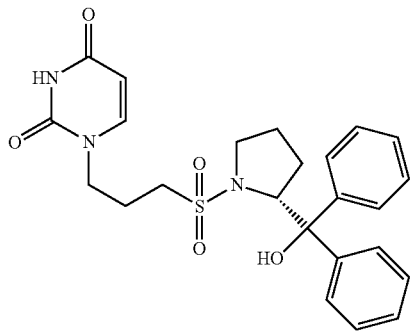

The (R)-1-(3-bromopropylsulfonyl)-2-((tert-butyldimethylsilyloxy)diphenylmethyl)pyrrolidine (1.18 g) obtained in Reference Example 217 was dissolved in DCE (50 mL). To the solution, 2,4-bis(trimethylsilyloxy)pyrimidine (1.11 g) obtained according to a method described in the document (Nucleosides & Nucleotides, 4, 565-585 (1985)) and iodine (55 mg) were added, and the mixture was heated to reflux at 93° C. for 10 hours. The reaction mixture was cooled to room temperature, water (20 mL) and an aqueous saturated sodium thiosulfate solution (1.0 mL) were then added thereto, and the mixture was then extracted with 10% methanol/chloroform (10 mL). The organic layer was washed with brine (20 mL), dried over anhydrous sodium sulfate, and then concentrated under reduced pressure. The residue was purified by silica gel column chromatography (2% methanol/chloroform). The obtained compound was dissolved in THF (3.0 mL). To the solution, a solution of TBAF in THF (1.0 M, 1.1 mL) was added, and the mixture was stirred at room temperature for 3 hours. The reaction mixture was concentrated under reduced pressure, and the residue was then purified by silica gel column chromatography (2.5% methanol/chloroform) to obtain the title compound (70 mg, yield: 5.4%) as a foam.

$^1$H-NMR (DMSO-d$_6$) δ (ppm): 1.62-1.67 (3H, m), 1.81-1.84 (2H, m), 1.98-2.12 (2H, m), 2.35-2.40 (1H, m), 3.22-3.24 (1H, m), 3.40-3.64 (3H, m), 5.22 (1H, d, J=6.2 Hz), 5.57 (1H, d, J=7.6 Hz), 5.65 (1H, brs), 7.05-7.53 (11H, m), 11.3 (1H, brs)

Example 131

Synthesis of (R)-1-(3-(2-(bis(4-fluorophenyl)(hydroxy)methyl)pyrrolidin-1-ylsulfonyl)propyl)pyrimidine-2,4(1H, 3H)-dione

[Formula 85]

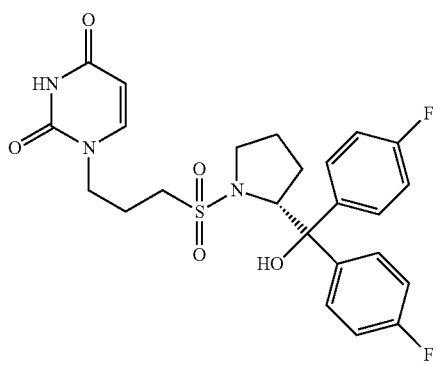

The title compound (80 mg, yield: 8.1%) was obtained as a foam by synthesis according to the method of Example 130 from the (R)-1-(3-bromopropylsulfonyl)-2-((tert-butyldimethylsilyloxy)bis(4-fluorophenyl)methyl)pyrrolidine (920 mg) obtained in Reference Example 218.

$^1$H-NMR (DMSO-d$_6$) δ (ppm): 1.71-1.79 (5H, m), 2.00-2.09 (1H, m), 2.43-2.72 (2H, m), 3.20-3.27 (1H, m), 3.51-3.70 (3H, m), 5.06 (1H, d, J=6.5 Hz), 5.56 (1H, d, J=7.8 Hz), 5.78 (1H, brs), 6.98-7.12 (4H, m), 7.38-7.57 (5H, m), 11.0 (1H, brs)

Example 132

Synthesis of (R)-1-(3-(2-(bis(3-fluorophenyl)(hydroxy)methyl)pyrrolidin-1-ylsulfonyl)propyl)pyrimidine-2,4(1H, 3H)-dione

[Formula 86]

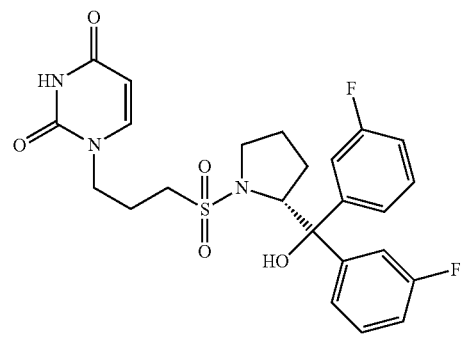

The title compound (40 mg, yield: 4.2%) was obtained as a foam by synthesis according to the method of Example 130 from the (R)-1-(3-bromopropylsulfonyl)-2-((tert-butyldimethylsilyloxy)bis(3-fluorophenyl)methyl)pyrrolidine (910 mg) obtained in Reference Example 219.

$^1$H-NMR (CDCl$_3$) δ (ppm): 1.53-1.58 (1H, m), 1.72-1.91 (2H, m), 2.02-2.17 (3H, m), 2.48-2.66 (2H, m), 3.03-3.10 (1H, m), 3.34 (1H, s), 3.67-3.79 (3H, m), 5.22 (1H, dd, J=3.8, 8.6 Hz), 5.73 (1H, d, J=7.8 Hz), 6.93-7.00 (2H, m), 7.17-7.33 (7H, m), 8.66 (1H, brs)

Example 133

Synthesis of 3-(2,4-dioxo-3,4-dihydropyrimidin-1(2H)-yl)-N-methyl-N-((1-phenylcyclopropyl)methyl)propane-1-sulfonamide

[Formula 87]

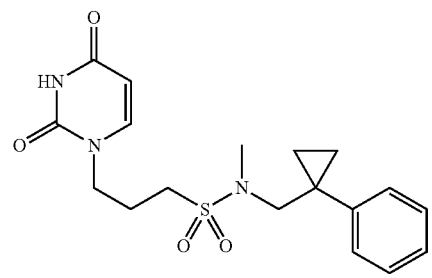

The 3-bromo-N-methyl-N-((1-phenylcyclopropyl)methyl)propane-1-sulfonamide (1.69 g) obtained in Reference Example 221 was dissolved in DCE (100 mL). To the solution, 2,4-bis(trimethylsilyloxy)pyrimidine (1.1 g) obtained according to a method described in the document (Nucleosides & Nucleotides, 4, 565-585 (1985)) and iodine (124 mg) were added, and the mixture was heated to reflux at 93° C. for 10 hours. The reaction mixture was cooled to room temperature, water (50 mL) and an aqueous saturated sodium thiosulfate solution (5 mL) were then added thereto, and the mixture was then extracted with 100 methanol/chloroform (50 mL). The organic layer was washed with brine (50 mL), dried over anhydrous sodium sulfate, and then concentrated under reduced pressure. The residue was purified by silica gel column chromatography (2% methanol/chloroform) to obtain the title compound (43 mg, yield: 3.0%) as a foam.

$^1$H-NMR (DMSO-d$_6$) δ (ppm): 0.83 (4H, s), 1.71-1.82 (2H, m), 2.66 (3H, s), 2.78 (2H, t, J=7.6 Hz), 3.33 (2H, m) 3.62 (2H, t, J=7.3 Hz), 5.56 (1H, d, J=7.8 Hz), 7.15-7.36 (5H, m), 7.54 (1H, d, J=7.8 Hz), 11.2 (1H, s)

Example 134

Synthesis of N-(3-(cyclopropylmethoxy)phenethyl)-3-(2,4-dioxo-3,4-dihydropyrimidin-1(2H)-yl)-N-methylpropane-1-sulfonamide

[Formula 88]

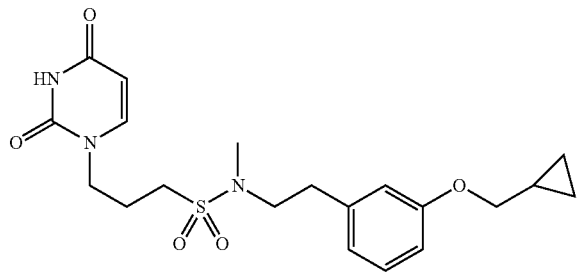

The title compound (34 mg, yield: 13%) was obtained as a foam by synthesis according to the method of Example 133 from the 3-bromo-N-(3-(cyclopropylmethoxy)phenethyl)-N-methylpropane-1-sulfonamide (249 mg) obtained in Reference Example 223.

$^1$H-NMR (CDCl$_3$) δ (ppm): 0.32-0.38 (2H, m), 0.61-0.68 (2H, m), 1.22-1.31 (1H, m), 2.08-2.18 (2H, m), 2.74 (2H, t, J=6.8 Hz), 2.83-2.88 (5H, m), 3.45 (2H, t, J=7.3 Hz), 3.79 (2H, d, J=6.8 Hz), 3.86 (2H, t, J=7.0 Hz), 5.71 (1H, d, J=7.8 Hz), 6.76-6.80 (3H, m), 7.18-7.27 (2H, m), 8.39 (1H, brs)

Example 135

Synthesis of N-(5-((2,4-dioxo-3,4-dihydropyrimidin-1(2H)-yl)methoxy)-2-methylpentan-2-yl)-3-methoxybenzenesulfonamide

[Formula 89]

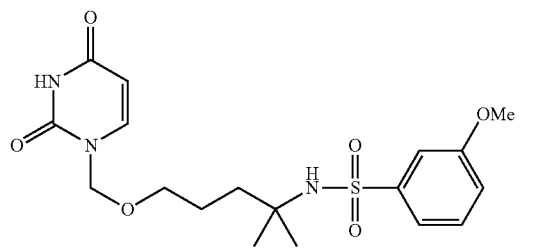

The benzyl 5-((2,4-dioxo-3,4-dihydropyrimidin-1(2H)-yl)methoxy)-2-methylpentan-2-ylcarbamate (2.80 g) obtained in Reference Example 226 was dissolved in methanol (40 mL). To the solution, 10% palladium-carbon (600 mg) was added, and the reaction mixture was stirred at room temperature for 2 hours under a hydrogen atmosphere. The precipitate was removed by filtration through a pad of Celite and washed with methanol (120 mL). Then, the combined filtrate was concentrated under reduced pressure. An aliquot (14.5 mg) of the residue was dissolved in dichloromethane (1.5 mL). To the mixture, triethylamine (17 μL) and 3-methoxybenzenesulfonyl chloride (13 μL) were added, and the mixture was stirred at room temperature for 3 days. To the reaction mixture, water (5.0 mL) was added, and the resultant mixture was then extracted with ethyl acetate (10 mL). The organic layer was washed with brine (5.0 mL), dried over anhydrous sodium sulfate, and then concentrated under reduced pressure. The residue was purified by silica gel column chromatography (4% methanol/chloroform) to obtain the title compound (10 mg, yield: 40%) as a foam.

$^1$H-NMR (DMSO-d$_6$) δ (ppm): 1.02 (6H, s), 1.34-1.46 (4H, m), 3.26-3.32 (2H, m), 3.79 (3H, s), 5.01 (2H, s), 5.60 (1H, d, J=7.9 Hz), 7.11-7.15 (1H, m), 7.32-7.48 (4H, m), 7.65 (1H, d, J=7.9 Hz), 11.31 (1H, brs)

Examples 136 to 156

Compounds shown below were synthesized according to the method of Example 135 from the compound of Reference Example 226. The results are shown in tables below.

Example 136

4-chloro-N-(5-((2,4-dioxo-3,4-dihydropyrimidin-1(2H)-yl)methoxy)-2-methylpentan-2-yl)benzenesulfonamide Example 137

3,4-dichloro-N-(5-((2,4-dioxo-3,4-dihydropyrimidin-1(2H)-yl)methoxy)-2-methylpentan-2-yl)benzenesulfonamide Example 138

4,5-dichloro-N-(5-((2,4-dioxo-3,4-dihydropyrimidin-1(2H)-yl)methoxy)-2-methylpentan-2-yl)thiophene-2-sulfonamide Example 139

3,5-dichloro-N-(5-((2,4-dioxo-3,4-dihydropyrimidin-1(2H)-yl)methoxy)-2-methylpentan-2-yl)benzenesulfonamide Example 140

N-(5-((2,4-dioxo-3,4-dihydropyrimidin-1(2H)-yl)methoxy)-2-methylpentan-2-yl)thiophene-2-sulfonamide

Example 141

3-bromo-N-(5-((2,4-dioxo-3,4-dihydropyrimidin-1(2H)-yl)methoxy)-2-methylpentan-2-yl)benzenesulfonamide

Example 142

2-chloro-N-(5-((2,4-dioxo-3,4-dihydropyrimidin-1(2H)-yl)methoxy)-2-methylpentan-2-yl)benzenesulfonamide

Example 143

N-(5-((2,4-dioxo-3,4-dihydropyrimidin-1(2H)-yl)methoxy)-2-methylpentan-2-yl)-3-(trifluoromethoxy)benzenesulfonamide

Example 144

N-(5-((2,4-dioxo-3,4-dihydropyrimidin-1(2H)-yl)methoxy)-2-methylpentan-2-yl)-2-methoxy-4-methylbenzenesulfonamide

Example 145

3-(difluoromethoxy)-N-(5-((2,4-dioxo-3,4-dihydropyrimidin-1(2H)-yl)methoxy)-2-methylpentan-2-yl)benzenesulfonamide

Example 146

3-(N-(5-((2,4-dioxo-3,4-dihydropyrimidin-1(2H)-yl)methoxy)-2-methylpentan-2-yl)sulfamoyl)phenylbenzoate

Example 147

5-(dimethylamino)-N-(5-((2,4-dioxo-3,4-dihydropyrimidin-1(2H)-yl)methoxy)-2-methylpentan-2-yl)naphthalene-1-sulfonamide

Example 148

3-chloro-N-(5-((2,4-dioxo-3,4-dihydropyrimidin-1(2H)-yl)methoxy)-2-methylpentan-2-yl)benzenesulfonamide

Example 149

4,5-dibromo-N-(5-((2,4-dioxo-3,4-dihydropyrimidin-1(2H)-yl)methoxy)-2-methylpentan-2-yl)thiophene-2-sulfonamide

Example 150

N-(5-((2,4-dioxo-3,4-dihydropyrimidin-1(2H)-yl)methoxy)-2-methylpentan-2-yl)-3-fluorobenzenesulfonamide

Example 151

N-(5-((2,4-dioxo-3,4-dihydropyrimidin-1(2H)-yl)methoxy)-2-methylpentan-2-yl)-2-methylbenzenesulfonamide

Example 152

2-cyano-N-(5-((2,4-dioxo-3,4-dihydropyrimidin-1(2H)-yl)methoxy)-2-methylpentan-2-yl)benzenesulfonamide

Example 153

N-(5-((2,4-dioxo-3,4-dihydropyrimidin-1(2H)-yl)methoxy)-2-methylpentan-2-yl)-4-methylbenzenesulfonamide

Example 154

N-(5-((2,4-dioxo-3,4-dihydropyrimidin-1(2H)-yl)methoxy)-2-methylpentan-2-yl)-3-methylbenzenesulfonamide

Example 155 methyl 2-(N-(5-((2,4-dioxo-3,4-dihydropyrimidin-1(2H)-yl)methoxy)-2-methylpentan-2-yl)sulfamoyl)benzoate

Example 156

2-bromo-N-(5-((2,4-dioxo-3,4-dihydropyrimidin-1(2H)-yl)methoxy)-2-methylpentan-2-yl)benzenesulfonamide

TABLE 68

| Example | Product | Yield (%) | $^1$H-NMR δ (ppm) Form |
|---|---|---|---|
| 136 | 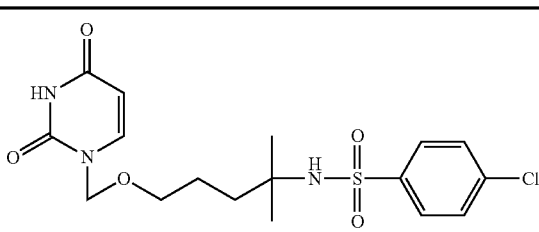 | 35 | (CD$_3$OD) 1.12 (6H, s), 1.45-1.54 (4H, m), 3.42-3.46 (2H, m), 5.11 (2H, s), 5.69 (1H, d, J = 7.8 Hz), 7.52-7.55 (2H, m), 7.60 (1H, d, J = 7.8 Hz), 7.82-7.85 (2H, m) Colorless gum |

TABLE 68-continued
| Example | Product | Yield (%) | ¹H-NMR δ (ppm) Form |
|---|---|---|---|
| 137 | 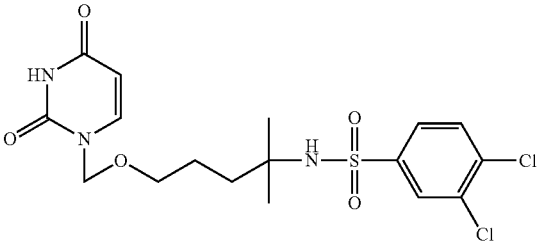 [SMILES: CC(C)(CCCOCn1ccc(=O)[nH]c1=O)NS(=O)(=O)c1ccc(Cl)c(Cl)c1] | 34 | (CD₃OD) 1.14 (6H, s), 1.52-1.54 (4H, m), 3.42-3.47 (2H, m), 5.11 (2H, s), 5.69 (1H, d, J = 7.8 Hz), 7.60 (1H, d, J = 7.8 Hz), 7.68-7.79 (2H, m), 7.89-7.99 (1H, m) Colorless gum |
| 138 | 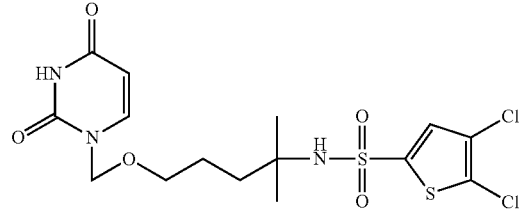 [SMILES: CC(C)(CCCOCn1ccc(=O)[nH]c1=O)NS(=O)(=O)c1cc(Cl)c(Cl)s1] | 66 | (CD₃OD) 1.10 (6H, s), 1.55-1.59 (4H, m), 3.48-3.50 (2H, m), 5.13 (2H, s), 5.69 (1H, d, J = 7.8 Hz), 7.45 (1H, s), 7.61 (1H, d, J = 7.8 Hz) Colorless gum |
TABLE 69
| Example | Product | Yield (%) | ¹H-NMR δ (ppm) Form |
|---|---|---|---|
| 139 | 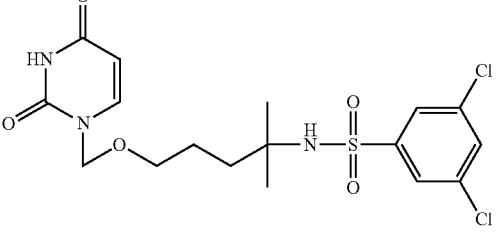 | 49 | (CD₃OD) 1.15 (6H, s), 1.51-1.55 (4H, m), 3.43-3.46 (2H, m), 5.11 (2H, s), 5.69 (1H, d, J = 7.8 Hz), 7.60 (1H, d, J = 7.8 Hz), 7.67-7.68 (1H, m), 7.78-7.80 (2H, m) Colorless gum |
| 140 | 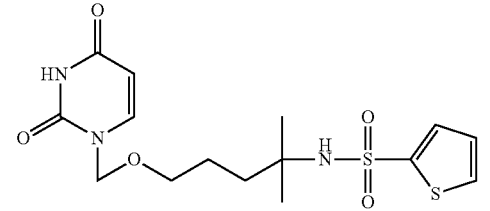 [SMILES: CC(C)(CCCOCn1ccc(=O)[nH]c1=O)NS(=O)(=O)c1cccs1] | 36 | (CD₃OD) 1.04 (6H, s), 1.50-1.58 (4H, m), 3.43-3.47 (2H, m), 5.12 (2H, s), 5.70 (1H, d, J = 7.9 Hz), 7.06-7.10 (1H, m), 7.56-7.58 (1H, m), 7.60 (1H, d, J = 7.9 Hz), 7.71-7.74 (1H, m) Colorless gum |
| 141 | 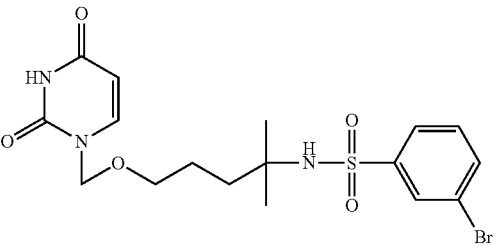 [SMILES: CC(C)(CCCOCn1ccc(=O)[nH]c1=O)NS(=O)(=O)c1cccc(Br)c1] | 40 | (CD₃OD) 1.13 (6H, s), 1.49-1.53 (4H, m), 3.39-3.45 (2H, m), 5.11 (2H, s), 5.70 (1H, d, J = 7.8 Hz), 7.43-7.47 (1H, m), 7.60 (1H, d, J = 7.8 Hz), 7.71-7.73 (1H, m), 7.81-7.83 (1H, m), 7.99-7.80 (1H, m) Colorless gum |

TABLE 70

| Example | Product | Yield (%) | $^1$H-NMR δ (ppm) Form |
|---|---|---|---|
| 142 | | 44 | (CD$_3$OD) 1.01 (6H, s), 1.40-1.49 (4H, m), 3.30-3.33 (2H, m), 5.00 (2H, s), 5.60 (1H, d, J = 7.8 Hz), 7.34-7.37 (1H, m), 7.40-7.52 (3H, m), 7.94-7.97 (1H, m) Colorless gum |
| 143 | | 74 | (CDCl$_3$) 1.17 (6H, s), 1.58-1.64 (4H, m), 3.51-3.55 (2H, m), 5.10 (1H, brs), 5.15 (2H, s), 5.79 (1H, d, J = 7.8 Hz), 7.34 (1H, d, J = 7.8 Hz), 7.37-7.41 (1H, m), 7.52-7.58 (1H, m), 7.73-7.75 (1H, m), 7.81-7.84 (1H, m), 8.86 (1H, brs) Colorless gum |
| 144 | | 48 | (CD$_3$OD) 1.08 (6H, s), 1.43-1.49 (2H, m), 1.52-1.56 (2H, m), 2.41 (3H, s), 3.37-3.40 (2H, m), 3.93 (3H, s), 5.10 (2H, s), 5.69 (1H, d, J = 7.8 Hz), 6.84-6.87 (1H, m), 6.97-6.99 (1H, m), 7.59-7.67 (2H, m) Colorless gum |

TABLE 71

| Example | Product | Yield (%) | $^1$H-NMR δ (ppm) Form |
|---|---|---|---|
| 145 | | 75 | (CDCl$_3$) 1.18 (6H, s), 1.56-1.62 (4H, m), 3.50-3.54 (2H, m), 4.97 (1H, brs), 5.14 (2H, s), 5.78 (1H, d, J = 8.1 Hz), 6.58 (1H, t, J = 78.3 Hz), 7.28-7.34 (2H, m), 7.47-7.53 (1H, m), 7.62-7.66 (1H, m), 7.72-7.75 (1H, m), 8.57 (1H, brs) Colorless gum |
| 146 | | 44 | (CDCl$_3$) 1.22 (6H, s), 1.54-1.57 (4H, m), 3.50-3.53 (2H, m), 4.81 (1H, brs), 5.12 (2H, s), 5.75 (1H, d, J = 8.1 Hz), 7.27-7.81 (8H, m), 8.19-8.22 (2H, m), 9.57 (1H, brs) Colorless gum |

TABLE 71-continued

| Example | Product | Yield (%) | ¹H-NMR δ (ppm) Form |
|---|---|---|---|
| 147 | | 53 | (CDCl₃) 1.09 (6H, s), 1.50-1.56 (4H, m), 2.89 (6H, s), 3.38-3.42 (2H, m), 4.75 (1H, brs), 5.09 (2H, s), 5.76 (1H, d, J = 8.1 Hz), 7.16-7.29 (3H, m), 7.50-7.54 (2H, m), 8.15-8.29 (2H, m), 8.51-8.54 (1H, m) Colorless gum |

TABLE 72

| Example | Product | Yield (%) | ¹H-NMR δ (ppm) Form |
|---|---|---|---|
| 148 | | 29 | (CD₃OD) 1.13 (6H, s), 1.49-1.53 (4H, m), 3.39-3.44 (2H, m), 5.11 (2H, s), 5.70 (1H, d, J = 7.9 Hz), 7.51-7.61 (2H, m), 7.61 (1H, d, J = 7.9 Hz), 7.77-7.85 (2H, m) Colorless gum |
| 149 | | 24 | (CD₃OD) 1.22 (6H, s), 1.55-1.58 (4H, m), 3.44-3.48 (2H, m), 5.13 (2H, s), 5.70 (1H, d, J = 7.9 Hz), 7.44 (1H, s), 7.61 (1H, d, J = 7.9 Hz) Colorless gum |
| 150 | | 42 | (CD₃OD) 1.03 (6H, s), 1.42-1.44 (4H, m), 3.33-3.35 (2H, m), 5.01 (2H, s), 5.60 (1H, d, J = 8.1 Hz), 7.20-7.25 (2H, m), 7.46-7.58 (3H, m) Colorless gum |

TABLE 73

| Example | Product | Yield (%) | ¹H-NMR δ (ppm) Form |
|---|---|---|---|
| 151 | | 39 | (DMSO-d₆) 1.01 (6H, s), 1.19-1.25 (4H, m), 2.57 (3H, s), 3.27-3.38 (2H, m), 5.00 (2H, s), 5.60 (1H, d, J = 7.9 Hz), 7.30-7.49 (4H, m), 7.63-7.86 (2H, m), 11.30 (1H, brs) Colorless solid |

TABLE 73-continued

| Example | Product | Yield (%) | $^1$H-NMR δ (ppm) Form |
|---|---|---|---|
| 152 | 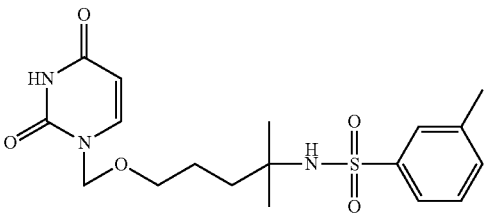 [SMILES: Cc1cccc(S(=O)(=O)NC(C)(C)CCCOCn2ccc(=O)[nH]c2=O)c1] | 23 | (DMSO-$d_6$) 1.07 (6H, s), 1.39-1.49 (4H, m), 3.28-3.33 (2H, m), 5.01 (2H, s), 5.60 (1H, d, J = 7.8 Hz), 7.65 (1H, d, J = 7.8 Hz), 7.75-7.81 (1H, m), 7.85-7.91 (2H, m), 8.04-8.07 (2H, m), 11.31 (1H, brs) Foam |
| 153 | 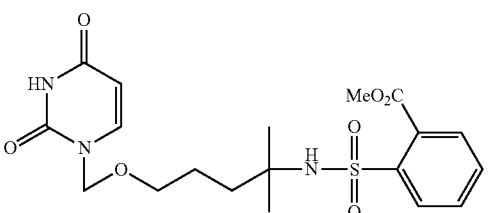 | 44 | (DMSO-$d_6$) 1.00 (6H, s), 1.32-1.45 (4H, m), 2.36 (3H, s), 3.31-3.38 (2H, m), 5.01 (2H, s), 5.60 (1H, d, J = 7.9 Hz), 7.32-7.35 (3H, m), 7.64-7.69 (3H, m), 11.31 (1H, brs) Colorless solid |

TABLE 74

| Example | Product | Yield (%) | $^1$H-NMR δ (ppm) Form |
|---|---|---|---|
| 154 | 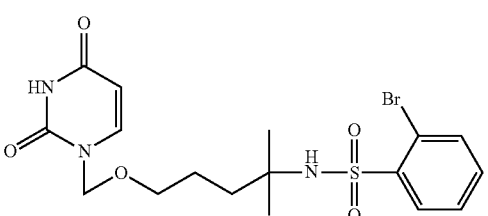 | 36 | (DMSO-$d_6$) 1.01 (6H, s), 1.32-1.45 (4H, m), 2.36 (3H, s), 3.25-3.38 (2H, m), 5.00 (2H, s), 5.60 (1H, d, J = 7.9 Hz), 7.36-7.44 (3H, m), 7.58-7.66 (3H, m), 11.31 (1H, brs) Foam |
| 155 | | 16 | (DMSO-$d_6$) 1.03 (6H, s), 1.38-1.45 (4H, m), 3.25-3.38 (2H, m), 3.82 (3H, s), 5.01 (2H, s), 5.60 (1H, d, J = 7.9 Hz), 7.15 (1H, s), 7.57-7.72 (4H, m), 7.94-7.97 (1H, m), 11.31 (1H, brs) Colorless gum |
| 156 | | 14 | (DMSO-$d_6$) 1.05 (6H, s), 1.43-1.46 (4H, m), 3.27-3.41 (2H, m), 5.02 (2H, s), 5.61 (1H, d, J = 7.8 Hz), 7.46-7.58 (3H, m), 7.66 (1H, d, J = 7.8 Hz), 7.79-7.83 (1H, m), 8.02-8.07 (1H, m), 11.32 (1H, brs) Colorless gum |

Example 157

Synthesis of N-(4-((2,4-dioxo-3,4-dihydropyrimidin-1(2H)-yl)methoxy)-2-methylbutan-2-yl)benzenesulfonamide

[Formula 90]

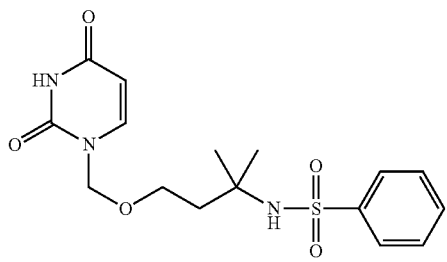

The N-(4-(methoxymethoxy)-2-methylbutan-2-yl)benzenesulfonamide (275 mg) obtained in Reference Example 227 was dissolved in dichloromethane (1.0 mL). To the solution, a solution of BCl$_3$ in dichloromethane (1.0 M, 0.32 mL) was gradually added at 0° C., and the mixture was stirred at room temperature for 2 hours. The reaction mixture was concentrated under reduced pressure, and the residue was then dissolved in DCE (10 mL). To the mixture, 2,4-bis(trimethylsilyloxy)pyrimidine (256 mg) obtained according to a method described in the document (Nucleosides & Nucleotides, 4, 565-585 (1985)) and iodine (10 mg) were added, and the mixture was heated to reflux at 93° C. for 1.5 hours. The reaction mixture was cooled to room temperature, an aqueous saturated sodium bisulfite solution (5.0 mL) was then added thereto, and the resultant mixture was then extracted with ethyl acetate (20 mL). The organic layer was washed with brine (10 mL), dried over anhydrous sodium sulfate, and then concentrated under reduced pressure. The residue was purified by silica gel column chromatography (3% methanol/chloroform) to obtain the title compound (120 mg, yield: 34%) as a foam.

$^1$H-NMR (DMSO-d$_6$) δ (ppm): 1.02 (6H, s), 1.66-1.71 (2H, m), 3.43-3.48 (2H, m), 4.99 (2H, s), 5.60 (1H, d, J=7.9 Hz), 7.49-7.61 (4H, m), 7.64 (1H, d, J=7.9 Hz), 7.77-7.81 (2H, m), 11.31 (1H, brs)

Examples 158 to 167

Compounds shown below were synthesized according to the method of Example 157 from the compounds obtained in Reference Examples 228 to 237, respectively. The results are shown in tables below.

Example 158

N-(5-((2,4-dioxo-3,4-dihydropyrimidin-1(2H)-yl)methoxy)-2-methylpentan-2-yl)benzenesulfonamide

Example 159

3-(cyclopropylmethoxy)-N-(5-((2,4-dioxo-3,4-dihydropyrimidin-1(2H)-yl)methoxy)-2-methylpentan-2-yl)benzenesulfonamide

Example 160

3-(2,2-difluoroethoxy)-N-(5-((2,4-dioxo-3,4-dihydropyrimidin-1(2H)-yl)methoxy)-2-methylpentan-2-yl)benzenesulfonamide

Example 161

3-(cyclopentyloxy)-N-(5-((2,4-dioxo-3,4-dihydropyrimidin-1(2H)-yl)methoxy)-2-methylpentan-2-yl)benzenesulfonamide

Example 162

(Z)—N-(5-((2,4-dioxo-3,4-dihydropyrimidin-1(2H)-yl)methoxy)-2-methylpentan-2-yl)-3-(prop-1-enyl)benzenesulfonamide

Example 163

N-(4-((2,4-dioxo-3,4-dihydropyrimidin-1(2H)-yl)methoxy)butyl)benzenesulfonamide

Example 164

N-(1-(3-((2,4-dioxo-3,4-dihydropyrimidin-1(2H)-yl)methoxy)propyl)cyclopropyl)benzenesulfonamide

Example 165

N-(1-(3-((2,4-dioxo-3,4-dihydropyrimidin-1(2H)-yl)methoxy)propyl)cyclopropyl)-3-methoxybenzenesulfonamide

Example 166

3-(cyclopropylmethoxy)-N-(4-((2,4-dioxo-3,4-dihydropyrimidin-1(2H)-yl)methoxy)butyl)benzenesulfonamide

Example 167

3-(cyclopropylmethoxy)-N-(1-(3-((2,4-dioxo-3,4-dihydropyrimidin-1(2H)-yl)methoxy)propyl)cyclopropyl)benzenesulfonamide

TABLE 75

| Example | Reference Example No. | Product | Yield (%) | ¹H-NMR δ (ppm) Form |
|---|---|---|---|---|
| 158 | 228 | (uracil-CH₂-O-(CH₂)₃-C(CH₃)₂-NH-SO₂-phenyl) | 82 | (DMSO-d₆) 1.00 (6H, s), 1.24-1.40 (4H, m), 3.22-3.27 (2H, m), 5.00 (2H, s), 5.61 (1H, d, J = 7.9 Hz), 7.42 (1H, brs), 7.50-7.60 (3H, m), 7.65 (1H, d, J = 7.9 Hz), 7.78-7.81 (2H, m), 11.31 (1H, brs) Foam |
| 159 | 229 | (uracil-CH₂-O-(CH₂)₃-C(CH₃)₂-NH-SO₂-phenyl-OCH₂-cyclopropyl) | 74 | (DMSO-d₆) 0.30-0.34 (2H, m), 0.53-0.56 (2H, m), 1.01 (6H, s), 1.15-1.24 (1H, m), 1.36-1.48 (4H, m), 3.32-3.39 (2H, m), 3.85 (2H, d, J = 6.9 Hz), 5.00 (2H, s), 5.60 (1H, d, J = 7.8 Hz), 7.09-7.13 (1H, m), 7.30-7.45 (4H, m), 7.64 (1H, d, J = 7.8 Hz), 11.30 (1H, brs) Pale yellow gum |

TABLE 76

| Example | Reference Example No. | Product | Yield (%) | ¹H-NMR δ (ppm) Form |
|---|---|---|---|---|
| 160 | 230 | (uracil-CH₂-O-(CH₂)₃-C(CH₃)₂-NH-SO₂-phenyl-O-CH₂-CHF₂) | 46 | (DMSO-d₆) 1.02 (6H, s), 1.36-1.46 (4H, m), 3.29-3.36 (2H, m), 4.38 (2H, td, J = 14.7, 3.5 Hz), 5.01 (2H, s), 5.60 (1H, d, J = 7.8 Hz), 6.40 (1H, tt, J = 54.2, 3.5 Hz), 7.20-7.24 (1H, m), 7.38-7.49 (4H, m), 7.65 (1H, d, J = 7.8 Hz), 11.32 (1H, brs) Foam |
| 161 | 231 | (uracil-CH₂-O-(CH₂)₃-C(CH₃)₂-NH-SO₂-phenyl-O-cyclopentyl) | 50 | (DMSO-d₆) 1.01 (6H, s), 1.32-1.47 (4H, m), 1.57-1.75 (6H, m), 1.87-1.96 (2H, m), 3.25-3.35 (2H, m), 4.81-4.85 (1H, m), 5.00 (2H, s), 5.60 (1H, d, J = 7.9 Hz), 7.06-7.10 (1H, m), 7.28-7.44 (4H, m), 7.64 (1H, d, J = 7.9 Hz), 11.31 (1H, brs) Foam |

TABLE 77

| Example | Reference Example No. | Product | Yield (%) | ¹H-NMR δ (ppm) Form |
|---|---|---|---|---|
| 162 | 232 | (uracil-CH₂-O-(CH₂)₃-C(CH₃)₂-NH-SO₂-phenyl-CH=CH-CH₃) | 62 | (CDCl₃) 1.18 (6H, s), 1.55-1.60 (4H, m), 1.88-1.92 (3H, m), 3.48-3.53 (2H, m), 4.75 (1H, brs), 5.13 (2H, s), 5.76-5.80 (1H, m), 5.84-5.97 (1H, m), 6.37-6.47 (1H, dd, J = 1.8, 11.7 Hz), 7.32 (1H, d, J = 8.1 Hz), 7.39-7.48 (2H, m), 7.69-7.74 (1H, m), 7.78-7.82 (1H, m), 8.36 (1H, brs) Foam |

TABLE 77-continued

| Example | Reference Example No. | Product | Yield (%) | ¹H-NMR δ (ppm) Form |
|---|---|---|---|---|
| 163 | 233 | 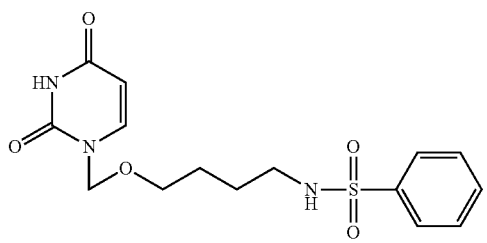 [SMILES: O=c1ccn(COCCCCNS(=O)(=O)c2ccccc2)c(=O)[nH]1] | 43 | (CDCl₃) 1.52-1.61 (4H, m), 2.91-2.98 (2H, m), 3.50-3.54 (2H, m), 5.12 (2H, s), 5.20-5.28 (1H, m), 5.78 (1H, d, J = 7.8 Hz), 7.32 (1H, d, J = 7.8 Hz), 7.48-7.60 (3H, m), 7.84-7.87 (2H, m), 9.47 (1H, brs) Colorless gum |

TABLE 78

| Example | Reference Example No. | Product | Yield (%) | ¹H-NMR δ (ppm) Form |
|---|---|---|---|---|
| 164 | 234 | 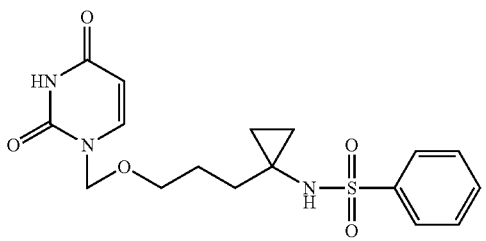 [SMILES: O=c1ccn(COCCCC2(NS(=O)(=O)c3ccccc3)CC2)c(=O)[nH]1] | 43 | (DMSO-d₆) 0.32-0.36 (2H, m), 0.48-0.53 (2H, m), 1.17-1.23 (2H, m), 1.44-1.49 (2H, m), 3.19-3.34 (2H, m), 4.96 (2H, s), 5.60 (1H, d, J = 7.9 Hz), 7.51-7.63 (4H, m), 7.76-7.78 (2H, m), 8.08 (1H, brs), 11.32 (1H, brs) Foam |
| 165 | 235 | 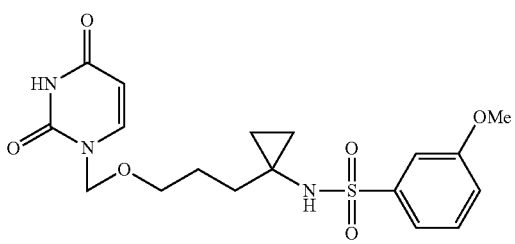 [SMILES: COc1cccc(S(=O)(=O)NC2(CCCOCn3ccc(=O)[nH]c3=O)CC2)c1] | 52 | (DMSO-d₆) 0.33-0.38 (2H, m), 0.51-0.55 (2H, m), 1.17-1.22 (2H, m), 1.43-1.51 (2H, m), 3.19-3.25 (2H, m), 3.79 (3H, s), 5.00 (2H, s), 5.60 (1H, d, J = 7.8 Hz), 7.13-7.46 (4H, m), 7.61 (1H, d, J = 7.8 Hz), 8.08 (1H, brs), 11.31 (1H, brs) Colorless gum |

TABLE 79

| Example | Reference Example No. | Product | Yield (%) | ¹H-NMR δ (ppm) Form |
|---|---|---|---|---|
| 166 | 236 | 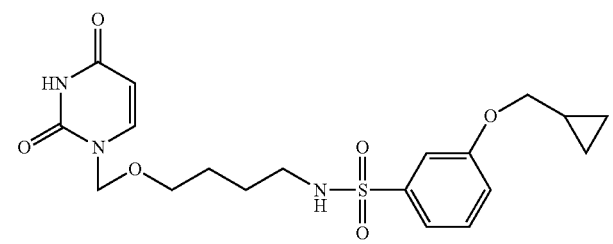 [SMILES: O=c1ccn(COCCCCNS(=O)(=O)c2cccc(OCC3CC3)c2)c(=O)[nH]1] | 47 | (DMSO-d₆) 0.32-0.36 (2H, m), 0.53-0.60 (2H, m), 1.19-1.24 (1H, m), 1.35-1.49 (4H, m), 2.66-2.73 (2H, m), 3.32-3.36 (2H, m), 3.86 (2H, d, J = 6.9 Hz), 5.00 (2H, s), 5.58 (1H, d, J = 7.8 Hz), 7.14-7.55 (5H, m), 7.64 (1H, d, J = 7.8 Hz), 11.31 (1H, brs) Pale yellow gum |

TABLE 79-continued

| Example | Reference Example No. | Product | Yield (%) | ¹H-NMR δ (ppm) Form |
|---|---|---|---|---|
| 167 | 237 | 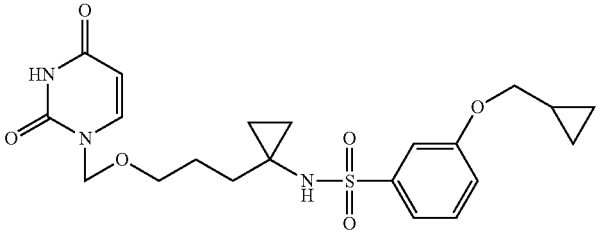 [SMILES: O=c1ccn(COCCCC2(NS(=O)(=O)c3cccc(OCC4CC4)c3)CC2)c(=O)[nH]1] | 56 | (DMSO-$d_6$) 0.30-0.37 (4H, m), 0.50-0.60 (4H, m), 1.18-1.24 (3H, m), 1.46-1.52 (2H, m), 3.21-3.27 (2H, m), 3.85 (2H, d, J = 6.9 Hz), 4.97 (2H, s), 5.59 (1H, d, J = 7.9 Hz), 7.12-7.16 (1H, m), 7.24-7.32 (2H, m), 7.40-7.46 (1H, m), 7.61 (1H, d, J = 7.9 Hz), 8.04 (1H, brs), 11.30 (1H, brs) Pale yellow gum |

Examples 168 to 171

Compounds shown below were synthesized according to the method of Example 135 from the compound of Reference Example 238. The results are shown in tables below.

Example 168

2-chloro-N-(5-(2,4-dioxo-3,4-dihydropyrimidin-1(2H)-yl)-2-methylpentan-2-yl)benzenesulfonamide

Example 169

2-bromo-N-(5-(2,4-dioxo-3,4-dihydropyrimidin-1(2H)-yl)-2-methylpentan-2-yl)benzenesulfonamide

Example 170

N-(5-(2,4-dioxo-3,4-dihydropyrimidin-1(2H)-yl)-2-methylpentan-2-yl)-2-nitrobenzenesulfonamide

Example 171

2-(N-(5-(2,4-dioxo-3,4-dihydropyrimidin-1(2H)-yl)-2-methylpentan-2-yl)sulfamoyl)benzoic acid

TABLE 80

| Example | Product | Yield (%) | ¹H-NMR δ (ppm) Form |
|---|---|---|---|
| 168 | 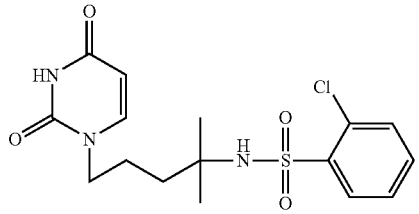 [SMILES: CC(C)(CCCn1ccc(=O)[nH]c1=O)NS(=O)(=O)c1ccccc1Cl] | 45 | (DMSO-$d_6$) 1.03 (6H, s), 1.39-1.45 (2H, m), 1.51-1.59 (2H, m), 3.57 (2H, t, J = 6.8 Hz), 5.54 (1H, d, J = 7.7 Hz), 7.48-7.65 (5H, m), 8.00 (1H, dd, J = 1.6, 7.7 Hz), 11.18 (1H, brs) Foam |
| 169 | 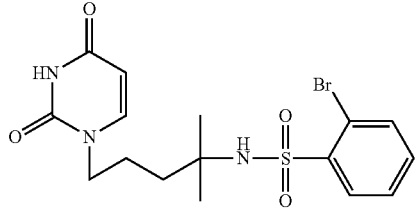 [SMILES: CC(C)(CCCn1ccc(=O)[nH]c1=O)NS(=O)(=O)c1ccccc1Br] | 39 | (DMSO-$d_6$) 1.04 (6H, s), 1.41-1.46 (2H, m), 1.55-1.59 (2H, m), 3.57 (2H, t, J = 6.7 Hz), 5.54 (1H, d, J = 7.7 Hz), 7.46-7.69 (4H, m), 7.81 (1H, dd, J = 1.5, 7.5 Hz), 8.04 (1H, dd, J = 1.9, 7.7 Hz), 11.19 (1H, brs) Foam |

TABLE 81

| Example | Product | Yield (%) | $^1$H-NMR δ (ppm) Form |
|---|---|---|---|
| 170 | (structure) | 35 | (DMSO-$d_6$) 1.07 (6H, s), 1.42-1.47 (2H, m), 1.53-1.58 (2H, m), 3.58 (2H, t, J = 6.5 Hz), 5.53 (1H, d, J = 7.8 Hz), 7.57 (1H, d, J = 7.8 Hz), 7.79-7.92 (4H, m), 8.04-8.09 (1H, m), 11.91 (1H, brs) Foam |
| 171 | (structure) | 65 | (DMSO-$d_6$) 1.06 (6H, s), 1.39-1.55 (4H, m), 3.54 (2H, t, J = 6.6 Hz), 5.52 (1H, dd, J = 2.3, 7.8 Hz), 7.13-7.27 (2H, m), 7.53 (1H, d, J = 7.9 Hz), 7.62-7.66 (3H, m), 7.91-7.94 (1H, m), 11.18 (1H, brs) Colorless solid |

Example 172

Synthesis of N-(5-((2,4-dioxo-3,4-dihydropyrimidin-1(2H)-yl)methylthio)-2-methylpentan-2-yl)benzenesulfonamide

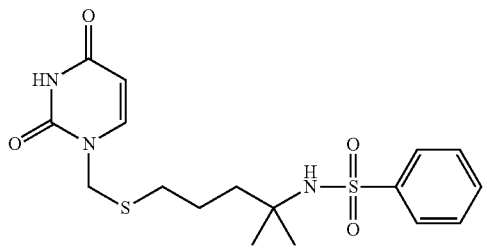

[Formula 91]

The tert-butyl 5-(methoxymethylthio)-2-methylpentan-2-ylcarbamate (780 mg) obtained in Reference Example 241 was dissolved in dichloromethane (3.0 mL). To the solution, a solution of BCl$_3$ in dichloromethane (1.0 M, 940 µL) was gradually added at 0° C., and the mixture was stirred at room temperature for 1.5 hours. The reaction mixture was concentrated under reduced pressure, and the residue was then dissolved in DCE (28 mL). To the mixture, 2,4-bis(trimethylsilyloxy)pyrimidine (1.08 g) obtained according to a method described in the document (Nucleosides & Nucleotides, 4, 565-585 (1985)) and iodine (28 mg) were added, and the mixture was heated to reflux at 93° C. for 24 hours. The reaction mixture was cooled to room temperature, an aqueous saturated sodium bisulfite solution (25 mL) was then added thereto, and the resultant mixture was then extracted with ethyl acetate (50 mL). The organic layer was washed with brine (20 mL), dried over anhydrous sodium sulfate, and then concentrated under reduced pressure. The residue was purified by silica gel column chromatography (85% ethyl acetate/hexane). An aliquot (220 mg) of the obtained colorless gum (503 mg) was dissolved in a hydrochloric acid-dioxane solution (4.0 M, 4.0 mL), and the solution was stirred at room temperature for 30 minutes. The reaction mixture was concentrated under reduced pressure, and the residue was then co-evaporated with toluene (5.0 mL×3). The residue was dissolved in dichloromethane (3.0 mL) and DMF (2.0 mL). To the mixture, triethylamine (260 µL) and benzenesulfonyl chloride (120 µL) were added, and the mixture was stirred at room temperature for 24 hours. To the reaction mixture, water (5.0 mL) was added, and the resultant mixture was then extracted with ethyl acetate (10 mL). The organic layer was washed with brine (5.0 mL), dried over anhydrous sodium sulfate, and then concentrated under reduced pressure. The residue was purified by silica gel column chromatography (90% ethyl acetate/hexane) to obtain the title compound (23.4 mg, yield: 9.5%) as a foam.

$^1$H-NMR (DMSO-$d_6$) δ (ppm): 1.00 (6H, s), 1.38-1.43 (4H, m), 2.40-2.45 (2H, m), 4.81 (2H, s), 5.62 (1H, dd, J=2.0, 7.9 Hz), 7.44 (1H, brs), 7.50-7.61 (3H, m), 7.70 (1H, d, J=7.9 Hz), 7.79-7.82 (2H, m), 11.34 (1H, brs)

Example 173

Synthesis of (E)-3-(cyclopropylmethoxy)-N-(7-(2,4-dioxo-3,4-dihydropyrimidin-1(2H)-yl)-2-methylhept-5-en-2-yl)benzenesulfonamide

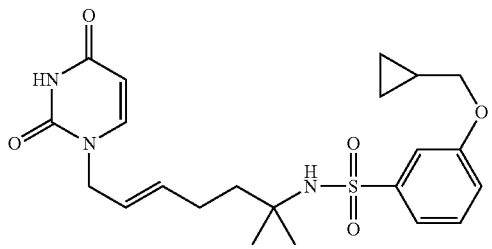

[Formula 92]

The (E)-N-(7-bromo-2-methylhept-5-en-2-yl)-3-(cyclopropylmethoxy)benzenesulfonamide (214 mg) obtained in Reference Example 242 was dissolved in DCE (5.0 mL). To the solution, 2,4-bis(trimethylsilyloxy)pyrimidine (198 mg) obtained according to a method described in the document (Nucleosides & Nucleotides, 4, 565-585 (1985)) and iodine (5 mg) were added, and the mixture was heated to reflux at 90° C. for 3 hours. The reaction mixture was cooled to room temperature, an aqueous saturated sodium bisulfite solution (5.0 mL) was then added thereto, and the resultant mixture was then extracted with ethyl acetate (15 mL). The organic layer was washed with brine (10 mL), dried over anhydrous sodium sulfate, and then concentrated under reduced pressure. The residue was purified by silica gel column chromatography (2% methanol/chloroform) to obtain the title compound (108 mg, yield: 47%) as a foam.

$^1$H-NMR (DMSO-d$_6$) δ (ppm): 0.29-0.35 (2H, m), 0.52-0.59 (2H, m), 1.05 (6H, s), 1.18-1.24 (1H, m), 1.38-1.44 (2H, m), 1.90-1.94 (2H, m), 3.84 (2H, d, J=6.9 Hz), 4.15 (2H, d, J=5.3 Hz), 5.32-5.51 (2H, m), 5.55 (1H, d, J=7.8 Hz), 7.08-7.11 (1H, m), 7.30-7.44 (4H, m), 7.51 (1H, d, J=7.8 Hz), 11.23 (1H, brs)

Example 174

Synthesis of N-(1-(3-(2,4-dioxo-3,4-dihydropyrimidin-1(2H)-yl)propoxy)-2-methylpropan-2-yl)benzenesulfonamide

[Formula 93]

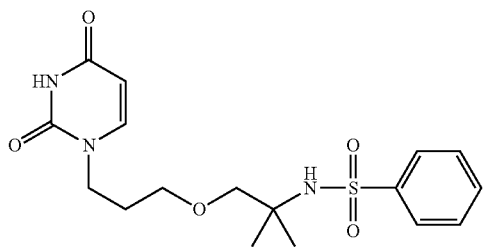

The N-(1-(3-aminopropoxy)-2-methylpropan-2-yl)benzenesulfonamide (600 mg) obtained in Reference Example 243 was dissolved in DMF (6.0 mL). To the solution, MS 4A (100 mg) and an aliquot (4.0 mL) of a solution of 3-methoxy-2-propenoyl isocyanate (442 mg) in toluene (6.0 mL) obtained according to a method described in the document (J. Heterocyclic Chem., 36, 293 (1999)) were gradually added at −40° C., and the mixture was stirred at room temperature for 14 hours. To the reaction mixture, water (10 mL) was added, and the resultant mixture was then extracted with ethyl acetate (20 mL). The organic layer was washed with brine (10 mL), dried over anhydrous sodium sulfate, and then concentrated under reduced pressure. The residue was purified by silica gel column chromatography (80% ethyl acetate/hexane). The obtained pale yellow solid (253 mg) was dissolved in ethanol. To the solution, concentrated hydrochloric acid (1.0 mL) was added, and the mixture was heated to reflux at 80° C. for 30 minutes. The reaction mixture was concentrated under reduced pressure, and the residue was co-evaporated with ethanol (5.0 mL×3). The residue was then purified by silica gel column chromatography (4% methanol/chloroform) to obtain the title compound (206 mg, yield: 27%) as a colorless gum.

$^1$H-NMR (DMSO-d$_6$) δ (ppm): 1.04 (6H, s), 1.67-1.76 (2H, m), 3.14 (2H, s), 3.22 (2H, t, J=6.0 Hz), 3.67 (2H, t, J=6.8 Hz), 5.52 (1H, d, J=7.9 Hz), 7.50-7.61 (5H, m), 7.78-7.84 (2H, m), 11.19 (1H, brs)

Example 175

Synthesis of 3-(cyclopropylmethoxy)-N-(1-(3-(2,4-dioxo-3,4-dihydropyrimidin-1(2H)-yl)propoxy)-2-methylpropan-2-yl)benzenesulfonamide

[Formula 94]

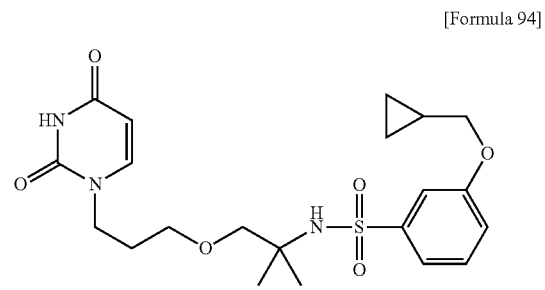 [SMILES: CC(C)(COCCCn1ccc(=O)[nH]c1=O)NS(=O)(=O)c1cccc(OCC2CC2)c1]

The title compound (215 mg, yield: 23%) was obtained as a pale yellow gum by synthesis according to the method of Example 174 from the N-(1-(3-aminopropoxy)-2-methylpropan-2-yl)-3-(cyclopropylmethoxy)benzenesulfonamide (730 mg) obtained in Reference Example 244.

$^1$H-NMR (DMSO-d$_6$) δ (ppm): 0.30-0.35 (2H, m), 0.53-0.58 (2H, m), 1.05 (6H, s), 1.17-1.24 (1H, m), 1.70-1.77 (2H, m), 3.14 (2H, s), 3.22 (2H, t, J=5.9 Hz), 3.67 (2H, t, J=6.8 Hz), 3.85 (2H, d, J=6.9 Hz), 5.52 (1H, d, J=7.7 Hz), 7.11-7.14 (1H, m), 7.33-7.48 (4H, m), 7.54 (1H, d, J=7.7 Hz), 11.20 (1H, brs)

Examples 176 to 179

Compounds shown below were synthesized according to the method of Example 173 from the compounds obtained in Reference Examples 245 to 248, respectively. The results are shown in tables below.

Example 176

N-(2-(4-((2,4-dioxo-3,4-dihydropyrimidin-1(2H)-yl)methyl)phenyl)propan-2-yl)benzenesulfonamide Example 177

N-(2-(4-((2,4-dioxo-3,4-dihydropyrimidin-1(2H)-yl)methyl)phenyl)propan-2-yl)-3-methoxybenzenesulfonamide Example 178

3-(cyclopropanemethoxy)-N-(2-(4-((2,4-dioxo-3,4-dihydropyrimidin-1(2H)-yl)methyl)phenyl)propan-2-yl)benzenesulfonamide Example 179

3-(cyclopropanemethoxy)-N-(2-(6-((2,4-dioxo-3,4-dihydropyrimidin-1(2H)-yl)methyl)pyridin-3-yl)propan-2-yl)benzenesulfonamide

TABLE 82

| Example | Reference Example No. | Product | Yield (%) | ¹H-NMR δ (ppm) Form |
|---|---|---|---|---|
| 176 | 245 | | 74 | (DMSO-d$_6$) 1.45 (6H, s), 4.76 (2H, s), 5.62 (1H, dd, J = 2.3, 7.9 Hz), 7.03 (2H, d, J = 8.4 Hz), 7.23 (2H, d, J = 8.4 Hz), 7.31-7.52 (5H, m), 7.72 (1H, d, J = 7.9 Hz), 8.06 (1H, brs), 11.33 (1H, brs) Foam |
| 177 | 246 | | 56 | (DMSO-d$_6$) 1.46 (6H, s), 3.72 (3H, s), 4.77 (2H, s), 5.61 (1H, d, J = 7.9 Hz), 6.96-7.10 (5H, m), 7.22-7.28 (3H, m), 7.70 (1H, d, J = 7.9 Hz), 8.04 (1H, brs), 11.31 (1H, brs) Foam |

TABLE 83

| Example | Reference Example No. | Product | Yield (%) | ¹H-NMR δ (ppm) Form |
|---|---|---|---|---|
| 178 | 247 | | 38 | (DMSO-d$_6$) 0.30-0.36 (2H, m), 0.54-0.61 (2H, m), 1.19-1.24 (1H, m), 1.45 (6H, s), 3.79 (2H, d, J = 6.9 Hz), 4.76 (2H, s), 5.60 (1H, d, J = 7.8 Hz), 6.97-7.06 (5H, m), 7.20-7.26 (3H, m), 7.69 (1H, d, J = 7.9 Hz), 8.02 (1H, brs), 11.32 (1H, brs) Foam |
| 179 | 248 | | 57 | (DMSO-d$_6$) 0.31-0.36 (2H, m), 0.54-0.61 (2H, m), 1.19-1.27 (1H, m), 1.48 (6H, s), 3.81 (2H, d, J = 7.1 Hz), 4.88 (2H, s), 5.61 (1H, d, J = 7.9 Hz), 7.01-7.09 (4H, m), 7.24-7.30 (1H, m), 7.63-7.68 (2H, m), 8.16 (1H, brs), 8.42 (1H, d, J = 2.5 Hz), 11.32 (1H, brs) Foam |

Comparative Example 1

1-((2-Trityloxy)ethoxy)methyl)pyrimidine-2,4-(1H,3H)-dione

[Formula 95]

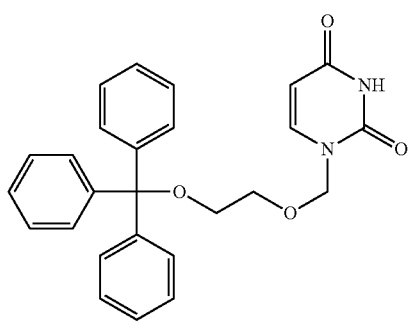

The title compound was synthesized according to a method described in WO2005-065689 (Patent Document 1).

Comparative Example 2

4-(2,4-Dioxo-3,4-dihydropyrimidin-1(2H)-yl)-N-hydroxy-2-(N-methyl-4-phenoxyphenylsulfonamide) butanamide

[Formula 96]

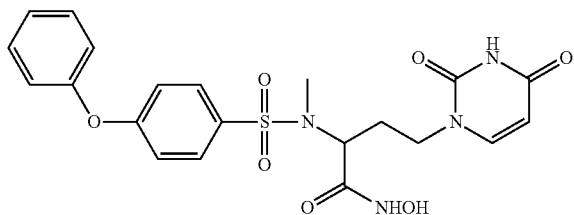

The title compound was synthesized according to a method described in JP-A-2002-284686.

Test Example 1

Human dUTPase Inhibitory Effect

The inhibitory activity of the compound of the present invention against human dUTPase was determined by measuring the production of [5-$^3$H]deoxyuridine monophosphate (hereinafter, referred to as [5-$^3$H]dUMP) from [5-$^3$H]deoxyuridine triphosphate (hereinafter, referred to as [5-$^3$H] dUTP) according to a method shown below.

Specifically, 0.2 mL in total of a solution containing 0.02 mL of 1 μM dUTP (including 588 Bq/mL [5-3H]dUTP), 0.05 mL of a 0.2 M Tris buffer solution (pH 7.4), 0.05 mL of 16 mM magnesium chloride, 0.02 mL of 20 mM 2-mercaptoethanol, 0.02 mL of a 1% aqueous solution of fetal bovine serum-derived albumin, 0.02 mL of varying concentrations of test compound solutions or pure water as a control, and 0.02 mL of a solution of human dUTPase (expressed using *E. coli* and purified) was reacted at 37° C. for 15 minutes. Immediately after the reaction, the solution was heated at 100° C. for 1 minute to terminate the reaction, followed by centrifugation at 15000 rpm for 2 minutes. An aliquot (150 μL) of the supernatant thus obtained by centrifugation was analyzed using an Atlantis dC18 column (manufactured by Waters Corp., 4.6×250 mm) and a high-performance liquid chromatograph (manufactured by Shimadzu Corp., Prominence). Elution was performed at a flow rate of 0.8 mL/min for 30 minutes by a concentration gradient from a 4:6 mixed solution of a mobile phase A (10 mM potassium dihydrogen phosphate (pH 6.7), 10 mM tetrabutylammonium, and 0.25% methanol) and a mobile phase B (50 mM potassium dihydrogen phosphate (pH 6.7), 5.6 mM tetrabutylammonium, and 30% methanol) to the mobile phase B. The eluate was mixed with a scintillator (manufactured by PerkinElmer Co., Ltd., Ultima-Flo AP) at a 1:2 ratio, and the radioactivity of the produced [5-$^3$H]dUMP (RT 10.2 min) was measured using Radiomatic Flow Scintillation Analyzer (manufactured by PerkinElmer Co., Ltd., 525TR).

The inhibitory activity of the test compound was determined according to the formula shown below. A concentration at which the test solution inhibits 50% of the amount of [5-$^3$H]dUMP produced by human dUTPase is shown as IC$_{50}$ (μM) in Tables 84 and 85.

$$\text{Inhibitory rate (\%)} = \left(1 - \frac{\text{Amount of } [5-^3H] \; dUMP \text{ in presence of test solution } (dpm)}{\text{Amount of } [5-^3H] \; dUMP \text{ as control } (dpm)}\right) \times 100$$

Data of the human dUTPase inhibitory activity is shown in tables below.

TABLE 84

| Example No. | IC$_{50}$ (μM) |
|---|---|
| 1 | 0.33 |
| 2 | 1.87 |
| 3 | 0.87 |
| 4 | 0.61 |
| 5 | 0.06 |
| 6 | 0.46 |
| 7 | 0.64 |
| 8 | 0.09 |
| 9 | 0.04 |
| 10 | 0.16 |
| 11 | 0.49 |
| 12 | 2.83 |
| 13 | 0.33 |
| 14 | 0.21 |
| 15 | 0.94 |
| 16 | 0.60 |
| 17 | 0.21 |
| 18 | 1.65 |
| 19 | 0.24 |
| 20 | 0.19 |
| 21 | 0.27 |
| 22 | 0.03 |
| 23 | 0.05 |
| 24 | 0.04 |
| 25 | 0.10 |
| 26 | 0.52 |
| 27 | 0.04 |
| 28 | 0.36 |
| 29 | 0.89 |
| 30 | 0.36 |
| 31 | 0.33 |
| 32 | 0.14 |
| 33 | 1.13 |

TABLE 84-continued

| Example No. | IC$_{50}$ (μM) |
|---|---|
| 34 | 0.03 |
| 35 | 1.55 |
| 36 | 0.15 |
| 37 | 0.10 |
| 38 | 0.03 |
| 39 | 0.28 |
| 40 | 0.10 |
| 41 | 0.04 |
| 42 | 0.33 |
| 43 | 0.09 |
| 44 | 0.16 |
| 45 | 2.01 |
| 46 | 2.35 |
| 47 | 0.21 |
| 48 | 0.14 |
| 49 | 0.94 |
| 50 | 2.03 |
| 51 | 0.83 |
| 52 | 0.51 |
| 53 | 0.23 |
| 54 | 0.23 |
| 55 | 0.41 |
| 56 | 0.85 |
| 57 | 1.18 |
| 58 | 0.31 |
| 59 | 0.72 |
| 60 | 0.49 |
| 61 | 0.14 |
| 62 | 0.37 |
| 63 | 0.47 |
| 64 | 0.41 |
| 65 | 1.00 |
| 66 | 0.46 |
| 67 | 0.43 |
| 68 | 0.11 |
| 69 | 0.74 |
| 70 | 0.76 |
| 71 | 0.93 |
| 72 | 0.66 |
| 73 | 0.51 |
| 76 | 2.10 |
| 77 | 5.69 |
| 78 | 2.58 |
| 79 | 1.65 |
| 80 | 1.30 |
| 81 | 9.44 |
| 83 | 4.78 |
| 87 | 7.13 |
| 93 | 4.63 |
| 96 | 4.62 |
| 97 | 0.58 |
| 98 | 0.66 |
| 99 | 1.81 |
| 100 | 0.04 |
| 101 | 0.07 |
| 102 | 0.61 |
| 103 | 0.52 |
| 104 | 1.46 |
| 105 | 0.17 |
| 106 | 0.12 |
| 107 | 1.72 |
| 108 | 1.71 |
| 109 | 0.12 |
| 110 | 0.05 |
| 111 | 8.27 |
| 112 | 2.23 |
| 113 | 0.41 |
| 114 | 0.58 |
| 115 | 0.25 |
| 116 | 0.35 |
| 118 | 9.80 |
| 128 | 0.27 |
| 130 | 0.48 |
| 131 | 0.40 |
| 132 | 0.38 |
| 133 | 6.56 |
| 134 | 4.54 |

TABLE 84-continued

| Example No. | IC$_{50}$ (μM) |
|---|---|
| 135 | 1.12 |
| 136 | 3.94 |
| 137 | 2.05 |
| 138 | 3.89 |
| 139 | 4.99 |
| 141 | 4.35 |
| 142 | 7.64 |
| 145 | 6.29 |
| 146 | 8.68 |
| 147 | 9.50 |
| 148 | 2.77 |
| 149 | 7.65 |
| 150 | 5.67 |
| 151 | 5.70 |
| 154 | 8.82 |
| 156 | 8.94 |
| 158 | 9.48 |
| 159 | 0.26 |
| 160 | 0.14 |
| 161 | 0.24 |
| 162 | 3.96 |
| 164 | 6.02 |
| 165 | 1.86 |
| 166 | 0.64 |
| 167 | 0.13 |
| 173 | 0.04 |

TABLE 85

| Example No. | IC$_{50}$ (μM) |
|---|---|
| 175 | 0.33 |
| 176 | 2.69 |
| 177 | 2.57 |
| 178 | 0.24 |
| 179 | 0.11 |
| Comparative Example 1 | 185 |
| Comparative Example 2 | 97.2 |

The compounds of the present invention exhibited much more potent human dUTPase inhibitory activity than each compound of Comparative Example 1 disclosed in Example of WO2005-065689 (Patent Document 1) which has dUTPase inhibitory effect and is structurally similar thereto, and Comparative Example 2 disclosed in Example of JP-A-2002-284686 which is structurally similar thereto.

The invention claimed is:

1. A uracil compound of formula (I) or a salt thereof:

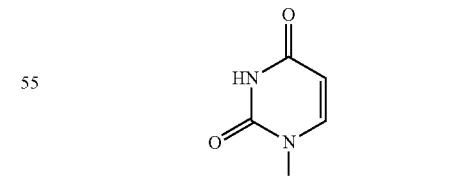

(I)

wherein:
n is an integer from 1 to 3;
X is a bond, an oxygen atom, a sulfur atom, an alkenylene group having comprising 2 to 6 carbon atoms, an optionally substituted divalent aromatic hydrocarbon group, or an optionally substituted divalent saturated or unsaturated heterocyclic group;

Y is a bond or a linear or branched alkylene group comprising 1 to 8 carbon atoms, which optionally has a cycloalkylidene structure on one carbon atom; and Z is $SO_2NR^1R^2$ or $-NR^3SO_2-R^4$, wherein:

$R^1$ and $R^2$ are each independently a hydrogen atom, an alkyl group comprising 1 to 6 carbon atoms, or an optionally substituted aralkyl group, wherein when an aromatic hydrocarbon group constituting the aralkyl group is a phenyl group, the phenyl group may form a condensed bicyclic hydrocarbon group, together with the substituent, or $R^1$ and $R^2$ are taken together with the adjacent nitrogen atom to form an optionally substituted saturated heterocyclic group;

$R^3$ is a hydrogen atom or an alkyl group comprising 1 to 6 carbon atoms; and $R^4$ is an optionally substituted aromatic hydrocarbon group or an optionally substituted unsaturated heterocyclic group excluding a uracil compound of formula (I), wherein n is 3, X is a bond, Y is a bond, Z is $-NR^3SO_2R^4$, $R^3$ is a hydrogen atom, and $R^4$ is a 5-(dimethylamino)-1-naphthyl group; and n is 3, X is a bond, Y is a bond, Z is $-NR^3SO_2R^4$, $R^3$ is a hydrogen atom, and $R^4$ is a 4-methylphenyl group.

2. The uracil compound or salt of claim 1, wherein:

n is 1 or 3;

X is a single bond, an oxygen atom, a sulfur atom, an alkenylene group comprising 2 to 4 carbon atoms, a divalent aromatic hydrocarbon group, or a divalent saturated or unsaturated heterocyclic group;

Y is a single bond or a linear or branched alkylene group comprising 1 to 6 carbon atoms, which optionally has a cycloalkylidene structure comprising 3 to 6 carbon atoms on one carbon atom, provided that when X is a single bond, the moiety $(CH_2)_n-X-Y$ is an alkylene group comprising 3 to 6 carbon atoms; and Z is $-SO_2NR^1R^2$ or $-NR^3SO_2-R^4$, wherein:

$R^1$ is a hydrogen atom or an alkyl group comprising 1 to 3 carbon atoms, and $R^2$ is a linear or branched alkyl group comprising 1 to 6 carbon atoms, which is substituted with an aromatic hydrocarbon group comprising having 6 to 14 carbon atoms, wherein each of the aromatic hydrocarbon group and the alkyl group is optionally substituted, and when the aromatic hydrocarbon group is a phenyl group, the phenyl group may form a condensed bicyclic hydrocarbon group, together with the substituent, or $R^1$ and $R^2$ are taken together with the adjacent nitrogen atom to form an optionally substituted pyrrolidinyl ring;

$R^3$ is a hydrogen atom; and $R^4$ a is an optionally substituted phenyl group, an optionally substituted naphthyl group, or an optionally substituted thienyl group.

3. The uracil compound or salt of claim 1, wherein:

n is 1 or 3;

X is a single bond, an oxygen atom, a sulfur atom, a vinylene group, a phenylene group, or a divalent group derived from a thienyl, piperidinyl, or pyridyl group;

Y is a single bond or a linear or branched alkylene group comprising 1 to 6 carbon atoms, which optionally has a cycloalkylidene structure comprising 3 to 6 carbon atoms on one carbon atom, provided that when X is a single bond, the moiety $(CH_2)_n-X-Y$ is an alkylene group comprising 3 to 6 carbon atoms; and Z is $-SO_2NR^1R^2$ or $-NR^3SO_2-R^4$, wherein:

$R^1$ is a hydrogen atom or an alkyl group comprising 1 to 3 carbon atoms, and $R^2$ is an optionally substituted benzyl group or an optionally substituted phenylethyl group (when a methylene group of the benzyl group or an ethylene group of the phenylethyl group comprises a substituent, each may comprise 1 to 3 substituents each independently selected from the group consisting of a hydroxyl group, an alkyl group comprising 1 to 6 carbon atoms, a cycloalkyl group comprising 3 to 7 carbon atoms, an optionally substituted aromatic hydrocarbon group, and an optionally substituted unsaturated heterocyclic group, wherein when two or more of the substituents are respectively an alkyl group comprising 1 to 6 carbon atoms, the carbon atoms of these alkyl groups may form together a cycloalkylidene structure; when a phenyl group of the benzyl or phenylethyl group comprises a substituent, each may comprise 1 to 2 substituents each independently selected from the group consisting of a halogen atom, an optionally substituted alkyl group comprising 1 to 6 carbon atoms, an optionally substituted alkynyl group comprising 2 to 6 carbon atoms, an optionally substituted linear or branched alkoxy group comprising 1 to 6 carbon atoms or a cycloalkylidene structure, a cycloalkoxy group comprising 3 to 7 carbon atoms, a cycloalkyl-alkoxy group comprising 3 to 7 carbon atoms, a cycloalkyl-alkylthio group comprising 3 to 7 carbon atoms, and a saturated heterocyclic oxy group; and the substituents in the methylene group of the benzyl group or ethylene group of the phenylethyl group and in the phenyl group of the benzyl or phenylethyl group may together form a condensed bicyclic hydrocarbon group with the phenyl group, or $R^1$ and $R^2$ are taken together with the adjacent nitrogen atom to form an optionally substituted pyrrolidinyl ring;

$R^3$ is a hydrogen atom; and $R^4$ is a phenyl group optionally comprising 1 to 2 substituents independently selected from the group consisting of a halogen atom, a cyano group, a nitro group, an alkyl group comprising 1 to 6 carbon atoms, an alkenyl group comprising 2 to 6 carbon atoms, an alkoxy group comprising 1 to 6 carbon atoms, a halogenoalkoxy group comprising 1 to 6 carbon atoms, a cycloalkyl-alkoxy group comprising 3 to 7 carbon atoms, a cycloalkoxy group comprising 3 to 7 carbon atoms, a carboxyl group, an alkoxycarbonyl group comprising 1 to 6 carbon atoms, and an acyloxy group; a naphthyl group optionally substituted with a mono- or dialkylamino group; or a thienyl group optionally substituted with a halogen atom.

4. The uracil compound or salt of claim 1, wherein:

n is 1;

X is a single bond, an oxygen atom, or a vinylene group;

Y is a linear alkylene group comprising 1 to 4 carbon atoms, provided that when X is a single bond, the moiety $(CH_2)_n-X-Y$ is a trimethylene or pentamethylene group; and Z is $-SO_2NR^1R^2$, wherein:

$R^1$ is a hydrogen atom and $R^2$ a is an optionally substituted benzyl group or an optionally substituted phenylethyl group (when a methylene group of the benzyl group or an ethylene group of the phenylethyl group comprises a substituent, each comprises 1 to 3 substituents each independently selected from the group consisting of a hydroxyl group, a methyl group, an ethyl group, an isopropyl group, an isobutyl group, a cyclopropyl group, an optionally substituted phenyl group, and an optionally substituted thienyl group, wherein when two or more of the substituents are respectively an alkyl group comprising 1 to 6 carbon atoms, the carbon atoms of these alkyl groups may together form a cycloalkylidene structure; when a phenyl group of the benzyl or phenylethyl group comprises a substituent, each may comprise 1 to 2 substituents each independently selected from the group consisting of a halogen atom, an alkyl group comprising 1 to 6 carbon atoms, a halogenoalkyl group comprising 1 to 6 carbon atoms, an alkynyl group comprising 2 to 6 carbon atoms, a linear or branched alkoxy group comprising 1 to 6 carbon atoms optionally comprising at least one substituent selected from the group consisting of a hydroxyl group, an alkenyl group comprising 2 to 6 carbon atoms, and an alkynyl group comprising 2 to 6 carbon atoms or a cycloalkylidene structure, a halogenoalkoxy group having comprising 1 to 6 carbon atoms, a cycloalkoxy group comprising 3 to 7 carbon atoms, a cycloalkyl-alkoxy group comprising 3 to 7 carbon atoms, a cycloalkyl-alkylthio group comprising 3 to 7 carbon atoms, and a saturated heterocyclic oxy group), or $R^1$ and $R^2$ together with the adjacent nitrogen atom form a pyrrolidinyl group optionally comprising an aralkyl group, wherein the aralkyl group is optionally substituted with at least one selected from the group consisting of a hydroxyl group, a halogen atom, and an optionally substituted phenyl group.

5. The uracil compound or salt of claim 1, wherein:
n is 1;
X is a single bond, an oxygen atom, or a vinylene group;
Y is an ethylene or trimethylene group, provided that when X is a single bond, the moiety $(CH_2)_n$—X—Y is a trimethylene or pentamethylene group; and
Z is —$SO_2NR^1R^2$,
wherein:
$R^1$ is a hydrogen atom;
$R^2$ is an optionally substituted benzyl group, wherein when a methylene group of the benzyl group comprises a substituent, it comprises 1 substituent selected from the group consisting of a methyl group, an ethyl group, an isopropyl group, a phenyl group, a 3-cyclopropylmethoxyphenyl group, and 4-fluorophenyl group; when a phenyl group of the benzyl group comprises a substituent, it comprises 1 to 2 substituents independently selected from the group consisting of a chlorine atom, a bromine atom, a fluorine atom, a methyl group, a trifluoromethyl group, an ethynyl group, an isobutoxy group, a 2-methylbutoxy group, an allyloxy group, a 2,2-difluoroethoxy group, a 2,2,2-trifluoroethoxy group, a cyclopentyloxy group, a cyclopropylmethoxy group, a tetrahydrofuran-3-yloxy group, and a tetrahydropyran-4-yloxy group.

6. The uracil compound or salt of claim 1, which is selected from the group consisting of:
N-(3-(cyclopropylmethoxy)benzyl)-3-((2,4-dioxo-3,4-dihydropyrimidin-1(2H)-yl)methoxy)propane-1-sulfonamide;
(R)—N-(1-(3-(cyclopentyloxy)phenyl)ethyl)-3-((2,4-dioxo-3,4-dihydropyrimidin-1(2H)-yl)methoxy)propane-1-sulfonamide;
3-((2,4-dioxo-3,4-dihydropyrimidin-1(2H)-yl)methoxy)-N—((R)-1-(3-((R)-tetrahydrofuran-3-yloxy)phenyl)ethyl)propane-1-sulfonamide;
N-(3-(cyclopropylmethoxy)-4-fluorobenzyl)-3-((2,4-dioxo-3,4-dihydropyrimidin-1(2H)-yl)methoxy)propane-1-sulfonamide;
(R)—N-(1-(3-(cyclopropylmethoxy)-4-fluorophenyl)ethyl)-3-((2,4-dioxo-3,4-dihydropyrimidin-1(2H)-yl)methoxy)propane-1-sulfonamide;
N-(1-(3-(cyclopropylmethoxy)phenyl)ethyl)-3-((2,4-dioxo-3,4-dihydropyrimidin-1(2H)-yl)methoxy)propane-1-sulfonamide;
N-(3-(cyclopentyloxy)benzyl)-3-((2,4-dioxo-3,4-dihydropyrimidin-1(2H)-yl)methoxy)propane-1-sulfonamide;
(R)—N-(1-(3-(cyclopropylmethoxy)-4-fluorophenyl)propyl)-3-((2,4-dioxo-3,4-dihydropyrimidin-1(2H)-yl)methoxy)propane-1-sulfonamide;
(R)—N-(1-(3-(cyclopropylmethoxy)phenyl)ethyl)-3-((2,4-dioxo-3,4-dihydropyrimidin-1(2H)-yl)methoxy)propane-1-sulfonamide;
(R)—N-(1-(3-(cyclopentyloxy)-4-fluorophenyl)ethyl)-3-((2,4-dioxo-3,4-dihydropyrimidin-1(2H)-yl)methoxy)propane-1-sulfonamide;
(R)-3-((2,4-dioxo-3,4-dihydropyrimidin-1(2H)-yl)methoxy)-N-(1-(3-(tetrahydro-2H-pyran-4-yloxy)phenyl)ethyl)propane-1-sulfonamide;
(R)-3-((2,4-dioxo-3,4-dihydropyrimidin-1(2H)-yl)methoxy)-N-(1-(3-(2,2,2-trifluoroethoxy)phenyl)ethyl)propane-1-sulfonamide;
(R)-3-((2,4-dioxo-3,4-dihydropyrimidin-1(2H)-yl)methoxy)-N-(1-(4-fluoro-3-(2,2,2-trifluoroethoxy)phenyl)ethyl)propane-1-sulfonamide;
(R)-3-((2,4-dioxo-3,4-dihydropyrimidin-1(2H)-yl)methoxy)-N-(1-(3-isobutoxyphenyl)ethyl)propane-1-sulfonamide;
3-((2,4-dioxo-3,4-dihydropyrimidin-1(2H)-yl)methoxy)-N—((R)-1-(3-((S)-2-methylbutoxy)phenyl)ethyl)propane-1-sulfonamide;
(R)—N-(1-(3-(2,2-difluoroethoxy)phenyl)ethyl)-3-((2,4-dioxo-3,4-dihydropyrimidin-1(2H)-yl)methoxy)propane-1-sulfonamide;
(R)—N-(1-(3-(allyloxy)phenyl)ethyl)-3-((2,4-dioxo-3,4-dihydropyrimidin-1(2H)-yl)methoxy)propane-1-sulfonamide;
(R)-3-((2,4-dioxo-3,4-dihydropyrimidin-1(2H)-yl)methoxy)-N-(1-phenylethyl)propane-1-sulfonamide;
(R)—N-(1-(3-(cyclopropylmethoxy)phenyl)propyl)-3-(2,4-dioxo-3,4-dihydropyrimidin-1(2H)-yl)propane-1-sulfonamide;
(R)-3-(2,4-dioxo-3,4-dihydropyrimidin-1(2H)-yl)-N-(1-phenylethyl)propane-1-sulfonamide;
(R)-3-(2,4-dioxo-3,4-dihydropyrimidin-1(2H)-yl)-N-(1-(2-fluorophenyl)ethyl)propane-1-sulfonamide;
(R)—N-(1-(2-chlorophenyl)ethyl)-3-(2,4-dioxo-3,4-dihydropyrimidin-1(2H)-yl)propane-1-sulfonamide;
(R)-3-(2,4-dioxo-3,4-dihydropyrimidin-1(2H)-yl)-N-(1-(2-ethynylphenyl)ethyl)propane-1-sulfonamide;
(R)—N-(1-(2-bromophenyl)ethyl)-3-(2,4-dioxo-3,4-dihydropyrimidin-1(2H)-yl)propane-1-sulfonamide; and
(R)-3-(2,4-dioxo-3,4-dihydropyrimidin-1(2H)-yl)-N-(1-o-tolylethyl)propane-1-sulfonamide.

7. A pharmaceutical composition, comprising:
a uracil compound or salt of claim 1.

8. A human dUTPase inhibitor, comprising:
a uracil compound or salt of claim 1.

* * * * *